(12) United States Patent
Boy et al.

(10) Patent No.: US 8,710,061 B2
(45) Date of Patent: *Apr. 29, 2014

(54) COMPOUNDS FOR THE REDUCTION OF β-AMYLOID PRODUCTION

(75) Inventors: Kenneth M. Boy, Durham, CT (US); Jason M. Guernon, Moodus, CT (US); John E. Macor, Guilford, CT (US); Richard E. Olson, Orange, CT (US); Jianliang Shi, Madison, CT (US); Lorin A. Thompson, III, Higganum, CT (US); Yong-Jin Wu, Madison, CT (US); Li Xu, Middletown, CT (US); Yunhui Zhang, Glastonbury, CT (US); Dmitry S. Zuev, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 15 days.

This patent is subject to a terminal disclaimer.

(21) Appl. No.: 13/358,822

(22) Filed: Jan. 26, 2012

(65) Prior Publication Data

US 2013/0030011 A1 Jan. 31, 2013

Related U.S. Application Data

(60) Provisional application No. 61/437,279, filed on Jan. 28, 2011.

(51) Int. Cl.
*A61K 31/497* (2006.01)
*A01N 43/54* (2006.01)
*A01N 43/90* (2006.01)

(52) U.S. Cl.
USPC .................................. 514/252.16; 514/258.1

(58) Field of Classification Search
USPC ................. 514/210.21, 230.5, 234.2, 252.16, 514/258.1, 260.1, 264.11, 371, 383
See application file for complete search history.

(56) References Cited

U.S. PATENT DOCUMENTS

| 8,349,880 B2 * | 1/2013 | Marcin et al. ................. 514/371 |
| 2011/0212937 A1 * | 9/2011 | Boy et al. ................. 514/210.16 |
| 2012/0028994 A1 * | 2/2012 | Boy et al. ................. 514/258.1 |

FOREIGN PATENT DOCUMENTS

| EP | 1 698 627 | 9/2006 |
| EP | 2 226 315 | 9/2010 |
| WO | WO 2010/083141 | 7/2010 |
| WO | WO 2011/014535 | 2/2011 |

OTHER PUBLICATIONS

Anderson, D.H. et al., "Characterization of β amyloid assemblies in drusen: the deposits associated with aging and age-related macular degeneration", Experimental Eye Research, vol. 78, pp. 243-256 (2004).

Barten, D.M. et al., "γ-Secretase Inhibitors for Alzheimer's Disease: Balancing Efficacy and Toxicity", Drugs R.D., vol. 7, No. 2, pp. 87-97 (2006).

Cleary, J.P. et al., "Natural oligomers of the amyloid-β protein specifically disrupt cognitive function", Nature Neuroscience, vol. 8, No. 1, pp. 79-84 (2005).

Deramecourt, V. et al., "Biochemical Staging of Synucleinopathy and Amyloid Deposition in Dementia with Lewy Bodies", J. Neuropathol. Exp. Neurol., vol. 65, No. 3, pp. 278-288 (2006).

Goldstein, L.E. et al., "Cytosolic β-amyloid deposition and supranuclear cataracts in lenses from people with Alzheimer's disease", The Lancet, vol. 361, pp. 1258-1265 (2003).

Grundman, M. et al., "Mild Cognitive Impairment Can Be Distinguished from Alzheimer Disease and Normal Aging for Clinical Trials", Arch. Neurol., vol. 61, pp. 59-66 (2004).

Hamilton, R.L. et al., "Alzheimer disease pathology in amyotrophic lateral sclerosis", Acta Neuropathol., vol. 107, pp. 515-522 (2004).

Loane, D.J. et al., "Amyloid precursor protein secretases as therapeutic targets for traumatic brain injury", Nature Medicine, vol. 15, No. 4, pp. 377-379 (2009).

Murphy, M.P. et al., "Inclusion-body myositis and Alzheimer disease: Two sides of the same coin, or different currencies altogether?", Neurology, vol. 66, Suppl. 1, pp. S65-S68 (2006).

Neumann, M. et al., "Ubiquitinated TDP-43 in Frontotemporal Lobar Degeneration and Amyotrophic Lateral Sclerosis", Science, vol. 314, pp. 130-133 (2006).

Selkoe, D.J., "Alzheimer's Disease: Genes, Proteins, and Therapy", Physiological Reviews, vol. 81, No. 2, pp. 741-766 (2001).

Thal, D.R. et al., "Two Types of Sporadic Cerebral Amyloid Angiopathy", Journal of Neuropathology and Experimental Neurology, vol. 61, No. 3, pp. 282-293 (2002).

The National Institute on Aging, and Reagan Institute Working Group on Diagnostic Criteria for the Neuropathological Assessment of Alzheimer's Disease, "Consensus Recommendations for the Postmortem Diagnosis of Alzheimer's Disease", Neurobiology of Aging, vol. 18, No. S4, pp. S1-S2 (1997).

Walsh, D.M. et al., "Deciphering the Molecular Basis of Memory Failure in Alzheimer's Disease", Neuron, vol. 44, pp. 181-193 (2004).

(Continued)

*Primary Examiner* — My-Chau T Tran
(74) *Attorney, Agent, or Firm* — John F. Levis

(57) ABSTRACT

The present disclosure provides a series of compounds of the formula (I)

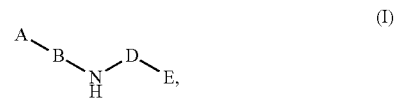

which modulate β-amyloid peptide (β-AP) production and are useful in the treatment of Alzheimer's Disease and other conditions affected by β-amyloid peptide (β-AP) production.

18 Claims, No Drawings

(56) References Cited

OTHER PUBLICATIONS

Watkins, T.A. et al., "Distinct Stages of Myelination Regulated by γ-Secretase and Astrocytes in a Rapidly Myelinating CNS Coculture System", Neuron, vol. 60, pp. 555-569 (2008).
Wolfe, M.S., "Secretase Targets for Alzheimer's Disease: Identification and Therapeutic Potential", Journal of Medicinal Chemistry, vol. 44, No. 13, pp. 2039-2060 (2001).
Wolfe, M.S. et al., "Intramembrane Proteolysis: Theme and Variations", Science, vol. 305, pp. 1119-1123 (2004).
Yokota, O. et al., "NACP/α-Synuclein, NAC, and β-amyloid pathology of familial Alzheimer's disease with the E184D presenilin-1 mutation: a clinicopathological study of two autopsy cases", Acta Neuropathol., vol. 104, pp. 637-648 (2002).
Yoshida, T. et al., "The potential role of amyloid β in the pathogenesis of age-related macular degeneration", The Journal of Clinical Investigation, vol. 115, No. 10, pp. 2793-2800 (2005).

\* cited by examiner

COMPOUNDS FOR THE REDUCTION OF β-AMYLOID PRODUCTION

CROSS-REFERENCE TO RELATED APPLICATION

This non-provisional application claims the benefit of U.S. Provisional Application Ser. No. 61/437,279 filed Jan. 28, 2011.

FIELD OF THE INVENTION

The present disclosure relates to methods of treating Alzheimer's Disease (AD) and other conditions related to β-amyloid production using compounds which are inhibitors of β-amyloid peptide (Aβ) production. The disclosure further relates to pharmaceutical compositions comprising these compounds.

BACKGROUND OF THE INVENTION

Alzheimer's disease (AD) is a progressive neurodegenerative disease which begins with memory loss and progresses to include severe cognitive impairment, altered behavior, and decreased motor function (Grundman, M. et al., *Arch Neurol.* (2004) 61: 59-66; Walsh, D. M. et al., *Neuron* (2004) 44: 181-193). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol Aging* (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme (BACE), to generate the N-terminus, and γ-secretase, to generate the C-terminus (Selkoe, D. J., *Physiol Rev.* (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., *Science* (2004) 305: 1119-1123). PS-1 and PS-2 are believed to contain the catalytic sites of γ-secretase.

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol Rev.*, (2001) 81: 741-766). Current evidence suggests that oligomeric, protofibrillar and intracellular Aβ42 play a significant role in the disease process (Cleary, J. P. et al., *Nat Neurosci.* (2005) 8: 79-84). Inhibitors of the enzymes that form Aβ42, such as γ-secretase, represent potential disease-modifying therapeutics for the treatment of AD.

Evidence suggests that a reduction in brain Aβ levels by inhibition of γ-secretase may prevent the onset and progression of AD (Selkoe, D. *Physiol. Rev.* (2001) 81: 741-766; Wolfe, M., *J. Med. Chem.* (2001) 44: 2039-2060). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit γ-secretase and reduce production of Aβ could be used to treat these or other Aβ-dependent diseases.

Excess production and/or reduced clearance of Aβ causes CAA (Thal, D. et al., *J. Neuropath. Exp. Neuro.* (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that reduce Aβ levels could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol (Berl)* (2002) 104: 637-648). Further, sporadic DLB patients have Aβ deposits similar to those in AD (Deramecourt, V. et al., *J Neuropathol Exp Neurol* (2006) 65: 278-288). Based on this data, Aβ likely drives Lewy body pathology in DLB and, therefore, compounds that reduce Aβ levels could reduce or prevent DLB.

Approximately 25% of ALS patients have significant dementia or aphasia (Hamilton, R. L. et al., *Acta Neuropathol (Berl)* (2004) 107: 515-522). The majority (~60%) of these patients, designated ALS-D, contain ubiquitin-positive inclusions comprised primarily of the TDP-43 protein (Neumann, M. et al., *Science* (2006) 314: 130-133). About 30% of the ALS-D patients have amyloid plaques consistent with Aβ causing their dementia (Hamilton, R. L. et al., *Acta Neuropathol (Berl)* (2004) 107: 515-522). These patients should be identifiable with amyloid imaging agents and potentially could be treated by compounds that reduce Aβ levels.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology* (2006) 66: S65-68). Compounds that reduce Aβ levels could reduce or prevent IBM.

In age-related macular degeneration, Aβ was identified as one of several components of drusen, extracellular deposits beneath the retinal pigment epithelium (RPE) (Anderson, D. H. et al., *Exp Eye Res* (2004) 78: 243-256). A recent study has shown potential links between Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that reduce Aβ levels could reduce or prevent age-related macular degeneration.

Compounds which inhibit gamma secretase may also be useful in treating conditions associated with loss of myelination, for example multiple sclerosis (Watkins, T. A., et al., *Neuron* (2008) 60: 555-569).

A recent study by Georgetown University Medical Center researchers suggests that gamma-secretase inhibitors may prevent long-term damage from traumatic brain injury (Loane, D. J., et al., *Nature Medicine* (2009): 1-3).

A logical approach to reducing Aβ levels is to block the action of the secretases. A complementary approach is to selectively reduce production of Aβ1-42 by the action of certain compounds that serve to direct the γ-secretase-mediated cleavage of APP to instead produce shorter forms of Aβ.

These shorter forms appear to aggregate less easily and solutions of the shorter forms of Aβ are less neurotoxic than solutions of Aβ1-42 (See Barten, Donna M.; Meredith, Jere E., Jr.; Zaczek, Robert; Houston, John G.; Albright, Charles F. *Drugs in R&D* (2006), 7(2), 87-97). Thus, compounds that selectively reduce Aβ1-42 production and their pharmaceutical compositions are beneficial agents that will prevent damage from overproduction of Aβ and are useful in treating Alzheimer's disease, Down syndrome, CAA, and inclusion body myositis, DLB, and other disorders where Aβ is overproduced.

SUMMARY OF THE INVENTION

In its first aspect the present disclosure provides a compound of formula (I)

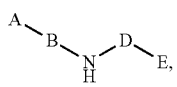

or a pharmaceutically acceptable salt thereof, wherein
A is a nitrile group;
B is selected from phenyl and pyridinyl, wherein the phenyl and pyridinyl are optionally substituted with one or two substituents independently selected from $C_{1-6}$alkoxy, $C_{1-6}$alkyl, $C_{1-3}$alkylamino-$C_{1-6}$alkoxy, cyano, $C_{1-3}$dialkylamino-$C_{1-6}$alkoxy, halo, halo$C_{1-6}$alkoxy, halo$C_{1-6}$alkyl, hydroxy, methylamino, and amino;
D is selected from the group of:

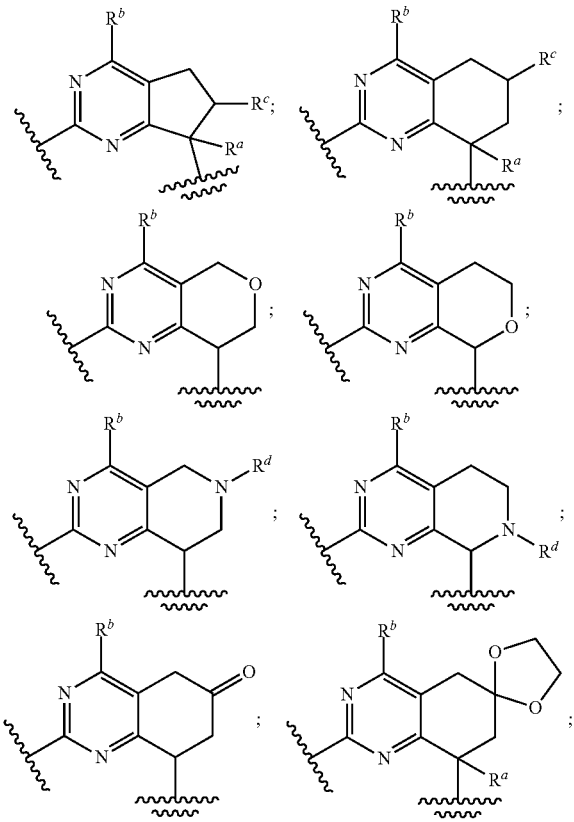

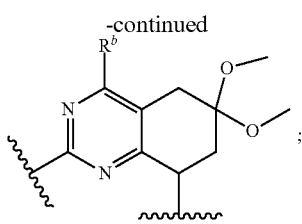

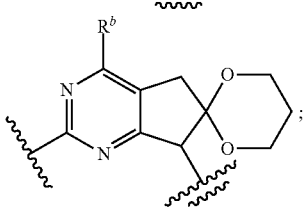

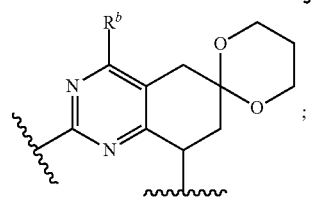

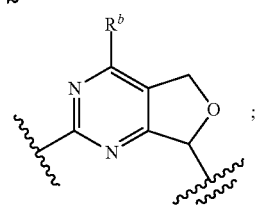

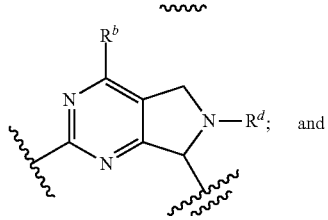

" $\xi$ " denotes the point of attachment to the nitrogen atom of the parent molecule;

" $\sim$ " denotes the point of attachment to the 'E' moiety;
$R^a$ is selected from hydrogen, $C_{1-6}$alkyl, $C_{2-6}$alkenyl, and hydroxy;
$R^b$ is —$NR^xR^y$, wherein $R^x$ and $R^y$ are independently selected from hydrogen, $C_{1-4}$alkoxy, $C_{1-4}$alkoxy$C_{1-4}$alkyl, $C_{1-4}$alkoxycarbonyl, $C_{1-6}$alkyl, $C_{3-7}$cycloalkyl, ($C_{3-7}$cycloalkyl)$C_{1-4}$alkyl, hydroxy$C_{1-4}$alkyl, and trideuteromethyl, wherein the alkyl part of the ($C_{3-7}$cycloalkyl)$C_{1-4}$alkyl can be optionally substituted with a $C_{1-4}$alkoxy group; or, $R^x$ and $R^y$, together with the nitrogen atom to which they are attached, form a four- to seven-membered monocyclic or bicyclic ring optionally containing one double bond and optionally containing one additional heteroatom selected from O, $NR^z$, and S; wherein $R^z$ is selected from hydrogen, $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —$NR^fR^g$, oxo, spirocyclic dioxolanyl; wherein $R^f$ and $R^g$ are independently selected from hydrogen, $C_{1-4}$alkoxycarbonyl, and $C_{1-6}$alkyl;
$R^c$ is selected from hydrogen, $C_{1-4}$alkylsulfonyl, $C_{1-4}$alkylsulfonylamido, amino, $C_{1-6}$alkylamino, $C_{1-6}$dialkylamino, $C_{3-7}$cycloalkylamino, hydroxy, and $C_{1-4}$alkoxy;
$R^d$ is selected from hydrogen, $C_{1-6}$alkyl, $C_{1-4}$alkoxy$C_{1-4}$alkylcarbonyl, $C_{1-6}$alkoxycarbonyl, $C_{1-6}$alkylcarbonyl, $C_{1-6}$alkylsulfonyl, $C_{3-7}$cycloalkylsulfonyl, $C_{3-7}$cycloalkylcarbonyl, $C_{1-6}$dialkylamino$C_{1-4}$alkylcarbonyl, and halo$C_{1-4}$alkyl, wherein the alkyl part of the alkoxycarbonyl, the alkylcarbonyl, and the alkylsulfonyl are optionally substituted with one substituent selected from $C_{1-4}$dialkylamino, and $C_{1-4}$alkoxy; and E is selected from $C_{1-6}$alkyl, $C_{4-6}$cycloalkyl, $(C_{4-7}$cycloalkyl$)C_{1-4}$alkyl, benzyl, phenyl, and a five- to six-membered heteroaromatic ring containing one or two nitrogen atoms, wherein the phenyl, the phenyl part of the benzyl, and the heteroaromatic ring are each optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl.

The present invention is directed to these, as well as other important ends, hereinafter described.

DETAILED DESCRIPTION OF THE EMBODIMENTS

In a first embodiment of the first aspect the present disclosure provides a compound of formula (I), or a pharmaceutically acceptable salt thereof, as set forth above wherein A is a nitrile group. In a second embodiment, B is selected from phenyl and pyridinyl, wherein the phenyl and pyridinyl are optionally substituted with one or two substituents independently selected from $C_{1-6}$alkoxy and halo. In a third embodiment, E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl. In a fourth embodiment, D is selected from

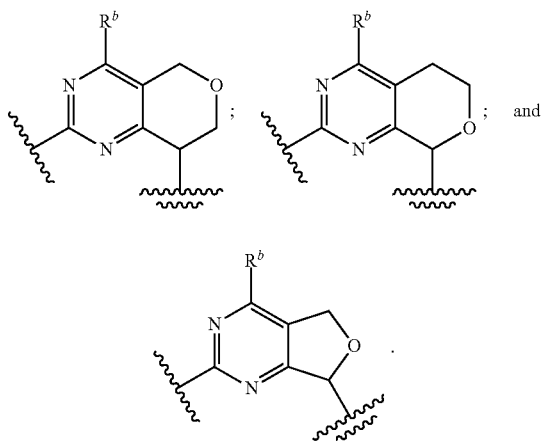

In a fifth embodiment, $R^b$ is —$NR^xR^y$, wherein $R^x$ and $R^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the $(C_{3-7}$cycloalkyl$)C_{1-4}$alkyl can be optionally substituted with a $C_{1-4}$alkoxy group.

In a sixth embodiment of the first aspect, the present disclosure provides a compound of formula (I), or a pharmaceutically acceptable salt thereof, wherein:

A is a nitrile group;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from the group of:

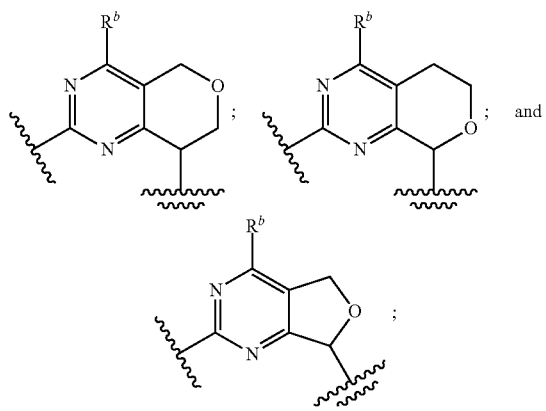

and $R^b$ is —$NR^xR^y$, wherein $R^x$ and $R^y$, together with the nitrogen atom to which they are attached, form a four- to seven-membered monocyclic or bicyclic ring optionally containing one additional heteroatom selected from O and $NR^z$; wherein $R^z$ is selected from $C_{1-4}$alkyl, and $C_{1-4}$alkoxycarbonyl; and wherein the ring is optionally substituted with one or two substituents independently selected from the group of $C_{1-6}$alkoxy, $C_{1-6}$alkyl, halo, halo$C_{1-4}$alkyl, hydroxy, —$NR^fR^g$, oxo, and spirocycle dioxolanyl; wherein $R^f$ and $R^g$ are independently selected from hydrogen, $C_{1-4}$alkoxycarbonyl, and $C_{1-6}$alkyl.

In a seventh embodiment of the first aspect, the present disclosure provides a compound of formula (I), or a pharmaceutically acceptable salt thereof, wherein:

A is a nitrile group;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl; and D is selected from the group of:

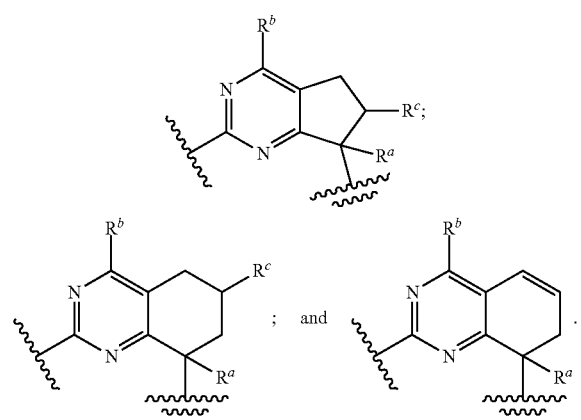

In an eighth embodiment of the first aspect, the present disclosure provides a compound of formula (I), or a pharmaceutically acceptable salt thereof, wherein:

A is a nitrile group;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from the group of:

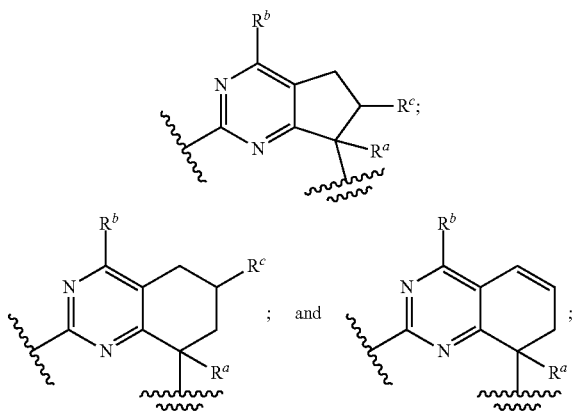

and $R^b$ is —$NR^xR^y$, wherein $R^x$ and $R^y$ are independently selected from hydrogen, $C_{1-4}$alkoxy$C_{1-4}$alkyl, $C_{1-6}$alkyl, $C_{3-7}$cycloalkyl, and hydroxy$C_{1-4}$alkyl, wherein the alkyl part of the ($C_{3-7}$cycloalkyl)$C_{1-4}$alkyl can be optionally substituted with a $C_{1-4}$alkoxy group.

In a ninth embodiment of the first aspect, the present disclosure provides a compound of formula (I), or a pharmaceutically acceptable salt thereof, wherein:

A is a nitrile group;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from the group of:

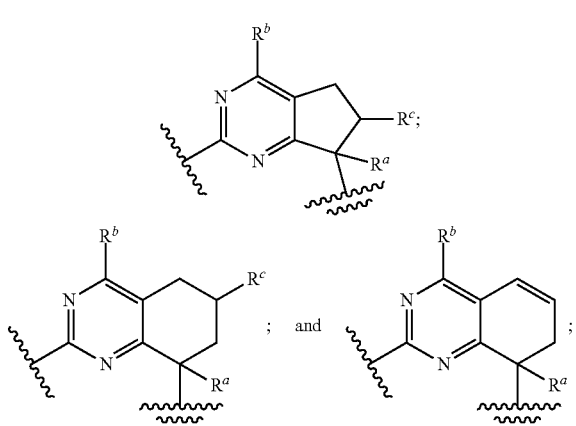

and $R^b$ is —$NR^xR^y$, wherein $R^x$ and $R^y$, together with the nitrogen atom to which they are attached, form a four- to seven-membered monocyclic or bicyclic ring optionally containing one additional heteroatom selected from O and $NR^z$; wherein $R^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —$NR^fR^g$, oxo, and spirocycle dioxolanyl; wherein $R^f$ and $R^g$ are independently selected from hydrogen, $C_{1-4}$alkoxycarbonyl, and $C_{1-6}$alkyl.

In a tenth embodiment of the first aspect, the present disclosure provides a compound of formula (I), or a pharmaceutically acceptable salt thereof, wherein:

A is a nitrile group;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl; and D is selected from

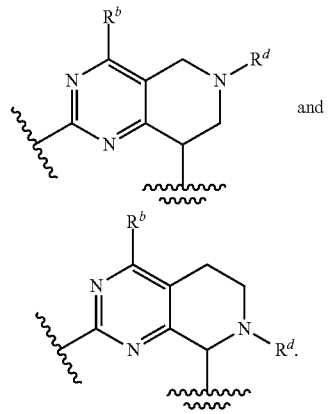

In an eleventh embodiment of the first aspect, the present disclosure provides a compound of formula (I), or a pharmaceutically acceptable salt thereof, wherein:

A is a nitrile group;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from

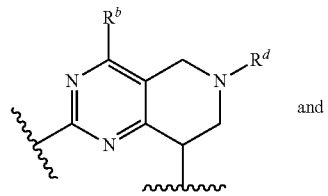

and

-continued

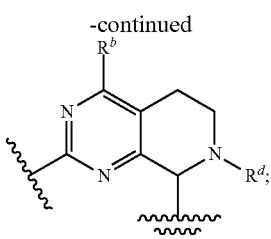

and $R^b$ is —$NR^xR^y$, wherein $R^x$ and $R^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the $(C_{3-7}$cycloalkyl)$C_{1-4}$alkyl can be optionally substituted with a $C_{1-4}$alkoxy group.

In a twelfth embodiment of the first aspect, the present disclosure provides a compound of formula (I), or a pharmaceutically acceptable salt thereof, wherein:

A is a nitrile group;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from

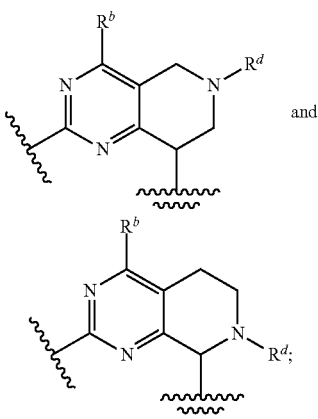

and $R^b$ is —$NR^xR^y$, wherein $R^x$ and $R^y$, together with the nitrogen atom to which they are attached, form a four- to seven-membered monocyclic or bicyclic ring optionally containing one additional heteroatom selected from O and $NR^z$; wherein $R^z$ is selected from $C_{1-6}$alkyl, and $C_{1-4}$alkoxycarbonyl; and wherein the ring is optionally substituted with one or two substituents independently selected from
$C_{1-6}$alkoxy, $C_{1-6}$alkyl, halo, halo$C_{1-4}$alkyl, hydroxy, —$NR^f R^g$, oxo, and spirocycle dioxolanyl; wherein $R^f$ and $R^g$ are independently selected from hydrogen,
$C_{1-4}$alkoxycarbonyl, and $C_{1-6}$alkyl.

In a thirteenth embodiment of the first aspect, B may also include pyrimidinyl.

In a fourteenth embodiment of the first aspect, $R^b$ as part of D may also include $SO_2C_{1-6}$alkyl, acetyl, and phenyl optionally substituted with 1-3$C_{1-6}$alkyl; and further wherein the ring as part of $R^z$ can also include spirocyclic tetrahydrofuranyl.

In a second aspect, the present disclosure provides a pharmaceutical composition for the treatment of disorders responsive to the reduction of β-amyloid peptide production comprising a therapeutically effective amount of a compound of formula (I), or a pharmaceutically acceptable salt thereof, in association with a pharmaceutically acceptable carrier or diluent.

In a third aspect, the present disclosure provides a method for the treatment of disorders responsive to the reduction of β-amyloid peptide production in a mammal in need thereof, which comprises administering to said mammal a therapeutically effective amount of a compound of formula (I), or a pharmaceutically acceptable salt thereof. In a first embodiment of the first aspect said disorder is selected from Alzheimer's Disease (AD), Down Syndrome, mild cognitive impairment (MCI), cerebral amyloid angiopathy (CAA), dementia with Lewy bodies (DLB), amyotrophic lateral sclerosis (ALS-D), inclusion body myositis (IBM), age-related macular degeneration, and cancer. In a second embodiment of the third aspect, said disorder is selected from Alzheimer's Disease and Down Syndrome. In a third embodiment of the third aspect, said disorder is Alzheimer's Disease.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

In some instances, the number of carbon atoms in any particular group is denoted before the recitation of the group. For example, the term "halo$C_{1-6}$alkoxy" denotes a haloalkoxy group containing one to six carbon atoms and the term "$C_{1-4}$alkoxy$C_{1-2}$alkyl" denotes an alkoxy group containing one to four alkoxy groups attached to the parent molecular moiety through an alkyl group of one or two carbon atoms. Where these designations exist they supersede all other definitions contained herein.

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylamino," as used herein, refers to —NHR$^x$, wherein R$^x$ is an alkyl group.

The term "alkylaminoalkoxy," as used herein, refers to an alkylamino group attached to the parent molecular moiety through an alkoxy group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "alkylsulfonylamido," as used herein refers to —C(O)NHS(O)$_2$R$^x$ wherein R$^x$ is an alkyl group.

The term "amino," as used herein, refers to —NH$_2$.

The term "carbonyl," as used herein, refers to —C(O)—.

The term "cyano," as used herein, refers to —CN.

The term "cycloalkyl," as used herein, refers to a saturated monocyclic hydrocarbon ring system having three to fourteen carbon atoms and zero heteroatoms.

The term "(cycloalkyl)alkyl," as used herein, refers to an alkyl group substituted with one, two, or three cycloalkyl groups.

The term "cycloalkylamino," as used herein, refers to —NHR$^x$ wherein R$^x$ is a cycloalkyl group.

The term "cycloalkylcarbonyl," as used herein, refers to a cycloalkyl group attached to the parent molecular moiety through a carbonyl group.

The term "cycloalkylsulfonyl," as used herein, refers to a cycloalkyl group attached to the parent molecular moiety through a sulfonyl group.

The term "dialkylamino," as used herein, refers to —NR$^x$R$^y$, wherein R$^x$ and R$^y$ are each alkyl groups.

The term "dialkylaminoalkoxy," as used herein, refers to a dialkylamino group attached to the parent molecular moiety through an alkoxy group.

The term "dialkylaminoalkyl," as used herein, refers to an alkyl group substituted with one, two, or three dialkylamino groups.

The term "dialkylaminoalkylcarbonyl," as used herein, refers to a dialkylaminoalkyl group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "hydroxy," as used herein, refers to —OH.

The term "hydroxyalkyl," as used herein, refers to an alkyl group substituted with one, two, or three hydroxy groups.

The term "methylamino," as used herein, refers to —NHCH$_3$.

The term "oxo," as used herein, refers to =O.

The term "sulfonyl," as used herein, refers to —SO$_2$—.

It should be understood that the disclosure encompasses all stereochemical forms, or mixtures thereof, which possess the ability to reduce β-amyloid peptide production.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Certain compounds of the present disclosure may exist in zwitterionic form and the present disclosure includes each zwitterionic form of these compounds and mixtures thereof.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

The dosage of the compounds of Formula I to achieve a therapeutic effect will depend not only on such factors as the age, weight and sex of the patient and mode of administration, but also on the degree of β-AP reduction desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to β-AP production as described herein, generally the daily dose will be from about 0.05 mg/kg to about 10 mg/kg and preferably, about 0.1 to 2 mg/kg when administered parenterally. For oral administration, the dose may be in the range from about 0.1 to about 75 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The abbreviations used in the present application, including particularly in the illustrative schemes and examples which follow, are well-known to those skilled in the art. Some of the abbreviations used are as follows:

Chemical abbreviations used in the specification and Examples are defined as follows: "dba" for dibenzylideneacetone; "t-Bu" for tert-butyl; "DCM" for dichloromethane; "LDA" for lithium diisopropylamide; "Ph" for phenyl; "TFA" for trifluoracetic acid; "Et" for ethyl; "DMF" for N,N-dimethylformamide; "OAc" for acetate; "h" for hours, "min" for minutes; and "THF" for tetrahydrofuran.

Examples of methods useful for the production of compounds of this disclosure are illustrated in Schemes 1-21.

The following schemes outline different routes for the synthesis of 2,4-dichloro-7-aryl-6,7-dihydro-5H-cyclopenta[d]pyrimidines used in the preparation of the title compounds. As illustrated on Scheme 1, cyclopentanone 15 can react with a variety of arylmagnesium halides to produce tertiary alcohols 16. In the presence of dehydrating agents, such as mineral acids or thionyl chloride, these tertiary alcohols can undergo elimination of water to yield olefins 17. Upon treatment with peroxidizing agents, such as performic acid, olefins 17 can be transformed to 2-arylcyclopentanones 18. Abu Thaher, B.; Koch, P.; Del Amo, V.; Knochel, P.; Laufer, S. *Synthesis* 2008, 2, 225-228.

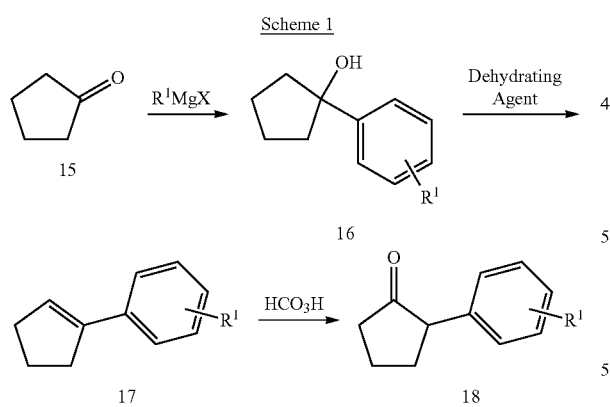

Alternatively, as indicated in Scheme 2,2-arylcyclopentanones 18 can be prepared by treatment of cyclopenteneoxide 19 with various arylmagnesium halides, in the presence of copper salts, such as copper iodide, followed by oxidation of resulting alcohols 20. The said oxidation can be carried out by a number of oxidation agents known to those skilled in the arts, with superior results achieved by the use of Dess-Martin periodinane. Dess, D. B.; Martin, J. C. *J. Org. Chem.* 1983, 48, 4155-4156.

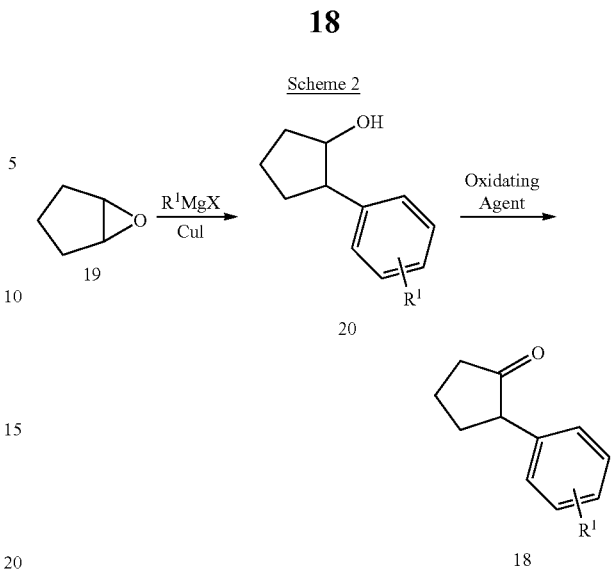

Additional ketones useful in the preparation of compounds of claim 1 can be prepared using the method described in O. Dirat et al, *Tetrahedron Letters*, 2006, 47, 1295. This method, described in Scheme 3, relies on alpha-arylation (Fox et al, *Journal of the American Chemical Society*, 2000, 122, 1360) of available ketones 21 that incorporate acetals or ketals at the 4-position. The corresponding ketone starting materials 21 are available commercially or can easily be prepared by those skilled in the art, and a variety of acetals can be used, including the shown ethylene glycol ketal or ketals of other alcohols including 1,3-propanediol, methanol, ethanol, and others. This chemistry works equally well to produce unsubstituted alpha-aryl ketones 24.

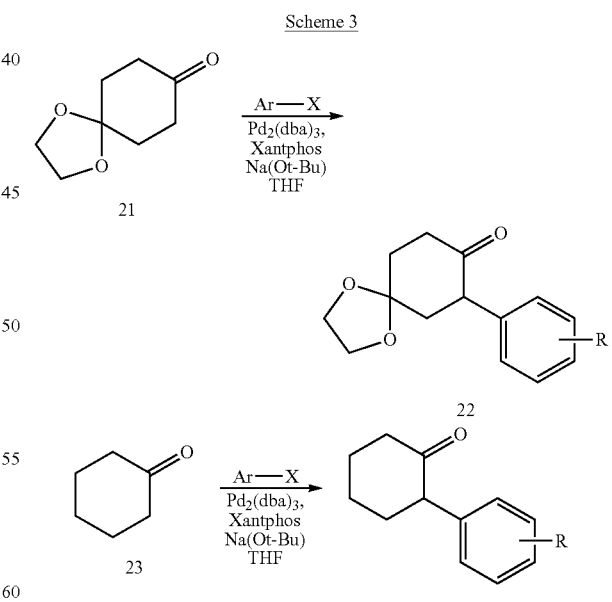

where X = Br, I

Additional alpha-aryl ketones can be prepared using the chemistry shown in Scheme 4, where tetrahydro-4H-pyran-4-one is brominated, typically using bromine in dichloromethane or pyrrolidine hydrotribromide as a brominating agent. The resulting alpha-bromo ketone can then be reacted with a Grignard reagent, and after migration of the aryl group the desired alpha-aryl ketone 27 is obtained.

Scheme 4

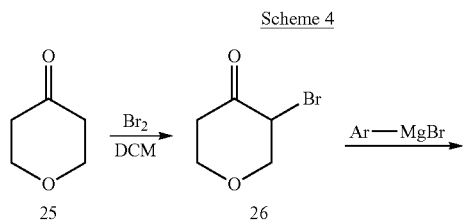

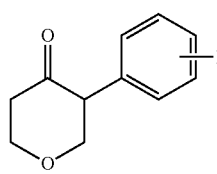

27

As indicated in Scheme 5, 2-arylcyclopentanones 18 can be deprotonated with a strong base, such as LDA and treated with alkylcyanoformate to give ketoesters 28, which upon reaction with 2-methyl-2-thiopseudourea provide 2-amino-7-aryl-6,7-dihydrocyclopenta[e][1,3]oxazin-4(5H)-ones 29. The latter compounds undergo acid-catalyzed hydrolysis to form 7-aryl-6,7-dihydrocyclopenta[e][1,3]oxazine-2,4(3H,5H)-diones 30. Larsen, J. S.; Christensen, L.; Ludvig, G.; Jorgensen, P. T.; Pedersen, E. B.; Nielsen, C. *J. Chem. Soc., Perkin Trans. I* 2000, 3035-3038.

Scheme 5

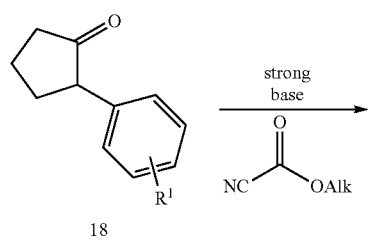

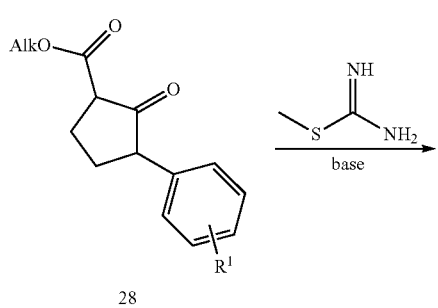

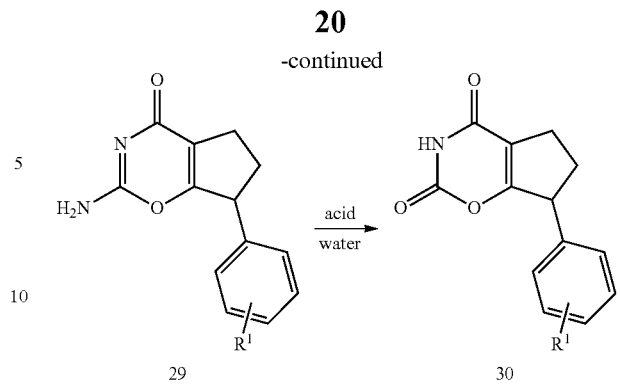

Alternatively, 7-aryl-6,7-dihydrocyclopenta[e][1,3]oxazine-2,4(3H,5H)-diones 31 are available by reaction of 2-arylcyclopentanones 18 with N-(chlorocarbonyl)isocyanate (Scheme 6). Subsequent treatment of 7-aryl-6,7-dihydrocyclopenta[e][1,3]oxazine-2,4(3H,5H)-diones 31 with ammonia in water, followed by chlorination with phosphorus oxychloride affords 2,4-dichloro-7-aryl-6,7-dihydro-5H-cyclopenta[d]pyrimidines 33.

Scheme 6

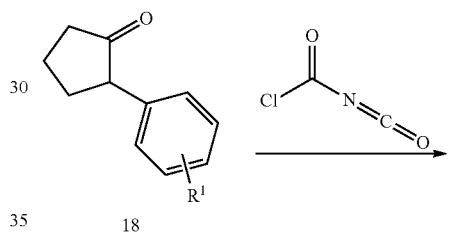

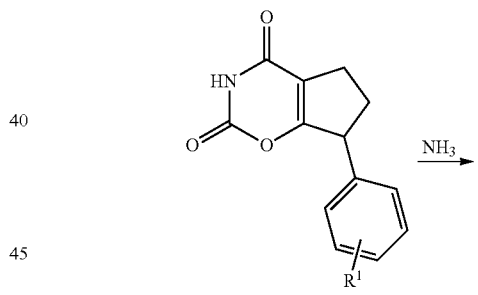

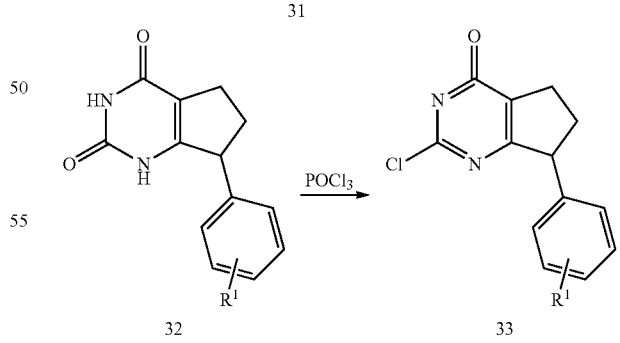

In a similar manner to the synthesis described in Scheme 6, additional ketones can be reacted with N-(chlorocarbonyl) isocyanate to provide additional oxazine diones 35 that can be reacted with ammonia to provide the pyrimidine diones 36 (Scheme 7). Chlorination then provides the intermediate dichlorides 37. In a similar way, this chemistry can be performed using the ketal-protected ketones produced in Scheme 3 to prepare the corresponding fused dichloropyrimidines (Scheme 8).

base, such as n-butyllithium or 2,2,6,6-tetramethylpiperidine, and quenched with allyl bromide to give 5-allyl-4-chloro-2,6-dimethoxypyrimidine 41. Nencka, R.; Votruba, I.; Hřebabecký, H.; Jansa, P.; Tloušt'ová, E.; Horská, K.; Masojídková, M.; Holý, A. *J. Med. Chem.* 2007, 50, 6016-6023. The latter compound can react with α-styrylborinic acids in the presence of a palladium catalyst, such as tetrakis(triphenylphosphine)palladium, to provide compounds of formula 42 which can undergo ring closure olefin metathesis under Grubbs conditions to form 2,4-dimethoxy-7-aryl-5H-cyclopenta[d]pyrimidines 43. Grubbs, R. H. *Handbook of Metathesis*, 2003, First Edition, Wiley-VCH. The double bond in compounds 43 can be reduced to give 2,4-dimethoxy-7-aryl-6,7-dihydro-5H-cyclopenta[d]pyrimidines 44, which upon acid-catalyzed hydrolysis, followed by chlorination with phosphorus oxychloride afford intermediates 33.

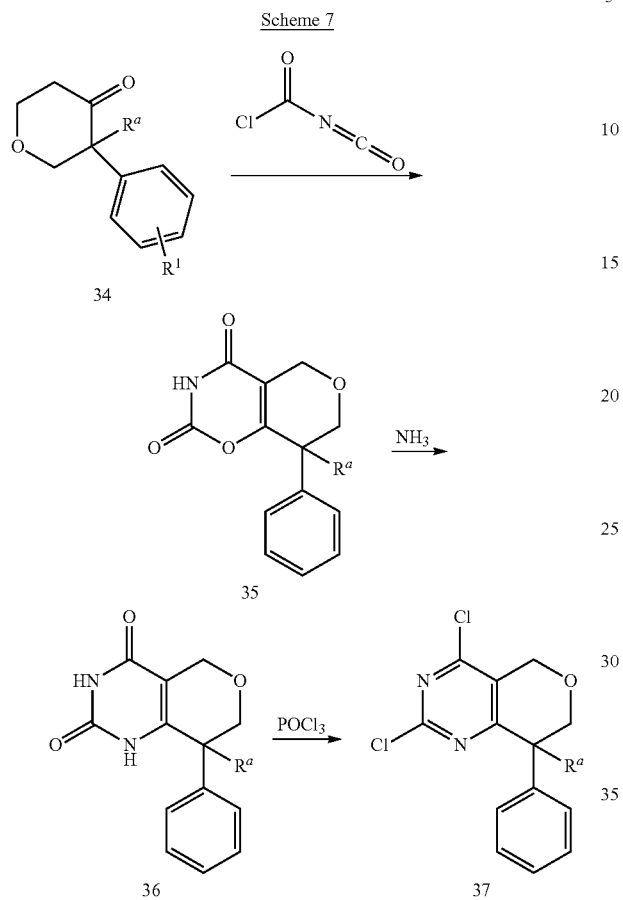

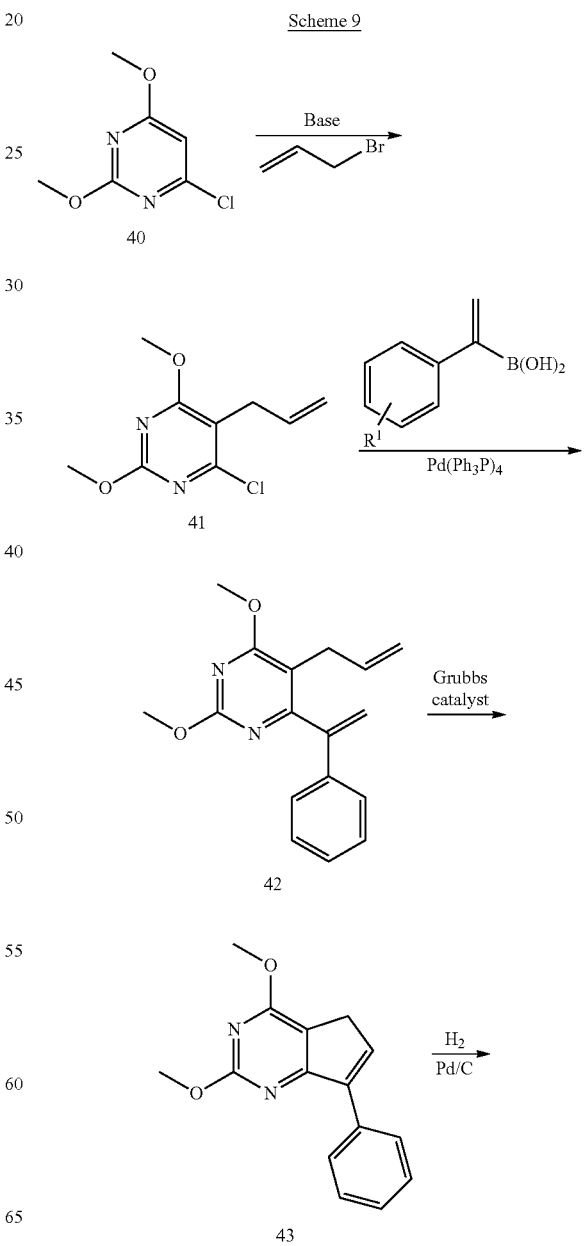

Synthesis of 2,4-dichloro-7-aryl-6,7-dihydro-5H-cyclopenta[d]pyrimidines 33 could also be performed according to the pathway described on Scheme 9. 4-Chloro-2,6-dimethoxypyrimidine 40 could be deprotonated with a strong

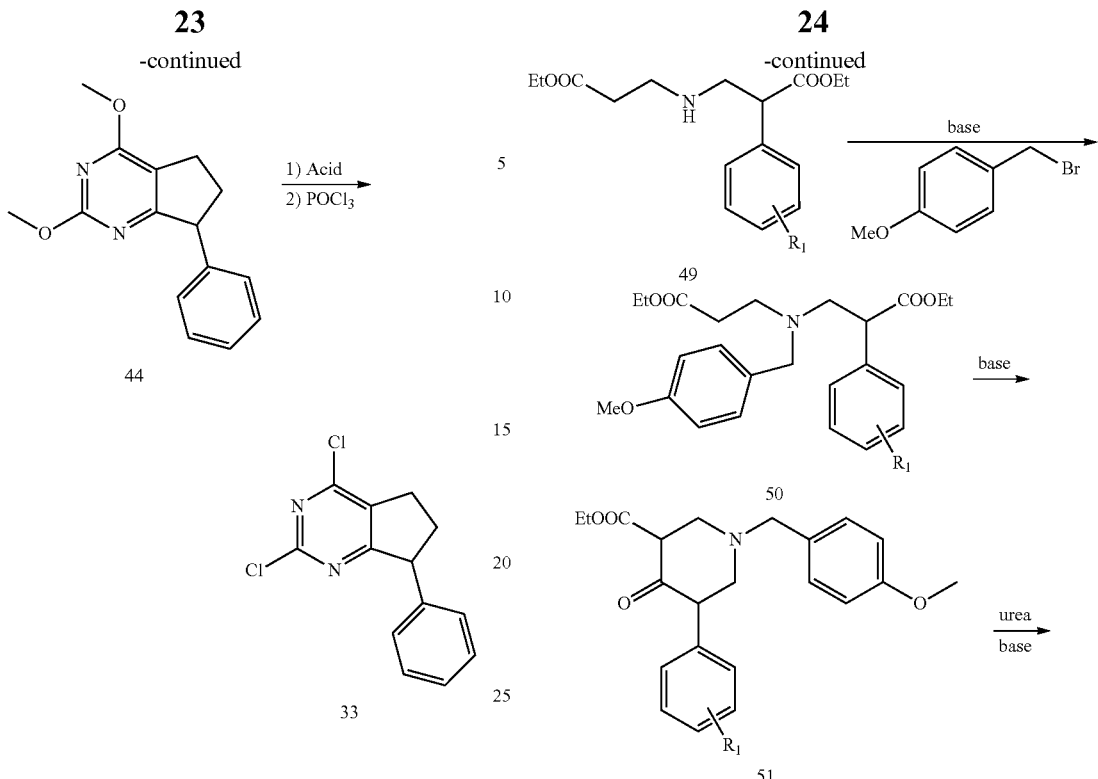

Additional members of the class of compounds of claim 1 can be prepared as is shown in Scheme 10. Carboxylation of benzonitriles followed by simple reduction using metal catalysis (Palladium on carbon or similar methods) provides the substituted beta-amino ester 48. Condensation with an acrylic ester provides intermediate 49, which can be alkylated on nitrogen to either directly provide access to $R^d$ substituents, or using the chemistry shown can be protected with a p-methoxybenzyl group for later deprotection and introduction of $R^d$. The intermediate 50 is then cyclized in the presence of base (usually KOt-Bu) to provide the beta-keto ester 51. Condensation of the beta-keto ester 51 with urea under basic conditions provides the pyrimidine dione intermediate 52, which can then be chlorinated under standard conditions to provide the dichloride 53. This dichloride can be converted into compounds of claim 1 in the usual way (vide infra).

Scheme 10

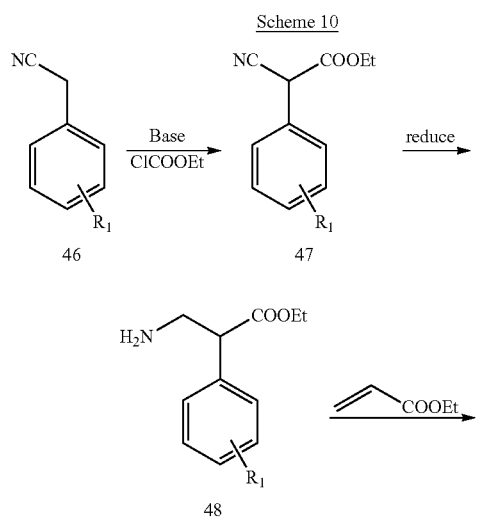

Additional members of the class of compounds of claim 1 can be prepared as is shown in Scheme 11. Esterification of an amino acid followed by alkylation with ethyl 4-bromobutyrate provides intermediate 56, which can be alkylated on nitrogen to either directly provide access to $R^d$ substituents, or using the chemistry shown can be protected with a p-methoxybenzyl group for later deprotection and introduction of $R^d$. The intermediate 57 is then cyclized in the presence of base (usually KOt-Bu) to provide the beta-keto ester 58. Condensation of the beta-keto ester 58 with urea under basic conditions provides the pyrimidine dione intermediate 59, which can then be chlorinated under standard conditions to provide the dichloride 60. This dichloride can be converted into compounds of claim 1 in the usual way (vide infra).

Scheme 11

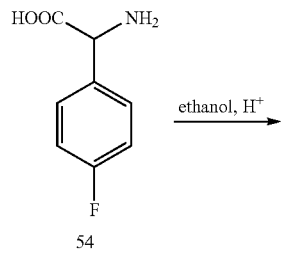
54

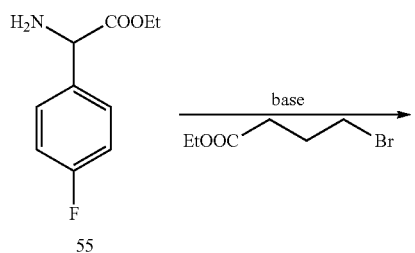
55

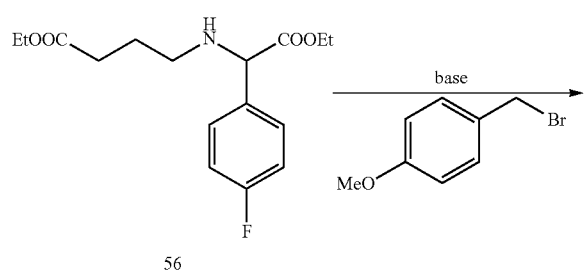
56

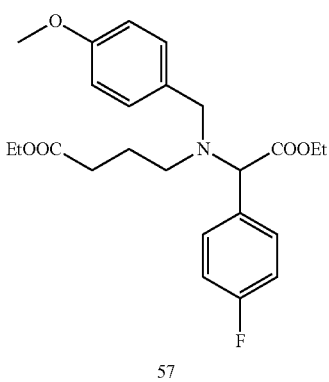
57

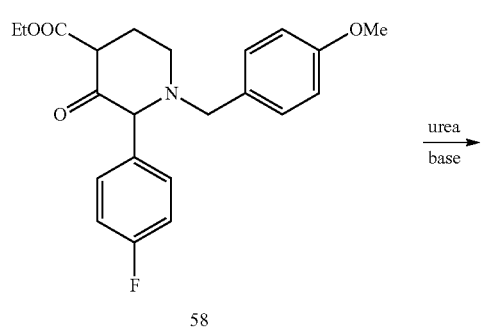
58

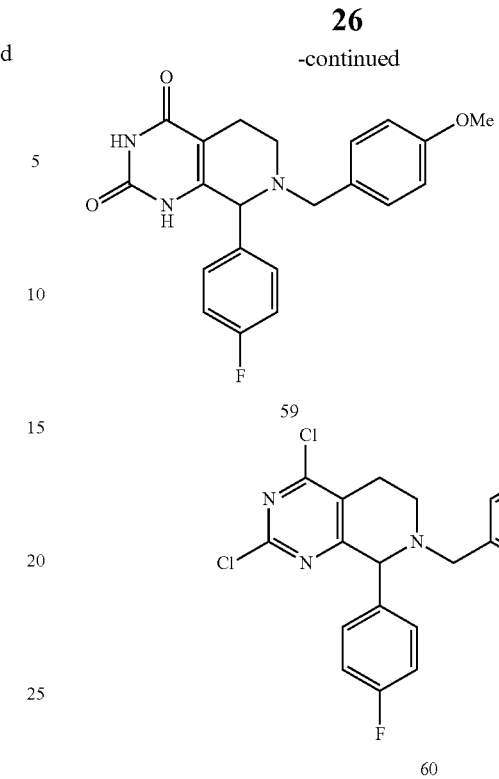
59

60

As shown in Scheme 12, the dimethoxybenzyl group used to protect the nitrogen atom on compounds of structure 61 can be deprotected, for instance by the action of a strong acid (TFA in the presence of anisole as a cation scavenger) to provide the free amine, which can then be further derivatized, for instance by acylation, sulfonylation, or alkylation in the usual ways to prepare additional compounds of claim 1. Similarly, amine the positional isomer 64 as shown in Scheme 13 participates in identical chemistry to access an additional class of compounds of claim 1.

Scheme 12

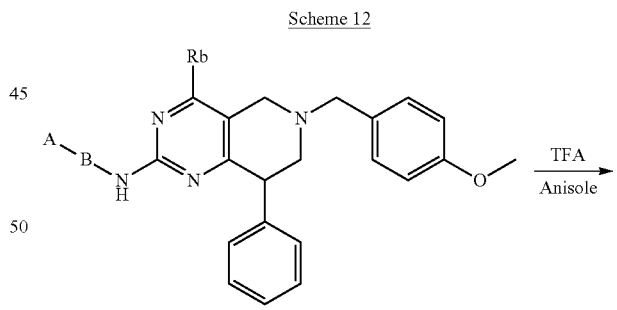
61

62

Scheme 13

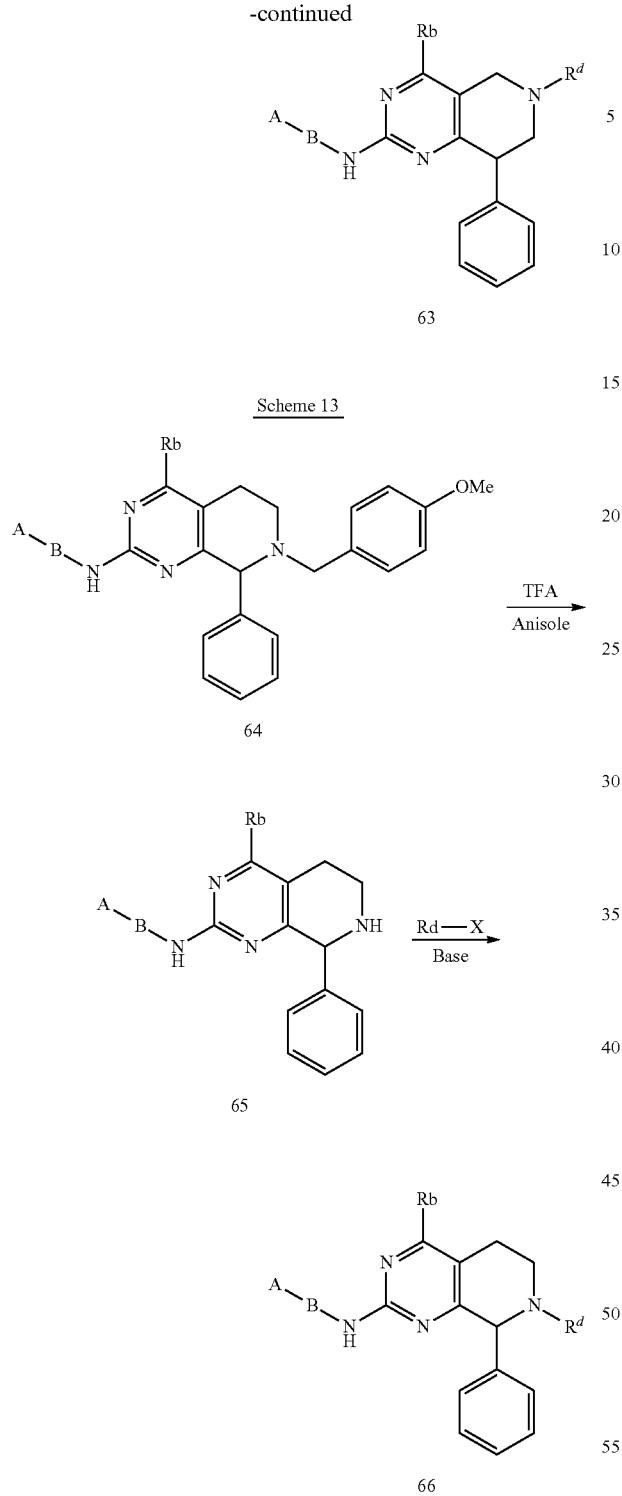

Scheme 14

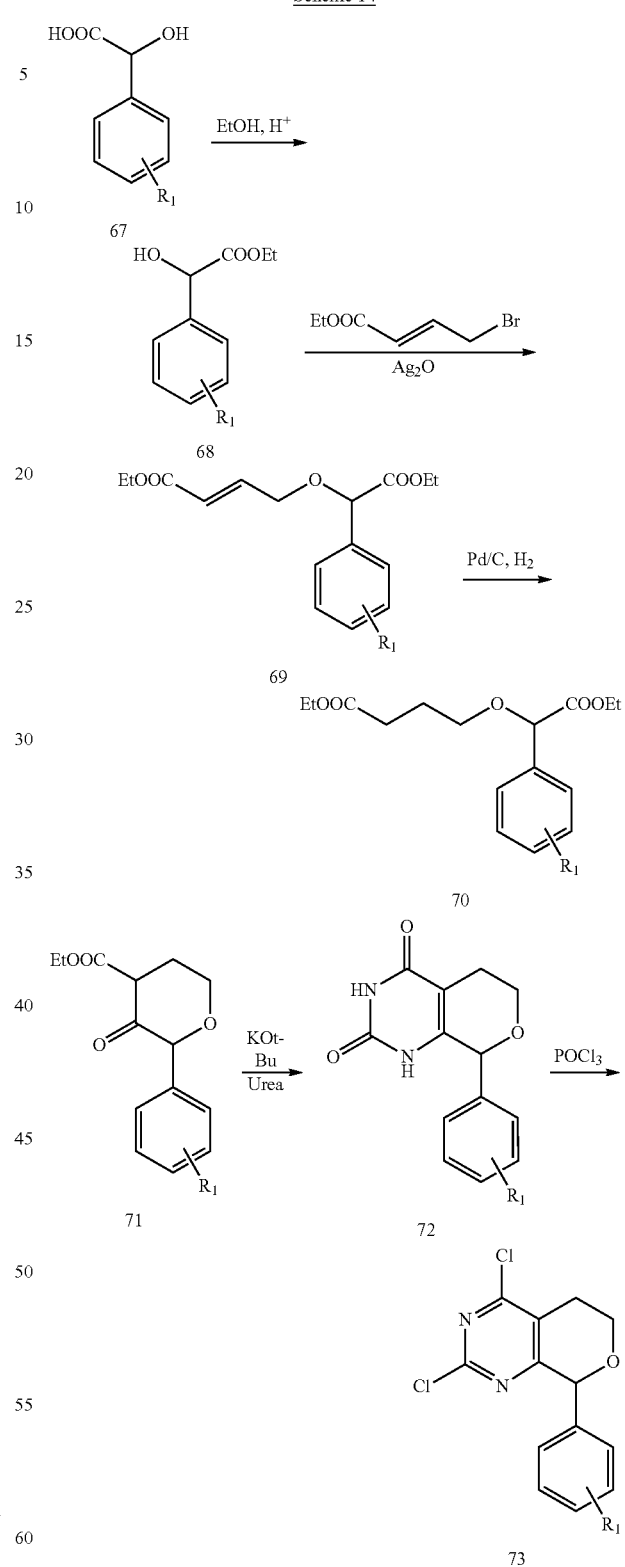

Further analogs can be prepared by the chemistry detailed in Scheme 14. Formation of the ester from commercial hydroxyacids 67 under Fisher conditions is followed by alkylation of the alcohol under silver(I) oxide catalysis. Reduction of the olefin and cyclization gives the beta-keto ester 71. Formation of the pyrimidine dione with KOt-Bu and urea followed by chlorination with POCl$_3$ gives the dichloride 73, which is carried forward to compounds of claim 1 as described in Scheme 19.

Additional analogs can be prepared using the chemistry shown in Scheme 15. Reaction of pyrimidine-2,4,6-triol with POCl$_3$ in DMF provides the chlorinated aldehyde 75. Protection of the aldehyde is followed by reaction with a Grignard reagent to produce the dichloride reagent 77. After hydrolytic deprotection and reduction of the aldehyde to the alcohol, the tetrahydrofuran ring can be closed by the action of lead tetraacetate to provide the substituted dichloride 80 which can then be used according to the methods described below to prepare further compounds of claim 1.

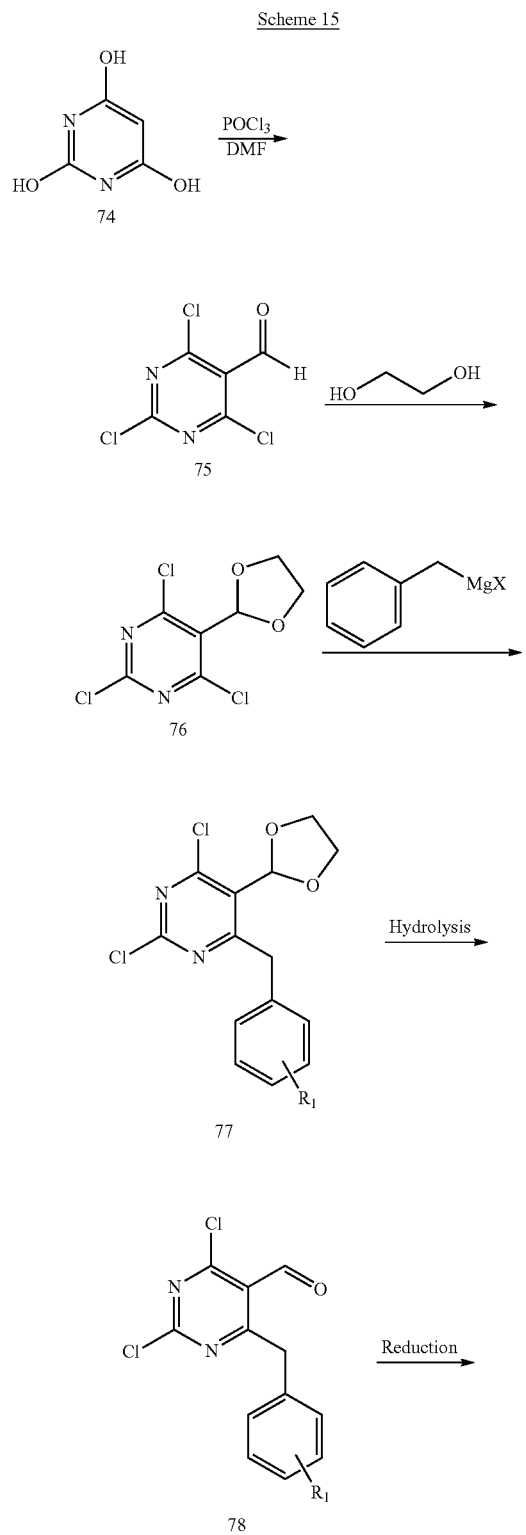

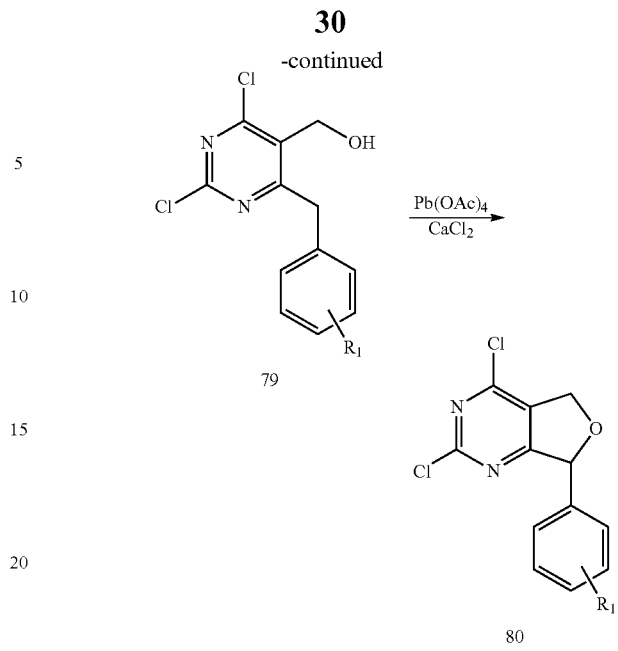

2,4-Dichloro-7-aryl-6,7-dihydro-5H-cyclopenta[d]pyrimidines 81 selectively react with primary and secondary amines to give 2-amino derivatives 82, which under heating can be coupled with anilines 4 to form title compounds 83. (Scheme 16). The said coupling can be performed either under acidic conditions (for example, using acetic acid), or under basic conditions, (for example, using sodium hydride). Alternatively, the coupling can be completed under metal catalysis, with conditions known in the literature, for instance the use of palladium Xantphos catalyst in the presence of a strong base (NaOt-Bu) or $Na_2CO_3$ in an aqueous cosolvent mixture (typically THF/water or dioxane/water).

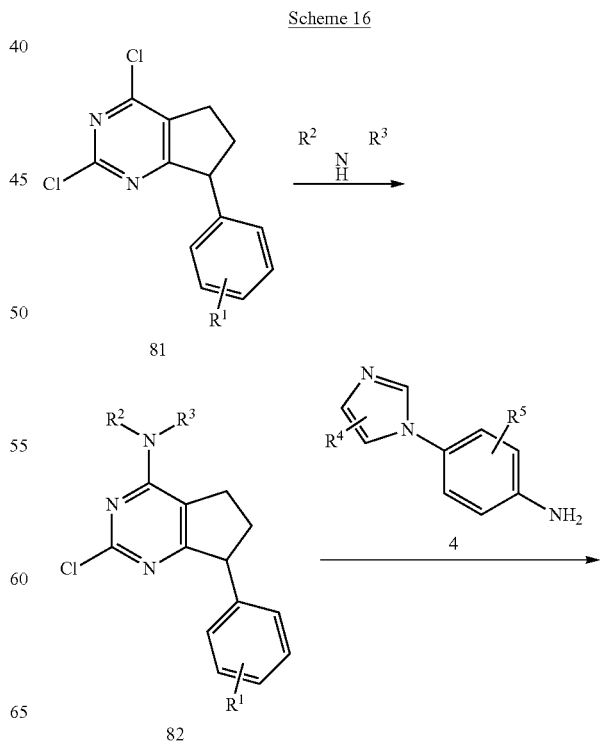

-continued

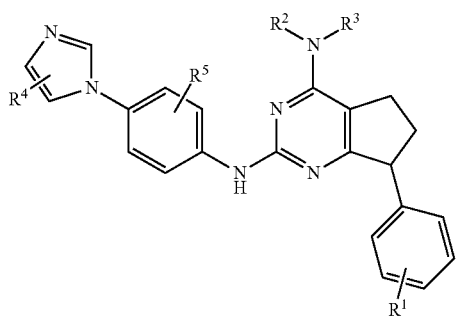

83

Additional compounds of claim 1 can be prepared by condensation of the appropriate ketal-containing dichlorides with animes and anilines in the manner already described to prepare intermediates 86 (Scheme 17). Deprotection of the ketal, for instance with aqueous acid produces the ketone 88 which is a very useful intermediate for the production of further compounds. The ketone can be directly condensed with amines under reductive conditions (reductive alkylation) to prepare substituted amine compounds 89. Alternatively, the ketone can be reduced with hydride reagents such as $NaBH_4$ or $LiAlH_4$ to provide the alcohol. The alcohol 90 can be activated, for instance as the methanesulfonate, and then displaced with nucleophiles including thiols, azide or other nucleophiles. Oxidation of the thiol prepares the sulfoxide and the sulfone. Reduction of the azide produces a facile entry into the amine, which can also be further alkylated to produce additional compounds of claim 1.

Scheme 17

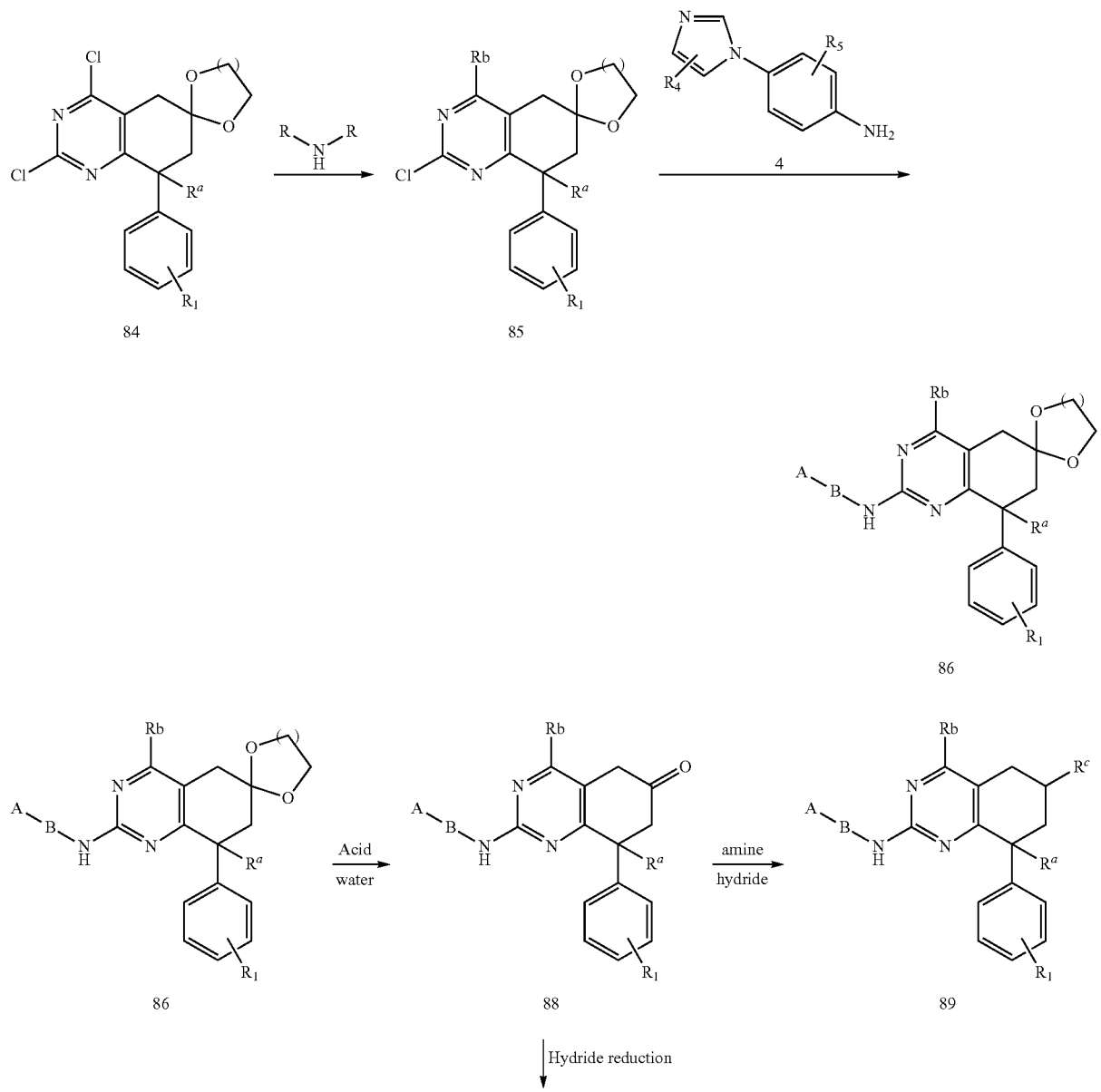

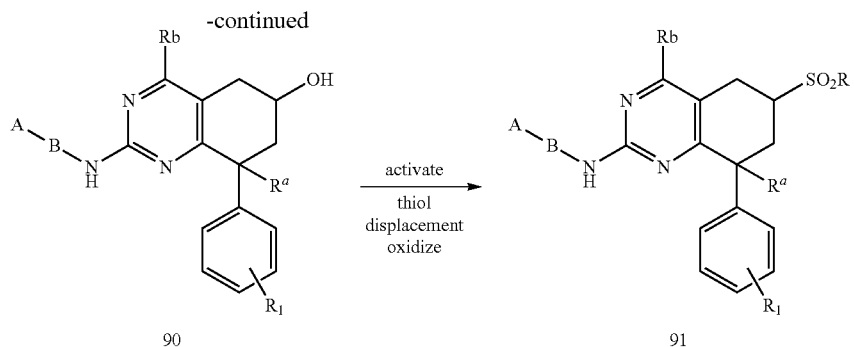

An additional method for the preparation of analogs of claim 1 is described in Scheme 18. Again starting with the aldehyde 76, addition of lithiated phenyldithiane provides intermediate 92. Deprotection of the protecting groups provides the keto aldehyde 93, which can be closed to the substituted pyrrolidine 94 by sequential reductive alkylation. The amine can either directly introduce a desired $R^d$ substituent, or as is described in the scheme an amine that introduces a protecting group (including 4-methoxybenzyl) can be used. According to the methods herein, the dichloride thus obtained can be transformed into compounds of claim 1. Additional analogs can then be prepared by deprotection of the 4-methoxybenzyl group using methods known to those in the art, such as TFA with Anisole as a cation scavenger, followed by additional alkylation, acylation, or sulfonylation using known methods.

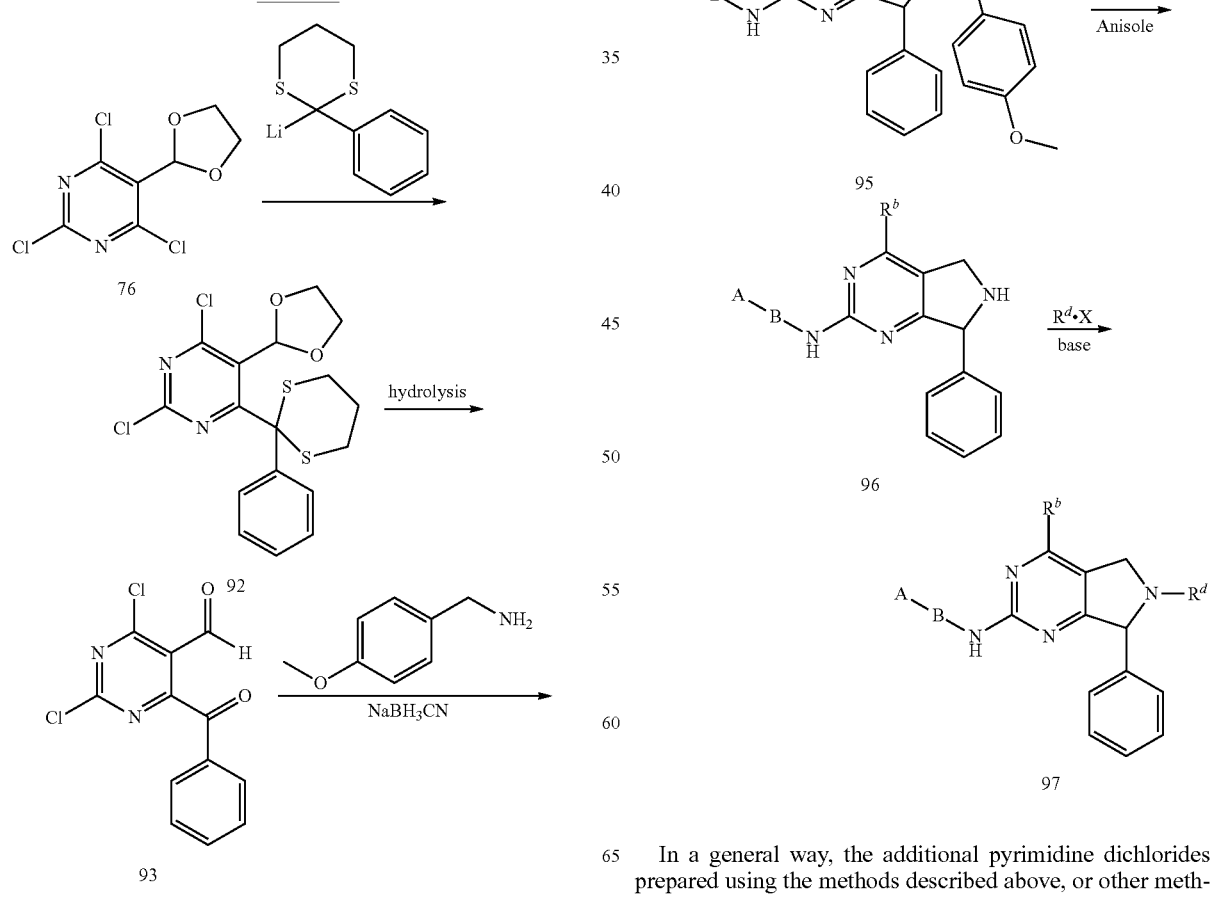

In a general way, the additional pyrimidine dichlorides prepared using the methods described above, or other methods known in the art can be transformed into additional analogs of claim 1 as demonstrated in Scheme 19. Pyrimidine dichlorides are reacted with amines to provide the chlorides 99 which correspond to the structures D-E as described in claim 1, where the bond that attaches the structure D-E to the ABNH fragment is activated as a displaceable chloride group. The title compounds of claim 1 are then prepared by condensing the chlorides 99 with the anilines $ABNH_2$ according to the methods previously described (Scheme 16).

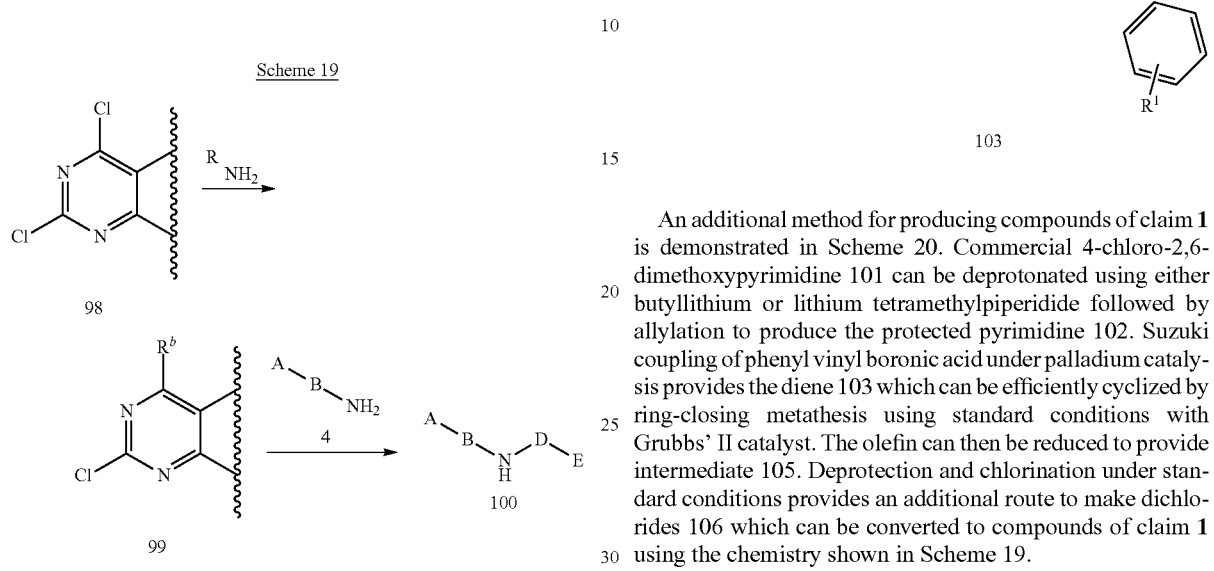

The racemic title compounds can be separated by chiral methods known to a reasonable person skilled in the arts, to provide individual enantiomers (Scheme 20). This is demonstrated below in the cyclopenta[d]pyrimidine series, but equally applies to the other racemic compounds described herein.

An additional method for producing compounds of claim 1 is demonstrated in Scheme 20. Commercial 4-chloro-2,6-dimethoxypyrimidine 101 can be deprotonated using either butyllithium or lithium tetramethylpiperidide followed by allylation to produce the protected pyrimidine 102. Suzuki coupling of phenyl vinyl boronic acid under palladium catalysis provides the diene 103 which can be efficiently cyclized by ring-closing metathesis using standard conditions with Grubbs' II catalyst. The olefin can then be reduced to provide intermediate 105. Deprotection and chlorination under standard conditions provides an additional route to make dichlorides 106 which can be converted to compounds of claim 1 using the chemistry shown in Scheme 19.

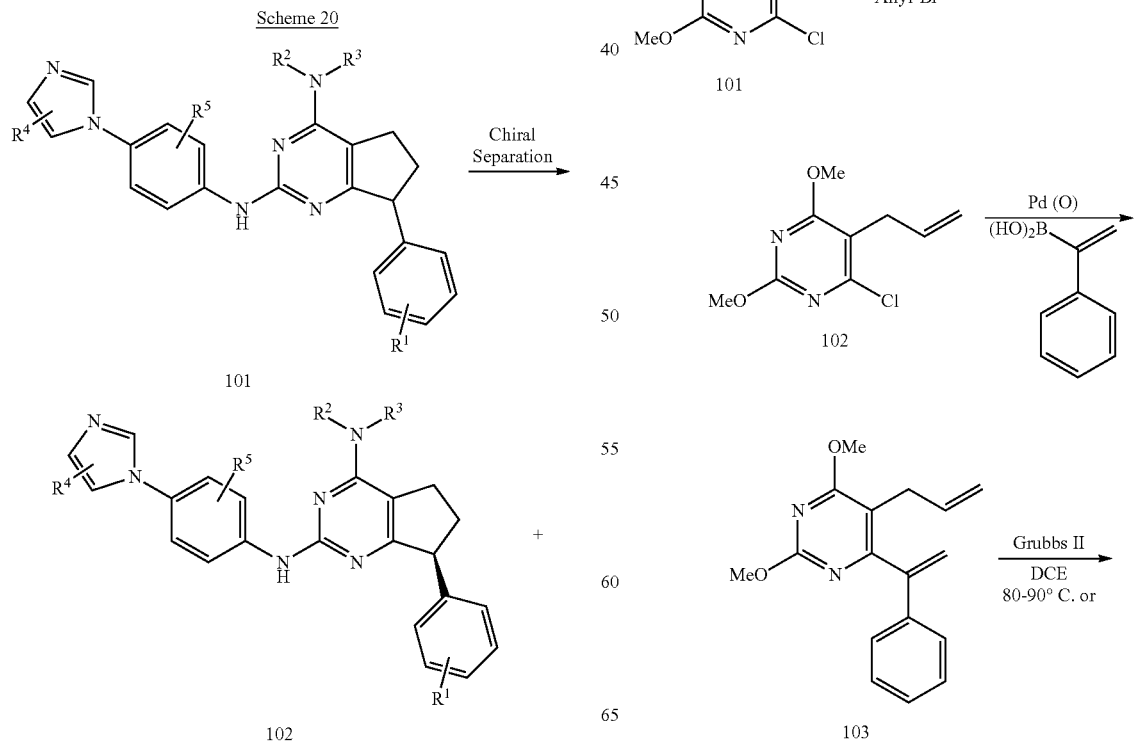

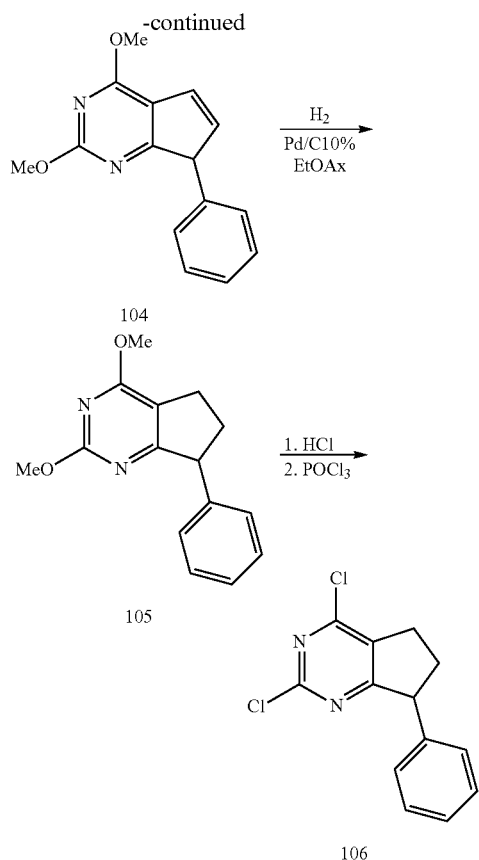

104

105

106

The racemic title compounds can be separated by chiral methods known to a reasonable person skilled in the arts, to provide individual enantiomers (Scheme 21). This is demonstrated below in the cyclopenta[d]pyrimidine series, but equally applies to the other racemic compounds described herein.

Scheme 21

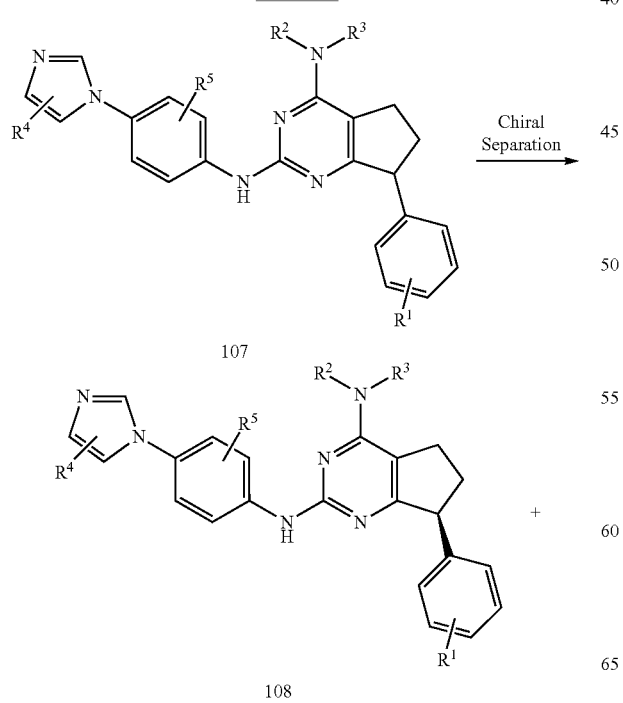

107

108

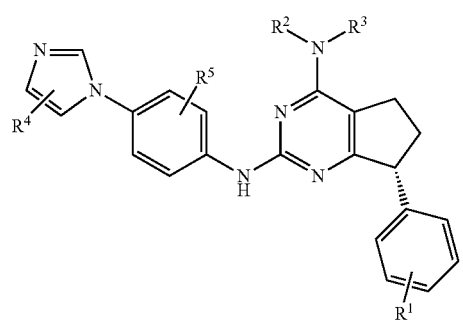

109

"HPLC" is an abbreviation used herein for high pressure liquid chromatography. "LC-MS" refers to high pressure liquid chromatography carried out according to the definition for HPLC with a mass spectrometry detector. HPLC solvent conditions: When described as performed under "standard conditions", samples were dissolved in methanol (1 mg/mL) and run using a gradient program with a solvent flow rate of 1.0 mL/min. Reverse phase preparatory HPLC: When described as performed under "standard conditions", samples (approx. 20 mg) were dissolved in methanol (10 mg/mL) and purified on a 30 mm×100 mm Waters-Atlantis S5 column using a 10 minute gradient elution from 0% to 100% buffer B in buffer A (buffer A=10% $CH_3OH$/90% water/0.1% TFA and buffer B=90% MeOH/10% water/0.1% TFA). at 40 mL/minute.

Proton NMR spectra were obtained on a Bruker 400 or 500 spectrometer. Data were referred to the lock solvent.

The examples provided are intended to assist in a further understanding of the present disclosure. Particular materials employed, species and conditions are intended to further illustrate the specific embodiments of the invention and not limit the reasonable scope thereof.

SYNTHESIS OF INTERMEDIATES

Preparation G 2,4-Dichloro-7-phenyl-6,7-dihydro-5H-cyclopenta[d]pyrimidine

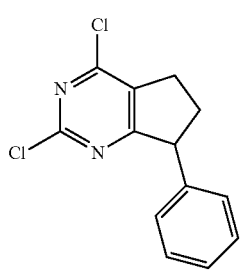 [SMILES: Clc1nc(Cl)c2c(n1)C(c1ccccc1)CC2]

Intermediate G(1)

Cyclopentenylbenzene

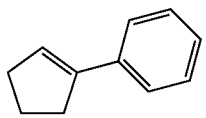 [SMILES: C1=C(c2ccccc2)CCC1]

To a solution of 3.0 M solution of phenylmagnesium bromide in ether (49.7 mL, 149 mmol) was added THF (300 mL). To this solution cooled to 0° C. cyclopentanone (13.23 mL, 149 mmol) was added. The reaction mixture was stirred at room temperature for 30 min, then—at reflux for 2 h. Ice (20 g) was added, followed by 6N HCl, until the precipitate dissolved. The product was extracted with ether. The combined etherial layers were washed with saturated sodium bicarbonate solution, dried over anhydrous magnesium sulfate and filtered. The solvent was removed in vacuum and the residue was purified by column chromatography on silica gel to give cyclopentenylbenzene (21.49 g, 149 mmol, 100% yield) as colorless oil. LC-MS (M+H)$^+$=145.1. $^1$H NMR (500 MHz, CDCl$_3$) δ ppm 7.48 (2H, d, J=7.3 Hz), 7.35 (2H, t, J=7.8 Hz), 7.22-7.27 (1H, m), 6.22 (1H, t, J=2.1 Hz), 2.70-2.80 (2H, m), 2.52-2.64 (2H, m), 2.01-2.12 (2H, m).

Intermediate G(2)

2-Phenylcyclopentanone

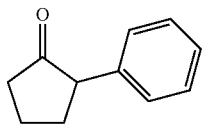 [SMILES: O=C1CCCC1c1ccccc1]

A mixture of 30% hydrogen peroxide (23 mL, 149 mmol) and 85% formic acid (100 mL, 2619 mmol) was heated at 40° C. for 15 minutes. The mixture was carefully added to cyclopentenylbenzene (21.49 g, 149 mmol) and the resulting two-phase system was vigorously stirred at room temperature for 4 h. An exothermic reaction was observed in the beginning. In the end of the stirring the solution became homogeneous. The reaction mixture was carefully quenched with saturated aqueous solution of sodium bicarbonate. The product was extracted with ether. The combined etherial layers were dried over anhydrous magnesium sulfate and filtered. The solvent was removed in vacuum and the product was purified by column chromatography on silica gel to give 2-phenylcyclopentanone (19.995 g, 125 mmol, 84% yield) as brown oil. LC-MS (M+H)$^+$=161.0. $^1$H NMR (500 MHz, CDCl$_3$) δ ppm 7.38 (1H, t, J=7.3 Hz), 7.30-7.35 (2H, m), 7.19 (2H, d, J=7.3 Hz), 3.28-3.37 (1H, m), 2.71 (1H, td, J=4.6, 2.7 Hz), 2.58-2.63 (1H, m), 2.43-2.55 (1H, m), 2.29 (1H, ddd, J=19.0, 10.5, 9.0 Hz), 2.07-2.21 (1H, m), 1.88-1.99 (1H, m).

Intermediate G(3)

Ethyl 2-oxo-3-phenylcyclopentanecarboxylate

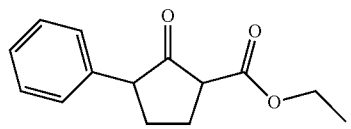 [SMILES: CCOC(=O)C1CCC(c2ccccc2)C1=O]

To a solution of diisopropylamine (6.62 mL, 46.8 mmol) in THF (200 mL) at −78° C. was added a 1.6 M solution of n-butyllithium in hexanes (29.3 mL, 46.8 mmol). The solution was stirred for 30 min at −78° C. and treated with a solution of 2-phenylcyclopentanone (5 g, 31.2 mmol) in 50 mL of dry THF. After stirring for 30 min at −78° C., ethyl carbonocyanidate (3.36 mL, 34.3 mmol) was added to the reaction mixture. The resulting solution was warmed to 25° C. with stirring over 3 h. The reaction mixture was quenched with 10 mL of water, washed with brine, dried over anhydrous sodium sulfate, concentrated in vacuum, and purified by column chromatography on silica gel to afford ethyl 2-oxo-3-phenylcyclopentanecarboxylate (5.3 g, 22.82 mmol, 73% yield) as colorless oil. LC-MS (M+K)$^+$=273.2. $^1$H NMR (500 MHz, CDCl$_3$) δ ppm 7.32-7.39 (2H, m), 7.25-7.31 (1H, m), 7.19-7.25 (2H, m), 4.18-4.32 (2H, m), 3.29-3.55 (2H, m), 1.87-2.62 (4H, m), 1.28-1.39 (3H, m).

Intermediate G(4)

2-Amino-7-phenyl-6,7-dihydrocyclopenta[e][1,3]oxazin-4(5H)-one

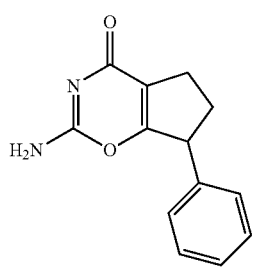 [SMILES: Nc1nc(=O)c2c(o1)C(c1ccccc1)CC2]

2-Methyl-2-thiopseudourea sulfate (1.336 g, 9.61 mmol) was dissolved in water (10 mL) and KOH (1.128 g, 20.10 mmol) was added. Under stirring, ethyl 2-oxo-3-phenylcyclopentanecarboxylate (2.03 g, 8.74 mmol) was added and the reaction mixture was stirred at room temperature overnight. The reaction mixture was filtered, washed with water and ether, and dried over anhydrous sodium sulfate to afford 2-amino-7-phenyl-6,7-dihydrocyclopenta[e][1,3]oxazin-4(5H)-one (1.22 g, 5.35 mmol, 61.2% yield) as white solid. LC-MS (M+H)$^+$=229.1. $^1$H NMR (500 MHz, dimethylsulfoxide-d6) δ ppm 7.57-7.85 (2H, m), 7.08-7.47 (5H, m), 4.25-4.38 (1H, m), 1.72-2.73 (3H, m), 1.09-1.31 (1H, m).

Intermediate G(5)

7-Phenyl-6,7-dihydrocyclopenta[e][1,3]oxazine-2,4(3H,5H)-dione

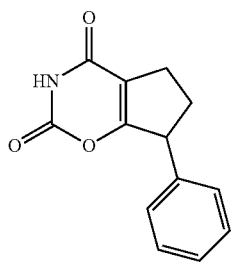 [SMILES: O=c1[nH]c(=O)c2c(o1)C(c1ccccc1)CC2]

2-Amino-7-phenyl-6,7-dihydrocyclopenta[e][1,3]oxazin-4(5H)-one (900 mg, 3.94 mmol) was dissolved in a 3M aqueous hydrogen chloride solution (32 mL, 96 mmol) under stirring. The mixture was heated at reflux for 1 h. The reaction mixture was cooled and extracted with ethyl acetate. The organic layer was washed with saturated aqueous sodium bicarbonate solution and brine, dried over anhydrous sodium sulfate, concentrated in vacuum and purified by column chromatography on silica gel to afford 7-phenyl-6,7-dihydrocyclopenta[e][1,3]oxazine-2,4(3H,5H)-dione (350 mg, 1.527 mmol, 38.7% yield). LC-MS $(M+H)^+=230.0$. $^1$H NMR (500 MHz, CDCl$_3$) δ ppm 8.34 (1H, br s), 7.35 (2H, t, J=7.3 Hz), 7.27-7.32 (1H, m), 7.18 (2H, d, J=7.3 Hz), 4.20 (1H, t, J=7.6 Hz), 2.82-2.91 (1H, m), 2.61-2.79 (2H, m), 2.11-2.21 (1H, m).

A solution of 2-phenylcyclopentanone (19.995 g, 125 mmol) and N-(chlorocarbonyl)isocyanate (23.70 g, 225 mmol) was stirred at 58° C. for 1 h and at 130° C. for 45 min. The resulting tarrified reaction mixture was dissolved in ethyl acetate and neutralized with saturated aqueous sodium bicarbonate solution. The organic layer was dried over anhydrous magnesium sulfate and filtered. The product was purified by column chromatography on silica gel to give 7-phenyl-6,7-dihydrocyclopenta[e][1,3]oxazine-2,4(3H,5H)-dione (3.751 g, 16.36 mmol, 13% yield) as brownish solid. LC-MS $(M+H)^+=230.0$. $^1$H NMR (500 MHz, CDCl$_3$) δ ppm 8.34 (1H, br s), 7.35 (2H, t, J=7.3 Hz), 7.27-7.32 (1H, m), 7.18 (2H, d, J=7.3 Hz), 4.20 (1H, t, J=7.6 Hz), 2.82-2.91 (1H, m), 2.61-2.79 (2H, m), 2.11-2.21 (1H, m).

Intermediate G(6)

7-Phenyl-6,7-dihydro-1H-cyclopenta[d]pyrimidine-2,4(3H,5H)-dione

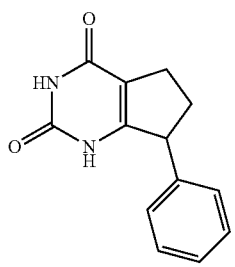 [SMILES: O=c1[nH]c2c(c(=O)[nH]1)CCC2c1ccccc1]

A solution of 7-phenyl-6,7-dihydrocyclopenta[e][1,3]oxazine-2,4(3H,5H)-dione (3.751 g, 16.36 mmol) in concentrated ammonia in water (80 mL, 16.36 mmol) was heated in a 350 mL high-pressure flask for 5 h. The solvent was removed in vacuum to give 7-phenyl-6,7-dihydro-1H-cyclopenta[d]pyrimidine-2,4(3H,5H)-dione (3.73 g, 16.34 mmol, 100% yield) as brown solid. LC-MS $(M+H)^+=229.1$. $^1$H NMR (500 MHz, dimethylsulfoxide-d6) δ ppm 7.34 (2H, t, J=7.5 Hz), 7.26 (1H, t, J=7.3 Hz), 7.18 (2H, d, J=7.3 Hz), 5.39 (1H, br s), 4.14 (1H, d, J=7.3 Hz), 2.43-2.68 (2H, m), 1.80-1.88 (2H, m).

Preparation G 2,4-Dichloro-7-phenyl-6,7-dihydro-5H-cyclopenta[d]pyrimidine

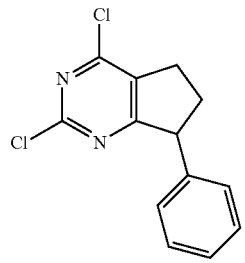 [SMILES: Clc1nc(Cl)c2c(n1)C(c1ccccc1)CC2]

A solution of 7-phenyl-6,7-dihydro-1H-cyclopenta[d]pyrimidine-2,4(3H,5H)-dione (1.241 g, 5.44 mmol) in phosphoryl trichloride (14.93 mL, 163 mmol) was heated in microwave at 110° C. for 1 h. Once ice melted, the product was extracted with dichloromethane. The combined organic extracts were dried over anhydrous magnesium sulfate and filtered. The solvent was removed in vacuum and the residue was purified by column chromatography on silica gel to give 2,4-dichloro-7-phenyl-6,7-dihydro-5H-cyclopenta[d]pyrimidine (3.132 g, 72%) as light brown solid. LC-MS $(M+H)^+=265.0$. $^1$H NMR (500 MHz, CDCl$_3$) δ ppm 7.31-7.37 (2H, m), 7.27 (1H, d, J=7.0 Hz), 7.15 (2H, d, J=7.9 Hz), 4.44 (1H, t, J=8.2 Hz), 3.09-3.18 (1H, m), 2.97-3.06 (1H, m), 2.73 (1H, ddd, J=9.0, 4.7, 4.6 Hz), 2.26 (1H, ddd, J=8.5, 7.0, 6.7 Hz).

Preparation Ga 2-chloro-N-methyl-7-phenyl-6,7-dihydro-5H-cyclopenta[d]pyrimidin-4-amine

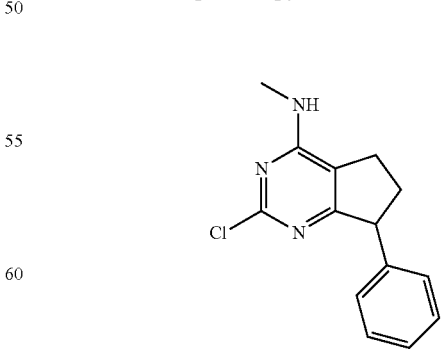

To a solution of 2,4-dichloro-7-phenyl-6,7-dihydro-5H-cyclopenta[d]pyrimidine (Preparation G) (395 mg, 1.49 mmol) in THF (3700 μL), 2 M MeNH$_2$ in THF (3700 μL, 7.45 mmol) was added. The reaction was allowed to stir at rt. When the reaction was complete, removed solvent and applied residue to silica gel. Eluted with EtOAc/Hex to afford the desired 2-chloro-N-methyl-7-phenyl-6,7-dihydro-5H-cyclopenta[d]pyrimidin-4-amine (80.8 mg, 0.220 mmol, 69.1% yield). LC-MS (M+H)$^+$=260.1. $^1$H NMR (500 MHz, CDCl$_3$) δ ppm 7.07 (3H, dd, J=8.5, 5.5 Hz), 6.96 (2H, t, J=8.7 Hz), 4.72 (1H, br s), 4.23 (1H, t, J=7.2 Hz), 3.09 (3H, d, J=4.9 Hz), 2.67-2.77 (1H, m), 2.58-2.67 (2H, m), 2.01-2.11 (1H, m).

Preparation Gb

2-Chloro-N,N-dimethyl-7-phenyl-6,7-dihydro-5H-cyclopenta[d]pyrimidin-4-amine

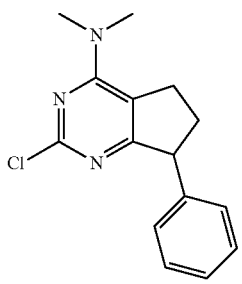 [SMILES: CN(C)c1nc(Cl)nc2c1CCC2c1ccccc1]

A solution of 2,4-dichloro-7-phenyl-6,7-dihydro-5H-cyclopenta[d]pyrimidine (200 mg, 0.754 mmol) and excess dimethylamine (3.77 mL, 7.54 mmol) in MeOH (2 mL) was stirred at rt for 1 h. The solvent was removed in vacuum to afford 2-chloro-N,N-dimethyl-7-phenyl-6,7-dihydro-5H-cyclopenta[d]pyrimidin-4-amine (207 mg, 0.756 mmol, 100% yield). LC-MS (M+H)$^+$=274.2.

Preparation Gc

2-Chloro-N-ethyl-N-methyl-7-phenyl-6,7-dihydro-5H-cyclopenta[d]pyrimidin-4-amine

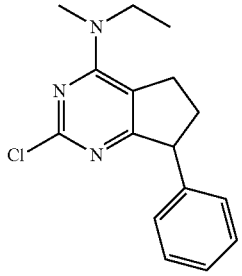 [SMILES: CCN(C)c1nc(Cl)nc2c1CCC2c1ccccc1]

A solution of 2,4-dichloro-7-phenyl-6,7-dihydro-5H-cyclopenta[d]pyrimidine (150 mg, 0.566 mmol) and excess N-methylethanamine (0.486 mL, 5.66 mmol) in MeOH (2 mL) was stirred at rt for 1 h. The solvent was removed in vacuum to afford 2-chloro-N-ethyl-N-methyl-7-phenyl-6,7-dihydro-5H-cyclopenta[d]pyrimidin-4-amine (163 mg, 0.566 mmol, 100% yield). LC-MS (M+H)$^+$=288.2.

Preparation Gd 4-(Azetidin-1-yl)-2-chloro-7-phenyl-6,7-dihydro-5H-cyclopenta[d]pyrimidine

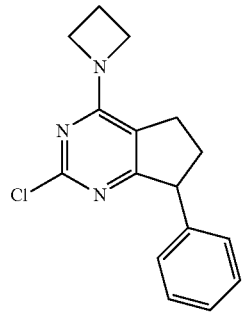 [SMILES: Clc1nc2c(c(N3CCC3)n1)CCC2c1ccccc1]

A solution of 2,4-dichloro-7-phenyl-6,7-dihydro-5H-cyclopenta[d]pyrimidine (150 mg, 0.566 mmol) and excess azetidine (162 mg, 2.83 mmol) in methanol (1 mL) was stirred at rt for 30 min. The solvent was removed in vacuum to afford 4-(azetidin-1-yl)-2-chloro-7-phenyl-6,7-dihydro-5H-cyclopenta[d]pyrimidine (162 mg, 0.567 mmol, 100% yield). LC-MS (M+H)$^+$=286.3.

Preparation Ge

2-Chloro-N-trideuteromethyl-7-phenyl-6,7-dihydro-5H-cyclopenta[d]pyrimidin-4-amine

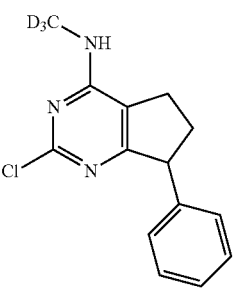 [SMILES: [2H]C([2H])([2H])Nc1nc(Cl)nc2c1CCC2c1ccccc1]

To a solution of 2,4-dichloro-7-(4-fluorophenyl)-6,7-dihydro-5H-cyclopenta[d]pyrimidine (350 mg, 1.236 mmol) and trideuteromethylamine hydrochloride (174 mg, 2.472 mmol) in methanol (3 mL) was added DIPEA (0.432 mL, 2.472 mmol). The reaction mixture was stirred at room temperature overnight. The solvent was removed in vacuum and the residue was purified by column chromatography on silica gel to give 2-chloro-N-trideuteromethyl-7-phenyl-6,7-dihydro-5H-cyclopenta[d]pyrimidin-4-amine as brown oil. LC-MS (M+H)$^+$=281.2.

Preparation Gf 2-chloro-N-cyclopropyl-7-phenyl-6,7-dihydro-5H-cyclopenta[d]pyrimidin-4-amine

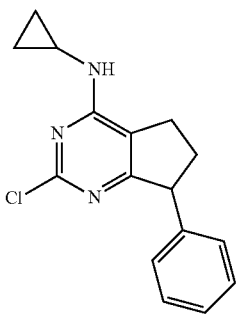 [SMILES: Clc1nc(NC2CC2)c2c(n1)C(c1ccccc1)CC2]

To a solution of 2,4-dichloro-7-phenyl-6,7-dihydro-5H-cyclopenta[d]pyrimidine (170 mg, 0.641 mmol) in NMP (2 mL) was added cyclopropanamine (110 mg, 1.924 mmol) dropwise. The mixture was stirred at RT for 3 hours. 8 mL of water was added to precipitate out the product. The solid was filtered out and air-dried to give a crude 2-chloro-N-cyclopropyl-7-phenyl-6,7-dihydro-5H-cyclopenta[d]pyrimidin-4-amine (175 mg, 0.612 mmol, 96% yield), which was used for the next step without any purification. LC-MS (M+H)$^+$= 286.1

Preparation Gg 2-chloro-N-cyclobutyl-7-phenyl-6,7-dihydro-5H-cyclopenta[d]pyrimidin-4-amine

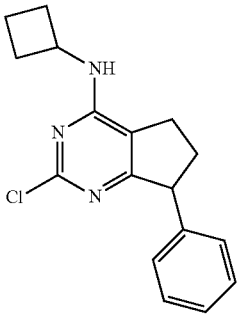 [SMILES: Clc1nc(NC2CCC2)c2c(n1)C(c1ccccc1)CC2]

To a solution of 2,4-dichloro-7-phenyl-6,7-dihydro-5H-cyclopenta[d]pyrimidine (160 mg, 0.60 mmol) in NMP (2 mL) was added cyclobutanamine (129 mg, 1.81 mmol) dropwise. The mixture was stirred at RT for 3 hrs. 8 mL of water was added to precipitate out the product. The solid was filtered out and air-dried to give a crude 2-chloro-N-cyclobutyl-7-phenyl-6,7-dihydro-5H-cyclopenta[d]pyrimidin-4-amine (177 mg, 0.57 mmol, 94% yield), which was used for the next step without any purification. LC-MS (M+H)$^+$=300.1

Preparation Gh 2-chloro-7-phenyl-N-isopropyl-6,7-dihydro-5H-cyclopenta[d]pyrimidin-4-amine

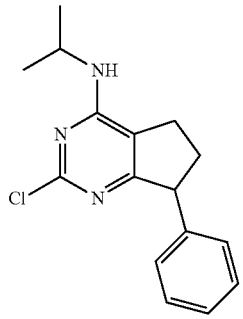 [SMILES: CC(C)Nc1nc(Cl)nc2c1CCC2c1ccccc1]

To a solution of 2,4-dichloro-7-phenyl-6,7-dihydro-5H-cyclopenta[d]pyrimidine (172 mg, 0.65 mmol) in NMP (2 mL) was added propan-2-amine (115 mg, 1.95 mmol) dropwise. The mixture was stirred at RT for 3 hrs. 8 mL of water was added to precipitate out the product. The solid was filtered out, air-dried, and purified via Biotage (12 g, hexanes-70% EtOAc) to give 2-chloro-N-isopropyl-7-phenyl-6,7-dihydro-5H-cyclopenta[d]pyrimidin-4-amine (154 mg, 0.535 mmol, 82% yield). $^1$H NMR (500 MHz, CDCl$_3$) δ ppm 7.30 (2 H, t, J=7.5 Hz), 7.20-7.25 (1 H, m), 7.15 (1 H, d, J=1.5 Hz), 7.13 (1 H, s), 4.53 (1 H, d, J=7.3 Hz), 4.37-4.45 (1 H, m), 4.23-4.28 (1 H, m), 2.58-2.78 (3 H, m), 2.10-2.17 (1 H, m), 1.27-1.29 (6 H, m).

Preparation Gi 2-chloro-4-(3-chloroazetidin-1-yl)-7-phenyl-6,7-dihydro-5H-cyclopenta[d]pyrimidine

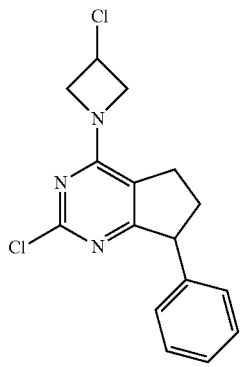 [SMILES: Clc1nc2c(c(N3CC(Cl)C3)n1)CCC2c1ccccc1]

The mixture of 3-chloroazetidine, HCl (217 mg, 1.697 mmol), 2,4-dichloro-7-phenyl-6,7-dihydro-5H-cyclopenta[d]pyrimidine (150 mg, 0.566 mmol) and DIEA (0.395 mL, 2.263 mmol) in N-Methyl-2-pyrrolidinone (2.0 mL) was stirred at RT for 3 h. Water (8 ml) was added to the reaction mixture. The product precipitated out which was filtered, rinsed with water and air dried. LC-MS (M+H)$^+$=320.0. $^1$H NMR (500 MHz, CHLOROFORM-d) δ ppm 7.21-7.39 (m, 3 H) 7.14 (d, J=7.02 Hz, 2 H) 4.65-4.84 (m, 3 H) 4.34-4.48 (m, 2 H) 4.23 (dd, J=9.16, 6.41 Hz, 1 H) 3.00 (dd, J=8.85, 5.80 Hz, 1 H) 2.83-2.93 (m, 1 H) 2.54-2.72 (m, 1 H) 2.02-2.20 (m, 1 H).

Preparation Gj

2-chloro-4-(3-fluoroazetidin-1-yl)-7-phenyl-6,7-dihydro-5H-cyclopenta[d]pyrimidine

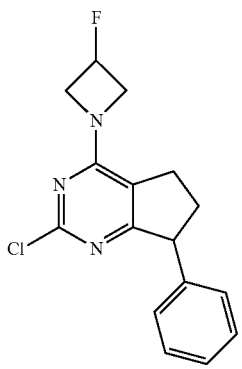 [SMILES: FC1CN(c2nc(Cl)nc3c2CCC3c2ccccc2)C1]

3-fluoroazetidine was reacted with Preparation G in the manner of Preparation Gi to afford the title compound. LC-MS (M+H)+=304.1. ¹H NMR (500 MHz, CHLOROFORM-d) δ ppm 7.19-7.37 (m, 3 H) 7.15 (d, J=7.32 Hz, 2 H) 5.39-5.52 (m, 1 H) 4.59 (dddd, J=14.88, 10.15, 5.19, 4.88 Hz, 2 H) 4.30-4.50 (m, 2 H) 4.23 (dd, J=9.00, 6.26 Hz, 1 H) 2.96-3.07 (m, 1 H) 2.84-2.96 (m, 1 H) 2.56-2.70 (m, 1 H) 2.05-2.21 (m, 1 H).

Preparation Gk

2-chloro-4-(3-methoxyazetidin-1-yl)-7-phenyl-6,7-dihydro-5H-cyclopenta[d]pyrimidine

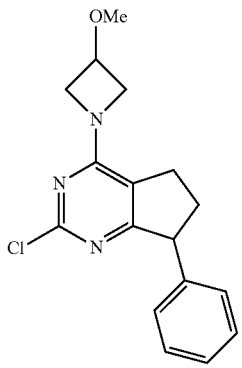 [SMILES: COC1CN(c2nc(Cl)nc3c2CCC3c2ccccc2)C1]

3-methoxyazetidine was reacted with Preparation G in the manner of Preparation Gi to afford the title compound. LC-MS (M+H)+=316.1.

Preparation Gl

2-(2-chloro-7-phenyl-6,7-dihydro-5H-cyclopenta[d]pyrimidin-4-yl)-5,8-dioxa-2-azaspiro[3.4]octane

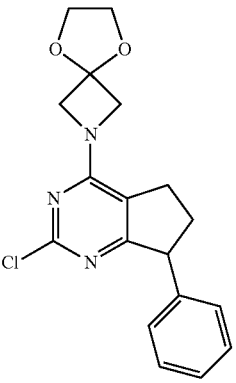 [SMILES: Clc1nc2c(c(N3CC4(C3)OCCO4)n1)CCC2c1ccccc1]

Azetidin-3-one was reacted with Preparation G in the manner of Preparation Gi to afford 1-(2-chloro-7-phenyl-6,7-dihydro-5H-cyclopenta[d]pyrimidin-4-yl)azetidin-3-one. LC-MS (M+H)+=300.0 A mixture of ethylene glycol (119 µL, 2.135 mmol), 1-(2-chloro-7-phenyl-6,7-dihydro-5H-cyclopenta[d]pyrimidin-4-yl)azetidin-3-one (320 mg, 1.068 mmol) and 4-methylbenzenesulfonic acid, H2O (20.31 mg, 0.107 mmol) in Benzene (2965 µL) was heated at reflux for 24 h in a Dean-stark apparatus. The resulting mixture was concentrated and purified by Prep-HPLC to afford the title compound. LC-MS (M+H)+=344.0. ¹H NMR (500 MHz, CHLOROFORM-d) δ ppm 7.21-7.40 (m, 3 H) 7.15 (d, J=7.63 Hz, 2 H) 4.35-4.53 (m, 4 H) 4.23 (dd, J=9.00, 6.26 Hz, 1 H) 4.03 (s, 4 H) 2.96-3.09 (m, 1 H) 2.80-2.96 (m, 1 H) 2.51-2.70 (m, 1 H) 2.03-2.16 (m, 1 H).

Preparation Gm

2-(2-chloro-7-phenyl-6,7-dihydro-5H-cyclopenta[d]pyrimidin-4-yl)-5-oxa-2-azaspiro[3.4]octane

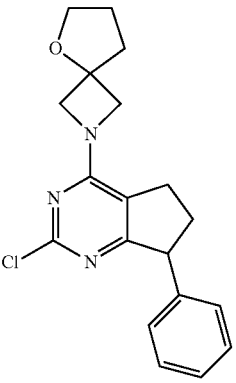 [SMILES: Clc1nc2c(c(N3CC4(CCCO4)C3)n1)CCC2c1ccccc1]

5-oxa-2-azaspiro[3.4]octane was reacted with Preparation G in the manner of Preparation Gi to afford the title compound. LC-MS (M+H)+=342.1.

Preparation Gn 1-(2-chloro-7-phenyl-6,7-dihydro-5H-cyclopenta[d]pyrimidin-4-yl)pyrrolidin-3-one

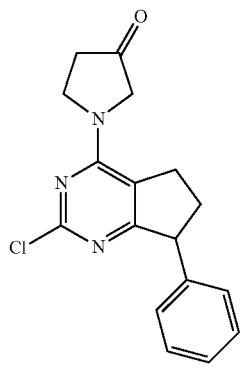 [SMILES: O=C1CCN(c2nc(Cl)nc3c2CCC3c2ccccc2)C1]

Pyrrolidin-3-one was reacted with Preparation G in the manner of Preparation Gi to afford the title compound. LC-MS (M+H)$^+$=314.1.

Preparation Go 7-(2-chloro-7-phenyl-6,7-dihydro-5H-cyclopenta[d]pyrimidin-4-yl)-1,4-dioxa-7-azaspiro[4.4]nonane

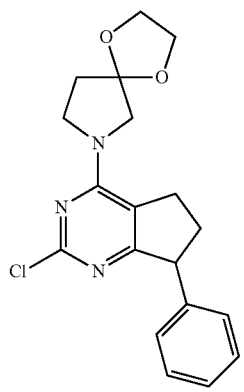 [SMILES: Clc1nc2c(c(N3CCC4(C3)OCCO4)n1)CCC2c1ccccc1]

The mixture of ethylene glycol (46.9 µL, 0.841 mmol), 1-(2-chloro-7-phenyl-6,7-dihydro-5H-cyclopenta[d]pyrimidin-4-yl)pyrrolidin-3-one (Intermediate Gn) (132 mg, 0.421 mmol) and 4-methylbenzenesulfonic acid, H2O (8.00 mg, 0.042 mmol) in Benzene (1169 µL) was heated at reflux for 24 h in a Dean-stark apparatus. The resulting mixture was concentrated and purified by Prep-HPLC (Column: PHENOMENEX LUNA C18 30×100 mm, Solvent A=10 mM Ammonium Acetate in 95:5 H2O/ACN, Solvent B=10 mM Ammonium Acetate in 5:95 H2O/ACN. Flow rate: 40 ml/min, 30-100, 20 min) to get 7-(2-chloro-7-phenyl-6,7-dihydro-5H-cyclopenta[d]pyrimidin-4-yl)-1,4-dioxa-7-azaspiro[4.4]nonane (24 mg, 0.067 mmol, 15.94% yield). LC-MS (M+H)$^+$=358.1. $^1$H NMR (500 MHz, CHLOROFORM-d) δ ppm 7.31 (2 H, t, J=7.63 Hz), 7.20-7.25 (1 H, m), 7.15 (2 H, d, J=7.63 Hz), 4.21 (1 H, dd, J=9.16, 6.10 Hz), 4.01-4.06 (4 H, m), 3.89-3.97 (2 H, m), 3.77-3.84 (2 H, m), 3.26 (1 H, ddd, J=15.03, 8.62, 5.95 Hz), 3.13 (1 H, ddd, J=14.95, 8.85, 5.80 Hz), 2.53-2.63 (1 H, m), 2.17 (2 H, t, J=7.17 Hz), 2.03-2.12 (1 H, m).

Preparation Gp 2-chloro-N-(5-isopropyl-2-methylphenyl)-7-phenyl-6,7-dihydro-5H-cyclopenta[d]pyrimidin-4-amine

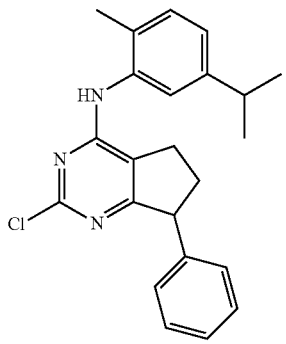 [SMILES: Cc1ccc(C(C)C)cc1Nc1nc(Cl)nc2c1CCC2c1ccccc1]

To a solution of 2,4-dichloro-7-phenyl-6,7-dihydro-5H-cyclopenta[d]pyrimidine (500 mg, 1.886 mmol) in NMP (Volume: 7543 µl) was added 5-isopropyl-2-methylaniline (281 mg, 1.886 mmol) and DIPEA (329 µl, 1.886 mmol). The resulting mixture was brought to 120° C. and stirred for 2 h. The mixture was then diluted with EtOAc (25 mL), washed with water(2×10 mL), brine (10 mL), dried over MgSO4, filtered, and concentrated in vacuo. Purification by flash chromatography (Silica, Thomson 40 g, 0-35% EtOAc/Hexanes) gave 2-chloro-N-(5-isopropyl-2-methylphenyl)-7-phenyl-6,7-dihydro-5H-cyclopenta[d]pyrimidin-4-amine (81421-078-01) (220 mg, 0.582 mmol, 30.9% yield). LC-MS (M+H)$^+$= 378.1. $^1$H NMR (500 MHz, MeOD) δ ppm 7.30-7.41 (3 H, m), 7.19-7.26 (3 H, m), 7.16 (2 H, d, J=7.93 Hz), 7.11 (1 H, d, J=7.63 Hz), 4.27 (1 H, t, J=7.63 Hz), 2.91 (1 H, ddd, J=13.89, 6.87, 6.71 Hz), 2.77-2.86 (1 H, m), 2.61-2.76 (2 H, m), 2.24 (3 H, s), 2.03-2.13 (1 H, m), 1.27 (5 H, dd, J=7.02, 1.53 Hz).

Preparation Gq

N2-(4-bromo-3-methoxyphenyl)-N4-methyl-7-phenyl-6,7-dihydro-5H-cyclopenta[d]pyrimidine-2,4-diamine

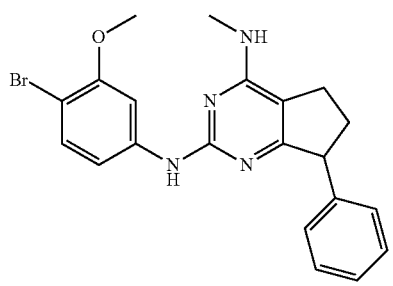 [SMILES: CNc1nc(Nc2ccc(Br)c(OC)c2)nc2c1CCC2c1ccccc1]

A mixture of 2-chloro-N-methyl-7-phenyl-6,7-dihydro-5H-cyclopenta[d]pyrimidin-4-amine (Preparation Ga) (0.24 g, 0.924 mmol), 4-bromo-3-methoxyaniline (0.187 g, 0.924 mmol) and H2SO4 (0.064 mL, 1.201 mmol) in NMP (Volume:

2 mL) was stirred in a sealed microwave tube at 90° C. overnight. The reaction was poured into 20 mL of water. The precipitate was collected by filtering. The cake was air dried. The cake was triturated with a minimum amount of cold MeOH to get 0.36 g (84%) of product as an off-white solid. LC-MS (M+H)$^+$=425.2. $^1$H NMR (400 MHz, DMSO-d$_6$) δ ppm 10.39 (1 H, br. s.), 7.68 (1 H, d, J=1.51 Hz), 7.53 (1 H, d, J=8.53 Hz), 7.34-7.42 (2 H, m), 7.24-7.34 (3 H, m), 6.94 (1 H, dd, J=8.66, 2.38 Hz), 4.36-4.51 (1 H, m), 3.83 (3 H, s), 3.05 (3 H, d, J=4.52 Hz), 2.79-2.95 (1 H, m), 2.59-2.77 (2 H, m), 1.93-2.12 (1 H, m).

Preparation H 2,4-Dichloro-7-(4-fluorophenyl)-6,7-dihydro-5H-cyclopenta[d]pyrimidine

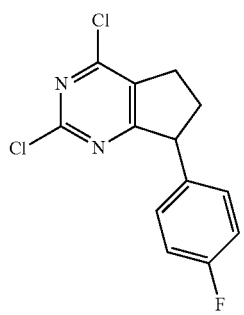 [SMILES: Fc1ccc(C2CCc3c(Cl)nc(Cl)nc32)cc1]

Intermediate H(1)

1-Cyclopentenyl-4-fluorobenzene

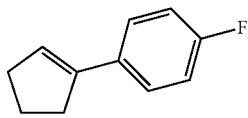 [SMILES: Fc1ccc(C2=CCCC2)cc1]

To a 0.5M solution of 4-fluorophenylmagnesium bromide (298 mL, 149 mmol) in THF at 0° C. was carefully added cyclopentanone (13.23 mL, 149 mmol). Upon the end of the addition, the reaction mixture was heated at reflux for 2 h. Ice (10 g) and 6N aqueous hydrochloric acid were added. The reaction mixture was extracted with ether. The combined organic extracts were washed with a saturated aqueous solution of sodium hydrogen sulfite, a saturated aqueous solution of sodium bicarbonate and water. The organic layer was dried over anhydrous magnesium sulfate and filtered. The solvent was removed in vacuum and the residue was purified by column chromatography on silica gel to give 1-cyclopentenyl-4-fluorobenzene (24.155 g, 149 mmol, 100% yield) as colorless oil. LC-MS (M+H)$^+$=163.0. $^1$H NMR (500 MHz, CDCl$_3$) δ ppm 7.35-7.42 (2H, m), 6.95-7.02 (2H, m), 6.06-6.13 (1H, m), 2.63-2.71 (2H, m), 2.47-2.56 (2H, m), 1.96-2.06 (2H, m).

Intermediate H(2)

2-(4-Fluorophenyl)cyclopentanone

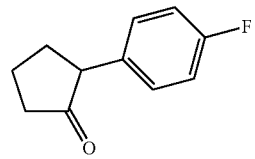 [SMILES: O=C1CCCC1c1ccc(F)cc1]

A mixture of 80% formic acid (100 mL, 2618 mmol) and 30% hydrogen peroxide (23 mL, 149 mmol) was warmed at 40° C. for 10 min. The resulting solution was carefully added to 1-cyclopentenyl-4-fluorobenzene (24.155 g, 149 mmol) under stirring. The two-phase system was initially stirred at room temperature. After a certain period of time, a spontaneous exothermic reaction took place, and the temperature rose to about 50° C. The reaction mixture was stirred at room temperature for 1 h. The reaction mixture was quenched by careful addition of a saturated sodium bicarbonate solution. Ether was added and the content of the separatory funnel was vigorously shaken. The organic layer was separated and the aqueous layer was extracted with ether. The combined organic extracts were dried over anhydrous magnesium sulfate and filtered. The solvent was removed in vacuum and the residue was purified by column chromatography on silica gel to give 2-(4-fluorophenyl)cyclopentanone (18.557 g, 104 mmol, 69.9% yield) as colorless oil. LC-MS (M+H)$^+$=177.2. $^1$H NMR (500 MHz, CDCl$_3$) δ ppm 7.12-7.18 (2H, m), 6.98-7.04 (2H, m), 3.29 (1H, dd, J=11.6, 8.5 Hz), 2.42-2.54 (2H, m), 2.27 (1H, ddd, J=19.1, 10.5, 8.9 Hz), 2.12-2.20 (1H, m), 2.01-2.12 (1H, m), 1.87-1.99 (1H, m, J=11.7, 11.7, 8.2, 6.3 Hz).

Intermediate H(3)

7-(4-Fluorophenyl)-6,7-dihydrocyclopenta[e][1,3]oxazine-2,4(3H,5H)-dione

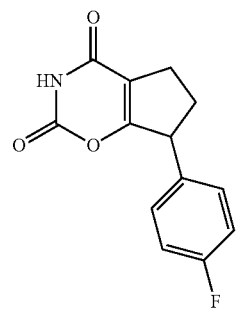 [SMILES: O=c1[nH]c(=O)c2c(o1)C(c1ccc(F)cc1)CC2]

A mixture of 2-(4-fluorophenyl)cyclopentanone (18.557 g, 104 mmol) and carbonisocyanatidic chloride (19.77 g, 187 mmol) was heated at 58° C. for 1 h and at 130° C. for 2 h. Upon cooling to room temperature, the tarrified reaction mixture was dissolved in ethyl acetate and washed with saturated aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(4-fluorophenyl)-6,7-dihydrocyclopenta[e][1,3]oxazine-2,4(3H,5H)-dione (13.527 g, 54.7 mmol, 52.5% yield) as brown solid. LC-MS (M+H)⁺=248.1. ¹H NMR (500 MHz, CDCl₃) δ ppm 11.80 (1H, br s), 7.31-7.39 (2H, m), 7.16-7.22 (2H, m), 4.30-4.38 (1H, m), 2.63-2.73 (1H, m), 2.53-2.63 (2H, m), 1.84-1.95 (1H, m).

Intermediate H(4)

7-(4-Fluorophenyl)-6,7-dihydro-1H-cyclopenta[d]pyrimidine-2,4(3H,5H)-dione

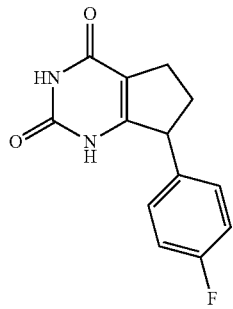 [SMILES: O=c1[nH]c2c(c(=O)[nH]1)CCC2c1ccc(F)cc1]

A solution of 7-(4-fluorophenyl)-6,7-dihydrocyclopenta[e][1,3]oxazine-2,4(3H,5H)-dione (13.527 g, 54.7 mmol) in concentrated ammonium hydroxide (150 mL, 3852 mmol) was heated at 100° C. in a high-pressure (350 mL) vessel overnight. The reaction mixture was cooled to 0° C. and filtered. The precipitate was consecutively washed with water and dried, first—by passing air through the filter, and then—in pump vacuum to give 7-(4-fluorophenyl)-6,7-dihydro-1H-cyclopenta[d]pyrimidine-2,4(3H,5H)-dione (4.670 g, 18.97 mmol, 34.7% yield). LC-MS (M+H)⁺=247.3. ¹H NMR (500 MHz, CDCl₃) δ ppm 11.70-11.81 (2H, br s), 7.31-7.39 (2H, m), 7.16-7.22 (2H, m), 4.30-4.38 (1H, m), 2.63-2.73 (1H, m), 2.53-2.63 (2H, m), 1.84-1.95 (1H, m).

Preparation H 2,4-Dichloro-7-(4-fluorophenyl)-6,7-dihydro-5H-cyclopenta[d]pyrimidine

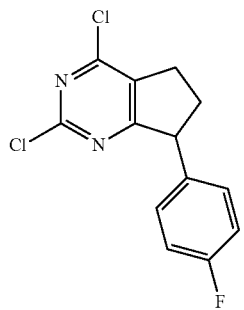 [SMILES: Fc1ccc(C2CCc3c(Cl)nc(Cl)nc32)cc1]

A solution of 7-(4-fluorophenyl)-6,7-dihydro-1H-cyclopenta[d]pyrimidine-2,4(3H,5H)-dione (1 g, 4.06 mmol) in phosphorus oxychloride (11.81 mL, 127 mmol) and N,N-dimethylaniline (3.94 mL, 31.1 mmol) was stirred at 110° C. overnight. The reaction mixture was carefully poured into ice. Once the ice melted, the aqueous layer was extracted with dichloromethane. The combined organic extracts were dried over anhydrous magnesium sulfate and filtered. The solvent was removed in vacuum and the residue was purified by column chromatography on silica gel to give 2,4-dichloro-7-(4-fluorophenyl)-6,7-dihydro-5H-cyclopenta[d]pyrimidine (700.0 mg, 2.472 mmol, 60.9% yield) as dark burgundy solid. LC-MS (M+H)⁺=283.1. ¹H NMR (500 MHz, CDCl₃) δ ppm 7.09-7.15 (2H, m), 7.03 (2H, t, J=8.5 Hz), 4.42 (1H, t, J=8.4 Hz), 3.10 (1H, dd, J=9.2, 4.6 Hz), 3.01 (1H, d, J=8.2 Hz), 2.73 (1H, d, J=8.9 Hz), 2.15-2.27 (1H, m).

Preparation Ha 2-chloro-4-(3,3-difluoroazetidin-1-yl)-7-(4-fluorophenyl)-6,7-dihydro-5H-cyclopenta[d]pyrimidine

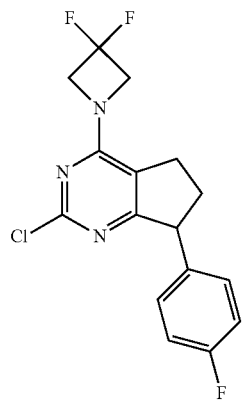 [SMILES: Fc1ccc(C2CCc3c2nc(Cl)nc3N2CC(F)(F)C2)cc1]

To a solution of 2,4-dichloro-7-(4-fluorophenyl)-6,7-dihydro-5H-cyclopenta[d]pyrimidine (Preparation H) (521 mg, 1.840 mmol) in MeOH (18.400 mL) was added DIPEA (0.803 mL, 4.60 mmol), then 3,3-difluoroazetidine, HCl (358 mg, 2.76 mmol). The reaction was allowed to stir at RT for 2 h and was then concentrated in vacuo. Purification by flash chromatography (silica, ethyl acetate/hexanes) gave 2-chloro-4-(3,3-difluoroazetidin-1-yl)-7-(4-fluorophenyl)-6,7-dihydro-5H-cyclopenta[d]pyrimidine (528 mg, 1.554 mmol, 84% yield) as a clear, colorless oil which crystallized on standing. LC-MS (M+H)⁺=340.0. ¹H NMR (500 MHz, CDCl₃) δ ppm 7.05-7.13 (2 H, m), 6.94-7.02 (2 H, m), 4.60 (4 H, td, J=11.75, 4.27 Hz), 4.18-4.30 (1 H, m), 2.93-3.06 (1 H, m), 2.80-2.95 (1 H, m), 2.56-2.70 (1 H, m), 1.96-2.18 (1 H, m).

Preparation Hb (1S,4S)-5-(2-chloro-7-(4-fluorophenyl)-6,7-dihydro-5H-cyclopenta[d]pyrimidin-4-yl)-2-oxa-5-azabicyclo[2.2.1]heptane

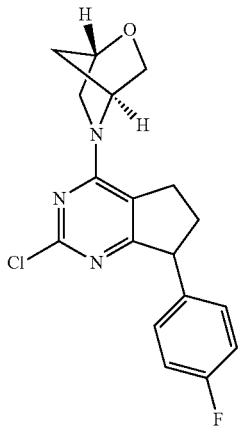 [SMILES: Fc1ccc(C2CCc3c2nc(Cl)nc3N2C[C@@H]3C[C@H]2CO3)cc1]

To a solution of 2,4-dichloro-7-(4-fluorophenyl)-6,7-dihydro-5H-cyclopenta[d]pyrimidine (Preparation H) (200 mg, 0.706 mmol) in MeOH (7064 μL) was added (1S,4S)-2-Oxa-5-azabicyclo[2.2.1]heptane monohydrochloride (115 mg, 0.848 mmol) and DIPEA (271 μL, 1.554 mmol). The resulting mixture was stirred at RT overnight. The reaction mixture was then concentrated in vacuo. The resulting oil was purified by flash chromatography (Silica, EtOAc/Hexanes) to give (1S,4S)-5-(2-chloro-7-(4-fluorophenyl)-6,7-dihydro-5H-cyclopenta[d]pyrimidin-4-yl)-2-oxa-5-azabicyclo[2.2.1]heptane (148 mg, 0.428 mmol, 60.6% yield). LC-MS (M+H)+= 346.1. $^1$H NMR (500 MHz, MeOD) δ ppm 7.12-7.21 (2 H, m), 7.00-7.08 (2 H, m), 5.11-5.21 (1 H, m), 4.69-4.74 (1 H, m), 4.15-4.26 (1 H, m), 3.88-3.94 (2 H, m), 3.68-3.86 (2 H, m), 3.11-3.21 (1 H, m), 2.56-2.69 (1 H, m), 1.92-2.11 (2 H, m), 1.24-1.42 (2 H, m).

Preparations Hc1 and Hc2

2-chloro-7-(4-fluorophenyl)-4-(2-methylpyrrolidin-1-yl)-6,7-dihydro-5H-cyclopenta[d]pyrimidine

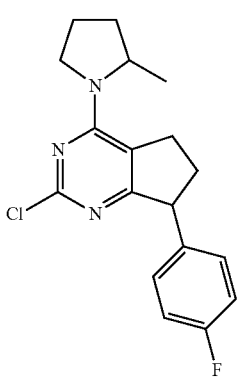

Diastereomer 1
Racemic

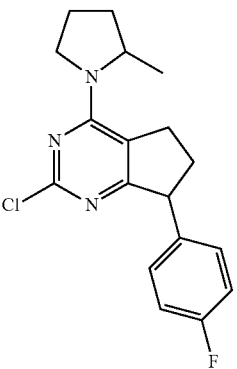

Diastereomer 2
Racemic

To a solution of 2,4-dichloro-7-(4-fluorophenyl)-6,7-dihydro-5H-cyclopenta[d]pyrimidine (Preparation H) (200 mg, 0.706 mmol) in MeOH (7064 mL) was added 2-Methylpyrrolidine (82 mL, 0.848 mmol). The resulting mixture was stirred at RT for 2 days. The reaction mixture was then concentrated in vacuo. The resulting oil was purified by flash chromatography (Silica, EtOAc/Hexanes) to give two racemic pairs of diasteriomers 2-chloro-7-(4-fluorophenyl)-4-(2-methylpyrrolidin-1-yl)-6,7-dihydro-5H-cyclopenta[d]pyrimidine. (Hc1, Diastereomer 1, racemic, first to elute) (79.5 mg, 0.240 mmol, 33.9% yield). LC-MS (M+H)+=332.1; $^1$H NMR (500 MHz, MeOD) δ ppm 7.16 (2 H, d, J=5.49 Hz), 7.04 (2 H, s), 4.42-4.54 (1 H, m), 4.09-4.22 (1 H, m), 3.86-4.00 (1 H, m), 3.71-3.82 (1 H, m), 3.24-3.31 (1 H, m), 3.10-3.22 (1 H, m), 2.54-2.65 (1 H, m), 2.05-2.16 (2 H, m), 1.94-2.05 (2 H, m), 1.69-1.80 (1 H, m), 1.27 (3 H, d, J=6.10 Hz). (Hc2, Diastereomer 2, racemic, second to elute) (89.5 mg, 0.270 mmol, 38% yield). LC-MS (M+H)+=332.1; $^1$H NMR (500 MHz, MeOD) δ ppm 7.14 (2 H, d, J=5.49 Hz), 6.99-7.08 (2 H, m), 4.42-4.54 (1 H, m), 4.13-4.22 (1 H, m), 3.86-4.00 (1 H, m), 3.71-3.83 (1 H, m), 3.25-3.32 (1 H, m), 3.14-3.25 (1 H, m), 2.52-2.67 (1 H, m), 2.05-2.19 (2 H, m), 1.94-2.05 (2 H, m), 1.68-1.78 (1 H, m), 1.19-1.32 (3 H, m). The relative stereochemistry for Hc1 and Hc2 was not determined

Preparation Hd (2S,6R)-4-(2-chloro-7-(4-fluorophenyl)-6,7-dihydro-5H-cyclopenta[d]pyrimidin-4-yl)-2,6-dimethylmorpholine

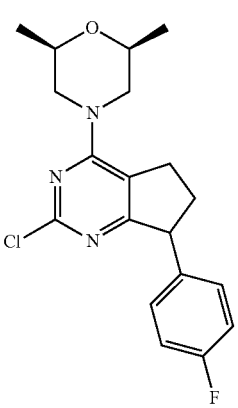 [SMILES: C[C@@H]1CN(c2nc(Cl)nc3c2CCC3c2ccc(F)cc2)C[C@H](C)O1]

To a solution of 2,4-dichloro-7-(4-fluorophenyl)-6,7-dihydro-5H-cyclopenta[d]pyrimidine (Preparation H) (200 mg, 0.706 mmol) in MeOH (7064 mL) was added cis-2,6-Dimethylmorpholine (105 mL, 0.848 mmol). The resulting mixture was stirred at RT overnight. An additional 2 equ. of cis-2,6-Dimethylmorpholine was then added and the mixture was again stirred overnight at RT. The reaction mixture was then concentrated in vacuo. The resulting oil was purified by flash chromatography (Silica, EtOAc/Hexanes) to give (2S, 6R)-4-(2-chloro-7-(4-fluorophenyl)-6,7-dihydro-5H-cyclopenta[d]pyrimidin-4-yl)-2,6-dimethylmorpholine (223 mg, 0.616 mmol, 87% yield). LC-MS (M+H)$^+$=332.1. $^1$H NMR (500 MHz, MeOD) δ ppm 7.11-7.24 (2 H, m), 6.99-7.09 (2 H, m), 4.39-4.51 (2 H, m), 4.20 (1 H, s), 3.70 (2 H, td, J=4.12, 2.44 Hz), 3.14-3.25 (1 H, m), 3.03-3.13 (1 H, m), 2.69-2.80 (2 H, m), 2.54-2.68 (1 H, m), 1.95-2.13 (1 H, m), 1.23 (6 H, d, J=6.10 Hz).

Preparation He 1-(2-chloro-7-(4-fluorophenyl)-6,7-dihydro-5H-cyclopenta[d]pyrimidin-4-yl)-4-methylpiperidin-4-ol

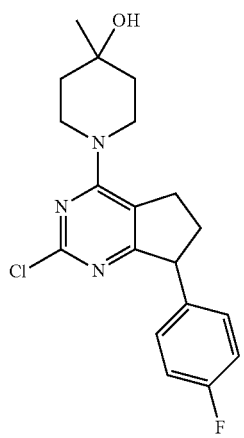 [SMILES: CC1(O)CCN(c2nc(Cl)nc3c2CCC3c2ccc(F)cc2)CC1]

To a solution of 2,4-dichloro-7-(4-fluorophenyl)-6,7-dihydro-5H-cyclopenta[d]pyrimidine (Preparation H) (400 mg, 1.413 mmol) in MeOH (14.100 mL) was added 4-methylpiperidin-4-ol (163 mg, 1.413 mmol). The resulting mixture was stirred at RT overnight. The reaction mixture was then concentrated in vacuo. Purification by flash chromatography (Silica, EtOAc/Hexanes) gave 1-(2-chloro-7-(4-fluorophenyl)-6,7-dihydro-5H-cyclopenta[d]pyrimidin-4-yl)-4-methylpiperidin-4-ol (374 mg, 1.034 mmol, 73.2% yield). LC-MS (M+H)$^+$=362.0. $^1$H NMR (500 MHz, MeOD) δ ppm 7.12-7.21 (2 H, m), 7.04 (2 H, t, J=8.85 Hz), 4.11-4.30 (3 H, m), 3.48-3.63 (2 H, m), 3.14-3.23 (1 H, m), 3.00-3.12 (1 H, m), 2.54-2.66 (1 H, m), 1.94-2.09 (1 H, m), 1.68 (4 H, t, J=4.12 Hz), 1.28 (3 H, s).

Preparations Hf1 and Hf2

2-chloro-4-(2-ethylpyrrolidin-1-yl)-7-(4-fluorophenyl)-6,7-dihydro-5H-cyclopenta[d]pyrimidine

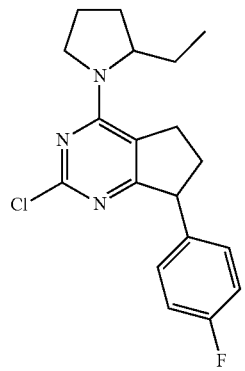

Hf1
Diastereomer 1
Racemic

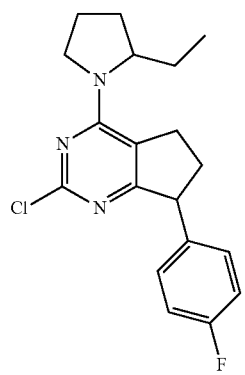

Hf2
Diastereomer 2
Racemic 2,4-dichloro-7-(4-fluorophenyl)-6,7-dihydro-5H-cyclopenta[d]pyrimidine (Preparation H) (200 mg, 0.706 mmol) and 2-ethylpyrrolidine (84 mg, 0.848 mmol) were combined and purified as per Preparation Hd to give two pairs of racemic diasteriomers 2-chloro-4-(2-ethylpyrrolidin-1-yl)-7-(4-fluorophenyl)-6,7-dihydro-5H-cyclopenta[d]pyrimidine. (Hf1, Diastereomer 1, racemic, first to elute) (77 mg, 0.223 mmol, 32% yield) LC-MS (M+H)$^+$=346. (Hf1, Diastereomer 2, racemic, second to elute) (80 mg, 0.232 mmol, 33% yield); LC-MS (M+H)$^+$=346.2. The relative stereochemistry for Hf1 and Hf2 was not determined

Preparation Hg tert-butyl 1-(2-chloro-7-(4-fluorophenyl)-6,7-dihydro-5H-cyclopenta[d]pyrimidin-4-yl)-4-methylpiperidin-4-ylcarbamate

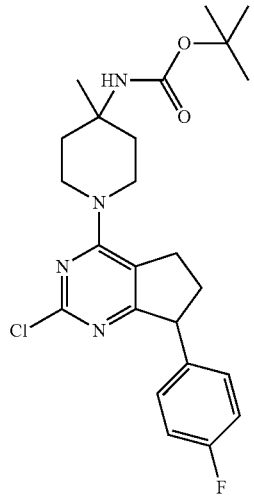 [SMILES: CC1(NC(=O)OC(C)(C)C)CCN(c2nc(Cl)nc3c2CCC3c2ccc(F)cc2)CC1]

To a solution of 2,4-dichloro-7-(4-fluorophenyl)-6,7-dihydro-5H-cyclopenta[d]pyrimidine (Preparation H) (400 mg, 1.413 mmol) in MeOH (14.100 mL) was added tert-butyl 4-methylpiperidin-4-ylcarbamate (303 mg, 1.413 mmol). The resulting mixture was stirred at RT for 7 days. At that time, the reaction mixture was concentrated in vacuo. Purification by flash chromatography (Silica, EtOAc/Hexanes) gave tert-butyl 1-(2-chloro-7-(4-fluorophenyl)-6,7-dihydro-5H-cyclopenta[d]pyrimidin-4-yl)-4-methylpiperidin-4-ylcarbamate (159 mg, 0.345 mmol, 24.41% yield) as a yellow foam. LC-MS (M+H)$^+$=461.2. $^1$H NMR (500 MHz, MeOD) δ ppm 7.12-7.22 (2 H, m), 6.98-7.09 (2 H, m), 4.19 (3 H, d, J=2.14 Hz), 3.38-3.56 (2 H, m), 3.13-3.25 (1 H, m), 3.02-3.13 (1 H, m), 2.53-2.67 (1 H, m), 2.11-2.24 (2 H, m), 1.96-2.08 (1 H, m), 1.53-1.65 (2 H, m), 1.47 (9 H, s), 1.37 (3 H, s).

Preparation Hh 2-chloro-7-(4-fluorophenyl)-N-methyl-6,7-dihydro-5H-cyclopenta[d]pyrimidin-4-amine

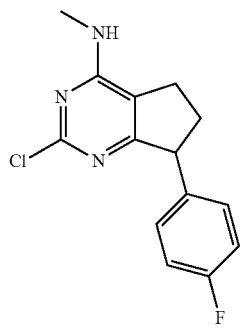

2,4-dichloro-7-(4-fluorophenyl)-6,7-dihydro-5H-cyclopenta[d]pyrimidine (Preparation H) (500 mg, 1.766 mmol) and methanamine hydrochloride (179 mg, 2.65 mmol) were combined and purified as per Preparation Ha to give 2-chloro-7-(4-fluorophenyl)-N-methyl-6,7-dihydro-5H-cyclopenta[d]pyrimidin-4-amine (344 mg, 1.239 mmol, 70.1% yield). LC-MS (M+H)$^+$=278.0. $^1$H NMR (500 MHz, CDCl$_3$) δ ppm 7.03-7.12 (2 H, m), 6.91-7.03 (2 H, m), 4.53-4.79 (1 H, m), 4.19-4.29 (1 H, m), 3.09 (3 H, d, J=4.88 Hz), 2.56-2.80 (3 H, m), 2.00-2.15 (1 H, m).

Preparation Hi 1-(2-chloro-7-(4-fluorophenyl)-6,7-dihydro-5H-cyclopenta[d]pyrimidin-4-yl)-3-(trifluoromethyl)pyrrolidin-3-ol

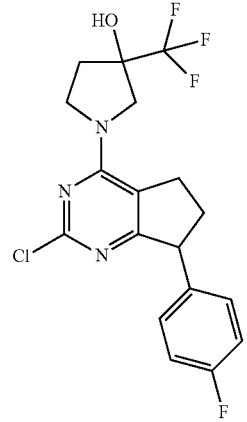 [SMILES: OC1(C(F)(F)F)CCN(c2nc(Cl)nc3c2CCC3c2ccc(F)cc2)C1]

2,4-dichloro-7-(4-fluorophenyl)-6,7-dihydro-5H-cyclopenta[d]pyrimidine (Preparation H) (286 mg, 1.010 mmol) and 3-(trifluoromethyl)pyrrolidin-3-ol (157 mg, 1.010 mmol) were combined and purified as per Preparation Hb to give 1-(2-chloro-7-(4-fluorophenyl)-6,7-dihydro-5H-cyclopenta[d]pyrimidin-4-yl)-3-(trifluoromethyl)pyrrolidin-3-ol (62% yield). LC-MS (M+H)$^+$=402.0.

Preparation Hj 1-(2-chloro-7-(4-fluorophenyl)-6,7-dihydro-5H-cyclopenta[d]pyrimidin-4-yl)-N,N-dimethylpyrrolidin-3-amine

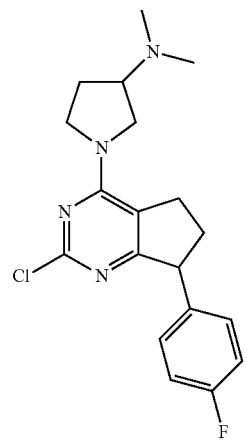 [SMILES: CN(C)C1CCN(c2nc(Cl)nc3c2CCC3c2ccc(F)cc2)C1]

2,4-dichloro-7-(4-fluorophenyl)-6,7-dihydro-5H-cyclopenta[d]pyrimidine (Preparation H) (100 mg, 0.353 mmol) and N,N-dimethylpyrrolidin-3-amine (44.3 µL, 0.353 mmol) were combined and purified as per Preparation Hb to give 1-(2-chloro-7-(4-fluorophenyl)-6,7-dihydro-5H-cyclopenta[d]pyrimidin-4-yl)-N,N-dimethylpyrrolidin-3-amine (109 mg, 86% yield). LC-MS (M+H)$^+$=361.2.

Preparation Hk 2-chloro-7-(4-fluorophenyl)-4-(4-methylpiperazin-1-yl)-6,7-dihydro-5H-cyclopenta[d]pyrimidine

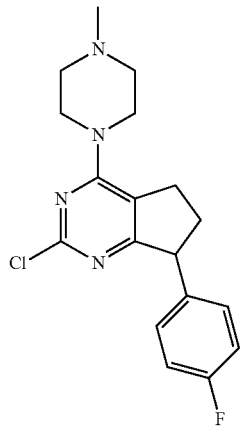 [SMILES: CN1CCN(c2nc(Cl)nc3c2CCC3c2ccc(F)cc2)CC1]

2,4-dichloro-7-(4-fluorophenyl)-6,7-dihydro-5H-cyclopenta[d]pyrimidine (Preparation H) (100 mg, 0.353 mmol) and 1-methylpiperazine (39.2 µL, 0.353 mmol) were combined and purified as per Preparation Hb to give 2-chloro-7-(4-fluorophenyl)-4-(4-methylpiperazin-1-yl)-6,7-dihydro-5H-cyclopenta[d]pyrimidine (109 mg, 0.314 mmol, 89% yield). LC-MS (M+H)$^+$=347.2.

Preparation Hl tert-butyl 4-(2-chloro-7-(4-fluorophenyl)-6,7-dihydro-5H-cyclopenta[d]pyrimidin-4-yl)piperazine-1-carboxylate

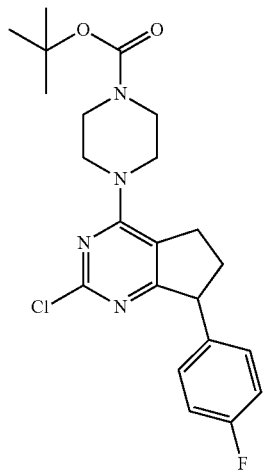 [SMILES: CC(C)(C)OC(=O)N1CCN(c2nc(Cl)nc3c2CCC3c2ccc(F)cc2)CC1]

2,4-dichloro-7-(4-fluorophenyl)-6,7-dihydro-5H-cyclopenta[d]pyrimidine (Preparation H) (100 mg, 0.353 mmol) and tert-Butyl 1-piperazinecarboxylate (65.8 mg, 0.353 mmol) were combined and purified as per Preparation Hb to give tert-butyl 4-(2-chloro-7-(4-fluorophenyl)-6,7-dihydro-5H-cyclopenta[d]pyrimidin-4-yl)piperazine-1-carboxylate (116.9 mg, 76% yield). LC-MS (M+H)$^+$=433.3.

Preparation Hm tert-butyl 1-(2-chloro-7-(4-fluorophenyl)-6,7-dihydro-5H-cyclopenta[d]pyrimidin-4-yl)pyrrolidin-3-ylmethyl)carbamate

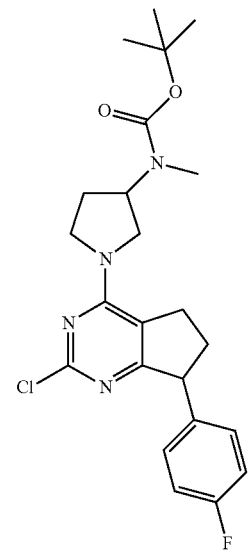 [SMILES: CN(C(=O)OC(C)(C)C)C1CCN(c2nc(Cl)nc3c2CCC3c2ccc(F)cc2)C1]

2,4-dichloro-7-(4-fluorophenyl)-6,7-dihydro-5H-cyclopenta[d]pyrimidine (Preparation H) (100 mg, 0.353 mmol) and 3-(N-tert-Butoxycarbonyl-N-methylamino)pyrrolidine (69.4 µL, 0.353 mmol) were combined and purified as per Preparation Hb to give tert-butyl 1-(2-chloro-7-(4-fluorophenyl)-6,7-dihydro-5H-cyclopenta[d]pyrimidin-4-yl)pyrrolidin-3-ylmethyl)carbamate (148 mg, 94% yield). LC-MS (M+H)$^+$=447.2.

Preparation Hn tert-butyl 1-(2-chloro-7-(4-fluorophenyl)-6,7-dihydro-5H-cyclopenta[d]pyrimidin-4-yl)azetidin-3-yl(methyl)carbamate

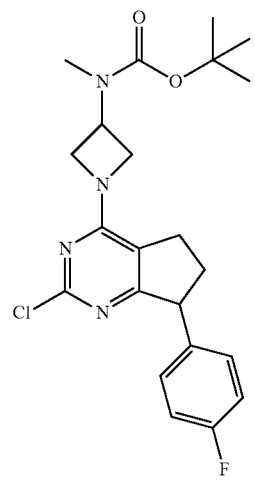 [SMILES: CN(C(=O)OC(C)(C)C)C1CN(c2nc(Cl)nc3c2CCC3c2ccc(F)cc2)C1]

2,4-Dichloro-7-(4-fluorophenyl)-6,7-dihydro-5H-cyclopenta[d]pyrimidine (Preparation H) (100 mg, 0.353 mmol) and carbamic acid, 3-azetidinylmethyl-, 1,1-dimethylethyl ester (82 mg, 0.441 mmol) were combined and purified as per Preparation Hb to give tert-butyl 1-(2-chloro-7-(4-fluorophenyl)-6,7-dihydro-5H-cyclopenta[d]pyrimidin-4-yl)azetidin-3-yl(methyl)carbamate (147 mg, 96% yield). LC-MS (M+H)$^+$=377.1.

Preparation Ho 1-(2-chloro-7-(4-fluorophenyl)-6,7-dihydro-5H-cyclopenta[d]pyrimidin-4-yl)-N,N-dimethylazetidin-3-amine

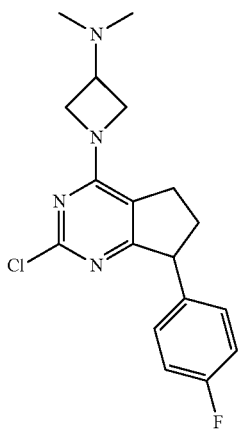 [SMILES: CN(C)C1CN(c2nc(Cl)nc3c2CCC3c2ccc(F)cc2)C1]

2,4-Dichloro-7-(4-fluorophenyl)-6,7-dihydro-5H-cyclopenta[d]pyrimidine (Preparation H) (100 mg, 0.353 mmol) and N,N-dimethylazetidin-3-amine, 2HCl (122 mg, 0.706 mmol) were combined and purified as per Preparation Hb to give 1-(2-chloro-7-(4-fluorophenyl)-6,7-dihydro-5H-cyclopenta[d]pyrimidin-4-yl)-N,N-dimethylazetidin-3-amine (quantitative). LC-MS (M+H)$^+$=347.2.

Preparation Hp1 and Hp2

2-chloro-7-(4-fluorophenyl)-4-((S)-3-fluoropyrrolidin-1-yl)-6,7-dihydro-5H cyclopenta[d]pyrimidine

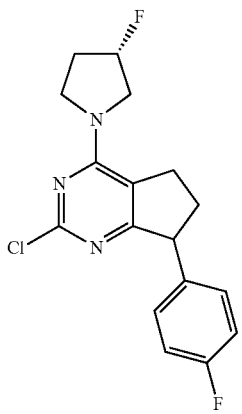 [SMILES: Fc1ccc(C2CCc3c2nc(Cl)nc3N2CC[C@H](F)C2)cc1]

To a solution of 2,4-dichloro-7-(4-fluorophenyl)-6,7-dihydro-5H-cyclopenta[d]pyrimidine (Preparation H) (135 mg, 0.477 mmol) in MeOH (4768 µL) was added DIPEA (208 µL, 1.192 mmol), then (S)-3-fluoropyrrolidine (46.7 mg, 0.524 mmol). The reaction was allowed to stir at ambient temperature for 2 h. The solvent was removed and the residue applied to Silica gel and eluted with an EtOAc/Hex gradient to afford two diasteriomers (Hp1 and Hp2). Hp1: LC-MS (M+H)$^+$=336.2. $^1$H NMR (500 MHz, CDCl$_3$) δ ppm 7.06-7.13 (2 H, m), 6.93-7.00 (2 H, m), 5.32 (1 H, td, J=52.57, 3.17 Hz), 4.17 (1 H, dd, J=9.16, 5.49 Hz), 4.06-4.14 (1 H, m), 3.98-4.06 (1 H, m), 3.76-3.90 (2 H, m), 3.25 (1 H, ddd, J=15.11, 8.55, 6.26 Hz), 3.08-3.16 (1 H, m), 2.51-2.60 (1 H, m, J=13.20, 9.12, 9.12, 6.41 Hz), 2.32-2.42 (1 H, m), 2.00-2.17 (2 H, m). Hp2: LC-MS (M+H)$^+$=336.2. $^1$H NMR (500 MHz, CDCl$_3$) δ ppm 7.06-7.14 (2 H, m), 6.94-7.02 (2 H, m), 5.25-5.40 (1 H, m), 3.99-4.24 (3 H, m), 3.75-3.92 (2 H, m), 3.19-3.28 (1 H, m), 3.10-3.19 (1 H, m), 2.57 (1 H, dddd, J=13.24, 8.74, 8.55, 4.58 Hz), 2.31-2.43 (1 H, m), 1.94-2.17 (2 H, m)

Preparation Hq 2-chloro-7-(4-fluorophenyl)-4-((R)-3-fluoropyrrolidin-1-yl)-6,7-dihydro-5H cyclopenta[d]pyrimidine

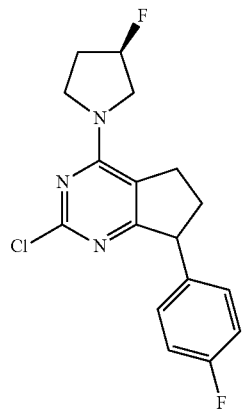 [SMILES: Fc1ccc(C2CCc3c2nc(Cl)nc3N2CC[C@@H](F)C2)cc1]

2,4-dichloro-7-(4-fluorophenyl)-6,7-dihydro-5H-cyclopenta[d]pyrimidine (Preparation H) was reacted as described in Preparation Hp1 and Hp2 with (R)-3-fluoropyrrolidine. The solvent was removed and the residue applied to Silica gel and eluted with an EtOAc/Hex gradient to afford the combined two diasteriomers (Hq).
Ha1: LC-MS (M+H)$^+$=336.0.

Preparation Hr 2-chloro-4-(4,4-difluoropiperidin-1-yl)-7-(4-fluorophenyl)-6,7-dihydro-5H-cyclopenta[d]pyrimidine

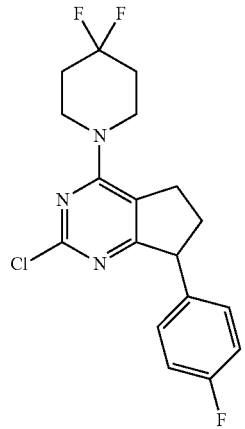 [SMILES: Fc1ccc(C2CCc3c2nc(Cl)nc3N2CCC(F)(F)CC2)cc1]

To a solution of 2,4-dichloro-7-(4-fluorophenyl)-6,7-dihydro-5H-cyclopenta[d]pyrimidine (Preparation H) (90 mg, 0.318 mmol) in MeOH (3179 µL), 4,4-difluoropiperidine (115 mg, 0.95 mmol) was added. The reaction was allowed to stir at rt. When the reaction was complete, removed solvent and applied residue to Silica gel. Eluted with EtOAc/Hex to afford the desired 2-chloro-4-(4,4-difluoropiperidin-1-yl)-7-(4-fluorophenyl)-6,7-dihydro-5H-cyclopenta[d]pyrimidine (80.8 mg, 0.220 mmol, 69.1% yield). LC-MS (M+H)$^+$= 368.0.

Preparation Hs 2-chloro-4-(4-fluoro-5,6-dihydropyridin-1(2H)-yl)-7-(4-fluorophenyl)-6,7-dihydro-5H-cyclopenta[d]pyrimidine

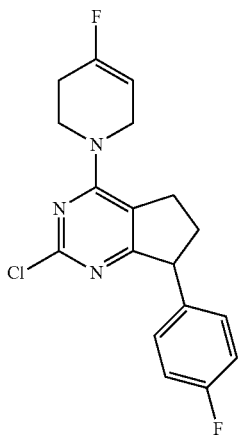 [SMILES: FC1=CCN(c2nc(Cl)nc3c2CCC3c2ccc(F)cc2)CC1]

2,4-dichloro-7-(4-fluorophenyl)-6,7-dihydro-5H-cyclopenta[d]pyrimidine (Preparation H) was reacted as described in Preparation Hc with 4-fluoro-1,2,3,6-tetrahydropyridine to afford 2-chloro-4-(4-fluoro-5,6-dihydropyridin-1(2H)-yl)-7-(4-fluorophenyl)-6,7-dihydro-5H-cyclopenta[d]pyrimidine (Preparation Hs).

Preparation Ht 2-chloro-7-(4-fluorophenyl)-4-(3-(trifluoromethyl)pyrrolidin-1-yl)-6,7-dihydro-5H-cyclopenta[d]pyrimidine-4-fluorophenyl)-6,7-dihydro-5H-cyclopenta[d]pyrimidine

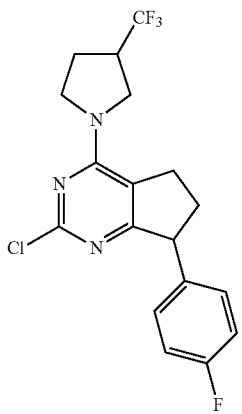 [SMILES: Fc1ccc(C2CCc3c2nc(Cl)nc3N2CCC(C(F)(F)F)C2)cc1]

2,4-dichloro-7-(4-fluorophenyl)-6,7-dihydro-5H-cyclopenta[d]pyrimidine (Preparation H) was reacted as described in Preparation Hr with 3-trifluoromethylpyrrolidine to afford 2-chloro-7-(4-fluorophenyl)-4-(3-(trifluoromethyl)pyrrolidin-1-yl)-6,7-dihydro-5H-cyclopenta[d]pyrimidine-4-fluorophenyl)-6,7-dihydro-5H-cyclopenta[d]pyrimidine (Preparation Ht) as a mixture of 4 diasteriomers. LC-MS (M+H)$^+$= 386.1. $^1$H NMR (500 MHz, CDCl$_3$) δ ppm 7.05-7.11 (2 H, m), 6.96 (2 H, t, J=8.70 Hz), 4.14-4.20 (1 H, m), 3.89-4.02 (2 H, m), 3.75-3.86 (2 H, m), 3.17-3.28 (1 H, m), 3.06-3.16 (1 H, m), 2.99 (1 H, dq, J=15.95, 8.01 Hz), 2.50-2.61 (1 H, m), 2.13-2.30 (2 H, m), 1.95-2.06 (1 H, m)

Preparation Hu 2-chloro-N-(3-ethoxypropyl)-7-(4-fluorophenyl)-6,7-dihydro-5H-cyclopenta[d]pyrimidin-4-amine

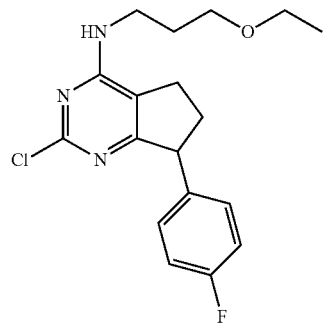 [SMILES: CCOCCCNc1nc(Cl)nc2c1CCC2c1ccc(F)cc1]

2,4-dichloro-7-(4-fluorophenyl)-6,7-dihydro-5H-cyclopenta[d]pyrimidine (Preparation H) was reacted as described in Preparation Hr with 3-ethoxypropan-1-amine to afford 2-chloro-N-(3-ethoxypropyl)-7-(4-fluorophenyl)-6,7-dihydro-5H-cyclopenta[d]pyrimidin-4-amine (Preparation Hu). LC-MS (M+H)$^+$=350.1.

Preparation Hv 3-(2-chloro-7-(4-fluorophenyl)-6,7-dihydro-5H-cyclopenta[d]pyrimidin-4-ylamino)propan-1-ol

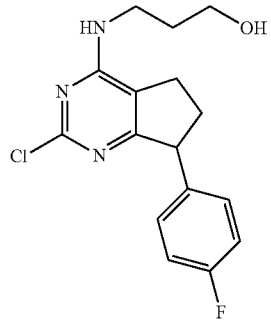 [SMILES: OCCCNc1nc(Cl)nc2c1CCC2c1ccc(F)cc1]

2,4-dichloro-7-(4-fluorophenyl)-6,7-dihydro-5H-cyclopenta[d]pyrimidine (Preparation H) was reacted as described in Preparation Hr with 3-hydroxypropan-1-amine to afford 3-(2-chloro-7-(4-fluorophenyl)-6,7-dihydro-5H-cyclopenta[d]pyrimidin-4-ylamino)propan-1-ol (Preparation Hv). LC-MS (M+H)$^+$=322.1. $^1$H NMR (500 MHz, CDCl$_3$) δ ppm 7.08 (2 H, dd, J=8.55, 5.49 Hz), 6.97 (2 H, t, J=8.70 Hz), 5.18 (1 H, br. s.), 4.22-4.27 (1 H, m), 3.66-3.75 (4 H, m), 3.18 (1 H, br. s.), 2.60-2.77 (3 H, m), 2.02-2.12 (1 H, m), 1.78-1.86 (2 H, m)

Preparation Hw 2-chloro-N-(1-cyclopropyl-2-methoxyethyl)-7-(4-fluorophenyl)-6,7-dihydro-5H-cyclopenta[d]pyrimidin-4-amine

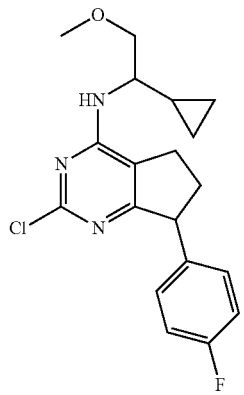 [SMILES: COCC(Nc1nc(Cl)nc2c1CCC2c1ccc(F)cc1)C1CC1]

2,4-dichloro-7-(4-fluorophenyl)-6,7-dihydro-5H-cyclopenta[d]pyrimidine (Preparation H) was reacted as described in Preparation Hr with 1-cyclopropyl-2-methoxyethanamine to afford 2-chloro-N-(1-cyclopropyl-2-methoxyethyl)-7-(4-fluorophenyl)-6,7-dihydro-5H-cyclopenta[d]pyrimidin-4-amine (Preparation Hw) as a mixture of 4 diasteriomers. LC-MS (M+H)$^+$=362.1.

Preparation Hx

2-Chloro-7-(4-fluorophenyl)-N,N-dimethyl-6,7-dihydro-5H-cyclopenta[d]pyrimidin-4-amine

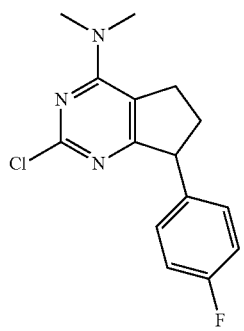 [SMILES: CN(C)c1nc(Cl)nc2c1CCC2c1ccc(F)cc1]

A solution of 2,4-dichloro-7-(4-fluorophenyl)-6,7-dihydro-5H-cyclopenta[d]pyrimidine (260 mg, 0.918 mmol) and excess dimethylamine (4.59 mL, 9.18 mmol) in methanol (2 mL) was stirred at rt for 30 min. The solvent was removed in vacuum to afford crude 2-chloro-7-(4-fluorophenyl)-N,N-dimethyl-6,7-dihydro-5H-cyclopenta[d]pyrimidin-4-amine (268 mg, 0.919 mmol, 100% yield). LC-MS (M+H)$^+$=292.3.

Preparation Hy

2-Chloro-7-(4-fluorophenyl)-N-trideuteromethyl-6,7-dihydro-5H-cyclopenta[d]pyrimidin-4-amine

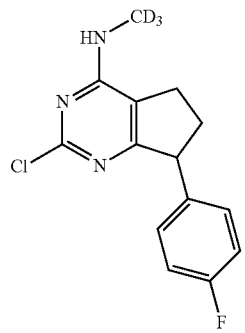 [SMILES: [2H]C([2H])([2H])Nc1nc(Cl)nc2c1CCC2c1ccc(F)cc1]

To a solution of 2,4-dichloro-7-(4-fluorophenyl)-6,7-dihydro-5H-cyclopenta[d]pyrimidine (350 mg, 1.236 mmol) and trideuteromethylamine hydrochloride (174 mg, 2.472 mmol) in methanol (3 mL) was added DIPEA (0.432 mL, 2.472 mmol). The reaction mixture was stirred at room temperature overnight. The solvent was removed in vacuum and the residue was purified by column chromatography on silica gel to give 2,4-dichloro-7-(4-fluorophenyl)-6,7-dihydro-5H-cyclopenta[d]pyrimidine (350 mg, 1.236 mmol) as brown oil. LC-MS (M+H)$^+$=281.2.

Preparation Hz 2-chloro-7-(4-fluorophenyl)-N-((R)-1-methoxybutan-2-yl)-6,7-dihydro-5H-cyclopenta[d]pyrimidin-4-amine

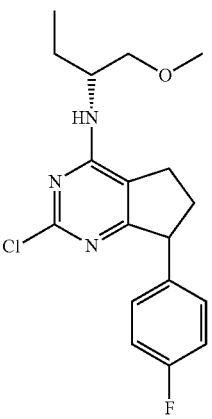

To a mixture of 2,4-dichloro-7-(4-fluorophenyl)-6,7-dihydro-5H-cyclopenta[d]pyrimidine (Preparation H) (100 mg, 0.353 mmol) in THF (1766 μL) was added (R)-1-methoxybutan-2-amine, HCl (197 mg, 1.413 mmol) and DIEA (493 μL, 2.83 mmol). The mixture was heated at 60° C. for 3 days. The crude product was purified by Prep-HPLC to get 2-chloro-7-(4-fluorophenyl)-N-((R)-1-methoxybutan-2-yl)-6,7-dihydro-5H-cyclopenta[d]pyrimidin-4-amine (Preparation Hz) (78 mg, 0.223 mmol, 63.1% yield). LC-MS (M+H)$^+$=350.4. $^1$H NMR (500 MHz, CDCl$_3$) δ ppm 7.12 (dd, J=8.24, 5.49 Hz, 2 H) 6.87-7.05 (m, 2 H) 4.86 (d, J=7.63 Hz, 1 H) 4.35 (d, J=3.05 Hz, 1 H) 4.18-4.30 (m, 1 H) 3.47-3.60 (m, 2 H) 3.40 (d, J=6.71 Hz, 3 H) 2.62-2.82 (m, 3 H) 2.03-2.15 (m, 1 H) 1.58-1.78 (m, 2 H) 0.89-1.07 (m, 3 H).

Preparation Haa 2-chloro-N-((R)-1-cyclopropylethyl)-7-(4-fluorophenyl)-6,7-dihydro-5H-cyclopenta[d]pyrimidin-4-amine

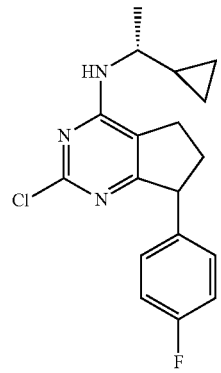 [SMILES: C[C@@H](Nc1nc(Cl)nc2c1CCC2c1ccc(F)cc1)C1CC1]

To a solution of 2,4-dichloro-7-(4-fluorophenyl)-6,7-dihydro-5H-cyclopenta[d]pyrimidine (Preparation H) (100 mg, 0.353 mmol) in THF (1766 µL) was added (R)-1-cyclopropylethanamine, HCl (172 mg, 1.413 mmol) and DIEA (493 µL, 2.83 mmol). The mixture was stirred at 60° C. for 5 days. The crude product was purified by Prep-HPLC get 2-chloro-N-((R)-1-cyclopropylethyl)-7-(4-fluorophenyl)-6,7-dihydro-5H-cyclopenta[d]pyrimidin-4-amine (Preparation Haa) (74 mg, 0.223 mmol, 63.1% yield). LC-MS (M+H)$^+$=332.3. $^1$H NMR (500 MHz, CDCl$_3$) δ ppm 7.06-7.18 (m, 2 H) 7.00 (td, J=8.70, 1.53 Hz, 2 H) 4.65 (d, J=5.80 Hz, 1 H) 4.26 (t, J=7.17 Hz, 1 H) 3.63-3.79 (m, 1 H) 2.62-2.82 (m, 3 H) 2.04-2.16 (m, 1 H) 1.26-1.40 (m, 3 H) 0.94 (qd, J=8.24, 3.36 Hz, 1 H) 0.42-0.62 (m, 3 H) 0.24-0.40 (m, 1 H).

Preparation Hab 2-chloro-N-((S)-1-cyclopropylethyl)-7-(4-fluorophenyl)-6,7-dihydro-5H-cyclopenta[d]pyrimidin-4-amine

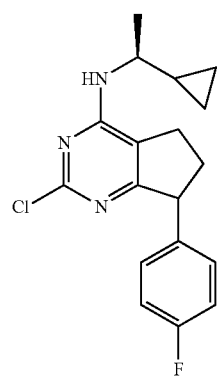 [SMILES: C[C@H](Nc1nc(Cl)nc2c1CCC2c1ccc(F)cc1)C1CC1]

2,4-dichloro-7-(4-fluorophenyl)-6,7-dihydro-5H-cyclopenta[d]pyrimidine (Preparation H) was reacted as described in Preparation Haa with (S)-1-cyclopropylethanamine, HCl to give 2-chloro-N-((S)-1-cyclopropylethyl)-7-(4-fluorophenyl)-6,7-dihydro-5H-cyclopenta[d]pyrimidin-4-amine (Preparation Hab). LC-MS (M+H)$^+$=332.3. $^1$H NMR (500 MHz, CDCl$_3$) δ ppm 7.07-7.21 (m, 2 H) 6.93-7.07 (m, 2 H) 4.65 (d, J=5.80 Hz, 1 H) 4.26 (t, J=7.32 Hz, 1 H) 3.61-3.79 (m, 1 H) 2.62-2.82 (m, 3 H) 2.05-2.16 (m, 1 H) 1.25-1.39 (m, 3 H) 0.84-1.00 (m, 1 H) 0.42-0.62 (m, 3 H) 0.29-0.40 (m, 1 H).

Preparation Hac 1-(2-chloro-7-(4-fluorophenyl)-6,7-dihydro-5H-cyclopenta[d]pyrimidin-4-yl)-3-methylazetidine-3-carbonitrile

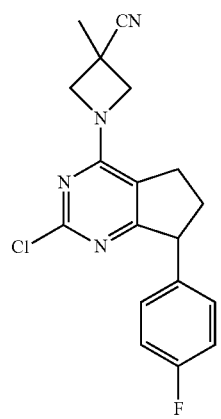 [SMILES: CC1(C#N)CN(c2nc(Cl)nc3c2CCC3c2ccc(F)cc2)C1]

3-cyano-3-methylazetidine was reacted with Preparation H in the manner of Preparation Gi to afford the title compound. LC-MS (M+H)$^+$=343.0 $^1$H NMR (500 MHz, CHLOROFORM-d) δ ppm 6.96-7.13 (m, 5 H) 4.73 (d, J=6.71 Hz, 1 H) 4.35 (d, J=7.32 Hz, 2 H) 4.33 (br. s., 1 H) 4.27 (dd, J=9.00, 2.90 Hz, 1 H) 2.99-3.09 (m, 1 H) 2.85-2.99 (m, 1 H) 2.64-2.78 (m, 1 H) 2.11 (dd, J=13.89, 7.48 Hz, 1 H) 1.76-1.91 (m, 3 H).

Preparation Had 2-chloro-4-(3-ethoxyazetidin-1-yl)-7-(4-fluorophenyl)-6,7-dihydro-5H-cyclopenta[d]pyrimidine

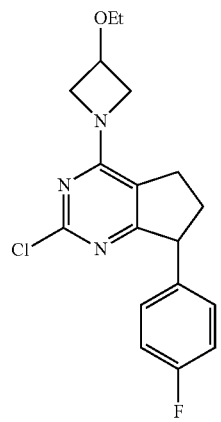 [SMILES: CCOC1CN(c2nc(Cl)nc3c2CCC3c2ccc(F)cc2)C1]

3-ethoxyazetidine was reacted with Preparation H in the manner of Preparation Gi to afford the title compound. LC-MS (M+H)+=348.0 ¹H NMR (500 MHz, CHLOROFORM-d) δ ppm 7.03-7.12 (m, 2 H) 6.91-7.01 (m, 2 H) 4.51 (br. s., 2 H) 4.36-4.48 (m, 1 H) 4.13-4.32 (m, 3 H) 3.50 (qd, J=6.97, 3.20 Hz, 2 H) 2.97-3.10 (m, 1 H) 2.82-2.96 (m, 1 H) 2.51-2.70 (m, 1 H) 1.93-2.11 (m, 1 H) 1.16-1.35 (m, 3 H).

Preparation Hae 1-(2-chloro-7-(4-fluorophenyl)-6,7-dihydro-5H-cyclopenta[d]pyrimidin-4-yl)-3-methylazetidin-3-ol

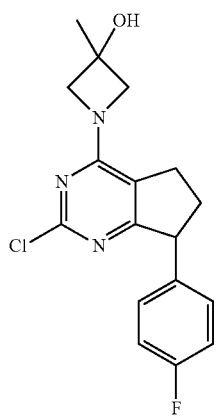

3-methylazetidin-3-ol was reacted with Preparation H in the manner of Preparation Gi to afford the title compound. LC-MS (M+H)+=334.0 ¹H NMR (500 MHz, CHLOROFORM-d) δ ppm 7.04-7.13 (m, 2 H) 7.00 (t, J=8.55 Hz, 2 H) 4.41 (d, J=6.71 Hz, 2 H) 4.39 (br. s., 3 H) 3.05-3.17 (m, 1 H) 2.90-3.04 (m, 1 H) 2.73 (ddd, J=9.08, 4.88, 4.65 Hz, 1 H) 2.03-2.19 (m, 1 H) 1.65 (s, 3 H).

Preparation Haf 2-chloro-7-(4-fluorophenyl)-4-(3-methoxy-3-methylazetidin-1-yl)-6,7-dihydro-5H-cyclopenta[d]pyrimidine

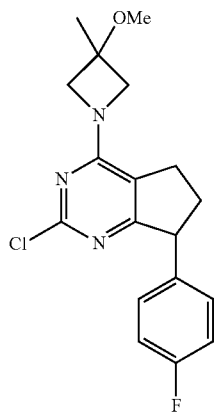 [SMILES: COC1(C)CN(c2nc(Cl)nc3c2CCC3c2ccc(F)cc2)C1]

3-methoxy-3-methylazetidine was reacted with Preparation H in the manner of Preparation Gi to afford the title compound. LC-MS (M+H)+=348.

Preparation I 2,4-dichloro-8-phenyl-7,8-dihydro-5H-pyrano[4,3-d]pyrimidine

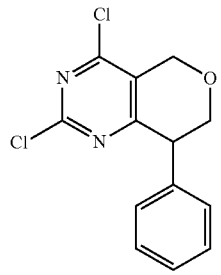 [SMILES: Clc1nc(Cl)c2c(n1)C(c1ccccc1)COC2]

Intermediate I(1)

3-iodo-4,4-dimethoxytetrahydro-2H-pyran

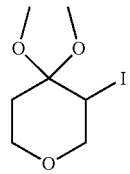

To a mixture of tetrahydro-4H-pyran-4-one (18.52 mL, 200 mmol) and trimethyl orthoformate (100 mL, 914 mmol) at 0° C. was added Iodine (49.2 mL, 200 mmol) slowly over 10 min. When the addition was complete, the reaction mixture was allowed to stir at 0° C. for 30 min. and was then allowed to come to RT and stir until TLC indicated all starting material had been consumed (approx. 1 h). The reaction was then cooled to 0° C. and quenched by the slow addition of sat. aqu. sodium thiosulfate (300 mL). The resulting mixture was extracted with EtOAc (3×75 mL). The combined organic layers were washed with brine (100 mL), dried over MgSO₄, filtered and concentrated in vacuo. Purification by flash chromatography (Silica, EtOAc/Hexanes) gave 3-iodo-4,4-dimethoxytetrahydro-2H-pyran (43.95 g, 162 mmol, 81% yield) as a yellow oil. ¹H NMR (500 MHz, CDCl₃) δ ppm 4.25 (1 H, q, J=2.44 Hz), 3.93-4.01 (1 H, m), 3.84-3.93 (2 H, m), 3.57 (1 H, td, J=11.75, 2.44 Hz), 3.19-3.30 (6 H, m), 2.34 (1 H, ddd, J=14.34, 12.21, 4.88 Hz), 1.80 (1 H, dq, J=14.34, 2.44 Hz).

Intermediate I(2)

3-phenyldihydro-2H-pyran-4(3H)-one

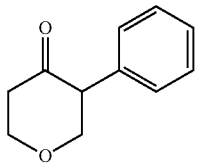 [SMILES: O=C1CCOCC1c1ccccc1]

To a stirred mixture of phenylboronic acid (16.81 g, 138 mmol), trans-2-Aminocyclohexanol hydrochloride (1.393 g, 9.19 mmol), and Nickel(II) chloride hexahydrate (1.092 g, 4.59 mmol) in THF (92 mL) at 0° C. was added Sodium bis(trimethylsilyl)amide (1.0 M in THF) (184 mL, 184 mmol) dropwise over 10 min. When the addition was complete, the reaction mixture was sparged with $N_2$ for 15 min. To the reaction mixture at 0° C. was then added 2-Propanol (375 mL) (previously sparged with $N_2$). The resulting mixture was allowed to come to RT at which time 3-iodo-4,4-dimethoxytetrahydro-2H-pyran (Intermediate I(1)) (25 g, 92 mmol) was added dropwise over 5 min. The reaction mixture was then brought to 60° C. and stirred overnight. The reaction mixture was then cooled to 0° C. and quenched by the careful addition of aqu. 1 N HCl until acidic. The resulting mixture was extracted with EtOAc (3×150 mL). The combined organic extracts were washed with Brine (100 mL), dried over $MgSO_4$, filtered and concentrated in vacuo. Purification by flash chromatography (Silica, EtOAc/Hexanes) gave 3-phenyldihydro-2H-pyran-4(3H)-one (8.37 g, 47.5 mmol, 51.7% yield) as a slightly orange oil. $^1$H NMR (500 MHz, $CDCl_3$) δ ppm 7.32-7.39 (2 H, m), 7.26-7.31 (1 H, m), 7.21-7.26 (2 H, m), 4.17-4.31 (2 H, m), 3.91-4.05 (2 H, m), 3.78 (1 H, dd, J=8.55, 6.10 Hz), 2.61-2.74 (1 H, m), 2.51-2.61 (1 H, m).

Intermediate I(3)

8-phenyl-7,8-dihydropyrano[3,4-e][1,3]oxazine-2,4(3H,5H)-dione

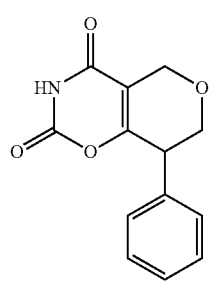 [SMILES: O=c1[nH]c(=O)c2c(o1)C(c1ccccc1)COC2]

A mixture of 3-phenyldihydro-2H-pyran-4(3H)-one (Intermediate I(2)) (3 g, 17.02 mmol) and carbonisocyanatidic chloride (10.48 g, 29.8 mmol) in a sealed tube was heated to 58° C. and stirred for 1 h. The mixture was then brought to 130° C. and stirred for an additional 2 h. The reaction turned black during this time. After cooling to RT, the tar was taken up in EtOAc (100 mL). The resulting solution was washed with saturated aqueous sodium bicarbonate (2×50 mL), brine (50 mL), dried over $MgSO_4$, filtered and concentrated in vacuo. Purification by flash chromatography (Silica, EtOAc/Hexanes) gave 8-phenyl-7,8-dihydropyrano[3,4-e][1,3]oxazine-2,4(3H,5H)-dione (2.58 g, 10.52 mmol, 61.8% yield) as a brown solid. LC-MS (M+H)$^+$=246.0. $^1$H NMR (500 MHz, MeOD) δ ppm 7.34-7.41 (4 H, m), 7.29-7.34 (1 H, m), 4.42-4.63 (2 H, m), 4.08-4.15 (1 H, m), 3.94 (1 H, dd, J=11.44, 4.12 Hz), 3.85 (1 H, ddd, J=4.20, 2.44, 2.21 Hz).

Intermediate I(4)

8-phenyl-7,8-dihydro-1H-pyrano[4,3-d]pyrimidine-2,4(3H,5H)-dione

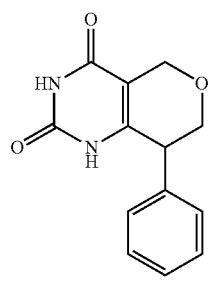 [SMILES: O=c1[nH]c2c(c(=O)[nH]1)COCC2c1ccccc1]

A solution of 8-phenyl-7,8-dihydropyrano[3,4-e][1,3]oxazine-2,4(3H,5H)-dione (Intermediate I(3)) (2.58 g, 10.52 mmol) in ammonium hydroxide (28.7 mL, 736 mmol) was heated to 80° C. in a sealed tube and stirred overnight. The reaction mixture was then concentrated to dryness giving 8-phenyl-7,8-dihydro-1H-pyrano[4,3-d]pyrimidine-2,4(3H,5H)-dione. The crude material was carried on as-is. LC-MS (M+H)$^+$=245.2.

Preparation I 2,4-dichloro-8-phenyl-7,8-dihydro-5H-pyrano[4,3-d]pyrimidine

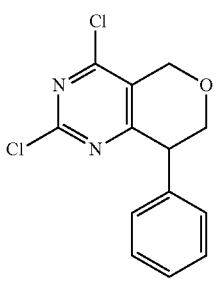 [SMILES: Clc1nc(Cl)c2c(n1)C(c1ccccc1)COC2]

A mixture of 8-phenyl-7,8-dihydro-1H-pyrano[4,3-d]pyrimidine-2,4(3H,5H)-dione (Intermediate 44)) (2569 mg, 10.52 mmol) and $POCl_3$ (29.400 mL, 315 mmol) was heated to 100° C. under microwave irradiation in a sealed tube for 1 h. The resulting mixture was poured over ice. When all the ice was melted, the mixture was extracted with EtOAc (3×15 mL). The combined organic extracts were washed with brine (20 mL), dried over $MgSO_4$, filtered and concentrated in vacuo. Purification by flash chromatography (Silica, EtOAc/Hexanes) gave 2,4-dichloro-8-phenyl-7,8-dihydro-5H-pyrano[4,3-d]pyrimidine (194 mg, 0.690 mmol, 6.56% yield). LC-MS (M+H)$^+$=281.1. $^1$H NMR (500 MHz, MeOD) δ ppm 7.30-7.37 (2 H, m), 7.25-7.30 (1 H, m), 7.18-7.25 (2 H, m), 4.90-5.00 (1 H, m), 4.75-4.84 (1 H, m), 4.16-4.26 (2 H, m), 4.02-4.15 (1 H, m).

Preparation Ia 2-chloro-N-methyl-8-phenyl-7,8-dihydro-5H-pyrano[4,3-d]pyrimidin-4-amine

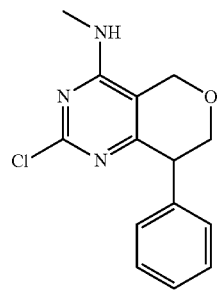 [SMILES: CNc1nc(Cl)nc2c1COCC2c1ccccc1]

To a solution of 2,4-dichloro-8-phenyl-7,8-dihydro-5H-pyrano[4,3-d]pyrimidine (Preparation I) (194 mg, 0.690 mmol) in MeOH (6901 μL) was added methanamine hydrochloride (69.9 mg, 1.035 mmol) and N,N-Diisopropylethylamine (301 μL, 1.725 mmol). The resulting mixture was stirred at RT for 2 h. The reaction mixture was then concentrated in vacuo. Purification by flash chromatography (Silica, EtOAc/Hexanes) gave 2-chloro-N-methyl-8-phenyl-7,8-dihydro-5H-pyrano[4,3-d]pyrimidin-4-amine (126 mg, 0.457 mmol, 66.2% yield). LC-MS $(M+H)^+$=276.0. $^1$H NMR (500 MHz, CDCl$_3$) δ ppm 7.28 (2 H, t, J=7.32 Hz), 7.20-7.25 (1 H, m), 7.14-7.20 (2 H, m), 4.47-4.62 (2 H, m), 4.47 (1 H, s), 4.00-4.11 (2 H, m), 3.95 (1 H, d, J=3.36 Hz), 3.08 (3 H, d, J=4.88 Hz).

Preparation Ib

2-Chloro-N,N-dimethyl-8-phenyl-7,8-dihydro-5H-pyrano[4,3-d]pyrimidin-4-amine

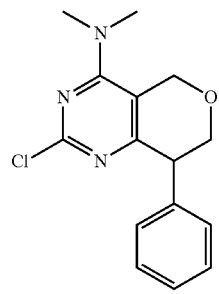 [SMILES: CN(C)c1nc(Cl)nc2c1COCC2c1ccccc1]

A solution of 2,4-dichloro-8-phenyl-7,8-dihydro-5H-pyrano[4,3-d]pyrimidine (135 mg, 0.480 mmol) and excess dimethylamine (216 mg, 4.80 mmol) in MeOH (2 mL) was stirred at rt for 1.5 h. The solvent was removed in vacuum to afford 2-chloro-N,N-dimethyl-8-phenyl-7,8-dihydro-5H-pyrano[4,3-d]pyrimidin-4-amine (139 mg, 0.480 mmol, 100% yield). LC-MS $(M+H)^+$=290.3.

Preparation Ic

2-Chloro-N-ethyl-N-methyl-8-phenyl-7,8-dihydro-5H-pyrano[4,3-d]pyrimidin-4-amine

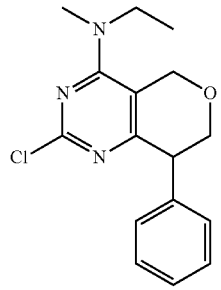 [SMILES: CCN(C)c1nc(Cl)nc2c1COCC2c1ccccc1]

A solution of 2,4-dichloro-8-phenyl-7,8-dihydro-5H-pyrano[4,3-d]pyrimidine (135 mg, 0.480 mmol) and excess N-methylethanamine (284 mg, 4.80 mmol) in MeOH (2 mL) was stirred at rt for 1 h. The solvent was removed in vacuum to afford 2-chloro-N-ethyl-N-methyl-8-phenyl-7,8-dihydro-5H-pyrano[4,3-d]pyrimidin-4-amine (146 mg, 0.481 mmol, 100% yield). LC-MS $(M+H)^+$=304.2.

Preparation J 2,4-dichloro-8-(4-fluorophenyl)-7,8-dihydro-5H-pyrano[4,3-d]pyrimidine

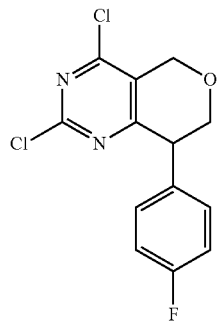 [SMILES: Fc1ccc(C2COCc3c(Cl)nc(Cl)nc32)cc1]

Intermediate J(1)

3-bromodihydro-2H-pyran-4(3H)-one

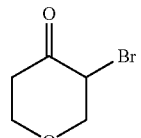

To a cooled solution of dihydro-2H-pyran-4(3H)-one (10.0 g, 99.8 mmol) in THF was added a solution of pyrrolidone hydrotribromide (49.54 g, 99.8 mmol) in THF over a period of 10 min. at 0° C. The reaction mixture was allowed to come to room temperature and stirred for 2 h. The solvent was removed under reduced pressure and the residue was diluted with ethyl acetate (300 mL). The organic solution was washed with aqueous saturated NaHCO$_3$ (100 mL), water (100 mL×2), brine solution (50 mL), dried over anhydrous Na$_2$SO$_4$ and evaporated under reduced pressure to give 3-bromodihydro-2H-pyran-4(3H)-one (12.0 g, 67%) as oily liquid. The crude compound was taken to the next step without further purification. $^1$H NMR (400 MHz, DMSO-d6): δ ppm 4.89-4.87 (1H, m) 4.28-4.27 (1H, m) 4.25-4.4.24 (1H, m) 3.85-3.74 (2H, m) 2.71-2.66 (2H, m).

Intermediate J(2)

3-(4-fluorophenyl)dihydro-2H-pyran-4(3H)-one

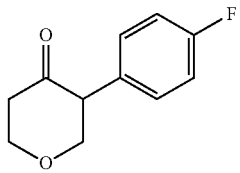 [SMILES: O=C1CCOCC1c1ccc(F)cc1]

To a solution of Intermediate J(1) (12.0 g, 66.9 mmol) in benzene was added 2 M solution of 4-fluorophenyl magnesium bromide in ether (13.34 g, 33.48 mL, 66.9 mmol) at 0° C. The reaction mixture was stirred at room temperature for 40 min. The reaction mixture was quenched with aqueous 1.5 N HCl (80 mL). The organic layer was separated and the aqueous layer was extracted with ethyl acetate (100×2). The combined organic layer was washed with water (100 mL×2), brine solution (50 mL), dried over anhydrous Na$_2$SO$_4$ and evaporated under reduced pressure to give crude compound as oily liquid. The crude compound was dissolved in benzene and was added a solution of 4-fluorophenyl magnesium bromide in ether (9.7 g, 24.5 mL, 49.0 mmol) at 0° C. The reaction mixture was heated at reflux for 30 min. The reaction mixture was quenched with aqueous 1.5 N HCl (50 mL). The organic layer was separated and the aqueous layer was extracted with ethyl acetate (100×2). The combined organic layer was washed with water (100 mL×2), brine solution (50 mL), dried over anhydrous Na$_2$SO$_4$ and evaporated under reduced pressure to give crude compound. The crude compound was purified by column chromatography (Silica gel, 230-400 mesh) using 5% ethyl acetate in pet-ether as mobile phase to give 3-(4-fluorophenyl)dihydro-2H-pyran-4(3H)-one (3.0 g, 36%) as oily liquid. LC-MS (M+H)$^+$=195.2. $^1$H NMR (400 MHz, chlorofom-d): δ ppm 7.7.21-7.18 (2H, m), 7.06-7.01 (2H, m), 4.28-4.21 (2H, m), 3.99-3.91 (2H, m), 3.79-3.76 (1H, m) 2.72-2.67 (1H, m) 2.64-2.55 (1H, m).

Intermediate J(3)

8-(4-fluorophenyl)-7,8-dihydropyrano[3,4-e][1,3]oxazine-2,4(3H,5H)-dione

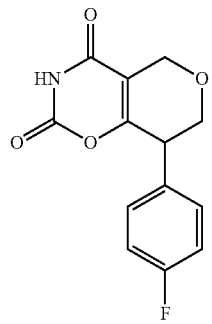 [SMILES: O=c1[nH]c(=O)c2c(o1)C(c1ccc(F)cc1)COC2]

A solution of Intermediate J(2) (1.5 g, 7.72 mmol) and N-chlorocarbonyl isocyanate (0.97 g, 9.2 mmol) was heated at 58° C. under nitrogen atmosphere for 1 h.

Then, the reaction temperature was increased to 130° C. and maintained for 2 h. The reaction mass was diluted with ethyl acetate (50 mL). The resulting organic solution was washed with saturated NaHCO$_3$ (25 mL), brine solution (25 mL), dried over anhydrous Na$_2$SO$_4$ and evaporated under reduced pressure to get crude compound. The crude compound was purified by column chromatography (Silica gel, 60-120 mesh) using 50% ethyl acetate in pet-ether as mobile phase to give 8-(4-fluorophenyl)-7,8-dihydropyrano[3,4-e][1,3]oxazine-2,4(3H,5H)-dione (0.8 g, 38%) as brown solid. LC-MS (M−H)$^+$=262.0. $^1$H NMR (400 MHz, DMSO-d6): δ ppm 11.97 (1H, s), 7.43-7.39 (2H, m), 7.21-7.16 (2H, m), 4.48-4.32 (2H, m), 4.05 (2H, m), 3.77 (1H, m).

Intermediate J(4)

8-(4-fluorophenyl)-7,8-dihydro-1H-pyrano[4,3-d]pyrimidine-2,4(3H,5H)-dione

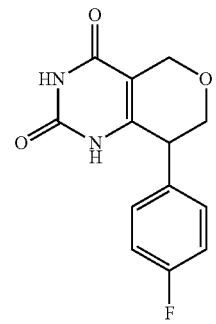 [SMILES: O=c1[nH]c2c(c(=O)[nH]1)COCC2c1ccc(F)cc1]

A solution of Intermediate J(3) (0.8 g, 3.0 mmol) in aqueous ammonia (50 mL) was heated at reflux for 18 h. The excess ammonia was removed under reduced pressure and the aqueous solution was extracted with ethyl acetate (25 mL×4). The combined organic layer was washed with brine solution (25 mL), dried over anhydrous Na$_2$SO$_4$ and evaporated under reduced pressure to give 8-(4-fluorophenyl)-7,8-dihydro-1H-pyrano[4,3-d]pyrimidine-2,4(3H,5H)-dione (0.4 g, 50%). The crude compound was taken to the next step without further purification. LC-MS (M+H)$^+$=263.4. $^1$H NMR (400 MHz, DMSO-d6): δ ppm 11.16 (1H, s), 10.79 (1H, s), 7.33-7.29 (2H, m), 7.19-7.15 (2H, m), 4.43 (1H, m), 4.25 (1H, m), 3.90 (1H, m), 3.75-3.68 (2H, m).

Preparation J 2,4-dichloro-8-(4-fluorophenyl)-7,8-dihydro-5H-pyrano[4,3-d]pyrimidine

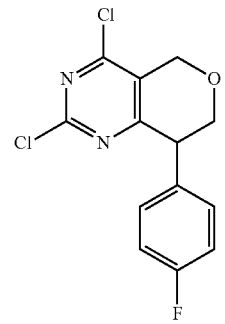 [SMILES: Fc1ccc(C2COCc3c(Cl)nc(Cl)nc32)cc1]

A solution of Intermediate J(4) (0.7 g, 2.6 mmol) and catalytic amount of DMF in POCl$_3$ (20 vol.) was heated at reflux for 18 h. The excess of POCl$_3$ was evaporated under reduced pressure. The residue was poured in to crushed ice and stirred for 15 min. The aqueous solution was extracted with ethyl acetate (20 mL×2). The combined organic layer was washed with aqueous saturated NaHCO₃ (50 mL×2), brine solution (25 mL), dried over Na₂SO₄ and evaporated under reduced pressure to give 2,4-dichloro-8-(4-fluorophenyl)-7,8-dihydro-5H-pyrano[4,3-d]pyrimidine (0.79 g) as crude compound. The crude compound was taken to the next step without further purification. LC-MS (M+H)⁺=299.0.

Preparation Ja 2-chloro-8-(4-fluorophenyl)-N-methyl-7,8-dihydro-5H-pyrano[4,3-d]pyrimidin-4-amine

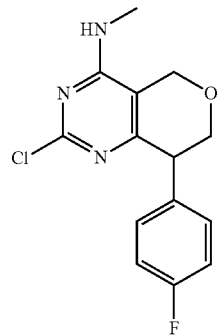 [SMILES: CNc1nc(Cl)nc2c1COCC2c1ccc(F)cc1]

To a solution of Preparation J (0.7 g, 2.3 mmol) in methanol was added Cs₂CO₃ (1.49 g, 4.6 mmol) followed by addition of methylamine hydrochloride (0.78 g, 11.7 mmol) at room temperature. The reaction mixture was stirred at room temperature for 18 h. The solvent was removed under reduced pressure and the residue diluted with ethyl acetate (25 mL), washed with water (25 mL), brine solution (25 mL), dried over anhydrous Na₂SO₄ and evaporated under reduced pressure to get crude compound. The crude compound was purified by column chromatography (60-120 mesh) using 50% ethyl acetate in pet-ether as mobile phase to give 2-chloro-8-(4-fluorophenyl)-N-methyl-7,8-dihydro-5H-pyrano[4,3-d]pyrimidin-4-amine (0.34 g, 49%) as off-white solid. LC-MS (M+H)⁺=294.2. ¹H NMR (400 MHz, DMSO-d6): δ ppm 7.22-7.19 (2H, m), 7.13-7.07 (2H, m), 4.91 (1H, m), 4.75 (1H, m), 4.12-4.08 (2H, m), 3.74 (1H, m), 3.05 (6H, s).

Preparation Jb 2-chloro-N-ethyl-8-(4-fluorophenyl)-7,8-dihydro-5H-pyrano[4,3-d]pyrimidin-4-amine

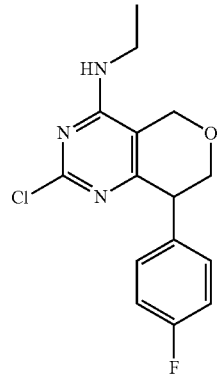 [SMILES: CCNc1nc(Cl)nc2c1COCC2c1ccc(F)cc1]

To a solution of Preparation J (0.350 g, 1.17 mmol) in methanol was added diisopropylethylamine (0.30 g, 2.2 mmol) followed by ethylamine hydrochloride (0.113 g, 1.17 mmol) at room temperature. The reaction mixture was stirred at room temperature for 18 h. The solvent was removed under reduced pressure and the residue diluted with ethyl acetate (25 mL), washed with water (25 mL), brine solution (25 mL), dried over anhydrous Na₂SO₄ and evaporated under reduced pressure to get crude compound. The crude compound was purified by column chromatography (60-120 mesh) using 50-55% ethyl acetate in pet-ether as mobile phase to give 2-chloro-N-ethyl-8-(4-fluorophenyl)-7,8-dihydro-5H-pyrano[4,3-d]pyrimidin-4-amine (0.16 g, 60%) as off-white solid. LC-MS (M+H)⁺=308.2.

Preparation Jc1 and Jc2

2-chloro-8-(4-fluorophenyl)-4-((S)-3-fluoropyrrolidin-1-yl)-7,8-dihydro-5H-pyrano[4,3-d]pyrimidine

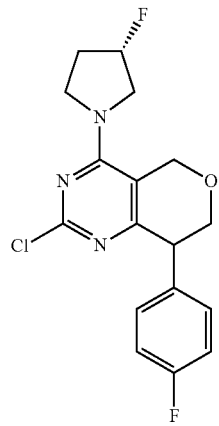

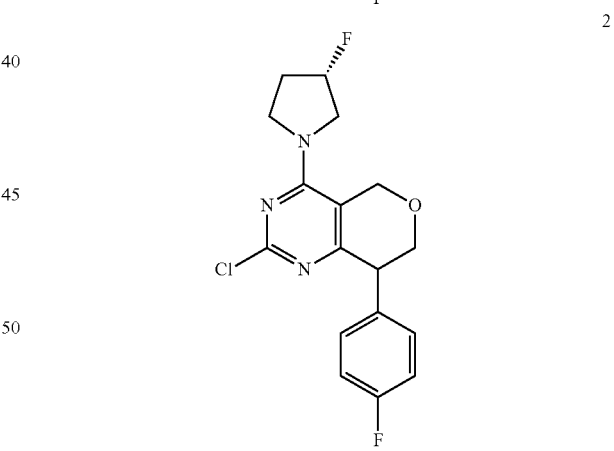

To a solution of Preparation J (0.70 g, 2.34 mmol) in methanol was added diisopropylethylamine (0.60 g, 4.6 mmol) followed by (R)-3-fluoropyrrolidine (0.58 g, 4.6 mmol) at room temperature. The reaction mixture was stirred at room temperature for 18 h. The solvent was removed under reduced pressure and the residue was purified by prep-HPLC (40% ethanol in hexane) to give 2-chloro-8-(4-fluorophenyl)-4-((S)-3-fluoropyrrolidin-1-yl)-7,8-dihydro-5H-pyrano[4,3-d]pyrimidine (0.90 g, 11% Isomer 1, 0.110 g, 13% Isomer 2) as off-white solid. LC-MS (M+H)⁺=352.2. ¹H NMR (400 MHz, DMSO-d6): δ ppm 7.24 (2H, m), 7.13 (2H, m), 5.40

(1H, m), 4.12 (1H, d, J=14.8 Hz), 4.88 (1H, d, J=14.8 Hz), 4.14-4.09 (2H, m), 3.91-3.81 (3H, m), 3.75-3.66 (2H, m), 2.51-2.18 (2H, m).

Preparation Jd1 and Jd2

2-chloro-8-(4-fluorophenyl)-4-((R)-3-fluoropyrrolidin-1-yl)-7,8-dihydro-5H-pyrano[4,3-d]pyrimidine

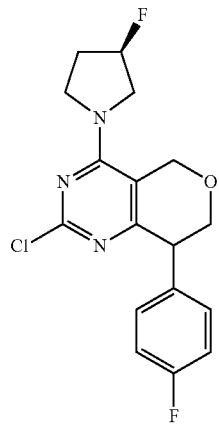

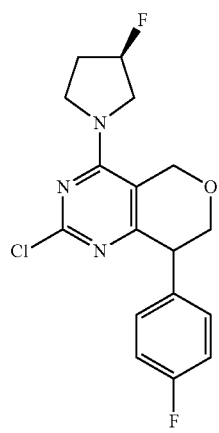

To a solution of Preparation J (0.70 g, 2.34 mmol) in methanol was added diisopropylethylamine (0.60 g, 4.6 mmol) followed by (S)-3-fluoropyrrolidine (0.58 g, 4.6 mmol) at room temperature. The reaction mixture was stirred at room temperature for 18 h. The solvent was removed under reduced pressure and the residue was purified by prep-HPLC (40% ethanol in hexane) to give 2-chloro-8-(4-fluorophenyl)-4-((R)-3-fluoropyrrolidin-1-yl)-7,8-dihydro-5H-pyrano[4,3-d]pyrimidine (0.100 g, 12% Isomer 1, 0.110 g, 13% Isomer 2) as off-white solid. LC-MS (M+H)$^+$=352.2.

Jd1: $^1$H NMR (400 MHz, DMSO-d6): δ ppm 7.24 (2H, m), 7.13 (2H, m), 5.40 (1H, m), 4.12 (1H, d, J=14.4 Hz), 4.88 (1H, d, J=14.4 Hz), 4.11 (2H, m), 3.94-3.89 (3H, m), 3.72-3.58 (2H, m), 2.20-2.01 (2H, m).

Jd2: $^1$H NMR (400 MHz, DMSO-d6): δ ppm 7.21 (2H, m), 7.13 (2H, m), 5.39 (1H, m), 5.02 (2H, m), 4.02-3.97 (2H, m), 3.91-3.84 (4H, m), 3.73 (1H, m), 2.23-2.01 (2H, m).

Preparation Je 2-chloro-8-(4-fluorophenyl)-N,N-dimethyl-7,8-dihydro-5H-pyrano[4,3-d]pyrimidin-4-amine

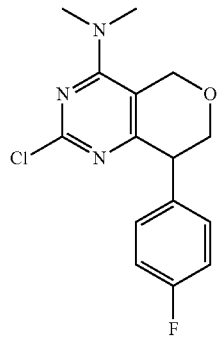 [SMILES: CN(C)c1nc(Cl)nc2c1COCC2c1ccc(F)cc1]

To a solution of Preparation J (0.7 g, 2.3 mmol) in methanol was added Cs$_2$CO$_3$ (1.49 g, 4.6 mmol) followed by addition of dimethylamine hydrochloride (0.95 g, 11.7 mmol) at room temperature. The reaction mixture was stirred at room temperature for 18 h. The solvent was removed under reduced pressure and the residue diluted with ethyl acetate (50 mL), washed with water (25 mL), brine solution (25 mL), dried over anhydrous Na$_2$SO$_4$ and evaporated under reduced pressure to get crude compound. The crude compound was purified by column chromatography (60-120 mesh) using 40% ethyl acetate in pet-ether as mobile phase to give 2-chloro-8-(4-fluorophenyl)-N,N-dimethyl-7,8-dihydro-5H-pyrano[4,3-d]pyrimidin-4-amine (0.35 g, 49%) as off-white solid. LC-MS (M+H)$^+$=308.2. This compound was taken to the next step without further purification.

Preparation Jf 2-chloro-N-ethyl-8-(4-fluorophenyl)-N-methyl-7,8-dihydro-5H-pyrano[4,3-d]pyrimidin-4-amine

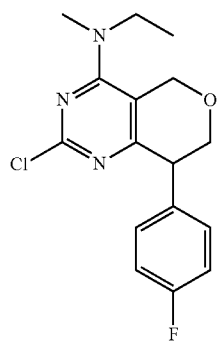 [SMILES: CCN(C)c1nc(Cl)nc2c1COCC2c1ccc(F)cc1]

To a solution of Preparation J (0.7 g, 2.3 mmol) in methanol was added Cs$_2$CO$_3$ (1.49 g, 4.6 mmol) followed by addition of ethylmethylamine hydrochloride (1.1 g, 11.7 mmol) at room temperature. The reaction mixture was stirred at room temperature for 18 h. The solvent was removed under reduced pressure and the residue diluted with ethyl acetate (25 mL), washed with water (25 mL), brine solution (25 mL), dried over anhydrous Na$_2$SO$_4$ and evaporated under reduced pressure to get crude compound. The crude compound was purified by column chromatography (60-120 mesh) using 50% ethyl acetate in pet-ether as mobile phase to give 2-chloro-N-ethyl-8-(4-fluorophenyl)-N-methyl-7,8-dihydro-5H-pyrano[4,3-d]pyrimidin-4-amine (0.39 g, 52%) as off-white solid.

Preparation Jg 2-chloro-4-(3,3-difluoroazetidin-1-yl)-8-(4-fluorophenyl)-7,8-dihydro-5H-pyrano[4,3-d]pyrimidine

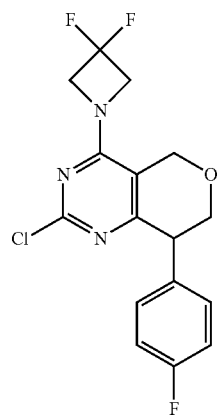 [SMILES: Fc1ccc(C2COCc3c2nc(Cl)nc3N2CC(F)(F)C2)cc1]

To a solution of Preparation J (0.7 g, 2.3 mmol) in methanol was added Cs$_2$CO$_3$ (1.49 g, 4.6 mmol) followed by addition of 3,3-difluoroazetidine hydrochloride (0.60 g, 4.6 mmol) at room temperature. The reaction mixture was stirred at room temperature for 18 h. The solvent was removed under reduced pressure and the residue diluted with ethyl acetate (25 mL), washed with water (25 mL), brine solution (25 mL), dried over anhydrous Na$_2$SO$_4$ and evaporated under reduced pressure to get crude compound. The crude compound was purified by column chromatography (60-120 mesh) using 50% ethyl acetate in pet-ether as mobile phase to give 2-chloro-4-(3,3-difluoroazetidin-1-yl)-8-(4-fluorophenyl)-7,8-dihydro-5H-pyrano[4,3-d]pyrimidine (0.42 g, 50%) as off-white solid. LC-MS (M+H)$^+$=355.2. This compound was taken to the next step without further purification.

Preparation K 2,4-dichloro-8-(4-chlorophenyl)-7,8-dihydro-5H-pyrano[4,3-d]pyrimidine

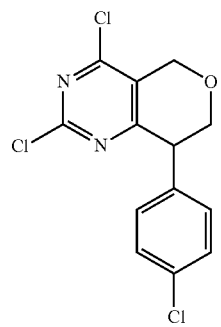 [SMILES: Clc1ccc(C2COCc3c(Cl)nc(Cl)nc32)cc1]

The title compound was prepared in the analogous fashion to Preparation J, as a pale yellow solid. LC-MS (M+H)$^+$= 315.0. $^1$H NMR (400 MHz, CDCl$_3$) δ ppm 7.30 (2H, dd, J=2.0, 6.4 Hz), 7.17 (2H, dd, J=2.0, 6.4 Hz), 4.91 (1H, d, J=16.4 Hz), 4.76 (1H, d, J=16.0 Hz), 4.18-4.09 (3H, m).

Preparation Ka 2-chloro-8-(4-chlorophenyl)-4-(3,3-difluoroazetidin-1-yl)-7,8-dihydro-5H-pyrano[4,3-d]pyrimidine

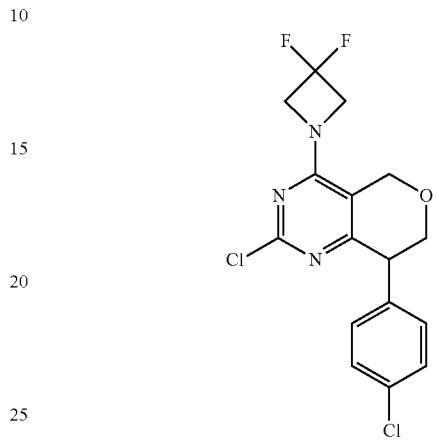

2,4-dichloro-8-(4-chlorophenyl)-7,8-dihydro-5H-pyrano[4,3-d]pyrimidine (Preparation K) (500 mg, 1.584 mmol) and 3,3-Difluoroazetidine hydrochloride (308 mg, 2.377 mmol) were combined and purified as per Preparation Ha to give 2-chloro-8-(4-chlorophenyl)-4-(3,3-difluoroazetidin-1-yl)-7,8-dihydro-5H-pyrano[4,3-d]pyrimidine (400 mg, 1.075 mmol, 67.8% yield) as a white solid. LC-MS (M+H)$^+$=372.0. $^1$H NMR (500 MHz, CDCl$_3$) δ ppm 7.22-7.34 (2 H, m), 7.12 (2 H, d, J=8.24 Hz), 4.63-4.85 (2 H, m), 4.46-4.64 (3 H, m), 4.04-4.17 (1 H, m), 3.91-4.04 (2 H, m).

Preparation Kb 2-chloro-8-(4-chlorophenyl)-N-methyl-7,8-dihydro-5H-pyrano[4,3-d]pyrimidin-4-amine

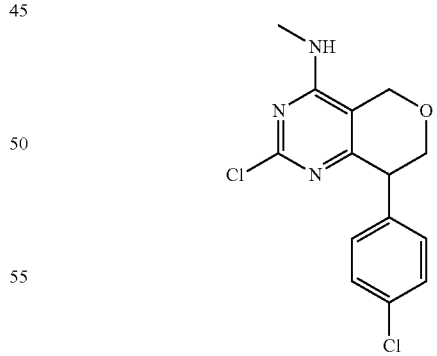

2,4-dichloro-8-(4-chlorophenyl)-7,8-dihydro-5H-pyrano[4,3-d]pyrimidine (Preparation K) (500 mg, 1.584 mmol) and methanamine hydrochloride (160 mg, 2.377 mmol) were combined and purified as per Preparation Ha to give 2-chloro-8-(4-chlorophenyl)-N-methyl-7,8-dihydro-5H-pyrano[4,3-d]pyrimidin-4-amine (150 mg, 0.484 mmol, 30.5% yield). LC-MS (M+H)$^+$=310.0. $^1$H NMR (500 MHz, CDCl$_3$) δ ppm 7.22-7.31 (2 H, m), 7.13 (2 H, d, J=8.55 Hz), 4.46-4.64 (1 H, m), 4.43 (1 H, br. s.), 3.97-4.14 (1 H, m), 3.91 (1 H, d, J=3.36 Hz), 3.09 (3 H, d, J=4.88 Hz).

Preparation Kc 2-chloro-8-(4-chlorophenyl)-N,N-dimethyl-7,8-dihydro-5H-pyrano[4,3-d]pyrimidin-4-amine

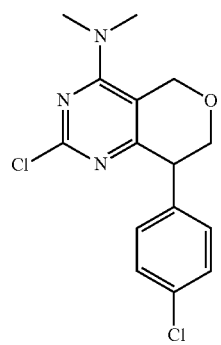 [SMILES: CN(C)c1nc(Cl)nc2c1COCC2c1ccc(Cl)cc1]

2,4-dichloro-8-(4-chlorophenyl)-7,8-dihydro-5H-pyrano[4,3-d]pyrimidine (Preparation K) (500 mg, 1.584 mmol) and Dimethylamine (2.0 M in THF) (1.188 mL, 2.377 mmol) were combined an purified as per Preparation Ha to give 2-chloro-8-(4-chlorophenyl)-N,N-dimethyl-7,8-dihydro-5H-pyrano[4,3-d]pyrimidin-4-amine (400 mg, 1.234 mmol, 78% yield) as a white solid. LC-MS (M+H)+=324.0. $^1$H NMR (500 MHz, CDCl$_3$) δ ppm 7.20-7.31 (2 H, m), 7.04-7.15 (2 H, m), 4.70-4.89 (2 H, m), 4.17 (1 H, dd, J=11.60, 5.49 Hz), 4.05 (1 H, t, J=5.49 Hz), 3.87 (1 H, dd, J=11.60, 5.49 Hz), 3.05-3.19 (6 H, m).

Preparation L 2,4-dichloro-8-(4-bromophenyl)-7,8-dihydro-5H-pyrano[4,3-d]pyrimidine

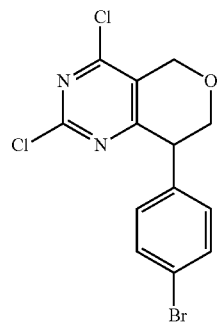 [SMILES: Clc1nc(Cl)c2c(n1)C(c1ccc(Br)cc1)COC2]

The title compound was prepared in the analogous fashion to Preparation J, as a pale yellow solid. LC-MS (M+H)+=359.0. $^1$H NMR (400 MHz, CD$_3$OD) δ ppm 7.52 (2H, d, J=8.4 Hz), 7.22 (2H, d, J=8.4 Hz), 4.87 (1H, d, J=16.0 Hz), 4.30 (1H, t, J=4.6 Hz), 4.14 (1H, dd, J=4.6, 11.4 Hz), 3.95 (1H, dd, J=4.8, 11.6 Hz).

Preparation La 8-(4-bromophenyl)-2-chloro-N-methyl-7,8-dihydro-5H-pyrano[4,3-d]pyrimidin-4-amine

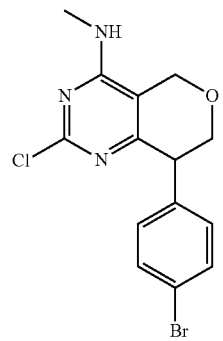 [SMILES: CNc1nc(Cl)nc2c1COCC2c1ccc(Br)cc1]

8-(4-bromophenyl)-2,4-dichloro-7,8-dihydro-5H-pyrano[4,3-d]pyrimidine (Preparation L) (500 mg, 1.389 mmol) and methanamine hydrochloride (141 mg, 2.083 mmol) were combined and purified as per Preparation Ha to give 8-(4-bromophenyl)-2-chloro-N-methyl-7,8-dihydro-5H-pyrano[4,3-d]pyrimidin-4-amine (210 mg, 0.592 mmol, 42.6% yield). LC-MS (M+H)+=356.0. $^1$H NMR (500 MHz, MeOD) δ ppm 7.46 (2 H, d, J=8.24 Hz), 7.13 (2 H, d, J=8.55 Hz), 4.43-4.71 (2 H, m), 4.09 (1 H, dd, J=11.44, 4.12 Hz), 3.92-4.03 (1 H, m), 3.86 (1 H, d, J=3.05 Hz), 3.00 (3 H, s).

Preparation M 2,4-dichloro-7-(4-fluorophenyl)-5,7-dihydrofuro[3,4-d]pyrimidine

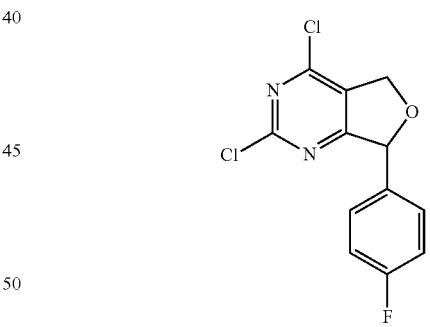

Intermediate M(1)

ethyl 2-hydroxy-2-phenylacetate

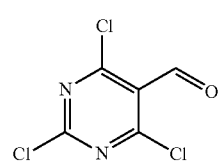 [SMILES: O=Cc1c(Cl)nc(Cl)nc1Cl]

A solution of pyrimidine-2,4,6-triol (10.0 g, 78.2 mmol), DMF (12 mL) in POCl₃ (10 vol.) was heated at reflux for 15 h. The excess of POCl₃ was evaporated under reduced pressure. The residue was poured in to crushed ice. The precipitated solid was filtered and washed with water to give 2,4,6-trichloropyrimidine-5-carbaldehyde (8.0 g, 47%) as yellow solid. This compound was taken to the next step without further purification.

Intermediate M(2)

2,4,6-trichloro-5-(1,3-dioxolan-2-yl)pyrimidine

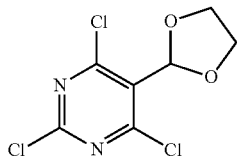 [SMILES: Clc1nc(Cl)c(C2OCCO2)c(Cl)n1]

To a solution of Intermediate M(1) (5.0 g, 23.6 mmol) in dry benzene was added ethylene glycol (4.0 mL, 64.5 mmol) followed by p-toluenesulfonic acid (0.15 g, 0.87 mmol) at room temperature. The reaction mixture was heated at reflux for 20 h. The reaction mixture was filtered and washed with warm benzene. The filtrate was evaporated under reduced pressure and the residue was purified by column chromatography (Silica gel, 60-120 mesh) using 10% ethyl acetate in pet-ether as mobile phase to give (4.5 g, 75%) as off-white solid. LC-MS (M+H)⁺=256.0. ¹H NMR (400 MHz, DMSO-d6): δ ppm 9.6 (1H, s), 7.99 (1H, s), 7.98 (1H, s), 7.76-7.41 (3H, m), 7.23-7.13 (4H, m), 5.87 (1H, s), 5.33 (1H, dd, J=27, 8 Hz), 5.17 (1H, dd, J=27, 8), 4.67 (4H, m), 3.72 (3H, s).

Intermediate M(3)

2,4-dichloro-5-(1,3-dioxolan-2-yl)-6-(4-fluorobenzyl)pyrimidine

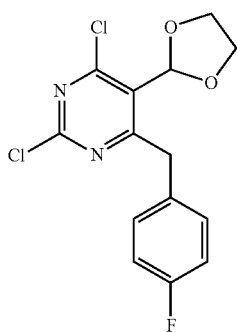 [SMILES: Fc1ccc(Cc2nc(Cl)nc(Cl)c2C2OCCO2)cc1]

To a solution of Intermediate M(2) (4.0 g, 15.6 mmol) in dry diethyl ether was added 4-fluorobenzyl magnesium bromide (75.2 mL, 18.8 mmol, 0.25 M solution in THF) at 0° C. The reaction mixture was allowed to come to room temperature and stirred for 4 h. The reaction mixture was quenched with aqueous saturated ammonium chloride. The organic layer was separated and the aqueous layer was extracted with diethyl ether (50 mL×2). The combined organic layer was washed with water, dried over anhydrous Na₂SO₄ and evaporated to get crude compound. The crude compound was purified by combiflash using 1.4% ethyl acetate in pet ether as mobile phase to give 2,4-dichloro-5-(1,3-dioxolan-2-yl)-6-(4-fluorobenzyl)pyrimidine (2.2 g, 43.1%) as off-white solid. LC-MS (M−H)⁺=327.0. ¹H NMR (400 MHz, DMSO-d6): δ ppm 7.26 (2H, m), 7.10 (2H, m), 6.19 (1H, s), 4.25 (2H, s), 4.19 (2H, m), 4.02 (2H, m).

Intermediate M(4)

(2,4-dichloro-6-(4-fluorobenzyl)pyrimidin-5-yl)methanol

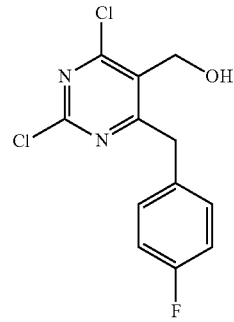 [SMILES: OCc1c(Cl)nc(Cl)nc1Cc1ccc(F)cc1]

To a solution of Intermediate M(3) (2.0 g, 6.07 mmol) in THF was added aqueous 6 N HCl over a period of 5 min. at room temperature. The reaction mixture was heated at reflux for 1 h. The reaction volume was reduced to half and the solution was extracted with diethyl ether (50 mL×2). The combined organic layer was washed with water (50 mL), brine solution (50 mL), dried over anhydrous Na₂SO₄ and evaporated under reduced pressure to get crude compound (1.2 g). The crude compound was dissolved in methanol and cooled to 0° C. Sodium borohydride (0.234 g) was added to the reaction mixture. The resulting solution was allowed to come to room temperature and stirred for 1 h. The reaction mixture was quenched with aqueous saturated ammonium chloride, and then solvent was evaporated under reduced pressure. The residue was diluted with ethyl acetate (50 mL). The organic solution was washed with water (25 mL), brine solution (25 mL), dried over anhydrous Na₂SO₄ and evaporated under reduced pressure to get crude compound. The crude compound was purified by column chromatography (Silica gel, 60-120 mesh) using 20% ethyl acetate in pet ether as mobile phase to give (2,4-dichloro-6-(4-fluorobenzyl)pyrimidin-5-yl)methanol (1.0 g, 58%) as oily liquid. LC-MS (M+H)⁺=488.1. ¹H NMR (300 MHz, CDCl₃): δ ppm 7.25 (2H, m), 7.01 (2H, m), 4.82 (2H, m), 4.27 (2H, s).

Preparation M 2,4-dichloro-7-(4-fluorophenyl)-5,7-dihydrofuro[3,4-d]pyrimidine

To a solution of Intermediate M(4) (1.0 g, 3.48 mmol) in dry benzene (100 mL) was added Cs$_2$CO$_3$ (0.4 g, 3.48 mmol) followed by lead tetra acetate (0.3 g, 3.48 mmol) at room temperature (the color of the reaction mixture was changed from colorless to brown). The reaction mass was heated at reflux for 18 h using Dean Stark apparatus. The reaction mixture was filtered through celite bed and washed with diethyl ether. The filtrate was evaporated under reduced pressure and the residue was diluted with diethyl ether. The organic solution was washed with water (25 mL×2), aqueous saturated NaHCO$_3$, brine solution (10 mL), dried over anhydrous Na$_2$SO$_4$ and evaporated under reduced pressure to get crude compound. The crude compound was purified by Combiflash using 0.9% ethyl acetate in pet-ether as mobile phase to give 2,4-dichloro-7-(4-fluorophenyl)-5,7-dihydrofuro[3,4-d]pyrimidine (0.250 mg, 30%) as oily liquid. LC-MS (M+H)$^+$=485.0. $^1$H NMR (400 MHz, methanol-d4): δ ppm 7.48-7.44 (2H, m), 7.16-7.12 (2H, m), 6.15 (1H, s), 5.40 (1H, dd, J=13.6 Hz), 5.27 (1H, dd, J=13.6).

Preparation Ma 2-chloro-7-(4-fluorophenyl)-N-methyl-5,7-dihydrofuro[3,4-d]pyrimidin-4-amine

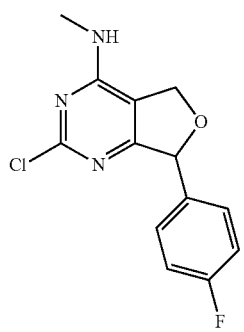 [SMILES: CNc1nc(Cl)nc2c1COC2c1ccc(F)cc1]

2,4-dichloro-7-(4-fluorophenyl)-5,7-dihydrofuro[3,4-d]pyrimidine (Preparation M) (250 mg, 0.877 mmol) and methanamine hydrochloride (89 mg, 1.315 mmol) were combined and purified as per Preparation Ia to give 2-chloro-7-(4-fluorophenyl)-N-methyl-5,7-dihydrofuro[3,4-d]pyrimidin-4-amine (149 mg, 0.533 mmol, 60.8% yield). LC-MS (M+H)$^+$=280.0. $^1$H NMR (500 MHz, MeOD) δ ppm 7.31-7.44 (2 H, m), 7.05-7.17 (2 H, m), 5.80-5.95 (1 H, m), 4.94-5.21 (2 H, m), 2.93-3.07 (3 H, m).

Preparation Mb 2-chloro-N-ethyl-7-(4-fluorophenyl)-5,7-dihydrofuro[3,4-d]pyrimidin-4-amine

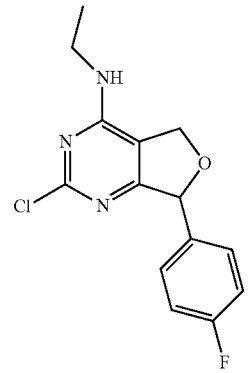 [SMILES: CCNc1nc(Cl)nc2c1COC2c1ccc(F)cc1]

2,4-dichloro-7-(4-fluorophenyl)-5,7-dihydrofuro[3,4-d]pyrimidine (Preparation M) (125 mg, 0.438 mmol) and ethylamine hydrochloride (53.6 mg, 0.658 mmol) were combined and purified as per Preparation Ha to give 2-chloro-N-ethyl-7-(4-fluorophenyl)-5,7-dihydrofuro[3,4-d]pyrimidin-4-amine (38.17 mg, 0.130 mmol, 29.6% yield). LC-MS (M+H)$^+$=294.0. $^1$H NMR (500 MHz, CDCl$_3$) δ ppm 7.24-7.38 (2 H, m), 6.92-7.08 (2 H, m), 5.73-5.98 (1 H, m), 4.83-5.21 (2 H, m), 3.36-3.63 (2 H, m), 1.13-1.28 (3 H, m).

Preparations Mc1 and Mc2

2-chloro-7-(4-fluorophenyl)-4-((S)-3-fluoropyrrolidin-1-yl)-5,7-dihydrofuro[3,4-d]pyrimidine

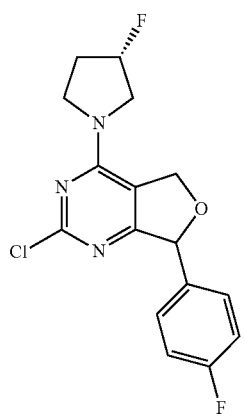

Diastereomer 1 Racemic

91

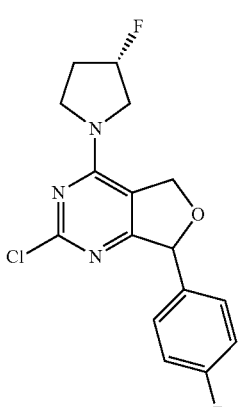

Diastereomer 2 Racemic 2,4-dichloro-7-(4-fluorophenyl)-5,7-dihydrofuro[3,4-d]pyrimidine (Preparation M) (125 mg, 0.438 mmol) and (S)-3-fluoropyrrolidine, HCl (83 mg, 0.658 mmol) were combined and purified as per Preparation Ha to give 2-chloro-7-(4-fluorophenyl)-4-((S)-3-fluoropyrrolidin-1-yl)-5,7-dihydrofuro[3,4-d]pyrimidine (Mc1, Diastereomer 1, first to elute) (49 mg, 0.145 mmol, 33.1% yield). LC-MS (M+H)$^+$=338.0.

(Mc2, Diastereomer 2, second to elute) (40 mg, 0.118 mmol, 27.0% yield). LC-MS (M+H)$^+$=338.0. The relative stereochemistry of Mc1 and Mc2 was not determined

Preparation Md 2-chloro-4-(3,3-difluoroazetidin-1-yl)-7-(4-fluorophenyl)-5,7-dihydrofuro[3,4-d]pyrimidine

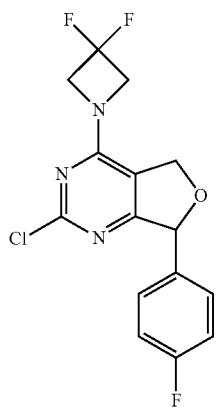 [SMILES: Fc1ccc(C2OCc3c2nc(Cl)nc3N2CC(F)(F)C2)cc1]

To a solution of Preparation M (0.05 g, 0.176 mmol) in methanol was added diisopropylethylamine (0.045 g, 0.30 mmol) followed by addition of 3,3-difluoroazitidine hydrochloride (0.03 g, 0.193 mmol) at room temperature. The reaction mixture was stirred at room temperature for 18 h. The solvent was removed under reduced pressure and the residue was purified by column chromatography (60-120 mesh) using 6% ethyl acetate in pet-ether as mobile phase to give 2-chloro-4-(3,3-difluoroazetidin-1-yl)-7-(4-fluorophenyl)-5,7-dihydrofuro[3,4-d]pyrimidine (0.035 g, 46%) as white solid. LC-MS (M+H)$^+$=342.2.

92

Preparation Me 2-chloro-7-(4-fluorophenyl)-4-((S)-2-methylpyrrolidin-1-yl)-5,7-dihydrofuro[3,4-d]pyrimidine

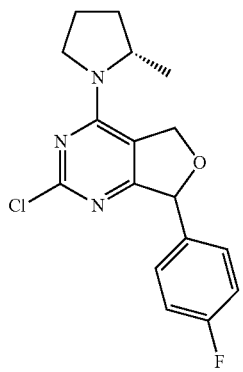 [SMILES: C[C@H]1CCCN1c1nc(Cl)nc2c1COC2c1ccc(F)cc1]

2,4-dichloro-7-(4-fluorophenyl)-5,7-dihydrofuro[3,4-d]pyrimidine (Preparation M) was reacted as described in Preparation Hp1 and Hp2 with (S)-2-methylpyrrolidine p-toluenesulfonate salt to afford 2-chloro-7-(4-fluorophenyl)-4-((S)-2-methylpyrrolidin-1-yl)-5,7-dihydrofuro[3,4-d]pyrimidine (Preparation Me) as a mixture of 2 diasteriomers. LC-MS (M+H)$^+$=334.1.

Preparation Mf 2-chloro-N-((R)-1-cyclopropylethyl)-7-(4-fluorophenyl)-5,7-dihydrofuro[3,4-d]pyrimidin-4-amine

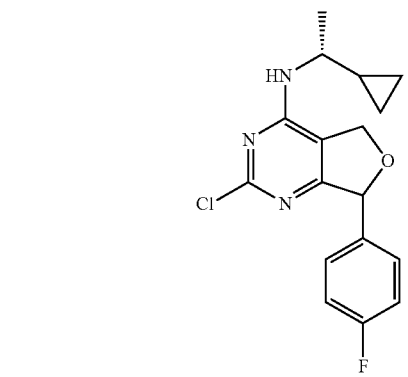 [SMILES: C[C@@H](Nc1nc(Cl)nc2c1COC2c1ccc(F)cc1)C1CC1]

To a solution of 2,4-dichloro-7-(4-fluorophenyl)-5,7-dihydrofuro[3,4-d]pyrimidine (Preparation M) (150 mg, 0.526 mmol) in THF (2631 μL) was added (R)-1-cyclopropylethanamine, HCl (128 mg, 1.052 mmol) and DIEA (368 μL, 2.105 mmol). The mixture was heated at 40° C. for 2 h and stirred at RT overnight. The mixture was concentrated and purified by column chromatography on silica gel to give 2-chloro-N-((R)-1-cyclopropylethyl)-7-(4-fluorophenyl)-5,7-dihydrofuro[3,4-d]pyrimidin-4-amine (Preparation Mf) (25 mg, 0.075 mmol, 14.24% yield) as a mixture of 2 diasteriomers. LC-MS (M+H)$^+$=334.1.

Preparation Mg 2-chloro-7-(4-fluorophenyl)-4-((R)-3-fluoropyrrolidin-1-yl)-5,7-dihydrofuro[3,4-d]pyrimidine

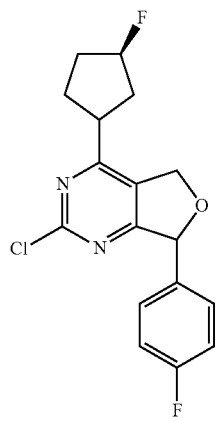 [SMILES: Fc1ccc(C2OCc3c(C4CC[C@@H](F)C4)nc(Cl)nc32)cc1]

2,4-dichloro-7-(4-fluorophenyl)-5,7-dihydrofuro[3,4-d]pyrimidine (Preparation M) was reacted as described in Preparation Xa with (R)-3-fluoropyrrolidine, HCl to give 2-chloro-7-(4-fluorophenyl)-4-((R)-3-fluoropyrrolidin-1-yl)-5,7-dihydrofuro[3,4-d]pyrimidine (Preparation Mg). LC-MS $(M+H)^+=338.1$. $^1$H NMR (400 MHz, CDCl$_3$) δ ppm 7.33-7.47 (m, 2 H) 7.00-7.14 (m, 2 H) 5.83-5.97 (m, 1 H) 5.54 (dd, J=11.33, 3.53 Hz, 1 H) 5.36-5.49 (m, 2 H) 3.88-4.00 (m, 1 H) 3.65-3.88 (m, 3 H) 2.30-2.52 (m, 1 H) 2.02-2.20 (m, 1 H).

Preparation Mh 2-chloro-4-((2S,6R)-2,6-dimethylmorpholino)-7-(4-fluorophenyl)-5,7-dihydrofuro[3,4-d]pyrimidine

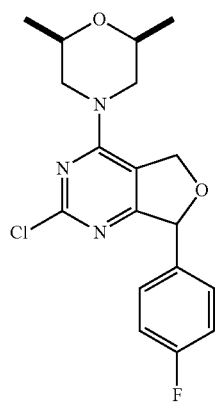 [SMILES: C[C@@H]1CN(c2nc(Cl)nc3c2COC3c2ccc(F)cc2)C[C@H](C)O1]

2,4-dichloro-7-(4-fluorophenyl)-5,7-dihydrofuro[3,4-d]pyrimidine (Preparation M) was reacted as described in Preparation Xa with (2R,6S)-2,6-dimethylmorpholine to give 2-chloro-4-((2S,6R)-2,6-dimethylmorpholino)-7-(4-fluorophenyl)-5,7-dihydrofuro[3,4-d]pyrimidine (Preparation Mh). LC-MS $(M+H)^+=364.2$. $^1$H NMR (500 MHz, CDCl$_3$) δ ppm 7.39 (dd, J=8.70, 5.34 Hz, 2 H) 7.07 (t, J=8.70 Hz, 2 H) 5.90 (br. s., 1 H) 5.34-5.42 (m, 1 H) 5.24-5.34 (m, 1 H) 4.14 (q, J=7.02 Hz, 2 H) 3.67 (ddd, J=10.38, 6.41, 2.44 Hz, 4 H), 1.20 (m, 6 H).

Preparation N 2,4-dichloro-8-phenyl-6,8-dihydro-5H-pyrano[3,4-d]pyrimidine

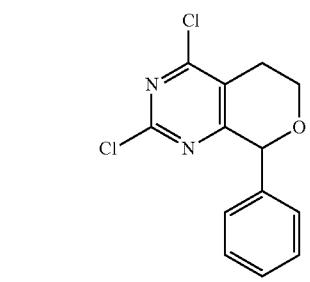 [SMILES: Clc1nc(Cl)c2c(n1)C(c1ccccc1)OCC2]

Intermediate N(1)

ethyl 2-hydroxy-2-phenylacetate

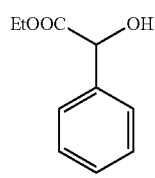

To a cooled solution of ethyl 2-hydroxy-2-phenylacetate (25.0 g, 164.3 mmol) in ethanol was added con. H$_2$SO$_4$ (15 mL) over a period of 10 min. The reaction mixture was heated at reflux for 5 h. The solvent was evaporated under reduced pressure and the residue was diluted with ethyl acetate (250 mL). The organic solution was washed with aqueous saturated NaHCO$_3$ (200 mL×2), water (100 mL×2), brine solution (100 mL), dried over anhydrous Na$_2$SO$_4$ and evaporated under reduced pressure to give ethyl 2-hydroxy-2-phenylacetate (24.5 g, 83%) as crude compound (oily liquid). The crude compound was taken to the next step without further purification. LC-MS $(M+H_2O)^+=198.2$. $^1$H NMR (400 MHz, DMSO-d6): δ ppm 7.41-7.28 (5H, m), 6.04 (1H, d, J=4.0 Hz), 5.11 (1H, d, J=4.0 Hz), 4.13 (2H, m), 1.13 (3H, t, J=7.2 Hz).

Intermediate N(2)

ethyl 4-(2-ethoxy-2-oxo-1-phenylethoxy)but-2-enoate

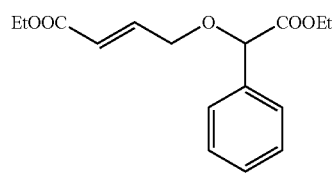 [SMILES: CCOC(=O)/C=C/COC(C(=O)OCC)c1ccccc1]

To a solution of Intermediate N(1) (20.0 g, 110.9 mmol) in hexane was added silver oxide (66.75 g, 288.5 mmol) followed by magnesium sulphate (2.66 g, 220 mmol) at room temperature. The reaction mixture was heated at reflux for 1 h. The reaction mixture was cooled to 0° C. and was added silver oxide (71.8 g, 310.9 mmol) followed by ethyl-4-bromochrotonate (32.0 g, 166 mmol). The resulting solution was stirred at room temperature for 3 days. The reaction mass was filtered through a bed of diatomaceous earth (Celite®) and washed with ethyl acetate. The filtrate was evaporated under reduced pressure to give ethyl 4-(2-ethoxy-2-oxo-1-phenylethoxy)but-2-enoate (20.0 g, 62.5%) as oily liquid. LC-MS (M+H$_2$O)$^+$=310.2. $^1$H NMR (400 MHz, DMSO-d6): δ ppm 7.42-7.35 (5H, m), 6.90 (1H, m), 6.05 (1H, m), 5.09 (1H, s), 4.26 (2H, m), 4.16 (4H, m), 1.21 (3H, t, J=7.2 Hz), 1.13 (3H, t, J=7.2 Hz).

Intermediate N(3)

ethyl 4-(2-ethoxy-2-oxo-1-phenylethoxy)butanoate

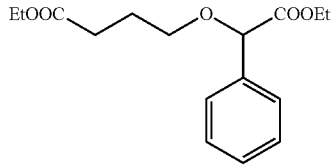 [SMILES: CCOC(=O)CCCOC(C(=O)OCC)c1ccccc1]

To a solution of Intermediate N(2) (20.0 g, 68.41 mmol) in ethanol was added palladium on carbon (10%, w/w) at room temperature. The reaction mixture was hydrogenated under balloon pressure of hydrogen for 30 h. The reaction mass was filtered through a bed of diatomaceous earth (Celite®) and washed with ethanol. The solvent was removed under reduced pressure and the residue was purified by column chromatography (Silica gel, 60-120 mesh) using 5% ethyl acetate in petroleum-ether as mobile phase to give ethyl 4-(2-ethoxy-2-oxo-1-phenylethoxy)butanoate (12.0 g, 59.5%) as oily liquid. LC-MS (M+H)$^+$=295.2. $^1$H NMR (400 MHz, DMSO-d6): δ ppm 7.41-7.27 (5H, m), 4.96 (1H, s), 4.07 (4H, m), 3.62 (1H, m), 3.49 (1H, m), 2.36 (2H, m), 1.79 (2H, m), 1.15 (6H, m).

Intermediate N(4)

ethyl 3-oxo-2-phenyltetrahydro-2H-pyran-4-carboxylate

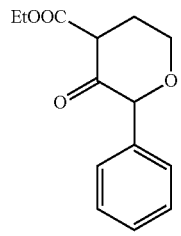

To a cooled solution of Intermediate N(3) (12.0 g, 40.76 mmol) in THF was added t-BuOK (9.13 g, 81.3 mmol) at 0° C. The reaction mixture was allowed to come to room temperature and stirred for 1 h. The reaction mixture was quenched with water and evaporated the solvent under reduced pressure. The residue was diluted with ethyl acetate (200 mL). The organic layer was washed with water (100 mL×2), brine solution (100 mL), dried over anhydrous Na$_2$SO$_4$ and evaporated under reduced pressure to get crude compound. The crude compound was purified by column chromatography (Silica gel, 60-120 mesh) using 50% ethyl acetate in pet-ether as mobile phase to give ethyl 3-oxo-2-phenyltetrahydro-2H-pyran-4-carboxylate (6.0 g, 59.4%) as oily liquid. LC-MS (M+H)$^+$=249.2. $^1$H NMR (400 MHz, DMSO-d6): δ ppm 11.81 (1H, s), 7.36 (5H, m), 5.20 (1H, s), 4.23 (2H, q, J=7.2.0 Hz), 3.71 (1H, m), 3.67 (1H, m), 2.36 (1H, m), 2.32 (1H, m), 1.29 (3H, t, J=7.2 Hz).

Intermediate N(5)

8-phenyl-5,6-dihydro-1H-pyrano[3,4-d]pyrimidine-2,4(3H,8H)-dione

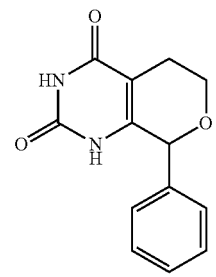 [SMILES: O=c1[nH]c2c(c(=O)[nH]1)CCOC2c1ccccc1]

To a solution of Intermediate N(4) (6.0 g, 24.16 mmol) in ethanol was added t-BuOK (6.76 g, 60.41 mmol) followed by urea (3.62 g, 60.41 mmol) at room temperature. The reaction mass was heated at reflux for 18 h. The reaction mixture was quenched with water and evaporated the solvent under reduced pressure. The residue was diluted with ethyl acetate (100 mL). The organic layer was washed with water (100 mL×2), brine solution (100 mL), dried over anhydrous Na$_2$SO$_4$ and evaporated under reduced pressure to get crude compound. The crude compound was purified by column chromatography (Silica gel, 60-120 mesh) using ethyl acetate as mobile phase to give 8-phenyl-5,6-dihydro-1H-pyrano[3,4-d]pyrimidine-2,4(3H,8H)-dione (3.0 g, 50.8%) as pale yellow solid. LC-MS (M–H)$^+$=243.2. $^1$H NMR (400 MHz, DMSO-d6): δ ppm 11.10 (1H, s), 10.57 (1H, s), 7.42-7.39 (3H, m), 7.32 (2H, m), 5.32 (1H, s), 3.71-3.56 (2H, m), 2.38-2.27 (2H, m).

Preparation N 2,4-dichloro-8-phenyl-6,8-dihydro-5H-pyrano[3,4-d]pyrimidine

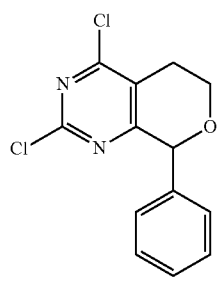 [SMILES: Clc1nc(Cl)c2c(n1)C(c1ccccc1)OCC2]

A solution of Intermediate N(5) (2.0 g, 8.18 mmol) and catalytic amount of DMF in POCl₃ (10 vol.) was heated at reflux for 18 h. The excess of POCl₃ was evaporated under reduced pressure. The residue was poured in to crushed ice and stirred for 15 min. The aqueous solution was extracted with ethyl acetate (50 mL×3). The combined organic layer was washed with aqueous saturated NaHCO₃ (50 mL×2), brine solution (50 mL), dried over Na₂SO₄ and evaporated under reduced pressure to give 2,4-dichloro-8-phenyl-6,8-dihydro-5H-pyrano[3,4-d]pyrimidine (2.0 g, crude) as brown solid. LC-MS (M+H)⁺=281.0.

Preparation Na 2-chloro-N-methyl-8-phenyl-6,8-dihydro-5H-pyrano[3,4-d]pyrimidin-4-amine

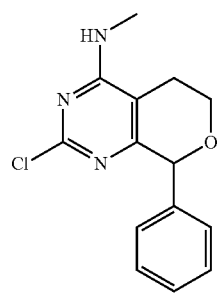 [SMILES: CNc1nc(Cl)nc2c1CCOC2c1ccccc1]

To a solution of Preparation N (2.1 g, crude) in acetonitrile was added diisopropylethylamine (1.83 g, 14.2 mmol) followed by addition of methylamine hydrochloride (0.96 g, 14.2 mmol) at room temperature. The reaction mixture was stirred at room temperature for 18 h. The solvent was removed under reduced pressure and the residue was purified by column chromatography (60-120 mesh) using 40% ethyl acetate in pet-ether as mobile phase to give 2-chloro-N-methyl-8-phenyl-6,8-dihydro-5H-pyrano[3,4-d]pyrimidin-4-amine (0.7 g, 35.7%) as off-white solid. LC-MS (M+H)⁺=276.0. ¹H NMR (400 MHz, DMSO-d6): δ ppm 7.49 (1H, m), 7.36-7.31 (3H, m), 7.25-7.23 (2H, m), 5.45 (1H, s), 4.0 (1H, m), 3.79 (1H, m), 2.87 (3H, d, J=4.4 Hz), 2.55 (1H, m), 2.44 (1H, m).

Preparation O 2,4-dichloro-8-(4-fluorophenyl)-6,8-dihydro-5H-pyrano[3,4-d]pyrimidine

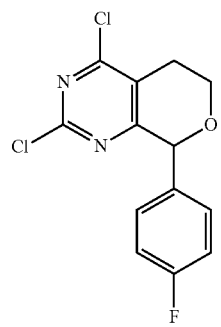 [SMILES: Fc1ccc(C2OCCc3c(Cl)nc(Cl)nc32)cc1]

Intermediate O(1)

ethyl 2-(4-fluorophenyl)-2-hydroxyacetate

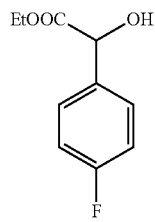

To a cooled solution of 2-(4-fluorophenyl)-2-hydroxyacetic acid (5.0 g, 29.4 mmol) in ethanol was added con. H₂SO₄ (10 mL) over a period of 10 min. The reaction mixture was heated at reflux for 5 h. The solvent was evaporated under reduced pressure and the residue was diluted with ethyl acetate (25 mL). The organic solution was washed with aqueous saturated NaHCO₃ (25 mL×2), water (20 mL), brine solution (10 mL), dried over anhydrous Na₂SO₄ and evaporated under reduced pressure to give ethyl 2-(4-fluorophenyl)-2-hydroxyacetate (5.0 g, 90%) as crude compound (oily liquid). The crude compound was taken to the next step without further purification. LC-MS (M+H₂O)⁺=216. ¹H NMR (400 MHz, DMSO-d6): δ 7.43-7.46 (2H, m), 7.17-7.20 (2H, m), 6.11-6.13 (1H, m), 5.14 (1H, d, J=5.20 Hz), 3.35-4.13 (2H, m), 1.12-1.15 (3H, m).

Intermediate O(2)

ethyl 4-(2-ethoxy-1-(4-fluorophenyl)-2-oxoethoxy)but-2-enoate

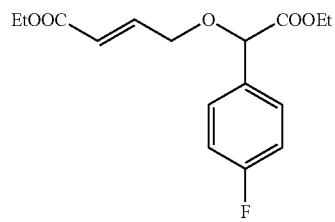 [SMILES: CCOC(=O)/C=C/COC(C(=O)OCC)c1ccc(F)cc1]

To a solution of Intermediate O(1) (3.0 g, 15.1 mmol) in hexane was added silver oxide (9.1 g, 39.3 mmol) followed by magnesium sulphate (1.8 g, 3.0 mmol) at room temperature. The reaction mixture was heated at reflux for 1 h. The reaction mixture was cooled to 0° C. and was added silver oxide (9.7 g, 39.9 mmol) followed by ethyl-4-bromochrotonate (4.3 g, 22.7 mmol). The resulting solution was stirred at room temperature for 3 days. The reaction mass was filtered through a bed of diatomaceous earth (Celite®) and washed with ethyl acetate. The filtrate was evaporated under reduced pressure to give ethyl 4-(2-ethoxy-1-(4-fluorophenyl)-2-oxoethoxy)but-2-enoate (3.0 g, 90%) as oily liquid. LC-MS (M+H₂O)⁺=328.2. ¹H NMR (400 MHz, CDCl₃): δ ppm 7.42-7.45 (2H, m), 7.04-7.26 (2H, m), 6.95 (1H, m), 6.12 (1H, m), 4.89 (1H, s), 4.13-4.28 (6H, m), 1.30 (3H, t, J=7.20 Hz), 1.26 (3H, J=6.8 Hz).

Intermediate O(3)

ethyl 4-(2-ethoxy-1-(4-fluorophenyl)-2-oxoethoxy)butanoate

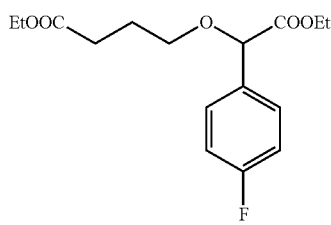 [SMILES: CCOC(=O)CCCOC(C(=O)OCC)c1ccc(F)cc1]

To a solution of Intermediate O(2) (3.0 g, 9.6 mmol) in ethanol was added palladium on carbon (10%, w/w) at room temperature. The reaction mixture was hydrogenated under balloon pressure of hydrogen for 30 h. The reaction mass was filtered through a bed of diatomaceous earth (Celite®) and washed with ethanol. The solvent was removed under reduced pressure and the residue was purified by column chromatography (Silica gel, 60-120 mesh) using 5% ethyl acetate in pet-ether as mobile phase to give ethyl 4-(2-ethoxy-1-(4-fluorophenyl)-2-oxoethoxy)butanoate (3.0 g, 63%) as oily liquid. LC-MS (M+H)$^+$=313.2 $^1$H NMR (400 MHz, CDCl$_3$): δ ppm 7.29-7.46 (2H, m), 7.05-7.09 (2H, m), 4.84 (1H, s), 4.10-4.23 (4H, m), 3.59-3.63 (1H, m), 3.42-3.53 (1H, m), 2.47 (2H, t, J=7.6 Hz), 1.99 (2H, t, J=7.6 Hz), 1.22-1.32 (6H, m).

Intermediate O(4)

ethyl 2-(4-fluorophenyl)-3-oxotetrahydro-2H-pyran-4-carboxylate

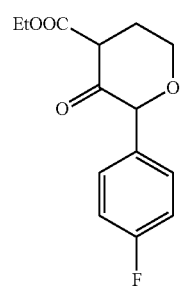 [SMILES: CCOC(=O)C1CCOC(c2ccc(F)cc2)C1=O]

To a cooled solution of Intermediate O(3) (3.0 g, 9.6 mmol) in THF was added t-BuOK (2.1 g, 19.0 mmol) at 0° C. The reaction mixture was allowed to come to room temperature and stirred for 1 h. The reaction mixture was quenched with water and evaporated the solvent under reduced pressure. The residue was diluted with ethyl acetate (200 mL). The organic layer was washed with water (100 mL×2), brine solution (100 mL), dried over anhydrous Na$_2$SO$_4$ and evaporated under reduced pressure to get crude compound. The crude compound was purified by column chromatography (Silica gel, 60-120 mesh) using 50% ethyl acetate in petroleum-ether as mobile phase to give ethyl 2-(4-fluorophenyl)-3-oxotetrahydro-2H-pyran-4-carboxylate (1.0 g, 55%) as oily liquid. LC-MS (M+H)$^+$=267.1. $^1$H NMR (400 MHz, DMSO-d6): δ ppm 11.81 (1H, s), 7.22-7.42 (2H, m), 7.12-7.20 (2H, m), 5.23 (1H, s), 4.22 (2H, q, J=7.2 Hz), 3.87-3.88 (1H, m), 3.69-3.84 (1H, m), 2.34-2.35 (1H, m), 2.30-2.33 (1H, m), 1.27 (3H, t, J=7.2 Hz).

Intermediate O(5)

8-(4-fluorophenyl)-5,6-dihydro-1H-pyrano[3,4-d]pyrimidine-2,4(3H,8H)-dione

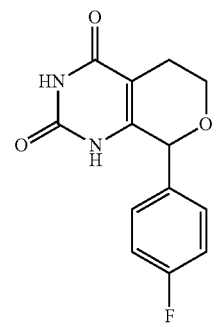 [SMILES: O=c1[nH]c2c(c(=O)[nH]1)CCOC2c1ccc(F)cc1]

To a solution of Intermediate O(4) (0.30 g, 1.12 mmol) in ethanol was added t-BuOK (0.253 g, 2.2 mmol) followed by urea (0.135 g, 2.2 mmol) at room temperature. The reaction mass was heated at reflux for 18 h. The reaction mixture was quenched with water and evaporated the solvent under reduced pressure. The residue was diluted with ethyl acetate (100 mL). The organic layer was washed with water (100 mL×2), brine solution (100 mL), dried over anhydrous Na$_2$SO$_4$ and evaporated under reduced pressure to get crude compound. The crude compound was purified by column chromatography (Silica gel, 60-120 mesh) using ethyl acetate as mobile phase to give 8-(4-fluorophenyl)-5,6-dihydro-1H-pyrano[3,4-d]pyrimidine-2,4(3H,8H)-dione (0.150 g, 40%) as pale yellow solid. LC-MS (M−H)$^+$=263.1. $^1$H NMR (400 MHz, DMSO-d6): δ ppm 11.14 (1H, s), 10.57 (1H, s), 7.35-7.36 (2H, m), 7.22 (2H, m), 5.34 (1H, s), 3.66-3.71 (1H, m), 3.58-3.64 (1H, m), 2.33 (2H, m).

Preparation O 2,4-dichloro-8-(4-fluorophenyl)-6,8-dihydro-5H-pyrano[3,4-d]pyrimidine

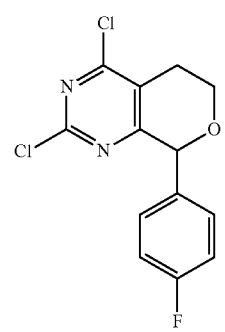 [SMILES: Fc1ccc(C2OCCc3c(Cl)nc(Cl)nc32)cc1]

A solution of Intermediate O(5) (0.30 g, 1.1 mmol) and catalytic amount of DMF in POCl$_3$ (10 vol.) was heated at reflux for 18 h. The excess of POCl$_3$ was evaporated under reduced pressure. The residue was poured in to crushed ice and stirred for 15 min. The aqueous solution was extracted with ethyl acetate (50 mL×3). The combined organic layer was washed with aqueous saturated NaHCO$_3$ (50 mL×2), brine solution (50 mL), dried over Na$_2$SO$_4$ and evaporated under reduced pressure to give 2,4-dichloro-8-(4-fluorophenyl)-6,8-dihydro-5H-pyrano[3,4-d]pyrimidine (0.20 g, crude) as brown liquid. LC-MS (M+H)$^+$=299.0.

Preparation Oa 2-chloro-N-ethyl-8-(4-fluorophenyl)-6,8-dihydro-5H-pyrano[3,4-d]pyrimidin-4-amine

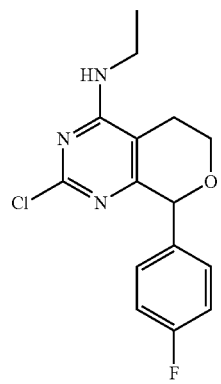 [SMILES: CCNc1nc(Cl)nc2c1CCOC2c1ccc(F)cc1]

To a solution of Preparation O (0.35 g, 1.1 mmol) in methanol was added diisopropylethylamine (0.30 g, 2.2 mmol) followed by addition of ethylamine hydrochloride (0.113 g, 1.1 mmol) at room temperature. The reaction mixture was stirred at room temperature for 18 h. The solvent was removed under reduced pressure and the residue was purified by column chromatography (60-120 mesh) using 35% ethyl acetate in pet-ether as mobile phase to give 2-chloro-N-ethyl-8-(4-fluorophenyl)-6,8-dihydro-5H-pyrano [3,4-d]pyrimidin-4-amine (0.15 g, crude) as off-white solid. LC-MS (M+H)$^+$=308.2.0.

Preparation Ob 2-chloro-N-ethyl-8-(4-fluorophenyl)-N-methyl-6,8-dihydro-5H-pyrano[3,4-d]pyrimidin-4-amine

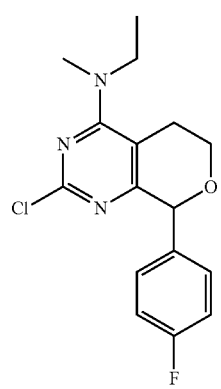 [SMILES: CCN(C)c1nc(Cl)nc2c1CCOC2c1ccc(F)cc1]

To a solution of Preparation O (0.20 g, 0.61 mmol) in methanol was added diisopropylethylamine (0.172 g, 1.3 mmol) followed by addition of ethylmethylamine hydrochloride (0.47 g, 0.81 mmol) at room temperature. The reaction mixture was stirred at room temperature for 18 h. The solvent was removed under reduced pressure and the residue was purified by column chromatography (60-120 mesh) using 40% ethyl acetate in pet-ether as mobile phase to give 2-chloro-N-ethyl-8-(4-fluorophenyl)-N-methyl-6,8-dihydro-5H-pyrano[3,4-d]pyrimidin-4-amine (0.020 g crude) as off-white solid. LC-MS (M+H)$^+$=322.2.

Preparation Oc1 and Oc2

2-chloro-8-(4-fluorophenyl)-4-((R)-3-fluoropyrrolidin-1-yl)-6,8-dihydro-5H-pyrano[3,4-d]pyrimidine

1

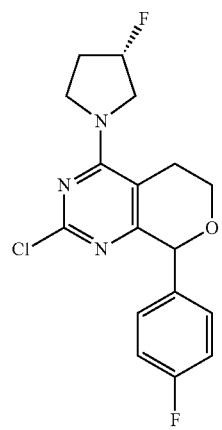

2

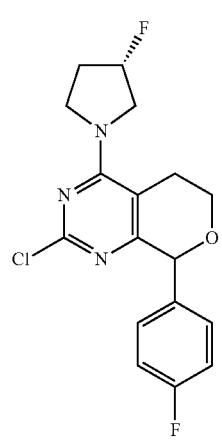

To a solution of Preparation O (0.60 g, 2.1 mmol) in methanol was added diisopropylethylamine (0.516 g, 4.6 mmol) followed by addition of (R)-3-fluoropyrrolidine (0.301 g, 2.2 mmol) at room temperature. The reaction mixture was stirred at room temperature for 18 h. The solvent was removed under reduced pressure and the residue was purified by pep-HPLC to give 2-chloro-8-(4-fluorophenyl)-4-((R)-3-fluoropyrrolidin-1-yl)-6,8-dihydro-5H-pyrano[3,4-d]pyrimidine (0.110 g, 40% Isomer 1, 0.109 g, 40% Isomer 2) as off-white solid. LC-MS (M+H)$^+$=352.0.

Oc1: $^1$H NMR (400 MHz, DMSO-d6): δ ppm 7.36-7.36 (2H, m), 7.16 (2H, m), 5.50 (2H, d, J=8.40 Hz), 5.35 (1H, s), 3.58-3.98 (7H, m), 3.24-3.34 (1H, m), 2.78 (1H, m), 2.04-2.28 (2H, m).

Oc2: $^1$H NMR (400 MHz, DMSO-d6): δ ppm 7.19-7.33 (2H, m), 7.15-7.20 (2H, m), 5.34 (1H, m), 5.40 (1H, m), 3.91-4.10 (2H, m), 3.75-3.90 (2H, m), 3.69-3.75 (2H, m), 3.05 (2H, t, J=5.20 Hz), 2.01 (2H, d, J=8.0 Hz).

Preparation Od1 and Od2

2-chloro-8-(4-fluorophenyl)-4-((S)-3-fluoropyrrolidin-1-yl)-6,8-dihydro-5H-pyrano[3,4-d]pyrimidine

1

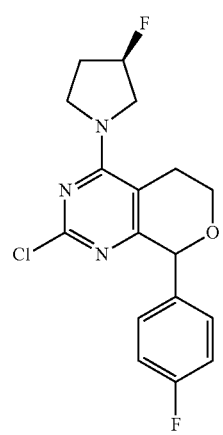

2

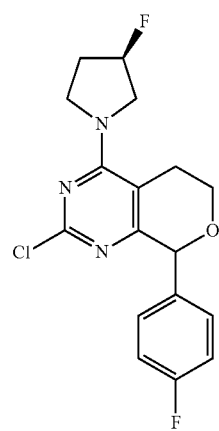

To a solution of Preparation O (0.60 g, 2.1 mmol) in methanol was added diisopropylethylamine (0.516 g, 4.6 mmol) followed by addition of (S)-3-fluoropyrrolidine (0.301 g, 2.2 mmol) at room temperature. The reaction mixture was stirred at room temperature for 18 h. The solvent was removed under reduced pressure and the residue was purified by pep-HPLC to give 2-chloro-8-(4-fluorophenyl)-4-((S)-3-fluoropyrrolidin-1-yl)-6,8-dihydro-5H-pyrano[3,4-d]pyrimidine (0.102 g, 39% Isomer 1, 0.111 g, 40% Isomer 2) as off-white solid. LC-MS (M+H)$^+$=352.0.

Od1: $^1$H NMR (400 MHz, DMSO-d6): δ ppm 7.36-7.36 (2H, m), 7.16 (2H, m), 5.50 (2H, d, J=8.4 Hz), 5.35 (1H, s), 3.58-3.98 (7H, m), 3.24-3.34 (1H, m), 2.78 (1H, d, J=8.4 Hz), 2.04-2.28 (2H, m).

Od2: $^1$H NMR (400 MHz, DMSO-d6): δ ppm 7.19-7.33 (2H, m), 7.15-7.20 (2H, m), 5.34 (1H, m), 5.40 ((1H, m), 3.91-4.10 (2H, m), 3.75-3.90 (2H, m), 3.69-3.75 (m, 2H), 3.05 (2H, t, J=5.20 Hz), 2.01 (2H, d, J=8.0 Hz).

Preparation P 2,4-Dichloro-7-(4-chlorophenyl)-6,7-dihydro-5H-cyclopenta[d]pyrimidine

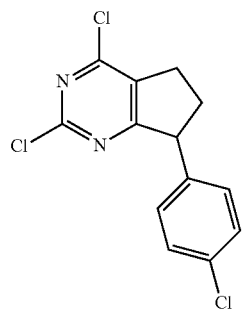 [SMILES: Clc1ccc(C2CCc3c(Cl)nc(Cl)nc32)cc1]

Intermediate P(1)

1-Chloro-4-cyclopentenylbenzene

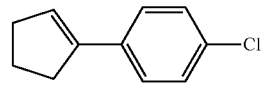 [SMILES: Clc1ccc(C2=CCCC2)cc1]

To a 1 M solution of 4-chlorophenyl)magnesium bromide (149 mL, 149 mmol) was added cyclopentanone (13.23 mL, 149 mmol). The solution turned warm upon the addition. The reaction mixture was stirred at reflux for 2 h. The reaction mixture was cooled to room temperature and quenched with 10 g of ice. 6N hydrochloric acid solution was added until the precipitate dissolved completely. Ether was added. The organic layer was separated and the aqueous phase was extracted with ether. The combined organic extracts were washed with saturated aqueous solution of sodium hydrogen sulfite, saturated aqueous solution of sodium bicarbonate and water. The organic layer was dried over anhydrous magnesium sulfate and filtered. The solvent was removed in vacuum and the residue was purified by column chromatography on silica gel to give 1-chloro-4-cyclopentenylbenzene (20.0 g, 112 mmol, 75% yield) as a colorless oil. LC-MS (M+H)$^+$= 179.2. $^1$H NMR (500 MHz, CDCl$_3$) δ ppm 7.27-7.39 (4H, m), 6.19 (1H, s), 2.66-2.74 (2H, m), 2.52-2.61 (2H, m), 2.01-2.12 (2H, m).

Intermediate P(2)

2-(4-Chlorophenyl)cyclopentanone

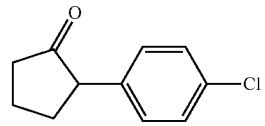 [SMILES: O=C1CCCC1c1ccc(Cl)cc1]

A mixture of formic acid (60 mL, 84 mmol) and hydrogen peroxide (15 mL, 84 mmol) was warmed at 40° C. for 10 min. The resulting solution was carefully added to 1-chloro-4- cyclopentenylbenzene (15 g, 84 mmol) under stirring. The two-phase system was initially stirred at room temperature. After a certain period of time, a spontaneous exothermic reaction took place, and the temperature rose to about 50° C. The reaction mixture was stirred at room temperature for 1 h. The LC/MS analysis of the reaction mixture shows the disappearance of the starting material and the formation of the product. The reaction mixture was quenched by careful addition of a saturated sodium bicarbonate solution. Ether was added and the reaction mixture was vigorously shaken. The organic layer was separated and the aqueous layer was extracted with ether. The combined organic extracts were dried over anhydrous magnesium sulfate and filtered. The solvent was removed in vacuum and the residue was purified by column chromatography on silica gel to give 2-(4-chlorophenyl)cyclopentanone (5.7 g, 29.3 mmol, 34.9% yield) as a colorless oil. LC-MS (M+H)$^+$=195.2. $^1$H NMR (500 MHz, CDCl$_3$) δ ppm 7.21-7.37 (2H, m), 7.11 (2H, d, J=8.5 Hz), 3.25 (1H, dd, J=11.6, 8.5 Hz), 2.44 (2H, d, J=6.1 Hz), 2.15-2.31 (1H, m), 1.96-2.15 (3H, m), 1.78-1.95 (1H, m).

Intermediate P(3)

7-(4-Chlorophenyl)-6,7-dihydrocyclopenta[e][1,3]oxazine-2,4(3H,5H)-dione

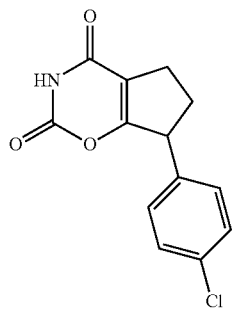

A solution of 2-(4-chlorophenyl)cyclopentanone (7.80 g, 40.1 mmol) and carbonisocyanatidic chloride (7.61 g, 72.1 mmol) was stirred at 58° C. in a high-pressure vessel for 1 h. The temperature was raised to 130° C. and the reaction mixture was stirred for an additional 2 h. After cooling to rt, the reaction mixture solidified. The solid residue was dissolved in ethyl acetate and washed with saturated aqueous solution of sodium bicarbonate. The organic layer was separated and the aqueous layer was extracted twice with ethyl acetate. The combined organic extracts were dried over anhydrous sodium sulfate and filtered. The solvent was removed in vacuum and the oily residue was purified by column chromatography on silica gel to provide 7-(4-chlorophenyl)-6,7-dihydrocyclopenta[e][1,3]oxazine-2,4(3H,5H)-dione (5.4 g, 20.48 mmol, 51.1% yield). LC-MS (M+H)$^+$=264.2. $^1$H NMR (500 MHz, CDCl$_3$) δ ppm 7.32 (2H, d, J=8.5 Hz), 7.12 (2H, d, J=8.5 Hz), 4.15-4.25 (1H, m), 2.56-2.93 (4H, m).

Intermediate P(4)

7-(4-Chlorophenyl)-6,7-dihydro-1H-cyclopenta[d]pyrimidine-2,4(3H,5H)-dione

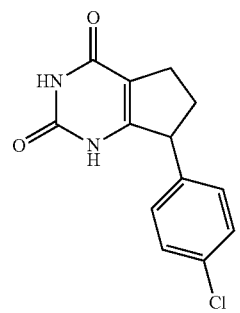

A solution of 7-(4-chlorophenyl)-6,7-dihydrocyclopenta[e][1,3]oxazine-2,4(3H,5H)-dione (5.4 g, 20.48 mmol) in concentrated ammonium hydroxide (59.8 mL, 1536 mmol) was stirred at 100° C. in a high-pressure vessel for 6 h. The formation of white precipitate was observed during the heating. The solvent was removed in vacuum to provide 7-(4-chlorophenyl)-6,7-dihydro-1H-cyclopenta[d]pyrimidine-2,4(3H,5H)-dione (4.9 g, 18.65 mmol, 91% yield) as a off-white solid. LC-MS (M+H)$^+$=263.2. $^1$H NMR (500 MHz, DMSO-d$_6$) δ ppm 7.37 (2H, d, J=8.2 Hz), 7.19 (1H, d, J=8.5 Hz), 4.16 (1H, d, J=5.2 Hz), 3.79 (1H, br s), 3.17 (1H, s), 2.51 (2H, d, J=1.8 Hz), 1.75-1.85 (1H, m).

Preparation P 2,4-Dichloro-7-(4-chlorophenyl)-6,7-dihydro-5H-cyclopenta[d]pyrimidine

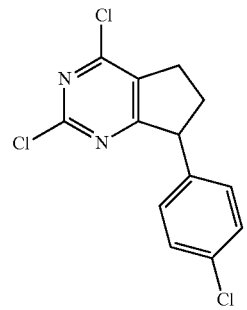

A mixture of 7-(4-chlorophenyl)-6,7-dihydro-1H-cyclopenta[d]pyrimidine-2,4(3H,5H)-dione (4.7 g, 17.89 mmol), POCl$_3$ (53.4 mL, 573 mmol) and N,N-dimethylaniline (18.26 mL, 143 mmol) was heated at 110° C. overnight. The reaction mixture was poured into a beaker with ice. The inside walls of the reaction vessel was washed with DCM. As soon as the ice completely melted, the organic layer was separated and the aqueous layer was extracted with DCM. The combined organic extracts were dried over anhydrous sodium sulfate and filtered. The solvent was removed in vacuum and the residue was purified by column chromatography on silica gel to provide 2,4-dichloro-7-(4-chlorophenyl)-6,7-dihydro-5H-cyclopenta[d]pyrimidine (1.2 g, 4.01 mmol, 22.39% yield). LC-MS (M+H)$^+$=299.0. $^1$H NMR (500 MHz, CDCl$_3$) δ ppm 7.41-7.99 (2H, m), 7.09 (2H, d, J=8.5 Hz), 4.41 (1H, t, J=8.4 Hz), 2.94-3.18 (2H, m), 2.73 (1H, dt, J=8.9, 4.5 Hz), 2.15-2.33 (1H, m).

Preparation Pa

2-Chloro-7-(4-chlorophenyl)-N,N-dimethyl-6,7-dihydro-5H-cyclopenta[d]pyrimidin-4-amine

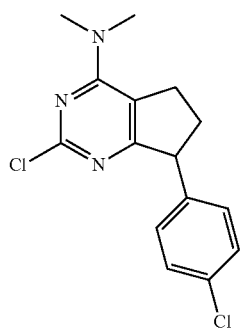

A solution of 2,4-dichloro-7-(4-chlorophenyl)-6,7-dihydro-5H-cyclopenta[d]pyrimidine (200 mg, 0.668 mmol) and excess dimethylamine (3.34 mL, 6.68 mmol) in MeOH (4 mL) was stirred at rt for 30 min. The solvent was removed in vacuum and the crude product was purified by column chromatography on silica gel to afford 2-chloro-7-(4-chlorophenyl)-N,N-dimethyl-6,7-dihydro-5H-cyclopenta[d]pyrimidin-4-amine (98 mg, 0.318 mmol, 47.6% yield). LC-MS (M+H)$^+$=308.1.

Preparation Pb

2-Chloro-7-(4-chlorophenyl)-4-(3,3-difluoroazetidin-1-yl)-6,7-dihydro-5H-cyclopenta[d]pyrimidine

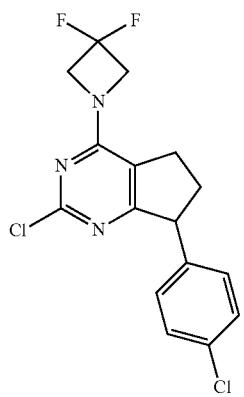 [SMILES: FC1(F)CN(c2nc(Cl)nc3c2CCC3c2ccc(Cl)cc2)C1]

A solution of 2,4-dichloro-7-(4-chlorophenyl)-6,7-dihydro-5H-cyclopenta[d]pyrimidine (325 mg, 1.085 mmol), N-ethyl-N-isopropylpropan-2-amine (0.945 mL, 5.42 mmol) and 3,3-difluoroazetidine, HCl salt (281 mg, 2.170 mmol) in MeOH (5 mL) was stirred at rt for 1 h. The solvent was removed in vacuum and the crude product was purified by column chromatography on silica gel to afford 2-chloro-7-(4-chlorophenyl)-4-(3,3-difluoroazetidin-1-yl)-6,7-dihydro-5H-cyclopenta[d]pyrimidine (70 mg, 0.197 mmol, 18.12% yield). LC-MS (M+H)$^+$=356.1.

Preparation Pc

2-Chloro-7-(4-chlorophenyl)-N-methyl-6,7-dihydro-5H-cyclopenta[d]pyrimidin-4-amine

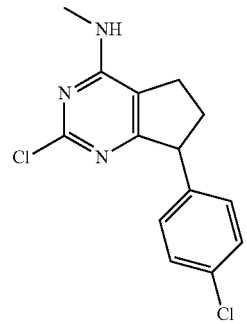 [SMILES: CNc1nc(Cl)nc2c1CCC2c1ccc(Cl)cc1]

A solution of 2,4-dichloro-7-(4-chlorophenyl)-6,7-dihydro-5H-cyclopenta[d]pyrimidine (300 mg, 1.001 mmol), methanamine, HCl salt (135 mg, 2.003 mmol) and DIPEA (0.700 mL, 4.01 mmol) in MeOH (6 mL) was stirred at rt for 30 min. The solvent was removed in vacuum and the crude product was purified by column chromatography on silica gel to afford 2-chloro-7-(4-chlorophenyl)-N-methyl-6,7-dihydro-5H-cyclopenta[d]pyrimidin-4-amine (101 mg, 0.343 mmol, 34.3% yield). LC-MS (M+H)$^+$=294.2.

Preparation Q 2,4-Dichloro-7-(3,4-difluorophenyl)-6,7-dihydro-5H-cyclopenta[d]pyrimidine

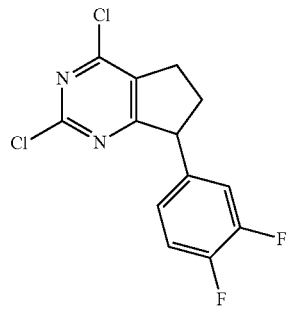 [SMILES: Fc1ccc(C2CCc3c(Cl)nc(Cl)nc32)cc1F]

Intermediate Q(1)

7-(3,4-Difluorophenyl)-6,7-dihydrocyclopenta[e][1,3]oxazine-2,4(3H,5H)-dione

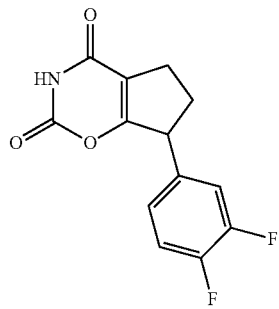 [SMILES: O=c1[nH]c(=O)c2c(o1)C(c1ccc(F)c(F)c1)CC2]

A solution of 2-(3,4-difluorophenyl)cyclopentanone, (prepared in the manner of Intermediate P(1) and P(2)) (1.5 g, 7.65 mmol) and carbonisocyanatidic chloride (1.129 g, 10.70 mmol) was stirred at 58° C. in a high-pressure vessel for 1 h. The temperature was raised to 130° C. and the reaction mixture was stirred for an additional 2 h. After cooling to rt, the reaction mixture solidified. The solid residue was dissolved in ethyl acetate and washed with saturated aqueous solution of sodium bicarbonate. The organic layer was separated and the aqueous layer was extracted twice with ethyl acetate. The combined organic extracts were dried over anhydrous sodium sulfate and filtered. The solvent was removed in vacuum and the oily residue was purified by column chromatography on silica gel to provide 7-(3,4-difluorophenyl)-6,7-dihydrocyclopenta[e][1,3]oxazine-2,4(3H,5H)-dione (1.05 g, 3.96 mmol, 51.8% yield) as a white solid. $^1$H NMR (500 MHz, CDCl$_3$) δ ppm 8.16 (1H, br s), 7.15 (1H, dt, J=10.0, 8.3 Hz), 6.97-7.05 (1H, m), 6.88-6.95 (1H, m), 2.80-2.90 (1H, m), 2.61-2.78 (2H, m), 0.78-0.86 (2H, m).

Intermediate Q(2)

7-(3,4-Difluorophenyl)-6,7-dihydro-1H-cyclopenta[d]pyrimidine-2,4(3H,5H)-dione

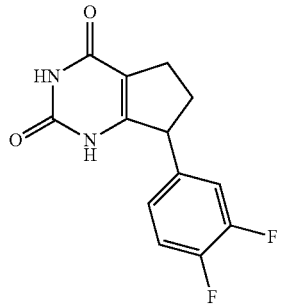 [SMILES: O=c1[nH]c2c(c(=O)[nH]1)CCC2c1ccc(F)c(F)c1]

A solution of 7-(3,4-difluorophenyl)-6,7-dihydrocyclopenta[e][1,3]oxazine-2,4(3H,5H)-dione (1.05 g, 3.96 mmol) in concentrated ammonium hydroxide (0.154 mL, 3.96 mmol) was stirred at 100° C. in a high-pressure vessel (75 mL) for 6 h. The formation of white precipitate was observed during the heating. The solvent was removed in vacuum to provide 7-(3,4-difluorophenyl)-6,7-dihydro-1H-cyclopenta[d]pyrimidine-2,4(3H,5H)-dione (1.046 g, 3.96 mmol, 100% yield) as a off-white solid. LC-MS (M+H)$^+$=265.2.

Preparation Q 2,4-Dichloro-7-(3,4-difluorophenyl)-6,7-dihydro-5H-cyclopenta[d]pyrimidine

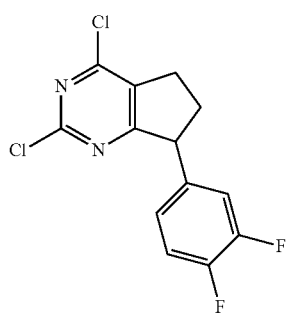 [SMILES: Fc1ccc(C2CCc3c(Cl)nc(Cl)nc32)cc1F]

A mixture of 7-(3,4-difluorophenyl)-6,7-dihydro-1H-cyclopenta[d]pyrimidine-2,4(3H,5H)-dione (500 mg, 1.892 mmol), POCl$_3$ (5644 µL, 60.6 mmol) and N,N-dimethylaniline (1931 µL, 15.14 mmol) was heated at 120° C. overnight. The reaction mixture was poured into a beaker with ice. The inside walls of the reaction vessel was washed with DCM. As soon as the ice completely melted, the content of the beaker was placed into a separatory funnel. The organic layer was separated and the aqueous layer was extracted with DCM. The combined organic extracts were dried over anhydrous sodium sulfate and filtered. The solvent was removed in vacuum and the residue was purified by column chromatography on silica gel to provide 2,4-dichloro-7-(3,4-difluorophenyl)-6,7-dihydro-5H-cyclopenta[d]pyrimidine (446 mg, 1.481 mmol, 78% yield). LC-MS (M+H)$^+$=301.1.

Preparation Qa

2-Chloro-7-(3,4-difluorophenyl)-N,N-dimethyl-6,7-dihydro-5H-cyclopenta[d]pyrimidin-4-amine

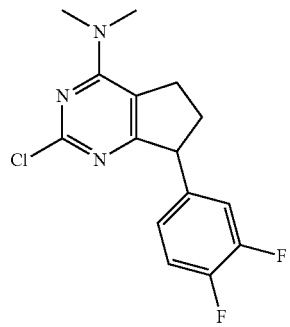 [SMILES: CN(C)c1nc(Cl)nc2c1CCC2c1ccc(F)c(F)c1]

A solution of 2,4-dichloro-7-(3,4-difluorophenyl)-6,7-dihydro-5H-cyclopenta[d]pyrimidine (446 mg, 1.481 mmol) and excess dimethylamine (2.222 mL, 4.44 mmol) in MeOH (6 mL) was stirred at rt for 30 min. The solvent was removed in vacuum and the crude product was purified by column chromatography on silica gel to afford 2-chloro-7-(3,4-difluorophenyl)-N,N-dimethyl-6,7-dihydro-5H-cyclopenta[d]pyrimidin-4-amine (146 mg, 0.471 mmol, 31.8% yield). LC-MS (M+H)$^+$=310.2.

Preparation Qb

2-Chloro-7-(3,4-difluorophenyl)-N-methyl-6,7-dihydro-5H-cyclopenta[d]pyrimidin-4-amine

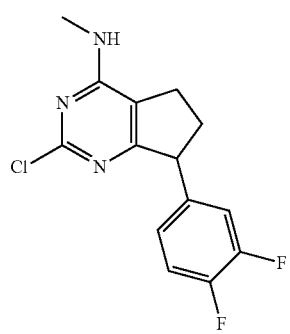 [SMILES: CNc1nc(Cl)nc2c1CCC2c1ccc(F)c(F)c1]

A solution of 2,4-dichloro-7-(3,4-difluorophenyl)-6,7-dihydro-5H-cyclopenta[d]pyrimidine (421 mg, 1.398 mmol), methanamine, HCl (283 mg, 4.19 mmol) and DIPEA (1.465 mL, 8.39 mmol) in methanol (10 mL) was stirred at rt for 1 h. The solvent was removed in vacuum and the crude product was purified by column chromatography on silica gel to afford 2-chloro-7-(3,4-difluorophenyl)-N-methyl-6,7-dihydro-5H-cyclopenta[d]pyrimidin-4-amine (154 mg, 0.521 mmol, 37.2% yield). LC-MS (M+H)$^+$=296.2.

Preparation R 2,4-dichloro-7-(4-(trifluoromethoxy)phenyl)-6,7-dihydro-5H-cyclopenta[d]pyrimidine

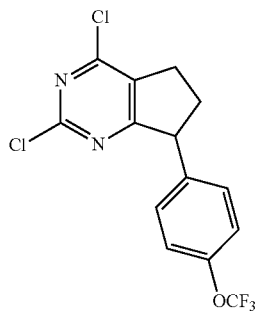 [SMILES: FC(F)(F)Oc1ccc(C2CCc3c(Cl)nc(Cl)nc32)cc1]

Intermediate R(1)

1-cyclopentenyl-4-(trifluoromethoxy)benzene

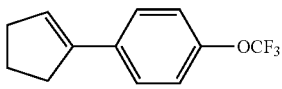

(4-(trifluoromethoxy)phenyl)magnesium bromide was reacted in the manner of Intermediate P(1) to give 1-cyclopentenyl-4-(trifluoromethoxy)benzene.

Intermediate R(2)

2-(4-(trifluoromethoxy)phenyl)cyclopentanone

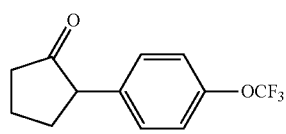

1-cyclopentenyl-4-(trifluoromethoxy)benzene was reacted in the manner of Intermediate P(2) to give 2-(4-(trifluoromethoxy)phenyl)cyclopentanone.

Intermediate R(3)

7-(4-(trifluoromethoxy)phenyl)-6,7-dihydrocyclopenta[e][1,3]oxazine-2,4(3H,5H)-dione

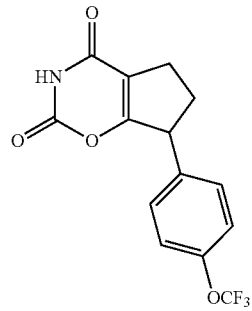 [SMILES: O=c1[nH]c(=O)c2c(o1)C(c1ccc(OC(F)(F)F)cc1)CC2]

2-(4-(trifluoromethoxy)phenyl)cyclopentanone was reacted in the manner of Intermediate P(3) to provide 7-(4-(trifluoromethoxy)phenyl)-6,7-dihydrocyclopenta[e][1,3]oxazine-2,4(3H,5H)-dione.

Intermediate R(4)

7-(4-(trifluoromethoxy)phenyl)-6,7-dihydro-1H-cyclopenta[d]pyrimidine-2,4(3H,5H)-dione

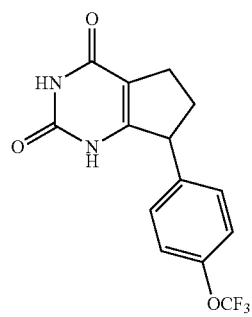 [SMILES: O=c1[nH]c2c(c(=O)[nH]1)CCC2c1ccc(OC(F)(F)F)cc1]

7-(4-(trifluoromethoxy)phenyl)-6,7-dihydrocyclopenta[e][1,3]oxazine-2,4(3H,5H)-dione was reacted in the manner of Intermediate P(4) to provide 7-(4-(trifluoromethoxy)phenyl)-6,7-dihydro-1H-cyclopenta[d]pyrimidine-2,4(3H,5H)-dione.

Preparation R 2,4-dichloro-7-(4-(trifluoromethoxy)phenyl)-6,7-dihydro-5H-cyclopenta[d]pyrimidine

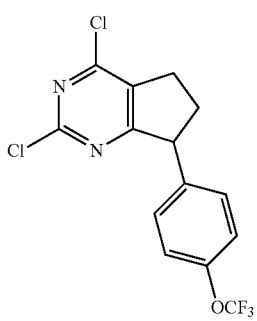 [SMILES: FC(F)(F)Oc1ccc(C2CCc3c(Cl)nc(Cl)nc32)cc1]

7-(4-(trifluoromethoxy)phenyl)-6,7-dihydro-1H-cyclopenta[d]pyrimidine-2,4(3H,5H)-dione was reacted in the manner of Preparation P to provide 2,4-dichloro-7-(4-(trifluoromethoxy)phenyl)-6,7-dihydro-5H-cyclopenta[d]pyrimidine as a pink solid. LC-MS (M+H)+=349.2. ¹H NMR (500 MHz, CD3OD) δ ppm 7.31 (2H, dd, J=2.0, 7.7 Hz), 7.25 (2H, d, J=7.4 Hz), 4.56 (1H, t, J=8.8 Hz), 3.15 (1H, ddd, J=3.8, 9.1, 16.9 Hz), 3.09-3.00 (1H, m), 2.81-2.72 (1H, m), 2.27-2.22 (1H, m).

Preparation Ra

2-Chloro-N-methyl-7-(4-(trifluoromethoxy)phenyl)-6,7-dihydro-5H-cyclopenta[d]pyrimidin-4-amine

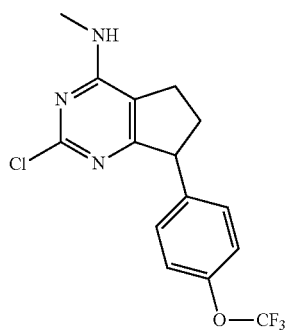 [SMILES: CNc1nc(Cl)nc2c1CCC2c1ccc(OC(F)(F)F)cc1]

A solution of 2,4-dichloro-7-(4-(trifluoromethoxy)phenyl)-6,7-dihydro-5H-cyclopenta[d]pyrimidine (200 mg, 0.573 mmol), and methanamine (0.286 mL, 0.573 mmol) in MeOH (5 mL) was stirred at rt for 1 h. The solvent was removed in vacuum to afford crude 2-chloro-N-methyl-7-(4-(trifluoromethoxy)phenyl)-6,7-dihydro-5H-cyclopenta[d]pyrimidin-4-amine (220 mg, 0.640 mmol, 112% yield). LC-MS (M+H)+=343.9.

Preparation Rb

2-Chloro-N-ethyl-7-(4-(trifluoromethoxy)phenyl)-6,7-dihydro-5H-cyclopenta[d]pyrimidin-4-amine

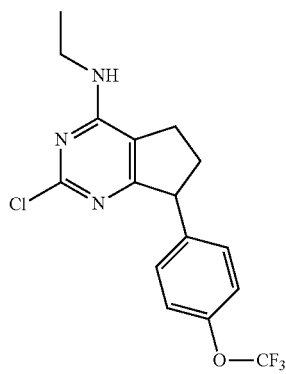 [SMILES: CCNc1nc(Cl)nc2c1CCC2c1ccc(OC(F)(F)F)cc1]

A solution of 2,4-dichloro-7-(4-(trifluoromethoxy)phenyl)-6,7-dihydro-5H-cyclopenta[d]pyrimidine (200 mg, 0.573 mmol), and ethanamine (0.286 mL, 0.573 mmol) in MeOH (2 mL) was stirred at rt for 1 h. The solvent was removed in vacuum and the crude product was purified by column chromatography on silica gel to afford 2-chloro-N-ethyl-7-(4-(trifluoromethoxy)phenyl)-6,7-dihydro-5H-cyclopenta[d]pyrimidin-4-amine (190 mg, 0.531 mmol, 93% yield). LC-MS (M+H)+=358.2.

Preparation Rc

2-Chloro-4-(3,3-difluoroazetidin-1-yl)-7-(4-(trifluoromethoxy)phenyl)-6,7-dihydro-5H-cyclopenta[d]pyrimidine

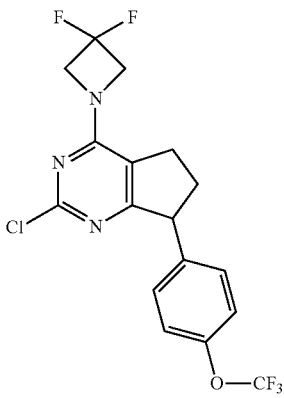 [SMILES: FC1(F)CN(c2nc(Cl)nc3c2CCC3c2ccc(OC(F)(F)F)cc2)C1]

A solution of 2,4-dichloro-7-(4-(trifluoromethoxy)phenyl)-6,7-dihydro-5H-cyclopenta[d]pyrimidine (250 mg, 0.716 mmol), 3,3-difluoroazetidine, HCl salt (186 mg, 1.432 mmol) and DIPEA (0.500 mL, 2.86 mmol) in MeOH (3 mL) was stirred at rt for 1.5 h. The solvent was removed in vacuum and the crude product was purified by column chromatography on silica gel to afford 2-chloro-4-(3,3-difluoroazetidin-1-yl)-7-(4-(trifluoromethoxy)phenyl)-6,7-dihydro-5H-cyclopenta[d]pyrimidine (244 mg, 0.601 mmol, 84% yield). LC-MS (M+H)+=406.0.

Preparation Rd

2-Chloro-N,N-dimethyl-7-(4-(trifluoromethoxy)phenyl)-6,7-dihydro-5H-cyclopenta[d]pyrimidin-4-amine

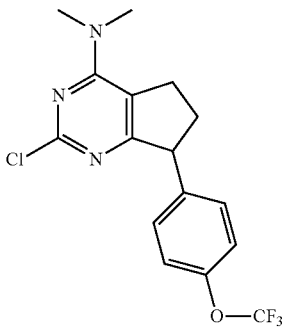 [SMILES: CN(C)c1nc(Cl)nc2c1CCC2c1ccc(OC(F)(F)F)cc1]

A solution of 2,4-dichloro-7-(4-(trifluoromethoxy)phenyl)-6,7-dihydro-5H-cyclopenta[d]pyrimidine (250 mg, 0.716 mmol) and dimethylamine (0.716 mL, 1.432 mmol) in MeOH (2 mL) was stirred at rt for 1 h. The solvent was removed in vacuum and the crude product was purified by column chromatography on silica gel to afford 2-chloro-N,N-dimethyl-7-(4-(trifluoromethoxy)phenyl)-6,7-dihydro- 5H-cyclopenta[d]pyrimidin-4-amine (250 mg, 0.699 mmol, 98% yield). LC-MS (M+H)$^+$=358.0.

Preparation Re 4-(Azetidin-1-yl)-2-chloro-7-(4-(trifluoromethoxy)phenyl)-6,7-dihydro-5H-cyclopenta[d]pyrimidine

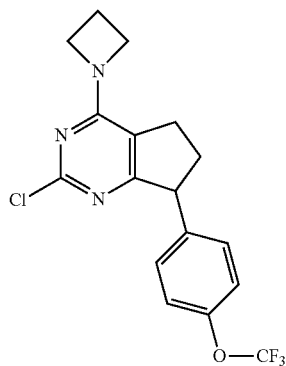 [SMILES: FC(F)(F)Oc1ccc(C2CCc3c2nc(Cl)nc3N2CCC2)cc1]

A solution of 2,4-dichloro-7-(4-(trifluoromethoxy)phenyl)-6,7-dihydro-5H-cyclopenta[d]pyrimidine (250 mg, 0.716 mmol) and azetidine (82 mg, 1.432 mmol) in MeOH (3 mL) was stirred at rt for 1 h. The solvent was removed in vacuum and the crude product was purified by column chromatography on silica gel to afford 4-(azetidin-1-yl)-2-chloro-7-(4-(trifluoromethoxy)phenyl)-6,7-dihydro-5H-cyclopenta[d]pyrimidine (238 mg, 0.644 mmol, 90% yield). LC-MS (M+H)$^+$=371.2.

Preparation S 2,4-Dichloro-7-(3,5-difluorophenyl)-6,7-dihydro-5H-cyclopenta[d]pyrimidine

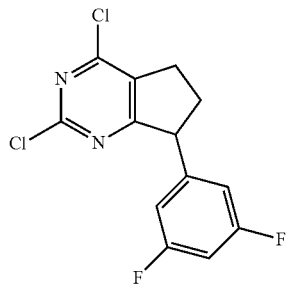 [SMILES: Fc1cc(F)cc(C2CCc3c(Cl)nc(Cl)nc32)c1]

Intermediate S(1)

(1S,2R)-2-(3,5-Difluorophenyl)cyclopentanol

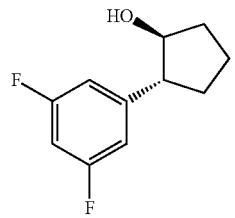 [SMILES: O[C@H]1CCC[C@@H]1c1cc(F)cc(F)c1]

A flask was charged with (3,5-difluorophenyl)magnesium bromide (149 mL, 149 mmol) and copper (I) iodide (1.901 g, 9.98 mmol). To this reaction mixture, 6-oxabicyclo[3.1.0]hexane (12.53 g, 149 mmol) dissolved in THF (25 mL) was added dropwise. The reaction mixture warmed upon the addition of the epoxide. The reaction was stirred at rt for 2 h at rt. The reaction mixture was quenched by the addition of a solution of ammonium chloride. Ether was added and the organic layer was collected, dried (Na$_2$SO$_4$) and concentrated. The crude product was purified by column chromatography on silica gel to afford (1S,2R)-2-(3,5-difluorophenyl)cyclopentanol (26.5 g, 134 mmol, 90% yield).

$^1$H NMR (500 MHz, CDCl$_3$) δ ppm 6.72 (2H, dd, J=8.7, 2.0 Hz), 6.50-6.63 (1H, m), 2.97 (1H, br s), 2.78 (1H, d, J=10.1 Hz), 1.96-2.15 (2H, m), 1.66-1.85 (2H, m), 1.53-1.65 (2H, m).

Intermediate S(2)

2-(3,5-Difluorophenyl)cyclopentanone

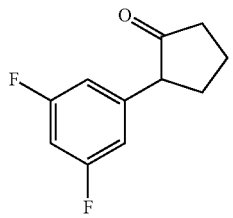 [SMILES: O=C1CCCC1c1cc(F)cc(F)c1]

To a solution of (1S,2R)-2-(3,5-difluorophenyl)cyclopentanol (6 g, 30.3 mmol) in CH$_2$Cl$_2$ (150 mL) was added Dess-Martin periodinane (15.41 g, 36.3 mmol). The reaction mixture was stirred at rt for 3 h. The reaction mixture was diluted with dichloromethane and quenched with the addition of 1 N NaOH. The organic layer was collected, dried (Na$_2$SO$_4$) and concentrated. The crude product was purified by column chromatography on silica gel to afford 2-(3,5-difluorophenyl)cyclopentanone (4.765 g, 24.29 mmol, 80% yield). LC-MS (M+H)$^+$=197.0. $^1$H NMR (500 MHz, CDCl$_3$) δ ppm 6.70 (2H, d, J=6.7 Hz), 6.52-6.67 (1H, m), 3.17-3.33 (1H, m), 2.33-2.56 (2H, m), 2.06-2.26 (2H, m), 2.01 (1H, dd, J=11.7, 6.3 Hz), 1.89 (1H, br s).

Intermediate S(3)

7-(3,5-difluorophenyl)-6,7-dihydrocyclopenta[e][1,3]oxazine-2,4(3H,5H)-dione

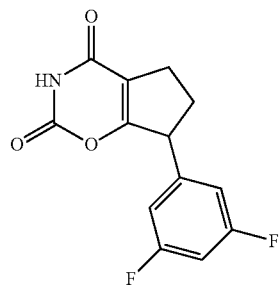 [SMILES: O=c1[nH]c(=O)c2c(o1)C(c1cc(F)cc(F)c1)CC2]

A mixture of 2-(3,5-difluorophenyl)cyclopentanone (4.765 g, 24.29 mmol) and carbonisocyanatidic chloride (4.61 g, 43.7 mmol) was heated at 58° C. for 1 h and at 130°

C. for 2 h. Upon cooling to room temperature, the reaction mixture was dissolved in ethyl acetate and washed with saturated aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(3,5-difluorophenyl)-6,7-dihydrocyclopenta[e][1,3]oxazine-2,4(3H,5H)-dione (700 mg, 2.64 mmol, 10.87% yield). LC-MS (M+H)$^+$=266.1. $^1$H NMR (500 MHz, CDCl$_3$) δ ppm 8.79 (1H, br s), 6.68-6.86 (3H, m), 4.22 (1H, br s), 2.87 (1H, dt, J=7.0, 4.4 Hz), 2.63-2.82 (2H, m), 2.15 (1H, br s).

Intermediate S(4)

7-(3,5-Difluorophenyl)-6,7-dihydro-1H-cyclopenta[d]pyrimidine-2,4(3H,5H)-dione

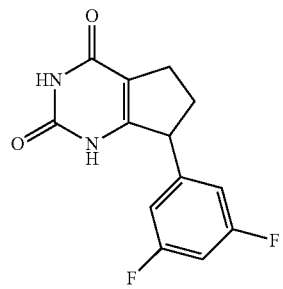 [SMILES: O=c1[nH]c2c(c(=O)[nH]1)CCC2c1cc(F)cc(F)c1]

A solution of 7-(3,5-difluorophenyl)-6,7-dihydrocyclopenta[e][1,3]oxazine-2,4(3H,5H)-dione (700 mg, 2.64 mmol) in concentrated ammonium hydroxide (50 mL, 1284 mmol) was heated at 100° C. in a high-pressure (350 mL) vessel overnight. The reaction mixture was cooled and concentrated in vacuum to give crude 7-(3,5-difluorophenyl)-6,7-dihydro-1H-cyclopenta[d]pyrimidine-2,4(3H,5H)-dione (740 mg, 2.80 mmol, 106% yield). LC-MS (M+H)$^+$=265.0.

Preparation S 2,4-Dichloro-7-(3,5-difluorophenyl)-6,7-dihydro-5H-cyclopenta[d]pyrimidine

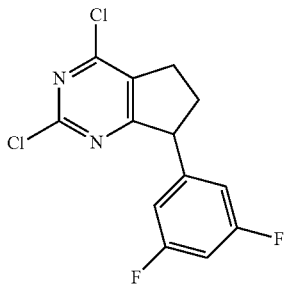 [SMILES: Fc1cc(F)cc(C2CCc3c(Cl)nc(Cl)nc32)c1]

A solution of 7-(3,5-difluorophenyl)-6,7-dihydro-1H-cyclopenta[d]pyrimidine-2,4(3H,5H)-dione (740 mg, 2.80 mmol) in phosphoryl trichloride (7.691 mL, 84 mmol) was heated in microwave at 110° C. for 1 h. The reaction mixture was poured into ice. Once ice melted, the product was extracted with dichloromethane. The combined organic extracts were dried over anhydrous magnesium sulfate and filtered. The solvent was removed in vacuum and the residue was purified by column chromatography on silica gel to give 2,4-dichloro-7-(3,5-difluorophenyl)-6,7-dihydro-5H-cyclopenta[d]pyrimidine (200 mg, 0.664 mmol, 23.72% yield). LC-MS (M+H)$^+$=301.0.

Preparation Sa

2-Chloro-7-(3,5-difluorophenyl)-N-methyl-6,7-dihydro-5H-cyclopenta[d]pyrimidin-4-amine

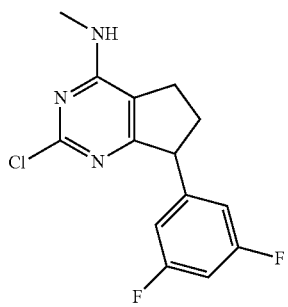 [SMILES: CNc1nc(Cl)nc2c1CCC2c1cc(F)cc(F)c1]

A solution of 2,4-dichloro-7-(3,5-difluorophenyl)-6,7-dihydro-5H-cyclopenta[d]pyrimidine (200 mg, 0.664 mmol) and methanamine (0.664 mL, 1.328 mmol) in MeOH (3 mL) was stirred at rt for 1 h. The solvent was removed in vacuum and the crude product was purified by column chromatography on silica gel to give 2-chloro-7-(3,5-difluorophenyl)-N-methyl-6,7-dihydro-5H-cyclopenta[d]pyrimidin-4-amine (60 mg, 0.203 mmol, 30.5% yield). LC-MS (M+H)$^+$=296.1.

Preparation T 2,4-Dichloro-7-(3,4,5-trifluorophenyl)-6,7-dihydro-5H-cyclopenta[d]pyrimidine

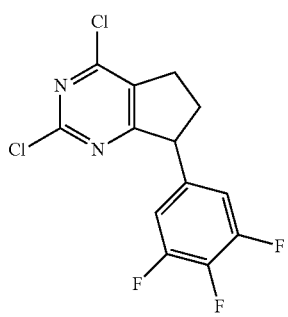 [SMILES: Fc1cc(C2CCc3c(Cl)nc(Cl)nc32)cc(F)c1F]

Intermediate T(1)

(1S,2R)-2-(3,4,5-Trifluorophenyl)cyclopentanol

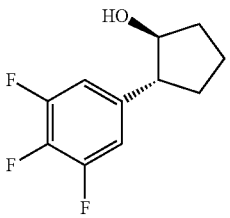 [SMILES: O[C@H]1CCC[C@@H]1c1cc(F)c(F)c(F)c1]

To a suspension of magnesium (2.88 g, 118 mmol) in THF (110 mL) was slowly added 5-bromo-1,2,3-trifluorobenzene (25 g, 118 mmol). After the addition, the reaction mixture was heated at reflux for 2 h. To this reaction mixture, copper (I) iodide (1.506 g, 7.91 mmol) and 6-oxabicyclo[3.1.0]hexane (9.93 g, 118 mmol) dissolved in THF (20 mL) were added dropwise. The reaction mixture warmed upon the addition of the epoxide. The reaction was stirred at rt for 2 h at rt. The reaction mixture was quenched by the addition of a solution of ammonium chloride. Ether was added and the organic layer was collected, dried (Na$_2$SO$_4$) and concentrated. The crude product was purified by column chromatography on silica gel to give (1S,2R)-2-(3,4,5-trifluorophenyl)cyclopentanol (20.2 g, 93 mmol, 79% yield).

$^1$H NMR (500 MHz, CDCl$_3$) δ ppm 6.79-7.02 (2H, m), 4.10-4.21 (1H, m), 2.75-2.91 (1H, m), 2.08-2.24 (2H, m), 1.75-1.93 (2H, m), 1.50-1.75 (2H, m).

Intermediate T(2)

2-(3,4,5-Trifluorophenyl)cyclopentanone

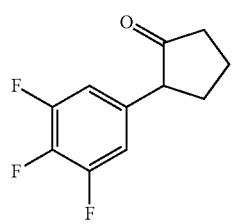

To a solution of (1S,2R)-2-(3,4,5-trifluorophenyl)cyclopentanol (1 g, 4.63 mmol) in CH$_2$Cl$_2$ (20 mL) was added Dess-Martin periodinane (2.354 g, 5.55 mmol). The reaction mixture was stirred at rt for 1 h. The reaction was diluted with dichloromethane and quenched with the addition of 1 N NaOH. The organic layer was collected, dried (Na$_2$SO$_4$) and concentrated. The crude product was purified by column chromatography on silica gel to afford 2-(3,4,5-trifluorophenyl)cyclopentanone (310 mg, 1.447 mmol, 31.3% yield). LC-MS (M+H)$^+$=215.1.

Intermediate T(3)

7-(3,4,5-Trifluorophenyl)-6,7-dihydrocyclopenta[e][1,3]oxazine-2,4(3H,5H)-dione

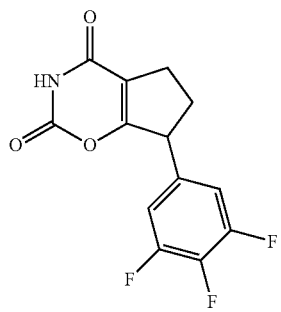 [SMILES: O=c1[nH]c(=O)c2c(o1)C(c1cc(F)c(F)c(F)c1)CC2]

A mixture of 2-(3,4,5-trifluorophenyl)cyclopentanone (2 g, 9.34 mmol) and carbonisocyanatidic chloride (1.773 g, 16.81 mmol) was heated at 58° C. for 1 h and at 130° C. for 2 h. Upon cooling to room temperature, the reaction mixture was dissolved in ethyl acetate and washed with saturated aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(3,4,5-trifluorophenyl)-6,7-dihydrocyclopenta[e][1,3]oxazine-2,4(3H,5H)-dione (1.227 g, 4.33 mmol, 46.4% yield). LC-MS (M+H)$^+$=284.0.

Intermediate T(4)

7-(3,4,5-Trifluorophenyl)-6,7-dihydro-1H-cyclopenta[d]pyrimidine-2,4(3H,5H)-dione

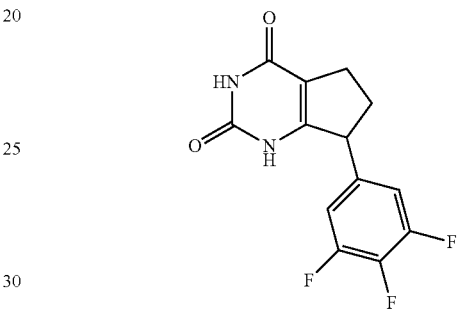

A solution of 7-(3,4,5-trifluorophenyl)-6,7-dihydrocyclopenta[e][1,3]oxazine-2,4(3H,5H)-dione (1.23 g, 4.34 mmol) in concentrated ammonium hydroxide (75 mL, 1926 mmol) was heated at 100° C. in a high-pressure (350 mL) vessel overnight. The reaction mixture was cooled and concentrated in vacuum to give crude 7-(3,4,5-trifluorophenyl)-6,7-dihydro-1H-cyclopenta[d]pyrimidine-2,4(3H,5H)-dione (1.3 g, 4.61 mmol, 106% yield). LC-MS (M+H)$^+$=283.0.

Preparation T 2,4-Dichloro-7-(3,4,5-trifluorophenyl)-6,7-dihydro-5H-cyclopenta[d]pyrimidine

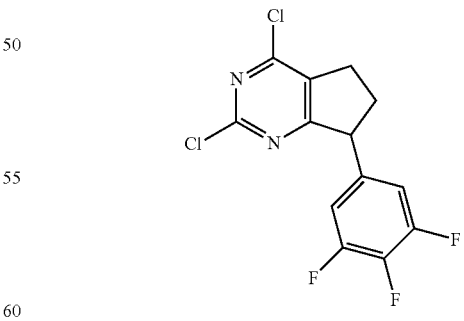

A solution of 7-(3,4,5-trifluorophenyl)-6,7-dihydro-1H-cyclopenta[d]pyrimidine-2,4(3H,5H)-dione (1.3 g, 4.61 mmol) in phosphoryl trichloride (5 mL, 54.6 mmol) was heated in microwave at 110° C. for 1 h. The reaction was repeated with an additional 800 mg of the starting material. The reaction mixtures was poured into ice and combined.

Once ice melted, the product was extracted with dichloromethane. The combined organic extracts were dried over anhydrous magnesium sulfate and filtered. The solvent was removed in vacuum and the residue was purified by column chromatography on silica gel to give 2,4-dichloro-7-(3,4,5-trifluorophenyl)-6,7-dihydro-5H-cyclopenta[d]pyrimidine (498 mg, 1.561 mmol, 33.9% yield). LC-MS (M+H)$^+$=318.9.

Preparation Ta

2-Chloro-N-methyl-7-(3,4,5-trifluorophenyl)-6,7-dihydro-5H-cyclopenta[d]pyrimidin-4-amine

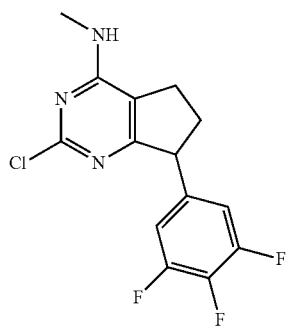 [SMILES: CNc1nc(Cl)nc2c1CCC2c1cc(F)c(F)c(F)c1]

A solution of 2,4-dichloro-7-(3,4,5-trifluorophenyl)-6,7-dihydro-5H-cyclopenta[d]pyrimidine (498 mg, 1.561 mmol) and methanamine (1.561 mL, 3.12 mmol) in MeOH (10 mL) was stirred at rt for 1 h. Incomplete reaction was observed. Additional portions of methanamine (1.561 mL, 3.12 mmol) were added to the reaction mixture until the reaction was complete. The solvent was removed in vacuum and the residue was purified by column chromatography on silica gel to give 2-chloro-7-(3,5-difluorophenyl)-N-methyl-6,7-dihydro-5H-cyclopenta[d]pyrimidin-4-amine (60 mg, 0.203 mmol, 30.5% yield). LC-MS (M+H)$^+$=314.0.

Preparation Tb

2-Chloro-4-(3,3-difluoropyrrolidin-1-yl)-7-(3,4,5-trifluorophenyl)-6,7-dihydro-5H-cyclopenta[d]pyrimidine

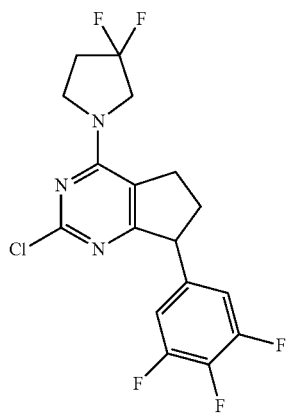 [SMILES: Fc1cc(C2CCc3c2nc(Cl)nc3N2CCC(F)(F)C2)cc(F)c1F]

A solution of 2,4-dichloro-7-(3,4,5-trifluorophenyl)-6,7-dihydro-5H-cyclopenta[d]pyrimidine (100 mg, 0.313 mmol), DIPEA (0.066 mL, 0.376 mmol) and 3,3-difluoropyrrolidine, HCl salt (45.0 mg, 0.313 mmol) were stirred at rt for 1 h. The solvent was removed in vacuum and the residue was purified by column chromatography on silica gel to give 2-chloro-4-(3,3-difluoropyrrolidin-1-yl)-7-(3,4,5-trifluorophenyl)-6,7-dihydro-5H-cyclopenta[d]pyrimidine (105 mg, 0.269 mmol, 86% yield). LC-MS (M+H)$^+$=390.0.

Preparation Tc

2-Chloro-4-(3,3-difluoroazetidin-1-yl)-7-(3,4,5-trifluorophenyl)-6,7-dihydro-5H-cyclopenta[d]pyrimidine

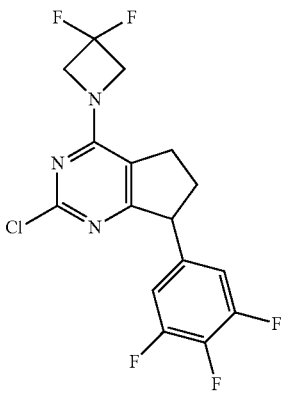 [SMILES: Fc1cc(C2CCc3c2nc(Cl)nc3N2CC(F)(F)C2)cc(F)c1F]

A solution of 2,4-dichloro-7-(3,4,5-trifluorophenyl)-6,7-dihydro-5H-cyclopenta[d]pyrimidine (100 mg, 0.313 mmol), DIPEA (0.109 mL, 0.627 mmol) and 3,3-difluoroazetidine, HCl salt (44.7 mg, 0.345 mmol) were stirred at rt for 1 h. The solvent was removed in vacuum and the residue was purified by column chromatography on silica gel to give 2-chloro-4-(3,3-difluoroazetidin-1-yl)-7-(3,4,5-trifluorophenyl)-6,7-dihydro-5H-cyclopenta[d]pyrimidine (105 mg, 0.279 mmol, 89% yield). LC-MS (M+H)$^+$=376.0.

Preparation U 2,4-Dichloro-7-(2,4-difluorophenyl)-6,7-dihydro-5H-cyclopenta[d]pyrimidine

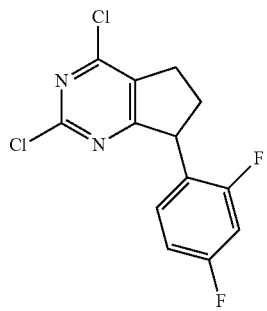 [SMILES: Fc1ccc(C2CCc3c(Cl)nc(Cl)nc32)c(F)c1]

Intermediate U(1)

1-Cyclopentenyl-2,4-difluorobenzene

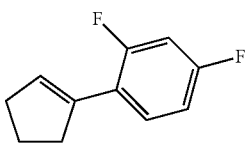 [SMILES: Fc1ccc(C2=CCCC2)c(F)c1]

To a 0.497M solution of (2,4-difluorophenyl)magnesium bromide (32.4 g, 149 mmol) in THF at 0° C. was carefully added cyclopentanone (13.23 mL, 149 mmol). Upon the end of the addition, the reaction mixture was heated at reflux for 2 h. Ice (10 g) and 6N aqueous hydrochloric acid were added. The reaction mixture was extracted with ether. The combined organic extracts were washed with a saturated aqueous solution of sodium hydrogen sulfite, a saturated aqueous solution of sodium bicarbonate and water. The organic layer was dried over anhydrous magnesium sulfate and filtered. The solvent was removed in vacuum and the residue was purified by column chromatography on silica gel to give 1-cyclopentenyl-2,4-difluorobenzene (7.064 g, 39.2 mmol, 26.3% yield) as colorless oil. LC-MS $(M+H)^+$=181.0. $^1$H NMR (500 MHz, CDCl$_3$) δ ppm 7.22-7.31 (1H, m), 6.75-6.85 (2H, m), 6.26-6.31 (1H, m), 2.68-2.74 (2H, m), 2.51-2.58 (2H, m), 1.93-2.02 (2H, m).

Intermediate U(2)

2-(2,4-Difluorophenyl)cyclopentanone

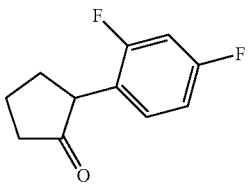 [SMILES: O=C1CCCC1c1ccc(F)cc1F]

A mixture of 90% formic acid (26.4 mL, 689 mmol) and 30% hydrogen peroxide (6.0 mL, 39.2 mmol) was warmed at 40° C. for 10 min. The resulting solution was carefully added to 1-cyclopentenyl-2,4-difluorobenzene (7.064 g, 39.2 mmol) under stirring. The two-phase system was initially stirred at room temperature. After a certain period of time, a spontaneous exothermic reaction took place, and the temperature rose to about 50° C. The reaction mixture was stirred at room temperature for 2 h. The reaction mixture was quenched by careful addition of a saturated sodium bicarbonate solution. Ether was added and the content of the separatory funnel was vigorously shaken. The organic layer was separated and the aqueous layer was extracted with ether. The combined organic extracts were dried over anhydrous magnesium sulfate and filtered. The solvent was removed in vacuum and the residue was purified by column chromatography on silica gel to give 2-(2,4-difluorophenyl)cyclopentanone (3.503 g, 17.85 mmol, 45.5% yield) as colorless oil. LC-MS $(M+H)^+$=195.2. $^1$H NMR (500 MHz, CDCl$_3$) δ ppm 7.08 (1H, td, J=8.4, 6.4 Hz), 6.76-6.86 (2H, m), 3.42 (1H, dd, J=12.2, 8.9 Hz), 2.42-2.53 (2H, m), 2.28-2.39 (1H, m), 2.13-2.23 (1H, m), 1.86-2.10 (2H, m).

Intermediate U(3)

7-(2,4-Difluorophenyl)-6,7-dihydrocyclopenta[e][1,3]oxazine-2,4(3H,5H)-dione

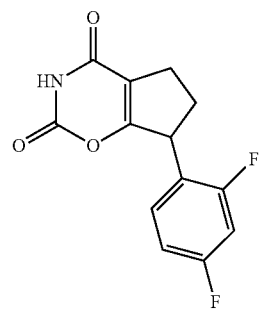 [SMILES: O=c1[nH]c(=O)c2c(o1)C(c1ccc(F)cc1F)CC2]

A mixture of 2-(2,4-difluorophenyl)cyclopentanone (1.014 g, 5.17 mmol) and 50% wt. carbonisocyanatidic chloride solution in toluene (1.963 g, 9.30 mmol) was heated at 58° C. for 1 h and at 120° C. for 3 h. The reaction mixture was dissolved in ethyl acetate and washed with an aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(2,4-difluorophenyl)-6,7-dihydrocyclopenta[e][1,3]oxazine-2,4(3H,5H)-dione (499.3 mg, 1.883 mmol, 36.4% yield) as brown solid. LC-MS $(M+H)^+$=266.2. $^1$H NMR (500 MHz, CDCl$_3$) δ ppm 8.19-8.64 (1H, m), 7.10 (1H, td, J=8.5, 6.3 Hz), 6.78-6.92 (2H, m), 4.36-4.49 (1H, m), 2.79-2.92 (1H, m), 2.59-2.78 (2H, m), 2.08 (1H, ddd, J=9.3, 6.9, 6.7 Hz).

Intermediate U(4)

7-(2,4-Difluorophenyl)-6,7-dihydro-1H-cyclopenta[d]pyrimidine-2,4(3H,5H)-dione

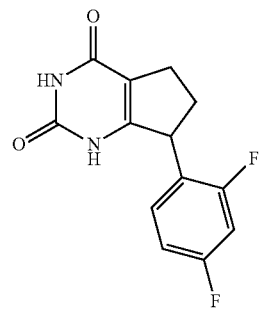 [SMILES: O=c1[nH]c2c(c(=O)[nH]1)CCC2c1ccc(F)cc1F]

A mixture of 2-(2,4-difluorophenyl)cyclopentanone (1.014 g, 5.17 mmol) and 50% wt. carbonisocyanatidic chloride solution in toluene (1.963 g, 9.30 mmol) was heated at 58° C. for 1 h and at 120° C. for 3 h. The reaction mixture was dissolved in ethyl acetate and washed with an aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(2,4-difluorophenyl)-6,7-dihydrocyclopenta[e][1,3]oxazine-2,4(3H,5H)-dione (499.3 mg, 1.883 mmol, 36.4% yield) as brown solid. LC-MS (M+H)$^+$= 265.1.

Preparation U 2,4-Dichloro-7-(2,4-difluorophenyl)-6,7-dihydro-5H-cyclopenta[d]pyrimidine

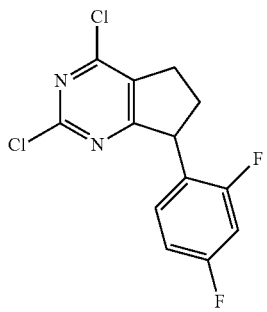

A solution of 7-phenyl-6,7-dihydro-1H-cyclopenta[d]pyrimidine-2,4(3H,5H)-dione (248.5 mg, 0.940 mmol) in phosphoryl trichloride (10 mL) was heated in microwave at 130° C. for 2 h. The reaction mixture was poured in a beaker with ice. Once ice melted, the product was extracted with dichloromethane. The combined organic extracts were dried over anhydrous magnesium sulfate and filtered. The solvent was removed in vacuum and the residue was purified by column chromatography on silica gel to give 2,4-dichloro-7-phenyl-6,7-dihydro-5H-cyclopenta[d]pyrimidine (267.9 mg, 95%) as light brown solid. LC-MS (M+H)$^+$=301.1.

Preparation Ua

2-Chloro-7-(2,4-difluorophenyl)-N-methyl-6,7-dihydro-5H-cyclopenta[d]pyrimidin-4-amine

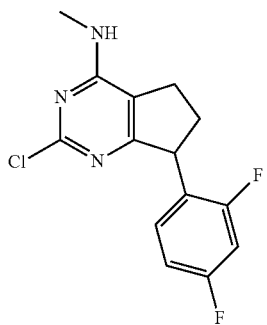 [SMILES: CNc1nc(Cl)nc2c1CCC2c1ccc(F)cc1F]

To a solution of 2,4-dichloro-7-(2,4-difluorophenyl)-6,7-dihydro-5H-cyclopenta[d]pyrimidine (267.9 mg, 0.890 mmol) in methanol (5 mL) was added a 2M solution of methylamine in methanol (0.890 mL, 1.779 mmol). The reaction mixture was stirred at room temperature overnight. The solvent was removed in vacuum and the residue was partitioned between ethyl acetate and water. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 2-chloro-7-(2,4-difluorophenyl)-N-methyl-6,7-dihydro-5H-cyclopenta[d]pyrimidin-4-amine (184.6 mg, 0.624 mmol, 70.2% yield) as brown solid. LC-MS (M+H)$^+$=296.1.

Preparation V 2,4-dichloro-7-methyl-7-phenyl-6,7-dihydro-5H-cyclopenta[d]pyrimidine

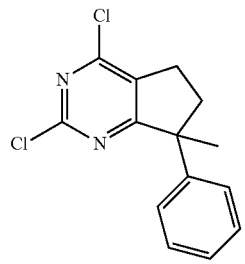 [SMILES: CC1(c2ccccc2)CCc2c(Cl)nc(Cl)nc21]

Intermediate V(1)

2-methyl-2-phenylcyclopentanone

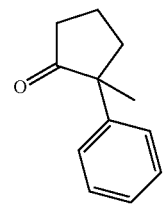

To a slurry of 60% NaH (125 mg, 3.12 mmol) in DME (3571 mL) at 0° C. was added 2-phenylcyclopentanone (500 mg, 3.12 mmol). After stirring for 1 h, MeI (898 µL, 14.36 mmol) was added, and the solution heated to reflux for 2 h. The reaction was poured onto ice and extracted 3 times into Et2O. The organic extracts were washed with brine, dried over MgSO4, filtered and concentrated in vacuo. Applied to Silica gel and eluted with an EtOAc/Hex gradient to afford 2-methyl-2-phenylcyclopentanone (401.7 mg, 2.305 mmol, 73.9% yield). LC-MS (M+H)$^+$=175.1. $^1$H NMR (500 MHz, CDCl$_3$) δ ppm 7.29-7.37 (4 H, m), 7.20-7.24 (1 H, m), 2.54 (1 H, dt, J=12.51, 6.26 Hz), 2.34 (2H, t, J=7.63 Hz), 1.82-2.05 (3 H, m), 1.38 (3 H, s).

Intermediate V(2)

7-methyl-7-phenyl-6,7-dihydrocyclopenta[e][1,3]oxazine-2,4(3H,5H)-dione

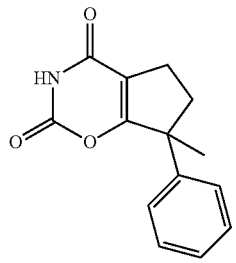 [SMILES: CC1(c2ccccc2)CCc2c1oc(=O)[nH]c2=O]

Combined 2-methyl-2-phenylcyclopentanone (Intermediate V(1) (705.5 mg, 4.05 mmol) and carbonisocyanatidic chloride (1700 mg, 8.06 mmol), flushed with N2, and sealed in a sealed tube. Heated at 58° C. for 1 h, then 130° C. for 1.75 h. Let cool to rt. Carefully opened the tube (HCl), and dissolved the residue in EtOAc. Partitioned with NaHCO3 (aq), and extracted 3 times into EtOAc. Washed combined organic layers with brine, dried over MgSO4, filtered, and concentrated in vacuo. Loaded the residue onto Silica gel and eluted with an EtOAc/Hexane gradient to afford 7-methyl-7-phenyl-6,7-dihydrocyclopenta[e][1,3]oxazine-2,4(3H,5H)-dione (43% yield) LC-MS (M+H)$^+$=244.1. $^1$H NMR (500 MHz, CDCl$_3$) δ ppm 8.12 (1 H, br. s.), 7.32-7.38 (2 H, m), 7.26-7.30 (3 H, m), 2.69-2.75 (2 H, m), 2.43-2.52 (1 H, m), 2.21-2.29 (1 H, m), 1.68 (3 H, s).

Intermediate V(3)

7-methyl-7-phenyl-6,7-dihydro-1H-cyclopenta[d]pyrimidine-2,4(3H,5H)-dione

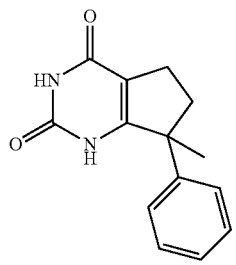 [SMILES: CC1(c2ccccc2)CCc2c1[nH]c(=O)[nH]c2=O]

To solid 7-methyl-7-phenyl-6,7-dihydrocyclopenta[e][1,3]oxazine-2,4(3H,5H)-dione (420 mg, 1.727 mmol) was added concentrated Ammonium Hydroxide (4706 µL, 121 mmol) in a sealed tube. The tube was heated for 4 h at 80° C. Cooled to rt. Removed the solvent under a stream of N2. Loaded the residue onto Silica gel and eluted with an EtOAc/Hexane gradient to afford 7-methyl-7-phenyl-6,7-dihydro-1H-cyclopenta[d]pyrimidine-2,4(3H,5H)-dione (293 mg, 1.209 mmol, 70.0% yield). LC-MS (M+H)$^+$=243.1.

Preparation V 2,4-dichloro-7-methyl-7-phenyl-6,7-dihydro-5H-cyclopenta[d]pyrimidine

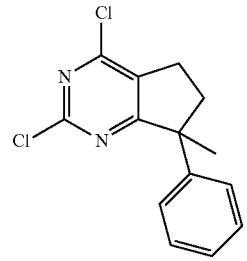 [SMILES: CC1(c2ccccc2)CCc2c(Cl)nc(Cl)nc21]

Dissolved 7-methyl-7-phenyl-6,7-dihydro-1H-cyclopenta[d]pyrimidine-2,4(3H,5H)-dione (48.2 mg, 0.199 mmol) in POCl$_3$ (742 µL, 7.96 mmol) and placed in a microwave vial. Heated the reaction for 1 h at 120° C. in the microwave. Cooled to rt, and poured into ice. As soon as the ice melted, extracted 3 times into EtOAc. Dried over MgSO4, filtered, and concentrated in vacuo. A quick EtOAc/Hex SG column provided 2,4-dichloro-7-methyl-7-phenyl-6,7-dihydro-5H-cyclopenta[d]pyrimidine (43.1 mg, 0.154 mmol, 78% yield). LC-MS (M+H)$^+$=279.1.

Preparation Va 2-chloro-N-ethyl-7-methyl-7-phenyl-6,7-dihydro-5H-cyclopenta[d]pyrimidin-4-amine

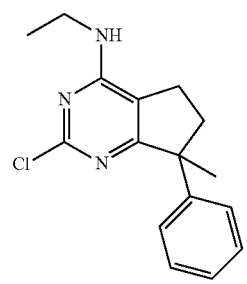 [SMILES: CCNc1nc(Cl)nc2c1CCC2(C)c1ccccc1]

To a solution of 2,4-dichloro-7-methyl-7-phenyl-6,7-dihydro-5H-cyclopenta[d]pyrimidine (Preparation V) (43.1 mg, 0.154 mmol) in THF (772 µL) at rt was added a solution of 2M Ethylamine (386 µL, 0.772 mmol) diluted with 390 uL MeOH (overall reaction is 0.1M in 1:1 THF/MeOH). Let stir at rt. Removed the solvent and subjected the residue to a Silica gel column with an EtOAc/Hex gradient to afford 2-chloro-N-ethyl-7-methyl-7-phenyl-6,7-dihydro-5H-cyclopenta[d]pyrimidin-4-amine (38.0 mg, 0.132 mmol, 86% yield).

Preparation W 2,4-dichloro-7-allyl-7-phenyl-6,7-dihydro-5H-cyclopenta[d]pyrimidine

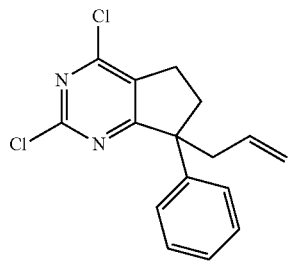 [SMILES: C=CCC1(c2ccccc2)CCc2c(Cl)nc(Cl)nc21]

Intermediate W(1)

2-allyl-2-phenylcyclopentanone

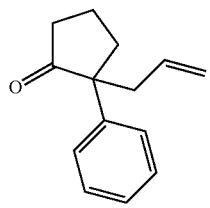

The procedure of Intermediate V(1) was utilized with allyl bromide to obtain 2-allyl-2-phenylcyclopentanone.

Intermediate W(2)

7-allyl-7-phenyl-6,7-dihydrocyclopenta[e][1,3]oxazine-2,4(3H,5H)-dione

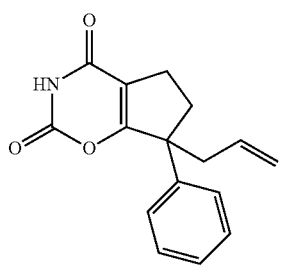 [SMILES: C=CCC1(c2ccccc2)CCc2c1oc(=O)[nH]c2=O]

The method of Intermediate V(2) was utilized to obtain 7-allyl-7-phenyl-6,7-dihydrocyclopenta[e][1,3]oxazine-2,4(3H,5H)-dione.

$^1$H NMR (500 MHz, CDCl$_3$) δ ppm 8.06 (1 H, br. s.), 7.23-7.43 (5 H, m), 5.59-5.72 (1H, m, J=17.09, 9.99, 7.21, 7.21 Hz), 5.08-5.23 (2 H, m), 2.73-2.87 (2 H, m), 2.63-2.71 (2 H, m), 2.38-2.49 (2 H, m)

Intermediate W(3)

7-allyl-7-phenyl-6,7-dihydro-1H-cyclopenta[d]pyrimidine-2,4(3H,5H)-dione

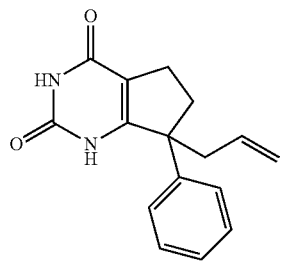 [SMILES: C=CCC1(c2ccccc2)CCc2c1[nH]c(=O)[nH]c2=O]

The method of Intermediate V(3) was utilized to obtain 7-allyl-7-phenyl-6,7-dihydro-1H-cyclopenta[d]pyrimidine-2,4(3H,5H)-dione. LC-MS (M+H)$^+$=269.1.

Preparation W 2,4-dichloro-7-allyl-7-phenyl-6,7-dihydro-5H-cyclopenta[d]pyrimidine

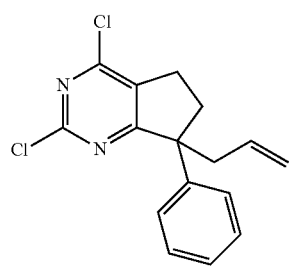 [SMILES: C=CCC1(c2ccccc2)CCc2c(Cl)nc(Cl)nc21]

The method of Preparation V was used to obtain 2,4-dichloro-7-allyl-7-phenyl-6,7-dihydro-5H-cyclopenta[d]pyrimidine. LC-MS (M+H)$^+$=305.0.

Preparation Wa 2-chloro-N-ethyl-7-allyl-7-phenyl-6,7-dihydro-5H-cyclopenta[d]pyrimidin-4-amine

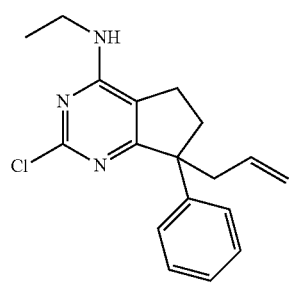 [SMILES: C=CCC1(c2ccccc2)CCc2c(NCC)nc(Cl)nc21]

Utilizing the procedure for Preparation Va, 2-chloro-N-ethyl-7-allyl-7-phenyl-6,7-dihydro-5H-cyclopenta[d]pyrimidin-4-amine was obtained. LC-MS (M+H)+=314.1.

Preparation X 2,4-dichloro-8-(3,5-difluorophenyl)-7,8-dihydro-5H-pyrano[4,3-d]pyrimidine

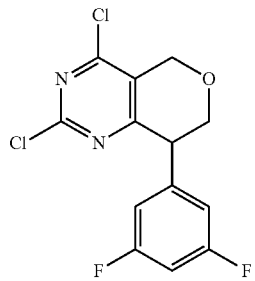 [SMILES: Fc1cc(F)cc(C2COCc3c(Cl)nc(Cl)nc32)c1]

Intermediate X(1)

3-iodo-4,4-dimethoxytetrahydro-2H-pyran

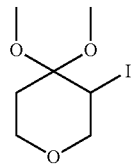

The mixture of trimethoxymethane (82 mL, 745 mmol) and dihydro-2H-pyran-4(3H)-one (14.92 g, 149 mmol) was cooled to 4° C. Added diiodine (37.8 g, 149 mmol) in lots and keep the temperature between 4° C. and 5° C. The reaction mixture was stirred at 4° C. for 10 min. Cooling bath was removed, stirred at 28° C. for 10 min. The mixture was cooled to 10° C. and stirred for 10 min, and then stirred at RT for 1 h.

The reaction mixture was diluted with $CH_2Cl_2$ and cooled in ice water. Slowly quenched with saturated $Na_2S_2O_3$ solution. The mixed layers were separated. The aqueous layer was extracted with $CH_2Cl_2$. The combined organic layer was washed with brine, dried over Na2SO4 and concentrated. The crude product was purified by column chromatography on silica gel to give 3-iodo-4,4-dimethoxytetrahydro-2H-pyran (33.05 g, 121 mmol, 82% yield). $^1$H NMR (500 MHz, CDCl$_3$) δ ppm 4.24 (1 H, t, J=2.29 Hz), 3.93-4.02 (1 H, m), 3.83-3.92 (2 H, m), 3.55 (1 H, d, J=2.44 Hz), 3.24 (3 H, s), 3.20 (3 H, s), 2.33 (1 H, dd, J=4.88, 2.14 Hz), 1.79 (1 H, dd, J=14.34, 2.44 Hz)

Intermediate X(2)

3-(3,5-difluorophenyl)dihydro-2H-pyran-4(3H)-one

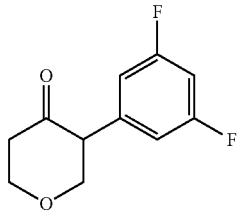 [SMILES: O=C1CCOCC1c1cc(F)cc(F)c1]

To a mixture of (1R,2R)-2-aminocyclohexanol hydrochloride (0.418 g, 2.76 mmol), nickel(II) chloride hexahydrate (0.328 g, 1.378 mmol) and 3,5-difluorophenylboronic acid (6.53 g, 41.3 mmol) was added NaHMDS in THF (55.1 mL, 55.1 mmol) at 10° C. dropwise under $N_2$. After addition, the mixture was stirred at 10° C. for 20 min. 2-Propanol (113 mL) (previously bubbled by N2) was added at 0° C. and then the mixture was stirred at RT for 10 min. 3-iodo-4,4-dimethoxytetrahydro-2H-pyran (Preparation X1) (7.5 g, 27.6 mmol). in THF was added dropwise and the mixture was heated at 60° C. overnight. The reaction mixture was cooled in ice bath, added 1.0HCl until acidic and stirred for 10 min. Concentrated in vacuum. Extracted with EtOAc and the organic layer was washed with brine and concentrated. The residue was purified by column chromatography on silica gel to give 3-(3,5-difluorophenyl)dihydro-2H-pyran-4(3H)-one (1.6 g, 7.54 mmol, 27.4% yield). $^1$H NMR (500 MHz, CDCl$_3$) δ ppm 6.78 (dd, J=8.24, 2.14 Hz, 2 H) 6.62-6.75 (m, 1 H) 4.21 (dd, J=11.44, 5.65 Hz, 2 H) 3.85-4.01 (m, 2 H) 3.76 (dd, J=8.55, 6.10 Hz, 1 H) 2.60-2.75 (m, 1 H) 2.48-2.60 (m, 1 H)

Intermediate X(3)

8-(3,5-difluorophenyl)-7,8-dihydropyrano[3,4-e][1,3]oxazine-2,4(3H,5H)-dione

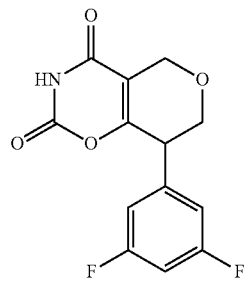 [SMILES: O=c1[nH]c(=O)c2c(o1)C(c1cc(F)cc(F)c1)COC2]

The mixture of 3-(3,5-difluorophenyl)dihydro-2H-pyran-4(3H)-one (Preparation X2) (800 mg, 3.77 mmol) and carbonisocyanatidic chloride (557 mg, 5.28 mmol) was heated in a sealed bottle at 55° C. for 1 h and then at 130° C. for 2 h. The mixture was cooled to RT. Partition between EtOAc and saturated NaHCO$_3$ solution. Extracted with EtOAc(×3 times). The combined organic layers was washed with brine, dried over Na$_2$SO$_4$ and concentrated. The crude product was purified by column chromatography on silica gel to give 8-(3,5-difluorophenyl)-7,8-dihydropyrano[3,4-e][1,3]oxazine-2,4(3H,5H)-dione (230 mg, 0.818 mmol, 21.69% yield). LC-MS (M+H)⁺=282.0. ¹H NMR (500 MHz, CDCl₃) δ ppm 8.94 (br, s., 1 H) 6.85-7.01 (m, 2 H) 6.81 (tt, J=8.81, 2.17 Hz, 1 H) 4.70 (d, J=15.56 Hz, 1 H) 4.49 (dd, J=15.56, 2.14 Hz, 1 H) 4.03-4.12 (m, 2 H) 3.68 (br. s., 1 H)

Intermediate X(4)

8-(3,5-difluorophenyl)-7,8-dihydro-1H-pyrano[4,3-d]pyrimidine-2,4(3H,5H)-dione

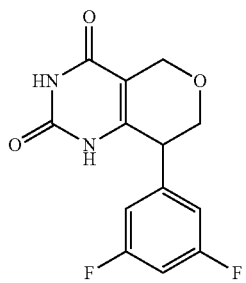

The mixture of 8-(3,5-difluorophenyl)-7,8-dihydropyrano[3,4-e][1,3]oxazine-2,4(3H,5H)-dione (Preparation X3) (230 mg, 0.818 mmol) and ammonium hydroxide (2229 μL, 57.3 mmol) in a sealed bottle was heated at 80° C. for 4 h. Blowed by N2 overnight to get 8-(3,5-difluorophenyl)-7,8-dihydro-1H-pyrano[4,3-d]pyrimidine-2,4(3H,5H)-dione (191 mg, 0.682 mmol, 83% yield) which was used as is. LC-MS (M+H)⁺=281.1.

Preparation X 2,4-dichloro-8-(3,5-difluorophenyl)-7,8-dihydro-5H-pyrano[4,3-d]pyrimidine

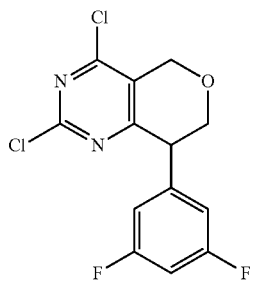 [SMILES: Fc1cc(F)cc(C2COCc3c(Cl)nc(Cl)nc32)c1]

The mixture of 8-(3,5-difluorophenyl)-7,8-dihydro-1H-pyrano[4,3-d]pyrimidine-2,4(3H,5H)-dione (Intermediate X(4)) (191 mg, 0.682 mmol) and POCl₃ (1906 μL, 20.45 mmol) in a microwave vial was heated by microwave at 100° C. for 2.5 h. The mixture was poured on ice, as long as ice was melted, extracted with EtOAc (×3 times), washed with brine, dried over Na₂SO₄ and concentrated. The crude product was purified by column chromatography on silica gel to give 2,4-dichloro-8-(3,5-difluorophenyl)-7,8-dihydro-5H-pyrano[4,3-d]pyrimidine (117 mg, 0.369 mmol, 54.1% yield). LC-MS (M+H)⁺=317.1. ¹H NMR (400 MHz, CDCl₃) δ ppm 6.66-6.91 (m, 3 H) 4.87-5.01 (m, 1 H) 4.70-4.83 (m, 1 H) 4.13-4.27 (m, 2 H) 4.10 (t, J=4.03 Hz, 1 H)

Preparation Xa 2-chloro-8-(3,5-difluorophenyl)-N-ethyl-7,8-dihydro-5H-pyrano[4,3-d]pyrimidin-4-amine

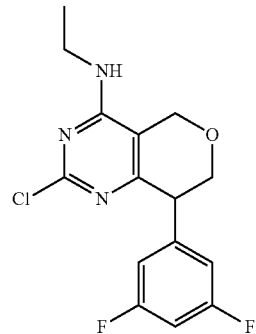 [SMILES: CCNc1nc(Cl)nc2c1COCC2c1cc(F)cc(F)c1]

The mixture of ethanamine (406 μL, 0.812 mmol), 2,4-dichloro-8-(3,5-difluorophenyl)-7,8-dihydro-5H-pyrano[4,3-d]pyrimidine (Preparation X) (117 mg, 0.369 mmol) and DIEA (161 μL, 0.922 mmol) in THF (1845 μL) was stirred at RT for 2 h. The mixture was concentrated and purified by column chromatography on silica gel to give 2-chloro-8-(3,5-difluorophenyl)-N-ethyl-7,8-dihydro-5H-pyrano[4,3-d]pyrimidin-4-amine (104 mg, 0.319 mmol, 87% yield). LC-MS (M+H)⁺=326.1.

Preparation Y 2,4-dichloro-8-(3,4-difluorophenyl)-7,8-dihydro-5H-pyrano[4,3-d]pyrimidine

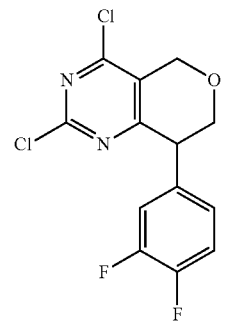 [SMILES: Fc1ccc(C2COCc3c(Cl)nc(Cl)nc32)cc1F]

Intermediate Y(2)

3-(3,4-difluorophenyl)dihydro-2H-pyran-4(3H)-one

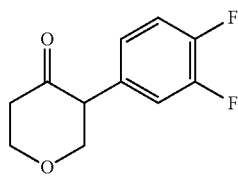 [SMILES: O=C1CCOCC1c1ccc(F)c(F)c1]

3,4-difluorophenylboronic acid was reacted as described in Intermediate X(2) with 3-iodo-4,4-dimethoxytetrahydro-2H-pyran (Intermediate X(1)) to give 3-(3,4-difluorophenyl)dihydro-2H-pyran-4(3H)-one (Intermediate Y(2)).

¹H NMR (500 MHz, CDCl₃) δ ppm 7.03-7.22 (m, 2 H) 6.95 (ddd, J=6.33, 4.20, 1.98 Hz, 1 H) 4.17-4.32 (m, 2 H) 3.96 (ddd, J=11.52, 9.84, 3.97 Hz, 1 H) 3.91 (dd, J=11.44, 9.00 Hz, 1 H) 3.77 (dd, J=8.85, 5.80 Hz, 1 H) 2.63-2.76 (m, 1 H) 2.49-2.62 (m, 1 H).

Intermediate Y(3)

8-(3,4-difluorophenyl)-7,8-dihydropyrano[3,4-e][1,3]oxazine-2,4(3H,5H)-dione

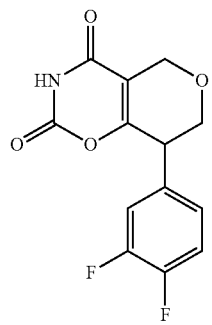 [SMILES: O=c1[nH]c(=O)c2c(o1)C(c1ccc(F)c(F)c1)COC2]

3-(3,4-difluorophenyl)dihydro-2H-pyran-4(3H)-one (Intermediate Y(2)) was reacted as described in Intermediate X(3) with carbonisocyanatidic chloride to give 8-(3,4-difluorophenyl)-7,8-dihydropyrano[3,4-e][1,3]oxazine-2,4(3H,5H)-dione (Intermediate Y(3)). LC-MS (M+H)⁺=282.1. ¹H NMR (500 MHz, CDCl₃) δ ppm 7.08-7.20 (m, 3 H) 4.67 (d, J=15.26 Hz, 1 H) 4.46 (dd, J=15.56, 2.14 Hz, 1 H) 3.98-4.10 (m, 2 H) 3.67 (br. s., 1 H).

Intermediate Y(4)

8-(3,4-difluorophenyl)-7,8-dihydro-1H-pyrano[4,3-d]pyrimidine-2,4(3H,5H)-dione

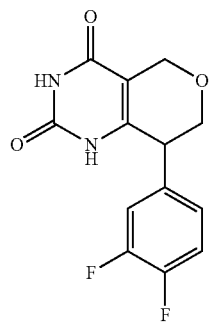 [SMILES: O=c1[nH]c2c(c(=O)[nH]1)COCC2c1ccc(F)c(F)c1]

8-(3,4-difluorophenyl)-7,8-dihydropyrano[3,4-e][1,3]oxazine-2,4(3H,5H)-dione (Intermediate Y(3)) was reacted as described in Intermediate X(4) with ammonium hydroxide to give 8-(3,4-difluorophenyl)-7,8-dihydro-1H-pyrano[4,3-d]pyrimidine-2,4(3H,5H)-dione (Intermediate Y(4)). LC-MS (M−H)⁺=279.1.

Preparation Y 2,4-dichloro-8-(3,4-difluorophenyl)-7,8-dihydro-5H-pyrano[4,3-d]pyrimidine

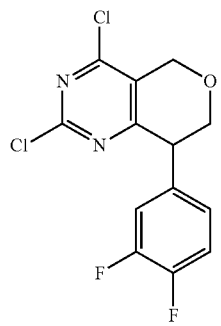 [SMILES: Fc1ccc(C2COCc3c(Cl)nc(Cl)nc32)cc1F]

2,4-dichloro-8-(3,4-difluorophenyl)-7,8-dihydro-5H-pyrano[4,3-d]pyrimidine (Intermediate Y(4)) was reacted as described in Preparation X with POCl₃ to give 2,4-dichloro-8-(3,4-difluorophenyl)-7,8-dihydro-5H-pyrano[4,3-d]pyrimidine (Preparation Y). LC-MS (M+H)⁺=317.1.

Preparation Ya 2-chloro-8-(3,4-difluorophenyl)-N-ethyl-7,8-dihydro-5H-pyrano[4,3-d]pyrimidin-4-amine

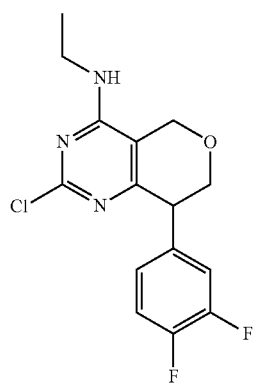 [SMILES: CCNc1nc(Cl)nc2c1COCC2c1ccc(F)c(F)c1]

2,4-dichloro-8-(3,4-difluorophenyl)-7,8-dihydro-5H-pyrano[4,3-d]pyrimidine (Preparation Y) was reacted as described in Preparation Xa with ethanamine to give 2-chloro-8-(3,4-difluorophenyl)-N-ethyl-7,8-dihydro-5H-pyrano[4,3-d]pyrimidin-4-amine (Preparation Ya). LC-MS (M+H)⁺=326.1.

Preparation Yb 2-chloro-4-(3,3-difluoroazetidin-1-yl)-8-(3,4-difluorophenyl)-7,8-dihydro-5H-pyrano[4,3-d]pyrimidine

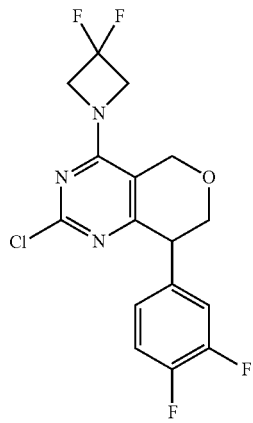 [SMILES: Fc1ccc(C2COCc3c2nc(Cl)nc3N2CC(F)(F)C2)cc1F]

2,4-dichloro-8-(3,4-difluorophenyl)-7,8-dihydro-5H-pyrano[4,3-d]pyrimidine (Preparation Y) was reacted as described in Preparation Xa with 3,3-difluoroazetidine, HCl to give 2-chloro-4-(3,3-difluoroazetidin-1-yl)-8-(3,4-difluorophenyl)-7,8-dihydro-5H-pyrano[4,3-d]pyrimidine (Preparation Yb). LC-MS (M+H)$^+$=374.1.

Preparation Yc 2-chloro-8-(3,4-difluorophenyl)-N-methyl-7,8-dihydro-5H-pyrano[4,3-d]pyrimidin-4-amine

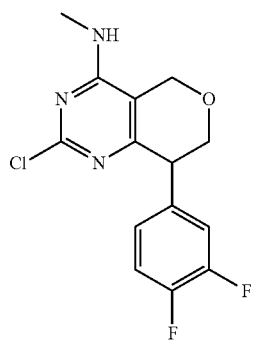 [SMILES: CNc1nc(Cl)nc2c1COCC2c1ccc(F)c(F)c1]

2,4-dichloro-8-(3,4-difluorophenyl)-7,8-dihydro-5H-pyrano[4,3-d]pyrimidine (Preparation Y) was reacted as described in Preparation Xa with methanamine to give 2-chloro-8-(3,4-difluorophenyl)-N-methyl-7,8-dihydro-5H-pyrano[4,3-d]pyrimidin-4-amine (Preparation Yc). LC-MS (M+H)$^+$=312.3.

Preparation Z 2,4-dichloro-8-(4-(trifluoromethyl)phenyl)-7,8-dihydro-5H-pyrano[4,3-d]pyrimidine

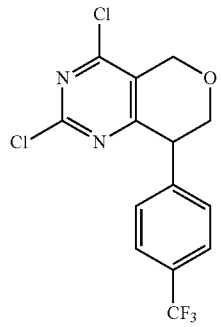 [SMILES: FC(F)(F)c1ccc(C2COCc3c(Cl)nc(Cl)nc32)cc1]

Intermediate Z(2)

3-(4-(trifluoromethyl)phenyl)dihydro-2H-pyran-4(3H)-one

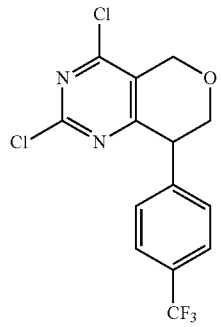 [SMILES: FC(F)(F)c1ccc(C2COCc3c(Cl)nc(Cl)nc32)cc1]

4-(trifluoromethyl)phenylboronic acid was reacted as described in Intermediate X(2) with 3-iodo-4,4-dimethoxytetrahydro-2H-pyran (Intermediate X(1)) to give 3-(4-(trifluoromethyl)phenyl)dihydro-2H-pyran-4(3H)-one (Intermediate Z(2)).

$^1$H NMR (500 MHz, CDCl$_3$) δ ppm 7.61 (m, J=8.24 Hz, 2 H) 7.37 (m, J=7.93 Hz, 2 H) 4.26 (dd, J=11.44, 5.95 Hz, 2 H) 3.93-4.05 (m, 2 H) 3.82-3.93 (m, 1 H) 2.64-2.81 (m, 1 H) 2.49-2.64 (m, 1 H)

Intermediate Z(3)

8-(4-(trifluoromethyl)phenyl)-7,8-dihydropyrano[3,4-e][1,3]oxazine-2,4(3H,5H)-dione

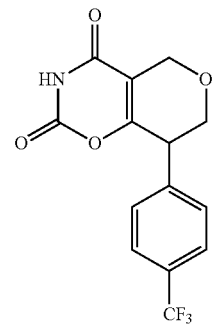 [SMILES: O=c1[nH]c(=O)c2c(o1)C(c1ccc(C(F)(F)F)cc1)COC2]

3-(4-(trifluoromethyl)phenyl)dihydro-2H-pyran-4(3H)-one (Intermediate Z(2)) was reacted as described in Intermediate X(3) with carbonisocyanatidic chloride to give 8-(4-(trifluoromethyl)phenyl)-7,8-dihydropyrano[3,4-e][1,3]oxazine-2,4(3H,5H)-dione (Intermediate Z(3)).

$^1$H NMR (500 MHz, CDCl$_3$) δ ppm 9.47 (br. s., 1 H) 7.58-7.75 (m, 2 H) 7.42-7.55 (m, 2 H) 4.68 (d, J=15.56 Hz, 1 H) 4.42-4.57 (m, 1 H) 4.03-4.22 (m, 2 H) 3.79 (br. s., 1 H)

Intermediate Z(4)

8-(4-(trifluoromethyl)phenyl)-7,8-dihydro-1H-pyrano[4,3-d]pyrimidine-2,4(3H,5H)-dione

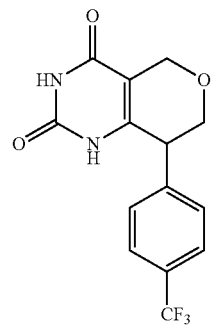 [SMILES: O=c1[nH]c2c(c(=O)[nH]1)COCC2c1ccc(C(F)(F)F)cc1]

8-(4-(trifluoromethyl)phenyl)-7,8-dihydropyrano[3,4-e][1,3]oxazine-2,4(3H,5H)-dione (Intermediate Z(3)) was reacted as described in Intermediate X(4) with ammonium hydroxide to give 8-(4-(trifluoromethyl)phenyl)-7,8-dihydro-1H-pyrano[4,3-d]pyrimidine-2,4(3H,5H)-dione (Intermediate Z(4)). LC-MS (M−H)$^+$=313.1.

Preparation Z 2,4-dichloro-8-(4-(trifluoromethyl)phenyl)-7,8-dihydro-5H-pyrano[4,3-d]pyrimidine

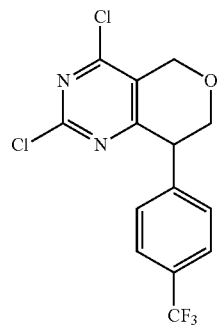 [SMILES: FC(F)(F)c1ccc(C2COCc3c(Cl)nc(Cl)nc32)cc1]

8-(4-(trifluoromethyl)phenyl)-7,8-dihydro-1H-pyrano[4,3-d]pyrimidine-2,4(3H,5H)-dione (Intermediate Z(4)) was reacted as described in Preparation X with POCl$_3$ to give 2,4-dichloro-8-(4-(trifluoromethyl)phenyl)-7,8-dihydro-5H-pyrano[4,3-d]pyrimidine (Preparation Z). LC-MS (M+H)$^+$=349.1.

Preparation Za 2-chloro-N-ethyl-8-(4-(trifluoromethyl)phenyl)-7,8-dihydro-5H-pyrano[4,3-d]pyrimidin-4-amine

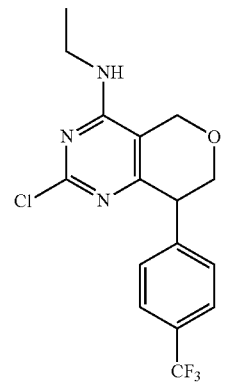 [SMILES: CCNc1nc(Cl)nc2c1COCC2c1ccc(C(F)(F)F)cc1]

2,4-dichloro-8-(4-(trifluoromethyl)phenyl)-7,8-dihydro-5H-pyrano[4,3-d]pyrimidine (Preparation Z) was reacted as described in Preparation Xa with ethanamine to give 2-chloro-N-ethyl-8-(4-(trifluoromethyl)phenyl)-7,8-dihydro-5H-pyrano[4,3-d]pyrimidin-4-amine (Preparation Za). LC-MS (M+H)$^+$=358.1.

Preparation Zb 2-chloro-N-methyl-8-(4-(trifluoromethyl)phenyl)-7,8-dihydro-5H-pyrano[4,3-d]pyrimidin-4-amine

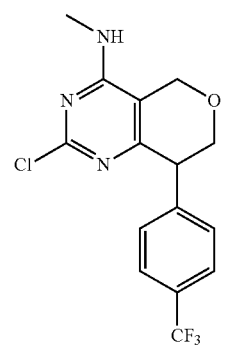 [SMILES: CNc1nc(Cl)nc2c1COCC2c1ccc(C(F)(F)F)cc1]

2,4-dichloro-8-(4-(trifluoromethyl)phenyl)-7,8-dihydro-5H-pyrano[4,3-d]pyrimidine (Preparation Z) was reacted as described in Preparation Xa with methanamine to give 2-chloro-N-methyl-8-(4-(trifluoromethyl)phenyl)-7,8-dihydro-5H-pyrano[4,3-d]pyrimidin-4-amine (Preparation Zb). LC-MS (M+H)$^+$=344.1.

Preparation Zc 2-chloro-N-((R)-1-cyclopropylethyl)-8-(4-(trifluoromethyl)phenyl)-7,8-dihydro-5H-pyrano[4,3-d]pyrimidin-4-amine

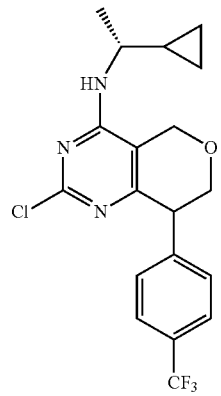 [SMILES: C[C@@H](Nc1nc(Cl)nc2c1COCC2c1ccc(C(F)(F)F)cc1)C1CC1]

2,4-dichloro-8-(4-(trifluoromethyl)phenyl)-7,8-dihydro-5H-pyrano[4,3-d]pyrimidine (Preparation Z) was reacted as described in Preparation Xa with (R)-1-cyclopropylethanamine, HCl to give 2-chloro-N-((R)-1-cyclopropylethyl)-8-(4-(trifluoromethyl)phenyl)-7,8-dihydro-5H-pyrano[4,3-d]pyrimidin-4-amine (Preparation Zc). LC-MS (M+H)$^+$=398.2.

Preparation AAa 4-(2-chloro-4-(ethylamino)-7,8-dihydro-5H-pyrano[4,3-d]pyrimidin-8-yl)benzonitrile

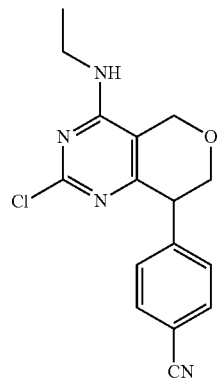 [SMILES: CCNc1nc(Cl)nc2c1COCC2c1ccc(C#N)cc1]

Intermediate AA(2)

4-(4-oxotetrahydro-2H-pyran-3-yl)benzonitrile

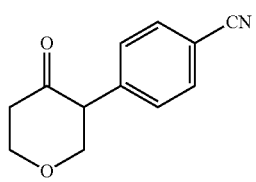 [SMILES: N#Cc1ccc(C2COCCC2=O)cc1]

4-cyanophenylboronic acid was reacted as described in Intermediate X(2) with 3-iodo-4,4-dimethoxytetrahydro-2H-pyran (Intermediate X(1)) to give 4-(4-oxotetrahydro-2H-pyran-3-yl)benzonitrile (Intermediate AA(2)). LC-MS (M+H)$^+$=202.1. $^1$H NMR (500 MHz, CDCl$_3$) δ ppm 7.66 (d, J=8.24 Hz, 2 H) 7.38 (d, J=8.55 Hz, 2 H) 4.23-4.31 (m, 2 H) 3.94-4.02 (m, 2 H) 3.85-3.92 (m, 1 H) 2.55-2.65 (m, 1 H) 2.52 (t, J=5.80 Hz, 1 H).

Intermediate AA(3)

4-(2,4-dioxo-2,3,4,5,7,8-hexahydropyrano[3,4-e][1,3]oxazin-8-yl)benzonitrile

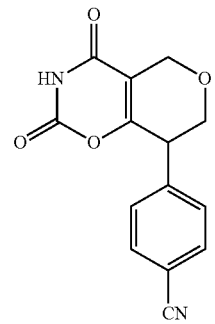 [SMILES: N#Cc1ccc(C2COCc3c2oc(=O)[nH]c3=O)cc1]

4-(4-oxotetrahydro-2H-pyran-3-yl)benzonitrile (Intermediate AA(2)) was reacted as described in Intermediate X(3) with carbonisocyanatidic chloride to give 4-(2,4-dioxo-2,3,4,5,7,8-hexahydropyrano[3,4-e][1,3]oxazin-8-yl)benzonitrile (Intermediate AA(3)). LC-MS (M+H)$^+$=271.1. $^1$H NMR (400 MHz, CDCl$_3$) δ ppm 7.57-7.78 (m, 2 H) 7.41-7.51 (m, 2 H) 4.61-4.75 (m, 1 H) 4.50 (dd, J=15.49, 2.14 Hz, 1 H) 4.04-4.20 (m, 2 H) 3.78 (br. s., 1 H).

Intermediate AA(4)

4-(2,4-dioxo-2,3,4,5,7,8-hexahydro-1H-pyrano[4,3-d]pyrimidin-8-yl)benzonitrile

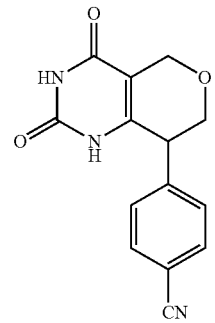 [SMILES: N#Cc1ccc(C2COCc3c2[nH]c(=O)[nH]c3=O)cc1]

4-(2,4-dioxo-2,3,4,5,7,8-hexahydropyrano[3,4-e][1,3]oxazin-8-yl)benzonitrile (Intermediate AA(3)) was reacted as described in Intermediate X(4) with ammonium hydroxide to give 4-(2,4-dioxo-2,3,4,5,7,8-hexahydro-1H-pyrano[4,3-d]pyrimidin-8-yl)benzonitrile (Intermediate AA(4)). LC-MS (M−H)$^+$=270.2.

Preparation AA 4-(2,4-dichloro-7,8-dihydro-5H-pyrano[4,3-d]pyrimidin-8-yl)benzonitrile

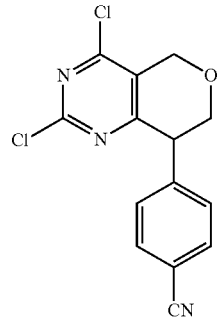 [SMILES: N#Cc1ccc(C2COCc3c(Cl)nc(Cl)nc32)cc1]

4-(2,4-dioxo-2,3,4,5,7,8-hexahydro-1H-pyrano[4,3-d]pyrimidin-8-yl)benzonitrile (Intermediate AA(4)) was reacted as described in Preparation X with POCl$_3$ to give 4-(2,4-dichloro-7,8-dihydro-5H-pyrano[4,3-d]pyrimidin-8-yl)benzonitrile (Preparation AA). LC-MS (M+H)$^+$=306.1.

Preparation AAa 4-(2-chloro-4-(ethylamino)-7,8-dihydro-5H-pyrano[4,3-d]pyrimidin-8-yl)benzonitrile

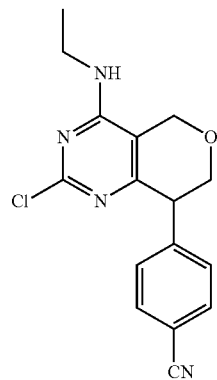 [SMILES: CCNc1nc(Cl)nc2c1COCC2c1ccc(C#N)cc1]

4-(2,4-dichloro-7,8-dihydro-5H-pyrano[4,3-d]pyrimidin-8-yl)benzonitrile (Preparation AA) was reacted as described in Preparation Xa with ethanamine to give 4-(2-chloro-4-(ethylamino)-7,8-dihydro-5H-pyrano[4,3-d]pyrimidin-8-yl)benzonitrile (Preparation AAa). LC-MS (M+H)$^+$=315.1.

Preparation AB 2,4-dichloro-8-(4-(trifluoromethoxy)phenyl)-7,8-dihydro-5H-pyrano[4,3-d]pyrimidine

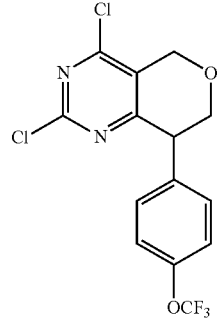 [SMILES: FC(F)(F)Oc1ccc(C2COCc3c(Cl)nc(Cl)nc32)cc1]

Intermediate AB(2)

3-(4-(trifluoromethoxy)phenyl)dihydro-2H-pyran-4(3H)-one

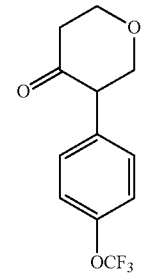

The procedure of Intermediate X(2) was utilized with 4-(trifluoromethoxy)phenylboronic acid to obtain 3-(4-(trifluoromethoxy)phenyl)dihydro-2H-pyran-4(3H)-one. $^1$H NMR (400 MHz, CDCl$_3$) δ ppm 7.29 (2 H, d, J=7.05 Hz), 7.19-7.25 (2 H, m), 4.23-4.32 (2 H, m), 3.91-4.04 (2 H, m), 3.84 (1 H, dd, J=8.81, 6.30 Hz), 2.66-2.77 (1 H, m), 2.56-2.63 (1 H, m)

Intermediate AB(3)

8-(4-(trifluoromethoxy)phenyl)-7,8-dihydropyrano[3,4-e][1,3]oxazine-2,4(3H,5H)-dione

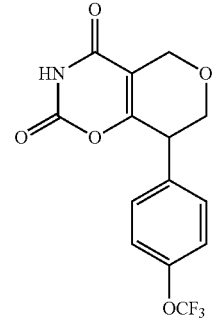 [SMILES: O=c1[nH]c(=O)c2c(o1)C(c1ccc(OC(F)(F)F)cc1)COC2]

The procedure of Intermediate X(3) was utilized to obtain 8-(4-(trifluoromethoxy)phenyl)-7,8-dihydropyrano[3,4-e][1,3]oxazine-2,4(3H,5H)-dione. $^1$H NMR (500 MHz, DMSO-d$_6$) δ ppm 11.98 (1 H, s), 7.52 (2 H, d, J=8.55 Hz), 7.37 (2H, d, J=7.93 Hz), 4.45-4.51 (1 H, m), 4.36 (1 H, dd, J=14.95, 2.14 Hz), 4.00-4.08 (2 H, m), 3.82 (1 H, dd, J=10.68, 3.36 Hz).

Intermediate AB(4)

8-(4-(trifluoromethoxy)phenyl)-7,8-dihydro-1H-pyrano[4,3-d]pyrimidine-2,4(3H,5H)-dione

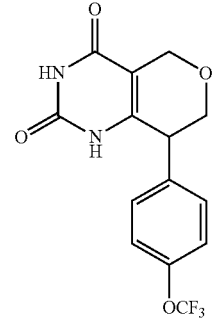 [SMILES: O=c1[nH]c2c(c(=O)[nH]1)COCC2c1ccc(OC(F)(F)F)cc1]

The procedure of Intermediate X(4) was utilized to obtain 8-(4-(trifluoromethoxy)phenyl)-7,8-dihydro-1H-pyrano[4,3-d]pyrimidine-2,4(3H,5H)-dione. LC-MS (M+H)⁺=329.0.

Preparation AB 2,4-dichloro-8-(4-(trifluoromethoxy)phenyl)-7,8-dihydro-5H-pyrano[4,3-d]pyrimidine

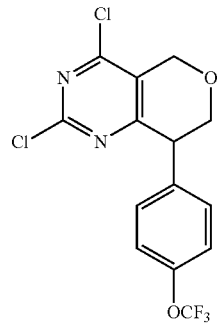 [SMILES: FC(F)(F)Oc1ccc(C2COCc3c(Cl)nc(Cl)nc32)cc1]

The procedure of Preparation X was utilized to obtain 2,4-dichloro-8-(4-(trifluoromethoxy)phenyl)-7,8-dihydro-5H-pyrano[4,3-d]pyrimidine. LC-MS (M+H)⁺=365.0.

Preparation ABa 2-chloro-N-methyl-8-(4-(trifluoromethoxy)phenyl)-7,8-dihydro-5H-pyrano[4,3-d]pyrimidin-4-amine

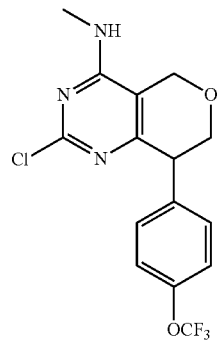 [SMILES: CNc1nc(Cl)nc2c1COCC2c1ccc(OC(F)(F)F)cc1]

To a solution of 2,4-dichloro-8-(4-(trifluoromethoxy)phenyl)-7,8-dihydro-5H-pyrano[4,3-d]pyrimidine (Preparation AB) (80.7 mg, 0.221 mmol) in MeOH (2210 μL) was added methylamine (1000 μL, 2.0 mmol) (2M in THF). The reaction was allowed to stir overnight. Removed the solvent and applied to silica gel, eluting with an EtOAc/Hex gradient to afford 2-chloro-N-methyl-8-(4-(trifluoromethoxy)phenyl)-7,8-dihydro-5H-pyrano[4,3-d]pyrimidin-4-amine (69.8 mg, 0.194 mmol, 88% yield). LC-MS (M+H)⁺=360.0.

Preparation ABb 2-chloro-4-((R)-3-fluoropyrrolidin-1-yl)-8-(4-(trifluoromethoxy)phenyl)-7,8-dihydro-5H-pyrano[4,3-d]pyrimidine

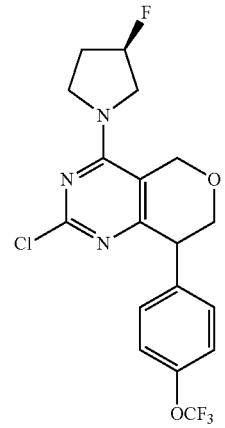 [SMILES: F[C@@H]1CCN(c2nc(Cl)nc3c2COCC3c2ccc(OC(F)(F)F)cc2)C1]

To a solution of 2,4-dichloro-8-(4-(trifluoromethoxy)phenyl)-7,8-dihydro-5H-pyrano[4,3-d]pyrimidine (Preparation AB) (56.4 mg, 0.154 mmol) in MeOH (1545 μL) was added DIPEA (67.4 μL, 0.386 mmol), then solid (R)-3-fluoropyrrolidine, HCl (21.34 mg, 0.170 mmol). The reaction was allowed to stir at rt. Removed the solvent and applied to silica gel. Eluted with a EtOAc/Hex gradient to afford the diasteriomeric mixture 2-chloro-4-((R)-3-fluoropyrrolidin-1-yl)-8-(4-(trifluoromethoxy)phenyl)-7,8-dihydro-5H-pyrano[4,3-d]pyrimidine (57.6 mg, 0.138 mmol, 89% yield). LC-MS (M+H)⁺=418.1.

Preparation AC 2,4-Dichloro-8-phenyl-5,6,7,8-tetrahydroquinazoline

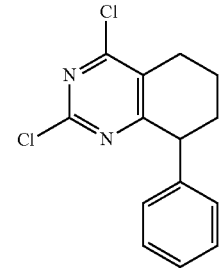 [SMILES: Clc1nc(Cl)c2c(n1)C(c1ccccc1)CCC2]

Intermediate AC(1)

8-Phenyl-5,6,7,8-tetrahydro-2H-benzo[e][1,3]oxazine-2,4(3H)-dione

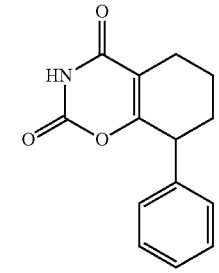 [SMILES: O=c1[nH]c(=O)c2c(o1)C(c1ccccc1)CCC2]

A solution of 2-phenylcyclohexanone (1.500 g, 8.61 mmol) and carbonisocyanatidic chloride (0.966 mL, 12 mmol) was stirred at 58° C. in a high-pressure vessel (75 mL) for 1 h. The temperature was raised to 130° C. and the reaction mixture was stirred for 2 h. After cooling to room temperature, the reaction mixture solidified. The solid residue was dissolved in ethyl acetate and washed with saturated aqueous solution of sodium bicarbonate. The organic layer was separated and the aqueous layer was extracted twice with ethyl acetate. The combined organic extracts were dried over anhydrous sodium sulfate and filtered. The solvent was removed in vacuum and the oily residue was purified by column chromatography on silica gel to provide 8-phenyl-5,6,7,8-tetrahydro-2H-benzo[e][1,3]oxazine-2,4(3H)-dione (415.0 mg, 1.689 mmol, 19.62% yield) as white solid and 4a-phenyl-4a,5,6,7-tetrahydro-2H-benzo[e][1,3]oxazine-2,4(3H)-dione (746.4 mg, 3.04 mmol, 35.3% yield) as white solid.

8-phenyl-5,6,7,8-tetrahydro-2H-benzo[e][1,3]oxazine-2,4(3H)-dione. LC-MS (M+H)$^+$=244.1. $^1$H NMR (500 MHz, CDCl$_3$) δ ppm 8.61 (1H, br s), 7.22-7.38 (3H, m), 7.09-7.19 (2H, m), 3.81 (1H, t, J=4.9 Hz), 2.39-2.63 (2H, m), 2.15 (1H, dddd, J=13.2, 9.8, 6.3, 3.1 Hz), 1.84-1.96 (1H, m), 1.52-1.84 (2H, m).

4a-phenyl-4a,5,6,7-tetrahydro-2H-benzo[e][1,3]oxazine-2,4(3H)-dione. LC-MS (M+H)$^+$=244.1. $^1$H NMR (500 MHz, CDCl$_3$) δ ppm 7.66 (1H, br s), 7.40-7.46 (2H, m), 7.29-7.39 (3H, m), 5.99-6.06 (1H, m), 2.37 (1H, ddd, J=14.0, 3.4, 3.1 Hz), 2.10-2.29 (3H, m), 1.54-1.64 (1H, m), 1.21-1.36 (1H, m).

Intermediate AC(2)

8-Phenyl-5,6,7,8-tetrahydroquinazoline-2,4(1H,3H)-dione

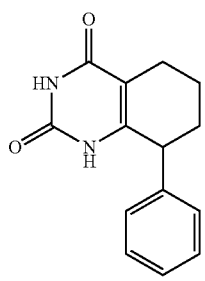 [SMILES: O=c1[nH]c2c(c(=O)[nH]1)CCCC2c1ccccc1]

A solution of 8-phenyl-5,6,7,8-tetrahydro-2H-benzo[e][1,3]oxazine-2,4(3H)-dione (415.0 mg, 1.706 mmol) in concentrated ammonium hydroxide (35 mL, 899 mmol) was stirred at 100° C. in a high-pressure vessel (75 mL) for 6 h. The formation of white precipitate was observed during the heating. The LC/MS analysis of the filtrate shows the presence of the product with the desired mass (M+H)=243.20. The solvent was removed in vacuum to provide 8-phenyl-5,6,7,8-tetrahydroquinazoline-2,4(1H,3H)-dione (435 mg, 1.706 mmol, 100% yield) as off-white solid. LC-MS (M+H)$^+$ =243.2. $^1$H NMR (500 MHz, DMSO-d$_6$) δ ppm 10.2 (2H, br. s.), 7.34 (2H, t, J=7.5 Hz), 7.26 (1H, t, J=7.3 Hz), 7.14 (2H, d, J=7.3 Hz), 3.80 (1H, br. s.), 2.32-2.43 (1H, m), 2.15 (1H, ddd, J=16.9, 10.5, 6.1 Hz), 1.93-2.04 (1H, m), 1.67-1.75 (1H, m), 1.56 (1H, ddd, J=7.8, 5.2, 2.6 Hz), 1.36 (1H, dt, J=13.1, 2.7 Hz).

Preparation AC 2,4-Dichloro-8-phenyl-5,6,7,8-tetrahydroquinazoline

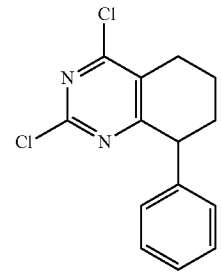 [SMILES: Clc1nc(Cl)c2c(n1)C(c1ccccc1)CCC2]

A mixture of 8-phenyl-5,6,7,8-tetrahydroquinazoline-2,4(1H,3H)-dione (233.1 mg, 0.962 mmol), phosphorus oxychloride (2798 mL, 30.0 mmol) and N,N-dimethylaniline (933 mL, 7.36 mmol) was heated at 110° C. in a capped vial overnight. The reaction mixture was poured into a beaker with ice and the inside of the reaction vessel was washed with dichloromethane. As soon as the ice completely melted, the content of the beaker was placed into a separatory funnel. The organic layer was separated and the aqueous layer was extracted with dichloromethane. The combined organic extracts were dried over anhydrous sodium sulfate and filtered. The solvent was removed in vacuum and the residue was purified by column chromatography on silica gel to provide 2,4-dichloro-8-phenyl-5,6,7,8-tetrahydroquinazoline (320.3 mg, 83%) as yellow oil. LC-MS (M+H)$^+$=279.1. $^1$H NMR (500 MHz, CDCl$_3$) δ ppm 7.28 (2H, t, J=7.5 Hz), 7.19-7.24 (1H, m), 6.95 (2H, d, J=7.3 Hz), 4.23 (1H, t, J=5.6 Hz), 2.82-2.92 (1H, m), 2.72-2.82 (1H, m), 2.10-2.22 (1H, m), 1.97-2.06 (1H, m), 1.76-1.93 (2H, m).

Preparation ACa

2-Chloro-N-ethyl-N-methyl-8-phenyl-5,6,7,8-tetrahydroquinazolin-4-amine

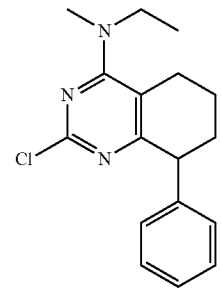 [SMILES: CCN(C)c1nc(Cl)nc2c1CCCC2c1ccccc1]

To a solution of 2,4-dichloro-8-phenyl-5,6,7,8-tetrahydroquinazoline (53.9 mg, 0.193 mmol) in methanol (1 mL) was added N-methylethanamine (0.033 mL, 0.386 mmol). The reaction mixture was stirred at room temperature for 2 h. The solvent was removed in vacuum and the residue was purified by column chromatography on silica gel to give 2-chloro-N-ethyl-N-methyl-8-phenyl-5,6,7,8-tetrahydroquinazolin-4-amine (42.9 mg, 0.141 mmol, 72.9% yield) as colorless oil. LC-MS (M+H)$^+$=302.2. $^1$H NMR (500 MHz, CDCl$_3$) δ ppm 7.25 (2H, t, J=7.5 Hz), 7.13-7.20 (1H, m), 7.01 (2H, d, J=7.3

Hz), 4.06-4.14 (1H, m), 3.42-3.53 (2H, m), 3.05 (3H, s), 2.56-2.74 (2H, m), 2.17-2.27 (1H, m), 1.76-1.89 (2H, m), 1.52-1.64 (1H, m), 1.24 (3H, t, J=7.2 Hz).

Preparation ACb

2-Chloro-8-phenyl-5,6,7,8-tetrahydroquinazoline

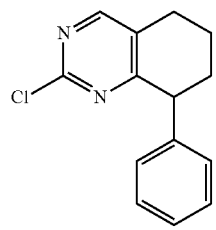 [SMILES: Clc1ncc2c(n1)C(c1ccccc1)CCC2]

A mixture of 2,4-dichloro-8-phenyl-5,6,7,8-tetrahydroquinazoline (51.9 mg, 0.186 mmol), ammonium chloride (13.0 mg, 0.243 mmol) and zinc (130 mg, 1.988 mmol) in acetone (0.75 mL) and water (0.75 mL) was heated at 90° C. with stirring for 2 h. The reaction mixture was filtered through a short plug of diatomaceous earth (Celite®). The solvent was removed in vacuum, and the residue was partitioned between dichloromethane and water. The organic layer was separated and the aqueous layer was extracted with dichloromethane. The combined organic extracts were dried over anhydrous magnesium sulfate and filtered. The solvent was removed in vacuum and the residue was purified by column chromatography on silica gel to give 2-chloro-8-phenyl-5,6,7,8-tetrahydroquinazoline (24.1 mg, 0.097 mmol, 52.4% yield) as white solid. LC-MS (M+H)$^+$=245.1. $^1$H NMR (500 MHz, CDCl$_3$) δ ppm 8.39 (1H, s), 7.27 (2H, t, J=7.6 Hz), 7.16-7.23 (1H, m), 6.95 (2H, d, J=7.3 Hz), 4.21 (1H, t, J=6.0 Hz), 2.72-2.91 (2H, m), 2.14-2.26 (1H, m), 1.95-2.06 (1H, m), 1.81-1.93 (1H, m), 1.71-1.81 (1H, m).

Preparation AD 2,4-dichloro-8-(4-fluorophenyl)-5,6,7,8-tetrahydroquinazoline

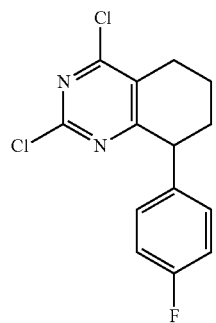 [SMILES: Fc1ccc(C2CCCc3c(Cl)nc(Cl)nc32)cc1]

Intermediate AD(1)

8-Phenyl-5,6,7,8-tetrahydro-2H-benzo[e][1,3]oxazine-2,4(3H)-dione

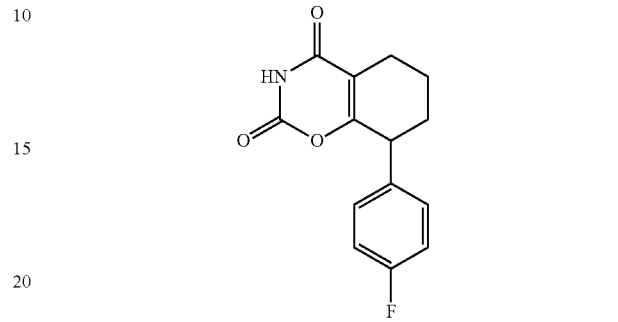

2-(4-fluorophenyl)cyclohexanone and carbonisocyanatidic chloride (0.966 mL, 12 mmol) was reacted as in Intermediate AC(1) to provide 8-(4-fluorophenyl)-5,6,7,8-tetrahydro-2H-benzo[e][1,3]oxazine-2,4(3H)-dione (415.0 mg, 1.689 mmol, 19.62% yield) as white solid and 4a-(4-fluorophenyl)-4a,5,6,7-tetrahydro-2H-benzo[e][1,3]oxazine-2,4(3H)-dione (746.4 mg, 3.04 mmol, 35.3% yield) as white solid. 8-(4-fluorophenyl)-5,6,7,8-tetrahydro-2H-benzo[e][1,3]oxazine-2,4(3H)-dione. LC-MS (M+H)$^+$=262.1. $^1$H NMR (500 MHz, CDCl$_3$) δ ppm 9.61 (1H, br s), 7.10 (2H, dd, J=5.0, 8.5 Hz), 6.98 (2H, app t, J=8.5 Hz), 3.77 (1H, t, J=4.9 Hz), 2.38-2.53 (2H, m), 2.16-2.07 (1H, m), 1.87-1.62 (3H, m).

Intermediate AD(2)

8-(4-fluorophenyl)-5,6,7,8-tetrahydroquinazoline-2,4 (1H,3H)-dione

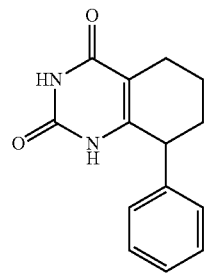 [SMILES: O=c1[nH]c2c(c(=O)[nH]1)CCCC2c1ccccc1]

A solution of 8-(4-fluorophenyl)-5,6,7,8-tetrahydro-2H-benzo[e][1,3]oxazine-2,4(3H)-dione was reacted in the manner of Intermediate AC(2) to provide 8-(4-fluorophenyl)-5,6,7,8-tetrahydroquinazoline-2,4(1H,3H)-dione. LC-MS (M+H)$^+$=261.2.

Preparation AD 2,4-dichloro-8-(4-fluorophenyl)-5,6,7,8-tetrahydroquinazoline

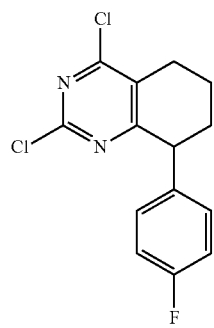 [SMILES: Fc1ccc(C2CCCc3c(Cl)nc(Cl)nc32)cc1]

A mixture of 8-(4-fluorophenyl)-5,6,7,8-tetrahydroquinazoline-2,4(1H,3H)-dione was reacted in the manner of Preparation AC to provide 2,4-dichloro-8-(4-fluorophenyl)-5,6,7,8-tetrahydroquinazoline, which was not characterized at this step.

Preparation ADa

2-Chloro-N-ethyl-8-(4-fluorophenyl)-N-methyl-5,6,7,8-tetrahydroquinazolin-4-amine

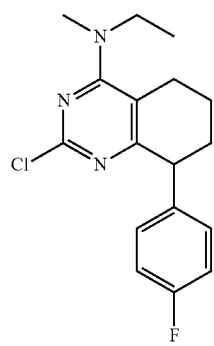 [SMILES: CCN(C)c1nc(Cl)nc2c1CCCC2c1ccc(F)cc1]

A solution of 2,4-dichloro-8-(4-fluorophenyl)-5,6,7,8-tetrahydroquinazoline (115 mg, 0.387 mmol) and excess N-methylethanamine (0.332 mL, 3.87 mmol) in MeOH (2 mL) was stirred at room temperature for 30 min. The solvent was removed in vacuum to afford 2-chloro-N-ethyl-8-(4-fluorophenyl)-N-methyl-5,6,7,8-tetrahydroquinazolin-4-amine (124 mg, 0.388 mmol, 100% yield). LC-MS (M+H)$^+$=320.2.

Preparation ADb

2-Chloro-8-(4-fluorophenyl)-N,N-dimethyl-5,6,7,8-tetrahydroquinazolin-4-amine

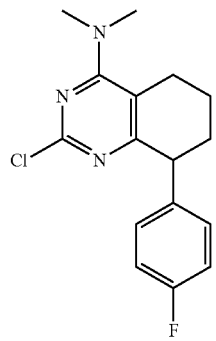 [SMILES: CN(C)c1nc(Cl)nc2c1CCCC2c1ccc(F)cc1]

A solution of 2,4-dichloro-8-(4-fluorophenyl)-5,6,7,8-tetrahydroquinazoline (115 mg, 0.387 mmol) and excess dimethylamine (1.935 mL, 3.87 mmol) in MeOH (1 mL) was stirred at room temperature for 1 h. The solvent was removed in vacuum to afford 2-chloro-8-(4-fluorophenyl)-N,N-dimethyl-5,6,7,8-tetrahydroquinazolin-4-amine (118 mg, 0.386 mmol, 100% yield). LC-MS (M+H)$^+$=306.2.

Preparation ADc

2-Chloro-8-(4-fluorophenyl)-5,6,7,8-tetrahydroquinazoline

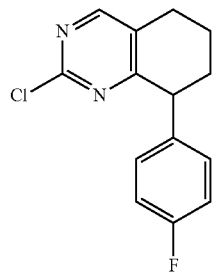 [SMILES: Fc1ccc(C2CCCc3cnc(Cl)nc32)cc1]

A mixture of 2,4-dichloro-8-(4-fluorophenyl)-5,6,7,8-tetrahydroquinazoline (115 mg, 0.387 mmol), Ammonium chloride (26.9 mg, 0.503 mmol) and zinc (266 mg, 4.06 mmol) in acetone (1 mL) and water (1.000 mL) was heated at 90° C. with stirring for 2 h. The reaction mixture was filtered through a short plug of celite. The solvent was removed in vacuum, and the residue was partitioned between dichloromethane and water. The organic layer was separated and the aqueous layer was extracted with dichloromethane. The combined organic extracts were dried over anhydrous magnesium sulfate and filtered. The solvent was removed in vacuum and the residue was purified by column chromatography on silica gel to give 2-chloro-8-(4-fluorophenyl)-5,6,7,8-tetrahydroquinazoline (20 mg, 0.076 mmol, 19.67% yield) as a white solid. LC-MS (M+H)$^+$=263.2.

Preparation AE 2,4-dichloro-6-(4-methoxybenzyl)-8-phenyl-5,6,7,8-tetrahydropyrido[4,3-d]pyrimidine

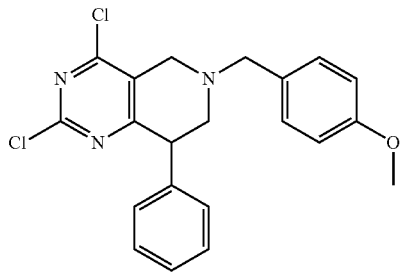 [SMILES: COc1ccc(CN2Cc3c(Cl)nc(Cl)nc3C(c3ccccc3)C2)cc1]

Intermediate AE(1)

Ethyl 2-cyano-2-phenylacetate

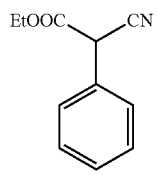

To a solution of sodium hydride (24.5 g, 1.02 mol) in THF was added benzyl cyanide (50.0 g, 0.426 mol) at −10° C. The reaction mixture was stirred for 15 min at the same temperature. Diethyl carbonate (60.5 g, 0.512 mol) was added to the reaction mixture and the reaction mixture was allowed to come to room temperature and heated to 40° C. (Caution: Reaction will start suddenly and exothermic). The heating path was removed immediately once the reaction was started and the reaction mixture was cooled under ice/acetone. The solution was allowed to come to room temperature and stirred for 1 h. The reaction mass was cooled to 0° C. and quenched with aqueous saturated ammonium chloride and extracted with ethyl acetate (250 mL×3). The combined organic layer was washed with water (200 mL), brine solution (200 mL), dried over anhydrous $Na_2SO_4$ and evaporated under reduced pressure to give ethyl 2-cyano-2-phenylacetate as crude compound as crude compound (71.0 g). The crude compound was taken to the next step without further purification. LC-MS $(M+H)^+$=190.1. $^1$H NMR (400 MHz, DMSO-d6) δ ppm 7.45 (5H, m), 5.65 (1H, s), 4.18 (2H, m), 1.18 (3H, t, J=7.2 Hz).

Intermediate AE(2)

ethyl 3-amino-2-phenylpropanoate

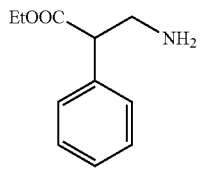 [SMILES: CCOC(=O)C(CN)c1ccccc1]

To a solution of Intermediate AE(1) (25.0 g, 0.132 mol) in methanol was added palladium on carbon (10%, w/w) followed by trifluoroacetic acid (2.0 vol., 50 mL) at room temperature. The reaction mixture was hydrogenated under 5 kg of hydrogen pressure for 3 h. The reaction mixture was filtered through celite bed and washed with methanol. The filtrate was evaporated under reduced pressure and the residue was neutralized with aqueous saturated bicarbonate solution. The aqueous solution was extracted with ethyl acetate (200 mL×4). The combined organic layer was washed with brine solution (200 mL), dried over anhydrous $Na_2SO_4$ and evaporated under reduced pressure to get crude compound. The crude compound was purified by column chromatography (Silica gel, 60-120 mesh) using 10% methanol in dichloromethane as mobile phase to give ethyl 3-amino-2-phenylpropanoate (17.0 g, 67%) as oily liquid. LC-MS $(M+H)^+$= 194.0. $^1$H NMR (400 MHz, DMSO-d6): δ ppm 7.42-7.2 (7H, m), 4.11 (2H, m), 4.09 (1H, m), 3.44 (1H, m), 3.09 (1H, m), 1.15 (3H, t, J=5.6 Hz).

Intermediate AE(3)

ethyl 3-(3-ethoxy-3-oxopropylamino)-2-phenylpropanoate

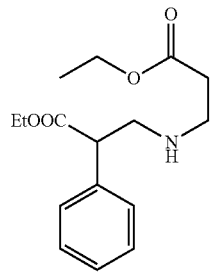 [SMILES: CCOC(=O)CCNCC(C(=O)OCC)c1ccccc1]

To a solution of Intermediate AE(2) (10.0 g, 51.7 mmol) in ethanol was added ethyl acrylate (4.1 g, 40.9 mmol) at room temperature. The reaction mixture was stirred at the same temperature for 18 h. The solvent was evaporated under reduced pressure and the crude compound was purified by column chromatography (Silica gel, 60-120 mesh) using 50% ethyl acetate in pet-ether as mobile phase to give ethyl 3-(3-ethoxy-3-oxopropylamino)-2-phenylpropanoate (12.1 g, 80%) as yellowish oily liquid. LC-MS $(M+H)^+$=294.1. $^1$H NMR (400 MHz, CDCl$_3$): δ ppm 7.29 (5H, m), 4.11 (4H, m), 3.76 (1H, m), 3.26 (1H, m), 2.90 (3H, m), 2.44 (2H, m), 1.20 (6H, m).

Intermediate AE(4)

ethyl 3-((3-ethoxy-3-oxopropyl)(4-methoxybenzyl)amino)-2-phenylpropanoate

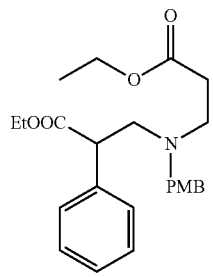

To a solution Intermediate AE(3) (15.0 g, 51.1 mmol) in acetone was added K$_2$CO$_3$ (8.4 g, 61.4 mmol) followed by p-methoxybenzyl bromide (15.4 g, 76.7 mmol) at room temperature. The reaction mixture was heated at reflux for 3 h. The solvent was removed under reduced pressure and the residue was diluted with water. The aqueous layer was extracted with ethyl acetate (100×3). The combined organic layer was washed with brine solution (100 mL), dried over anhydrous Na$_2$SO$_4$ and evaporated under reduced pressure to get crude compound. The crude compound was purified by column chromatography (Silica gel, 60-120 mesh) using 30% ethyl acetate in pet-ether as mobile phase to give ethyl 3-((3-ethoxy-3-oxopropyl)(4-methoxybenzyl)amino)-2-phenyl-propanoate (12.1 g, 60%) as oily liquid. LC-MS (M+H)$^+$= 414.2. $^1$H NMR (400 MHz, CDCl$_3$): δ ppm 7.27 (5H, m), 7.13, (2H, m), 6.82 (2H, m), 4.11 (4H, m), 4.08 (3H, s), 4.06 (1H, m), 3.81 (1H, d, J=4.0 Hz), 3.79 (1H, d, J=4.0 Hz), 3.25 (1H, m), 2.73 (3H, m), 2.43 (2H, m), 1.24 (6H, m).

Intermediate AE(5)

ethyl 1-(4-methoxybenzyl)-4-oxo-5-phenylpiperidine-3-carboxylate

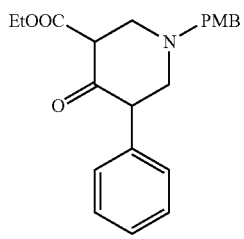

To a cooled solution of Intermediate AE(4) (12.0 g, 29.0 mmol) in THF was added t-BuOK (6.5 g, 58.0 mmol). The reaction mixture was stirred at room temperature for 2 h. The reaction mass was quenched with water then evaporated the solvent under reduced pressure. The residue was diluted with water and extracted with ethyl acetate (100 mL×2). The combined organic layer was washed with brine solution (100 mL), dried over anhydrous Na$_2$SO$_4$ and evaporated under reduced pressure to get crude compound. The crude compound was purified by column chromatography (Silica gel, 60-120 mesh) using 25% ethyl acetate in pet-ether as mobile phase to give ethyl 1-(4-methoxybenzyl)-4-oxo-5-phenylpiperidine-3-carboxylate (7.1 g, 67%) as oily liquid. LC-MS (M+H)$^+$= 368.2. $^1$H NMR (400 MHz, CDCl$_3$): δ ppm 7.26 (4H, m), 7.15 (2H, m), 6.88 (2H, m), 4.15 (2H, m), 4.09 (3H, s), 3.82 (2H, m), 3.66 (2H, m), 2.80 (3H, m), 2.40 (1H, m), 1.24 (3H, m).

Intermediate AE(6)

6-(4-methoxybenzyl)-8-phenyl-5,6,7,8-tetrahydropyrido[4,3-d]pyrimidine-2,4(1H,3H)-dione

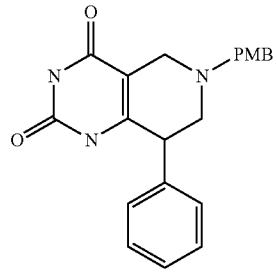

To a cooled solution of Intermediate AE(5) (7.0 g, 19.0 mmol) in ethanol was added t-BuOK (5.3 g, 47.6 mmol) followed by urea (2.8 g, 47.6 mmol). The reaction mixture was heated at reflux for 24 h. The reaction mass was quenched with water and evaporated the solvent under reduced pressure. The residue was diluted with water and extracted with ethyl acetate (100 mL×3). The combined organic layer was washed with brine solution (100 mL), dried over Na2SO4 and evaporated under reduced pressure to get crude compound. The crude compound was purified by column chromatography (Silica gel, 60-120 mesh) using 10% pet-ether in ethyl acetate as mobile phase to give 6-(4-methoxybenzyl)-8-phenyl-5,6,7,8-tetrahydropyrido[4,3-d]pyrimidine-2,4(1H,3H)-dione (4.0 g, 57%) as pale yellow solid. LC-MS (M+H)$^+$= 364.2. $^1$H NMR (400 MHz, DMSO-d6): δ ppm 11.05 (1H, s), 10.60 (1H, s), 7.30 (5H, m), 6.99 (2H, m), 6.77 (2H, m), 3.72 (2H, m), 3.57 (3H, s), 3.44 (1H, m), 3.34 (1H, m), 2.90 (1H, m), 2.51 (2H, m).

Preparation AE 2,4-dichloro-6-(4-methoxybenzyl)-8-phenyl-5,6,7,8-tetrahydropyrido[4,3-d]pyrimidine

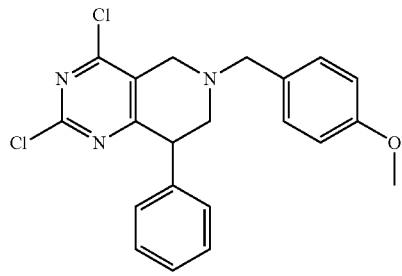 [SMILES: COc1ccc(CN2Cc3c(Cl)nc(Cl)nc3C(c3ccccc3)C2)cc1]

A solution of Intermediate AE(6) (2.0 g, 5.5 mmol) and catalytic amount of DMF in POCl$_3$ (20 vol.) was heated at reflux for 10 h. The excess of POCl$_3$ was evaporated under reduced pressure. The residue was poured in to crushed ice and stirred for 15 min. The aqueous solution was extracted with ethyl acetate (75 mL×3). The combined organic layer was washed with aqueous saturated NaHCO$_3$ (50 mL×2), brine solution (100 mL), dried over Na$_2$SO$_4$ and evaporated under reduced pressure to give 2,4-dichloro-6-(4-methoxybenzyl)-8-phenyl-5,6,7,8-tetrahydropyrido[4,3-d]pyrimidine (1.5 g, 69%) as brown solid. LC-MS (M+H)$^+$=400.0. $^1$H NMR (400 MHz, CDCl$_3$): δ ppm 7.30 (3H, m), 7.26 (4H, m), 6.81 (2H, m), 4.20 (1H, m), 3.79 (2H, m), 3.72 (3H, s), 3.68 (2H, m), 3.57 (1H, m), 3.02 (1H, m), 2.98 (1H, m).

Preparation AEa 2-chloro-6-(4-methoxybenzyl)-N-methyl-8-phenyl-5,6,7,8-tetrahydropyrido[4,3-d]pyrimidin-4-amine

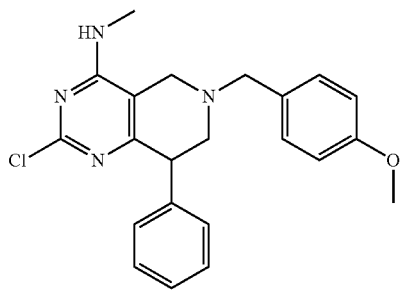 [SMILES: CNc1nc(Cl)nc2c1CN(Cc1ccc(OC)cc1)CC2c1ccccc1]

To a solution of Preparation AE (1.1 g, 2.7 mmol) in acetonitrile was added diisopropylethylamine (1.0 g, 8.3 mmol) followed by addition of methylamine hydrochloride (0.28 g, 4.1 mmol) at room temperature. The reaction mixture was stirred at room temperature for 18 h. The solvent was removed under reduced pressure and the residue was purified by column chromatography (60-120 mesh) using 30% ethyl acetate in pet-ether as mobile phase to give 2-chloro-6-(4-methoxybenzyl)-N-methyl-8-phenyl-5,6,7,8-tetrahydropyrido[4,3-d]pyrimidin-4-amine (0.8 g, 74%) as off-white solid. LC-MS (M+H)$^+$=395.2. $^1$H NMR (400 MHz, DMSO-d6): δ ppm 7.29 (4H, m), 7.16 (4H, m), 6.80 (2H, m), 3.93 (1H, m), 3.73 (3H, s), 3.66 (2H, m), 3.57 (1H, m), 3.46 (1H, m), 3.23 (1H, m), 2.67 (3H, d, J=4.0 Hz), 2.51 (1H, m).

Preparation AEb 2-chloro-N-ethyl-6-(4-methoxybenzyl)-8-phenyl-5,6,7,8-tetrahydropyrido[4,3-d]pyrimidin-4-amine

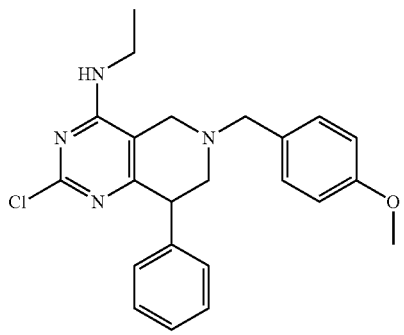 [SMILES: CCNc1nc(Cl)nc2c1CN(Cc1ccc(OC)cc1)CC2c1ccccc1]

To a solution of Preparation AE (1.6 g, 4.0 mmol) in acetonitrile was added diisopropylethylamine (1.5 g, 12.0 mmol) followed by addition of ethylamine hydrochloride (0.52 g, 6.0 mmol) at room temperature. The reaction mixture was stirred at the same temperature for 18 h. The solvent was removed under reduced pressure and the residue was purified by column chromatography (60-120 mesh) using 30% ethyl acetate in pet-ether as mobile phase to give 2-chloro-N-ethyl-6-(4-methoxybenzyl)-8-phenyl-5,6,7,8-tetrahydropyrido[4,3-d]pyrimidin-4-amine (0.9 g, 56%) as off-white solid. LC-MS (M−H)$^+$=407.0. $^1$H NMR (400 MHz, DMSO-d6): δ ppm 7.31-7.12 (7H, m), 6.83-6.79 (2H, m), 4.47 (1H, bs), 4.06 (1H, m), 3.83 (3H, s), 3.66 (2H, m), 3.58 (2H, m), 3.44 (1H, m), 3.20 (1H, m), 3.08 (1H, m), 2.88 (1H, m), 1.25 (3H, d, J=7.2 Hz).

Preparation AEc 2-chloro-N,N-dimethyl-6-(4-methoxybenzyl)-8-phenyl-5,6,7,8-tetrahydropyrido[4,3-d]pyrimidin-4-amine

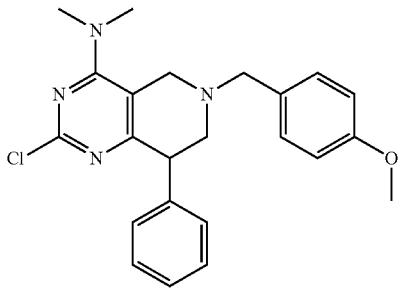 [SMILES: COc1ccc(CN2Cc3c(nc(Cl)nc3N(C)C)C(c3ccccc3)C2)cc1]

Using the procedure of Preparation AEb, utilized dimethylamine to produce 2-chloro-N,N-dimethyl-6-(4-methoxybenzyl)-8-phenyl-5,6,7,8-tetrahydropyrido[4,3-d]pyrimidin-4-amine Preparation AF 2,4-dichloro-6-methyl-8-phenyl-5,6,7,8-tetrahydropyrido[4,3-d]pyrimidine

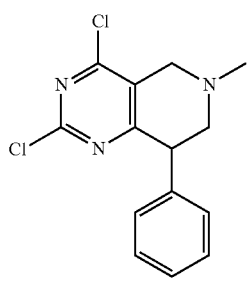 [SMILES: CN1Cc2c(Cl)nc(Cl)nc2C(c2ccccc2)C1]

Intermediate AF(1)

ethyl 3-((3-ethoxy-3-oxopropyl)(methyl)amino)-2-(4-fluorophenyl)propanoate

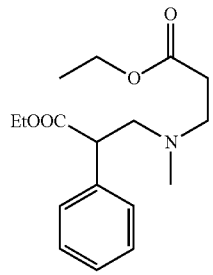 [SMILES: CCOC(=O)CCN(C)CC(C(=O)OCC)c1ccccc1]

To a solution of Intermediate AE(3) (4.0 g, 13.65 mmol) in acetone was added K$_2$CO$_3$ (3.7 g, 27.3 mmol) followed by methyl iodide (2.3 g, 16.3 mmol) at 0° C. The reaction mixture was stirred at room temperature for 2 h. The solvent was removed under reduced pressure and the residue was diluted with water. The aqueous layer was extracted with ethyl acetate (25×3). The combined organic layer was washed with brine solution (50 mL), dried over anhydrous Na$_2$SO$_4$ and evaporated under reduced pressure to get crude compound. The crude compound was purified by column chromatography (Silica gel, 60-120 mesh) using 40% ethyl acetate in pet-ether as mobile phase to give ethyl 3-((3-ethoxy-3-oxopropyl)(methyl)amino)-2-phenylpropanoate (0.9 g, 22%) as oily liquid. LC-MS (M+H)$^+$=308.0. $^1$H NMR (400 MHz, DMSO-d): δ ppm 7.33-7.26 (5H, m), 4.07-4.01 (4H, m), 3.83 (1H, m), 3.07 (1H, m), 2.69-2.52 (2H, m), 2.47-2.41 (3H, m), 2.21 (3H, s), 1.19-0.10 (6H, m).

Intermediate AF(2)

ethyl 1-methyl-4-oxo-5-phenylpiperidine-3-carboxylate

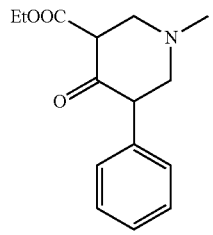

To a cooled solution of Intermediate AF(1) (0.9 g, 2.93 mmol) in THF was added t-BuOK (0.65 g, 5.86 mmol). The reaction mixture was stirred at room temperature for 2 h. The reaction mass was quenched with water then evaporated the solvent under reduced pressure. The residue was diluted with water and extracted with ethyl acetate (25 mL×2). The combined organic layer was washed with brine solution (25 mL), dried over anhydrous Na$_2$SO$_4$ and evaporated under reduced pressure to get crude compound. The crude compound was purified by column chromatography (Silica gel, 60-120 mesh) using 10% ethyl acetate in pet-ether as mobile phase to give ethyl 1-methyl-4-oxo-5-phenylpiperidine-3-carboxylate (7.1 g, 67%) as oily liquid. LC-MS (M+H)$^+$=262.2.

Intermediate AF(3)

6-methyl-8-phenyl-5,6,7,8-tetrahydropyrido[4,3-d]pyrimidine-2,4(1H,3H)-dione

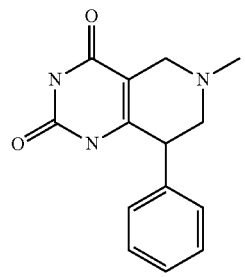 [SMILES: CN1Cc2c([nH]c(=O)[nH]c2=O)C(c2ccccc2)C1]

To a cooled solution of Intermediate AF(2) (4.5 g, 17.2 mmol) in ethanol was added t-BuOK (4.8 g, 43.1 mmol) followed by urea (2.58 g, 43.1 mmol). The reaction mixture was heated at reflux for 24 h. The reaction mass was quenched with water and evaporated the solvent under reduced pressure. The residue was diluted with water and extracted with ethyl acetate (50 mL×3). The combined organic layer was washed with brine solution (50 mL), dried over Na$_2$SO$_4$ and evaporated under reduced pressure to get crude compound. The crude compound was purified by column chromatography (Silica gel, 60-120 mesh) using 10% methanol in dichloromethane as mobile phase to give 6-methyl-8-phenyl-5,6,7,8-tetrahydropyrido[4,3-d]pyrimidine-2,4(1H,3H)-dione (2.5 g, 56%) as pale yellow solid. LC-MS (M+H)$^+$=258.2 $^1$H NMR (400 MHz, DMSO-d6): δ ppm 11.04 (1H, s), 10.56 (1H, s), 7.33-7.23 (5H, m), 3.73 (1H, m), 4.75 (1H, m), 2.83 (1H, m), 2.78 (1H, m), 2.68 (1H, m), 2.22 (3H, s).

Preparation AF 2,4-dichloro-6-methyl-8-phenyl-5,6,7,8-tetrahydropyrido[4,3-d]pyrimidine

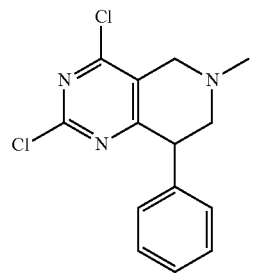 [SMILES: CN1Cc2c(Cl)nc(Cl)nc2C(c2ccccc2)C1]

A solution of Intermediate AF(3) (4.0 g, 15.56 mmol) and catalytic amount of DMF in POCl$_3$ (20 vol.) was heated at reflux for 10 h. The excess of POCl$_3$ was evaporated under reduced pressure. The residue was poured in to crushed ice and stirred for 15 min. The aqueous solution was extracted with ethyl acetate (75 mL×3). The combined organic layer was washed with aqueous saturated NaHCO$_3$ (50 mL×2), brine solution (75 mL), dried over Na$_2$SO$_4$ and evaporated under reduced pressure to give 2,4-dichloro-6-methyl-8-phenyl-5,6,7,8-tetrahydropyrido[4,3-d]pyrimidine (1.2 g, 27%) as brown solid. LC-MS (M+H)⁺=294.0.

Preparation AFa 2-chloro-N,6-dimethyl-8-phenyl-5,6,7,8-tetrahydropyrido[4,3-d]pyrimidin-4-amine

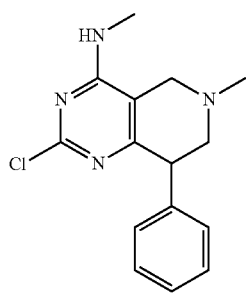 [SMILES: CNc1nc(Cl)nc2c1CN(C)CC2c1ccccc1]

To a solution of Preparation AF (1.0 g, 3.4 mmol) in acetonitrile was added diisopropylethylamine (1.3 g, 10.2 mmol) followed by addition of methylamine hydrochloride (0.34 g, 5.1 mmol) at room temperature. The reaction mixture was stirred at room temperature for 18 h. The solvent was removed under reduced pressure and the residue was purified by column chromatography (60-120 mesh) using 10% methanol in dichloromethane as mobile phase to give 2-chloro-N,6-dimethyl-8-phenyl-5,6,7,8-tetrahydropyrido[4,3-d]pyrimidin-4-amine (0.9 g, 91%) as off-white solid. LC-MS (M+H)⁺= 289.2.

Preparation AFb 2-chloro-N-ethyl-6-methyl-8-phenyl-5,6,7,8-tetrahydropyrido[4,3-d]pyrimidin-4-amine

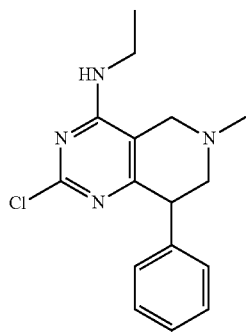 [SMILES: CCNc1nc(Cl)nc2c1CN(C)CC2c1ccccc1]

To a solution of Preparation AF (0.4 g, 1.36 mmol) in acetonitrile was added diisopropylethylamine (0.52 g, 4.0 mmol) followed by addition of ethylamine hydrochloride (0.16 g, 2.0 mmol) at room temperature. The reaction mixture was stirred at the same temperature for 18 h. The solvent was removed under reduced pressure and the residue was purified by column chromatography (60-120 mesh) using 50% ethyl acetate in pet-ether as mobile phase to give 2-chloro-N-ethyl-6-methyl-8-phenyl-5,6,7,8-tetrahydropyrido[4,3-d]pyrimidin-4-amine (0.4 g, 97%) as off-white solid. LC-MS (M−H)⁺=303.2.

Preparation AG 2,4-dichloro-8-(4-fluorophenyl)-6-(4-methoxybenzyl)-5,6,7,8-tetrahydropyrido[4,3-d]pyrimidine

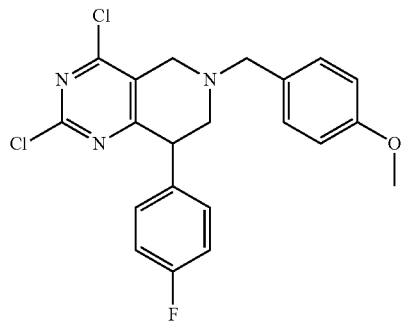 [SMILES: COc1ccc(CN2Cc3c(Cl)nc(Cl)nc3C(c3ccc(F)cc3)C2)cc1]

Intermediate AG(1)

ethyl 2-cyano-2-(4-fluorophenyl)acetate

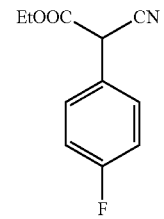 [SMILES: CCOC(=O)C(C#N)c1ccc(F)cc1]

To a solution of sodium hydride (4.2 g, 177.7 mmol) in THF was added 4-fluoro phenyl acetonitrile (10 g, 74.0 mmol) at −10° C. The reaction mixture was stirred for 15 min at the same temperature. Diethyl carbonate (10.5 g, 88.0 mmol) was added to the reaction mixture and the reaction mixture was allowed to come to room temperature and heated to 40° C. (Caution: Reaction will start suddenly and exothermic). The heating path was removed immediately once the reaction was started and the reaction mixture was cooled under ice/acetone. The solution was allowed to come to room temperature and stirred for 1 h. The reaction mass was cooled to 0° C. and quenched with aqueous saturated ammonium chloride and extracted with ethyl acetate (50 mL×3). The combined organic layer was washed with water (50 mL), brine solution (50 mL), dried over anhydrous Na₂SO₄ and evaporated under reduced pressure to give ethyl 2-cyano-2-(4-fluorophenyl)acetate as crude compound as crude compound (10 g). The crude compound was taken to the next step without further purification. LC-MS (M−H)⁺=206.2. ¹H NMR (400 MHz, CDCl₃) δ ppm 7.44 (2H, m), 7.11 (2H, m), 4.69 (1H, s), 4.27-4.22 (2H, q, J=7.2 Hz). 1.26 (3H, m)

Intermediate AG(2)

ethyl 3-amino-2-(4-fluorophenyl)propanoate

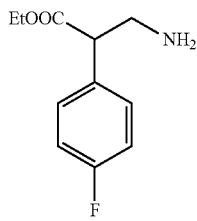 [SMILES: CCOC(=O)C(CN)c1ccc(F)cc1]

To a solution of Intermediate AG(1) (10.0 g, 40.0 mmol) in acetic acid was added palladium on carbon (10%, w/w) followed by $H_2SO_4$ (0.5 vol., 5 mL) at room temperature. The reaction mixture was hydrogenated under 5 kg of hydrogen pressure for 18 h. The reaction mixture was filtered through celite bed and washed with methanol. The filtrate was evaporated under reduced pressure and the residue was neutralized with aqueous saturated bicarbonate solution. The aqueous solution was extracted with ethyl acetate (100 mL×4). The combined organic layer was washed with brine solution (100 mL), dried over anhydrous $Na_2SO_4$ and evaporated under reduced pressure to get crude compound. The crude compound was purified by column chromatography (Silica gel, 60-120 mesh) using 10% methanol in dichloromethane as mobile phase to give ethyl 3-amino-2-(4-fluorophenyl)propanoate (6.0 g, 59%) as oily liquid. LC-MS (M+H)$^+$=212.2. $^1$H NMR (400 MHz, CDCl$_3$): δ ppm 7.26-7.22 (2H, m), 7.04-6.98 (2H, m), 4.15 (2H, m), 3.66 (1H, m), 3.28 (1H, m), 2.99 (1H, m). 1.20 (3H, m).

Intermediate AG(3)

ethyl 3-(3-ethoxy-3-oxopropylamino)-2-(4-fluorophenyl)propanoate

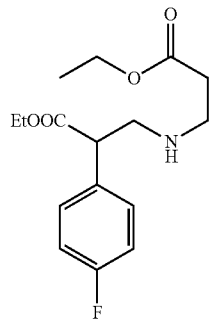 [SMILES: CCOC(=O)CCNCC(C(=O)OCC)c1ccc(F)cc1]

To a solution of Intermediate AG(2) (3.0 g, 14.0 mmol) in ethanol was added ethyl acrylate (1.7 g, 17.0 mmol) at room temperature. The reaction mixture was stirred at the same temperature for 18 h. The solvent was evaporated under reduced pressure and the crude compound was purified by column chromatography (Silica gel, 60-120 mesh) using 50% ethyl acetate in pet-ether as mobile phase to give ethyl 3-(3-ethoxy-3-oxopropylamino)-2-(4-fluorophenyl)propanoate (2.5 g, 60%) as yellowish oily liquid. LC-MS (M+H)$^+$=313.2. $^1$H NMR (400 MHz, CDCl$_3$): δ ppm 7.27-7.21 (2H, m), 7.03-6.97 (2H, m), 4.13 (4H, m), 3.77 (1H, m), 3.23 (1H, m), 2.89 (3H, m), 2.48 (2H, m). 1.22 (6H, m).

Intermediate AG(4)

ethyl 3-((3-ethoxy-3-oxopropyl)(4-methoxybenzyl)amino)-2-(4-fluorophenyl)propanoate

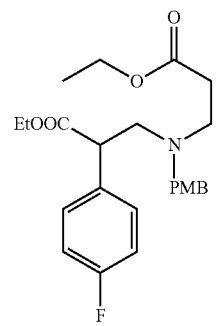

To a solution of Intermediate AG(3) (2.0 g, 6.42 mmol) in acetone was added $K_2CO_3$ (1.39 g, 9.6 mmol) followed by p-methoxybenzyl bromide (1.68 g, 8.35 mmol) at room temperature. The reaction mixture was heated at reflux for 3 h. The solvent was removed under reduced pressure and the residue was diluted with water. The aqueous layer was extracted with ethyl acetate (25×2). The combined organic layer was washed with brine solution (25 mL), dried over anhydrous $Na_2SO_4$ and evaporated under reduced pressure to get crude compound. The crude compound was purified by column chromatography (Silica gel, 60-120 mesh) using 30% ethyl acetate in pet-ether as mobile phase to give ethyl 3-((3-ethoxy-3-oxopropyl)(4-methoxybenzyl)amino)-2-(4-fluorophenyl)propanoate (1.6 g, 60%) as oily liquid. LC-MS (M+H)$^+$=432.2. $^1$H NMR (400 MHz, CDCl$_3$): δ ppm 7.22 (2H, m), 7.09, (2H, m), 6.95 (2H, m), 6.78 (2H, m) 4.14 (4H, m), 3.80 (3H, s), 3.77 (2H, m), 3.53 (2H, m), 3.16 (1H, m), 2.79 (2H, m), 2.43 (2H, m), 1.24 (6H, m).

Intermediate AG(5)

ethyl 5-(4-fluorophenyl)-1-(4-methoxybenzyl)-4-oxopiperidine-3-carboxylate

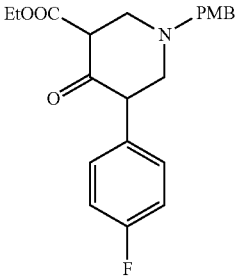

To a cooled solution of Intermediate AG(4) (1.6 g, 3.71 mmol) in THF was added t-BuOK (0.62 g, 5.56 mmol). The reaction mixture was stirred at room temperature for 2 h. The reaction mass was quenched with water then evaporated the solvent under reduced pressure. The residue was diluted with water and extracted with ethyl acetate (25 mL×2). The combined organic layer was washed with brine solution (30 mL), dried over anhydrous $Na_2SO_4$ and evaporated under reduced pressure to get crude compound. The crude compound was purified by column chromatography (Silica gel, 60-120 mesh) using 25% ethyl acetate in pet-ether as mobile phase to give ethyl 5-(4-fluorophenyl)-1-(4-methoxybenzyl)-4-oxopiperidine-3-carboxylate (1.0 g, 70%) as oily liquid. LC-MS (M+H)⁺=386.2. ¹H NMR (400 MHz, CDCl₃): δ ppm 12.0 (1H, s) 7.26 (4H, m), 7.15 (2H, m), 6.88 (2H, m), 4.15 (2H, m), 3.80 (3H, s), 3.77 (2H, m), 3.57 (2H, m), 2.80 (1H, m), 2.40 (1H, m), 1.24 (3H, m).

Intermediate AG(6)

8-(4-fluorophenyl)-6-(4-methoxybenzyl)-5,6,7,8-tetrahydropyrido[4,3-d]pyrimidine-2,4(1H,3H)-dione

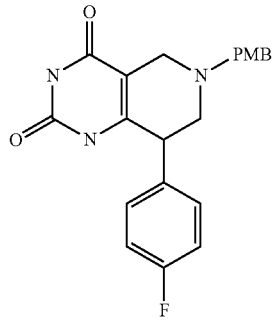

To a cooled solution of Intermediate AG(5) (1.0 g, 2.59 mmol) in ethanol was added t-BuOK (0.436 g 3.89 mmol) followed by urea (0.233 g, 3.89 mmol). The reaction mixture was heated at reflux for 24 h. The reaction mass was quenched with water and evaporated the solvent under reduced pressure. The residue was diluted with water and extracted with ethyl acetate (25 mL×2). The combined organic layer was washed with brine solution (30 mL), dried over Na₂SO₄ and evaporated under reduced pressure to get crude compound. The crude compound was purified by column chromatography (Silica gel, 60-120 mesh) using 10% pet-ether in ethyl acetate as mobile phase to give 8-(4-fluorophenyl)-6-(4-methoxybenzyl)-5,6,7,8-tetrahydropyrido[4,3-d]pyrimidine-2,4(1H,3H)-dione (0.6 g, 63%) as pale yellow solid. LC-MS (M+H)⁺=382.2. ¹H NMR (400 MHz, DMSO-d6): δ ppm 11.06 (1H, s), 10.60 (1H, s), 7.35 (2H, m), 7.29 (2H, m), 7.05 (2H, m), 6.77 (2H, m), 4.05 (1H, m), 3.75 (3H, s), 3.53 (1H, m), 3.44 (2H, m), 2.88 (1H, m), 2.65 (2H, m).

Preparation AG 2,4-dichloro-8-(4-fluorophenyl)-6-(4-methoxybenzyl)-5,6,7,8-tetrahydropyrido[4,3-d]pyrimidine

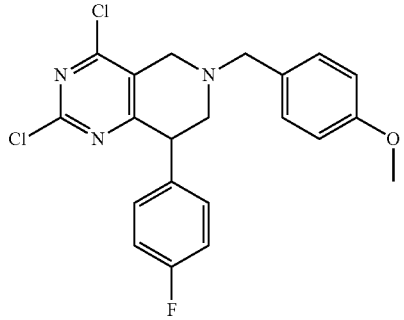 [SMILES: COc1ccc(CN2Cc3c(Cl)nc(Cl)nc3C(c3ccc(F)cc3)C2)cc1]

A solution of Intermediate AG(6) (0.6 g, 1.57 mmol) and catalytic amount of DMF in POCl₃ (20 vol.) was heated at reflux for 10 h. The excess of POCl₃ was evaporated under reduced pressure. The residue was poured in to crushed ice and stirred for 15 min. The aqueous solution was extracted with ethyl acetate (20 mL×3). The combined organic layer was washed with aqueous saturated NaHCO₃ (10 mL×2), brine solution (10 mL), dried over anhydrous Na₂SO₄ and evaporated under reduced pressure to give 2,4-dichloro-8-(4-fluorophenyl)-6-(4-methoxybenzyl)-5,6,7,8-tetrahydropyrido[4,3-d]pyrimidine (0.35 g,) as brown solid. LC-MS (M+H)⁺=418.3.

Preparation AGa 2-chloro-8-(4-fluorophenyl)-6-(4-methoxybenzyl)-N-methyl-5,6,7,8-tetrahydropyrido[4,3-d]pyrimidin-4-amine

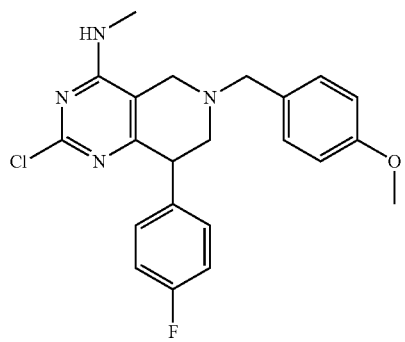 [SMILES: CNc1nc(Cl)nc2c1CN(Cc1ccc(OC)cc1)CC2c1ccc(F)cc1]

To a solution of Preparation AG (1.0 g, 2.39 mmol) in methanol was added diisopropylethylamine (0.62 g, 4.79 mmol) followed by methylamine hydrochloride (0.192 g, 2.87 mmol) at room temperature. The reaction mixture was stirred at room temperature for 18 h. The solvent was removed under reduced pressure and the residue was purified by column chromatography (60-120 mesh) using 35% ethyl acetate in pet-ether as mobile phase to give 2-chloro-8-(4-fluorophenyl)-6-(4-methoxybenzyl)-N-methyl-5,6,7,8-tetrahydropyrido[4,3-d]pyrimidin-4-amine (0.408 g, 41%) as off-white solid. LC-MS (M+H)⁺=413.0. ¹H NMR (400 MHz, DMSO-d6): δ ppm 7.32 (1H, m), 7.24-7.20 (2H, m), 7.14-7.06 (4H, m), 6.82 (2H, m), 3.96 (1H, m), 3.72 (3H, s), 3.67 (1H, m), 3.59 (1H, m), 3.50 (1H, m), 3.20 (1H, m), 2.82 (3H, d, J=4.0 Hz), 2.80 (1H, m), 2.51 (1H, m).

Preparation AGb 2-chloro-N-ethyl-8-(4-fluorophenyl)-6-(4-methoxybenzyl)-5,6,7,8-tetrahydropyrido[4,3-d]pyrimidin-4-amine

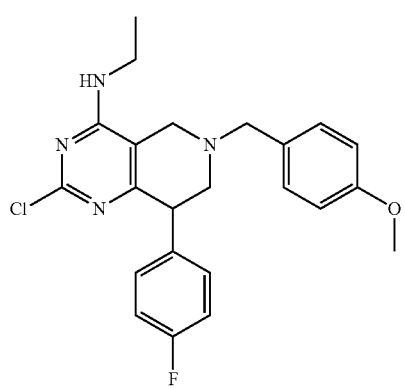 [SMILES: CCNc1nc(Cl)nc2c1CN(Cc1ccc(OC)cc1)CC2c1ccc(F)cc1]

To a solution of Preparation AG (1.0 g, 2.39 mmol) in methanol was added diisopropylethylamine (0.61 g, 4.79 mmol) followed by ethylamine hydrochloride (0.23 g, 2.86 mmol) at room temperature. The reaction mixture was stirred at room temperature for 18 h. The solvent was removed under reduced pressure and the residue was purified by column chromatography (60-120 mesh) using 30-35% ethyl acetate in pet-ether as mobile phase to give 2-chloro-N-ethyl-8-(4-fluorophenyl)-6-(4-methoxybenzyl)-5,6,7,8-tetrahydropyrido[4,3-d]pyrimidin-4-amine (0.54 g, 54%) as off-white solid. LC-MS (M+H)⁺=427.2. ¹H NMR (400 MHz, DMSO-d6): δ ppm 7.32 (1H, m), 7.30-7.19 (2H, m), 7.13-7.05 (4H, m), 6.80 (2H, m), 3.93 (1H, m), 3.71 (3H, s), 3.68-3.48 (5H, m), 3.22 (1H, m), 2.80 (1H, m), 2.68 (1H, m), 1.15 (3H, m).

Preparation AGc 2-chloro-N-ethyl-8-(4-fluorophenyl)-6-(4-methoxybenzyl)-N-methyl-5,6,7,8-tetrahydropyrido[4,3-d]pyrimidin-4-amine

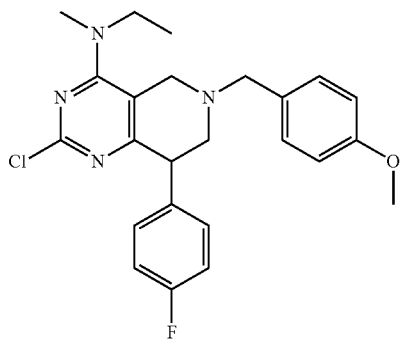 [SMILES: CCN(C)c1nc(Cl)nc2c1CN(Cc1ccc(OC)cc1)CC2c1ccc(F)cc1]

To a solution of Preparation AG (1.2 g, 2.87 mmol) in methanol was added diisopropylethylamine (0.74 g, 5.75 mmol) followed by ethylmethylamine (0.20 g, 3.44 mmol) at room temperature. The reaction mixture was stirred at room temperature for 18 h. The solvent was removed under reduced pressure and the residue was purified by column chromatography (60-120 mesh) using 30-35% ethyl acetate in petroleum-ether as mobile phase to give 2-chloro-N-ethyl-8-(4-fluorophenyl)-6-(4-methoxybenzyl)-N-methyl-5,6,7,8-tetrahydropyrido[4,3-d]pyrimidin-4-amine (0.50 g, 41%) as off-white solid. LC-MS (M+H)⁺=441.2. ¹H NMR (400 MHz, DMSO-d6): δ ppm 7.23-7.16 (4H, m), 7.11-7.07 (2H, m), 6.84 (2H, m), 4.10 (1H, m), 3.73 (3H, s), 3.65-3.56 (3H, m), 3.51-3.40 (3H, m), 3.04 (1H, m), 2.99 (3H, s), 2.58 (1H, m), 1.11 (3H, t, J=7.0 Hz).

Preparation AGd 2-chloro-4-(3,3-difluoroazetidin-1-yl)-8-(4-fluorophenyl)-6-(4-methoxybenzyl)-5,6,7,8-tetrahydropyrido[4,3-d]pyrimidine

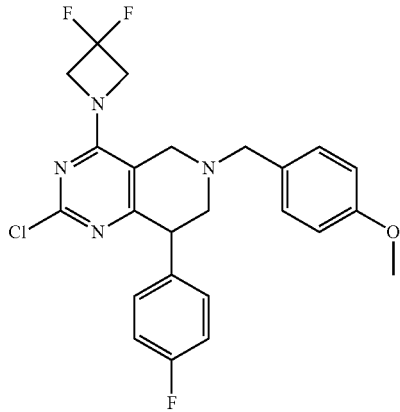 [SMILES: COc1ccc(CN2Cc3c(nc(Cl)nc3N3CC(F)(F)C3)C(c3ccc(F)cc3)C2)cc1]

To a solution of Preparation AG (0.75 g, 1.79 mmol) in methanol was added diisopropylethylamine (0.58 g, 4.49 mmol) followed by 3,3-difluoroazetidine (0.25 g, 1.97 mmol) at room temperature. The reaction mixture was stirred at room temperature for 18 h. The solvent was removed under reduced pressure and the residue was purified by column chromatography (60-120 mesh) using 30% ethyl acetate in pet-ether as mobile phase to give 2-chloro-4-(3,3-difluoroazetidin-1-yl)-8-(4-fluorophenyl)-6-(4-methoxybenzyl)-5,6,7,8-tetrahydropyrido[4,3-d]pyrimidine (0.4 g, 48%) as off-white solid. LC-MS (M+H)⁺=475.2. ¹H NMR (400 MHz, CDCl₃): δ ppm 7.25-7.10 (4H, m), 6.97-6.82 (2H, m), 6.80 (2H, m), 4.52 (4H, m), 4.07 (1H, m), 3.80 (3H, s), 3.59 (3H, m), 3.36 (1H, m), 2.93 (1H, m), 2.80 (1H, m).

Preparation AH 2,4-dichloro-8-(4-fluorophenyl)-6-methyl-5,6,7,8-tetrahydropyrido[4,3-d]pyrimidine

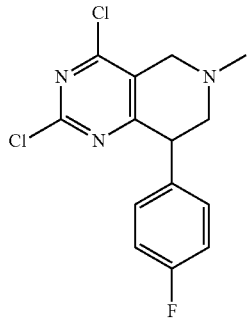 [SMILES: CN1Cc2c(Cl)nc(Cl)nc2C(c2ccc(F)cc2)C1]

Intermediate AH(1)

ethyl 3-((3-ethoxy-3-oxopropyl)(4-methoxybenzyl)amino)-2-(4-fluorophenyl)propanoate

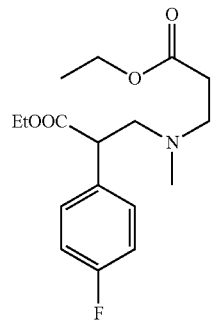 [SMILES: CCOC(=O)CCN(C)CC(C(=O)OCC)c1ccc(F)cc1]

To a solution of Intermediate AG(3) (12.0 g, 38.5 mmol) in acetone was added K₂CO₃ (6.38 g, 46.3 mmol) followed by methyl iodide (6.5 g, 46.3 mmol) at 0° C. The reaction mixture was stirred at room temperature for 2 h. The solvent was removed under reduced pressure and the residue was diluted with water. The aqueous layer was extracted with ethyl acetate (50×3). The combined organic layer was washed with brine solution (75 mL), dried over anhydrous Na₂SO₄ and evaporated under reduced pressure to get crude compound. The crude compound was purified by column chromatography (Silica gel, 60-120 mesh) using 20% ethyl acetate in pet-ether as mobile phase to give ethyl 3-((3-ethoxy-3-oxopropyl)(methyl)amino)-2-phenylpropanoate (6.0 g, 50%) as oily liquid. LC-MS (M+H)+=326.2. ¹H NMR (400 MHz, CDCl₃): δ ppm 7.01 (2H, m), 6.98, (2H, m), 4.16-4.07 (4H, m), 3.77 (1H, m), 3.13 (1H, t, J=2.4 Hz), 2.75-2.51 (5H, m), 2.17 (3H, s), 1.26-1.19 (6H, m).

Intermediate AH(2)

ethyl 5-(4-fluorophenyl)-1-methyl-4-oxopiperidine-3-carboxylate

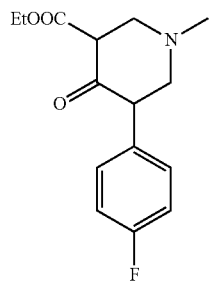

To a cooled solution of Intermediate AH(1) (6.0 g, 18.4 mmol) in THF was added t-BuOK (4.1 g, 36.9 mmol). The reaction mixture was stirred at room temperature for 2 h. The reaction mass was quenched with water then evaporated the solvent under reduced pressure. The residue was diluted with water and extracted with ethyl acetate (25 mL×4). The combined organic layer was washed with brine solution (30 mL), dried over anhydrous Na₂SO₄ and evaporated under reduced pressure to get crude compound. The crude compound was purified by column chromatography (Silica gel, 60-120 mesh) using 20% ethyl acetate in pet-ether as mobile phase to give ethyl 5-(4-fluorophenyl)-1-methyl-4-oxopiperidine-3-carboxylate (3.0 g, 51%) as oily liquid. LC-MS (M+H)+=278.2. ¹H NMR (400 MHz, DMSO-d6): δ ppm 7.35 (1H, m), 7.15 (1H, m), 7.12 (1H, m), 6.98 (1H, m), 4.01 (2H, m), 3.88 (1H, m), 2.60 (1H, m), 2.38 (2H, m), 2.19 (3H, s), 1.19-1.08 (3H, m).

Intermediate AH(3)

8-(4-fluorophenyl)-6-methyl-5,6,7,8-tetrahydropyrido[4,3-d]pyrimidine-2,4(1H,3H)-dione

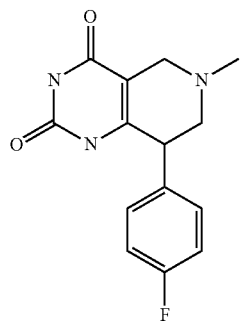 [SMILES: CN1Cc2c([nH]c(=O)[nH]c2=O)C(c2ccc(F)cc2)C1]

To a cooled solution of Intermediate AH(2) (3.0 g, 10.75 mmol) in ethanol was added t-BuOK (3.0 g 26.8 mmol) followed by urea (1.6 g, 26.8 mmol). The reaction mixture was heated at reflux for 36 h. The reaction mass was quenched with water and evaporated the solvent under reduced pressure. The residue was diluted with water and extracted with ethyl acetate (25 mL×3). The combined organic layer was washed with brine solution (30 mL), dried over Na₂SO₄ and evaporated under reduced pressure to get crude compound. The crude compound was purified by column chromatography (Silica gel, 60-120 mesh) using 100% ethyl acetate as mobile phase to give 8-(4-fluorophenyl)-6-methyl-5,6,7,8-tetrahydropyrido[4,3-d]pyrimidine-2,4(1H,3H)-dione (1.5 g, 51%) as pale yellow solid. LC-MS (M+H)+=276.0. ¹H NMR (400 MHz, DMSO-d6): δ ppm 11.08 (1H, s), 10.59 (1H, s), 7.31 (2H, m), 7.13 (2H, m), 3.74 (1H, m), 3.17 (1H, m), 2.80-2.59 (2H, m), 2.23 (3H, s).

Preparation AH 2,4-dichloro-8-(4-fluorophenyl)-6-methyl-5,6,7,8-tetrahydropyrido[4,3-d]pyrimidine

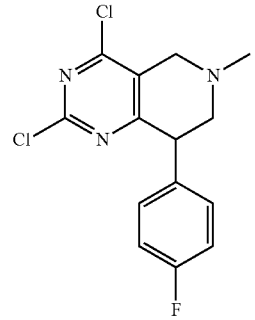 [SMILES: CN1Cc2c(Cl)nc(Cl)nc2C(c2ccc(F)cc2)C1]

A solution of Intermediate AH(3) (1.5 g, 5.45 mmol) and catalytic amount of DMF in POCl₃ (20 vol.) was heated at reflux for 10 h. The excess of POCl₃ was evaporated under reduced pressure. The residue was poured in to crushed ice and stirred for 15 min. The aqueous solution was extracted with ethyl acetate (20 mL×2). The combined organic layer was washed with aqueous saturated NaHCO₃ (10 mL×2), brine solution (10 mL), dried over anhydrous Na₂SO₄ and evaporated under reduced pressure to give 2,4-dichloro-8-(4-fluorophenyl)-6-methyl-5,6,7,8-tetrahydropyrido[4,3-d]pyrimidine (0.7 g, 56%) as brown solid. LC-MS (M+H)+= 312.2.

Preparation AHa 2-chloro-8-(4-fluorophenyl)-N,6-dimethyl-5,6,7,8-tetrahydropyrido[4,3-d]pyrimidin-4-amine

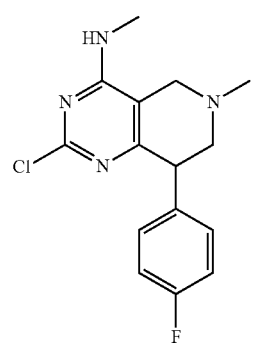 [SMILES: CNc1nc(Cl)nc2c1CN(C)CC2c1ccc(F)cc1]

To a solution of Preparation AH (0.4 g, 1.28 mmol) in methanol was added diisopropylethylamine (0.33 g, 2.57 mmol) followed by methylamine hydrochloride (0.16 g, 2.57 mmol) at room temperature. The reaction mixture was stirred at room temperature for 18 h. The solvent was removed under reduced pressure and the residue was purified by column chromatography (60-120 mesh) using 50% ethyl acetate in pet-ether as mobile phase to give 2-chloro-8-(4-fluorophenyl)-N,6-dimethyl-5,6,7,8-tetrahydropyrido[4,3-d]pyrimidin-4-amine (0.20 g, 51.2%) as off-white solid. LC-MS (M+H)$^+$=307.2.

Preparation AHb 2-chloro-N-ethyl-8-(4-fluorophenyl)-6-methyl-5,6,7,8-tetrahydropyrido[4,3-d]pyrimidin-4-amine

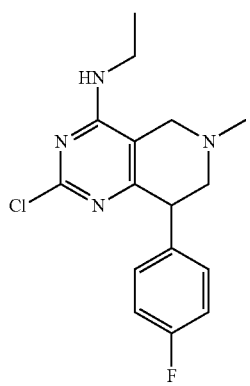 [SMILES: CCNc1nc(Cl)nc2c1CN(C)CC2c1ccc(F)cc1]

To a solution of Preparation AH (0.7 g, 2.25 mmol) in methanol was added diisopropylethylamine (0.58 g, 4.50 mmol) followed by ethylamine hydrochloride (0.4 g, 4.50 mmol) at room temperature. The reaction mixture was stirred at room temperature for 18 h. The solvent was removed under reduced pressure and the residue was purified by column chromatography (60-120 mesh) using 30-35% ethyl acetate in pet-ether as mobile phase to give 2-chloro-N-ethyl-8-(4-fluorophenyl)-6-methyl-5,6,7,8-tetrahydropyrido[4,3-d]pyrimidin-4-amine (0.21 g, 29%) as off-white solid. LC-MS (M+H)$^+$=321.2.

Preparation AHc 2-chloro-N-ethyl-8-(4-fluorophenyl)-N,6-dimethyl-5,6,7,8-tetrahydropyrido[4,3-d]pyrimidin-4-amine

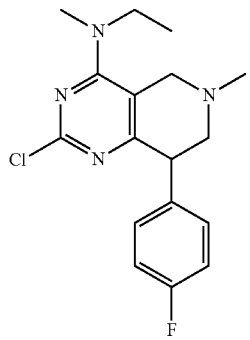 [SMILES: CCN(C)c1nc(Cl)nc2c1CN(C)CC2c1ccc(F)cc1]

To a solution of Preparation AH (0.35 g, 1.1 mmol) in methanol was added diisopropylethylamine (0.29 g, 2.2 mmol) followed by ethylmethylamine (0.67 g, 1.35 mmol) at room temperature. The reaction mixture was stirred at room temperature for 18 h. The solvent was removed under reduced pressure and the residue was purified by column chromatography (60-120 mesh) using 35% ethyl acetate in pet-ether as mobile phase to give 2-chloro-N-ethyl-8-(4-fluorophenyl)-N,6-dimethyl-5,6,7,8-tetrahydropyrido[4,3-d]pyrimidin-4-amine (0.22 g, 58%) as off-white solid. LC-MS (M+H)$^+$=333.9.

Preparation AI 2,4-dichloro-8-(4-fluorophenyl)-7-(4-methoxybenzyl)-5,6,7,8-tetrahydropyrido[3,4-d]pyrimidine

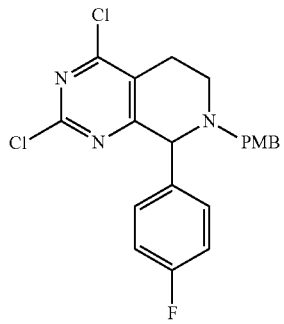

Intermediate AI(1)

ethyl 2-amino-2-(4-fluorophenyl)acetate

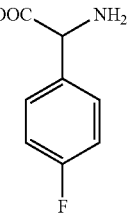

To a cooled solution of 2-amino-2-(4-fluorophenyl)acetic acid (1.0 g, 6.17 mmol) in ethanol was added con. H$_2$SO$_4$ (1 mL) over a period of 1 min. The reaction mixture was heated at reflux for 5 h. The solvent was evaporated under reduced pressure and the residue was diluted with ethyl acetate (20 mL). The organic solution was washed with aqueous saturated NaHCO$_3$ (15 mL×2), water (20 mL), brine solution (10 mL), dried over anhydrous Na$_2$SO$_4$ and evaporated under reduced pressure to give ethyl 2-amino-2-(4-fluorophenyl) acetate (0.75 g, 65%) as crude compound (oily liquid). The crude compound was taken to the next step without further purification. LC-MS (M+H$_2$O)$^+$=198.0. $^1$H NMR (400 MHz, DMSO-d6): δ 7.44-7.40 (2H, m), 7.18-7.13 (2H, m), 4.51 (1H, s), 4.12-4.01 (2H, m), 2.26 (2H, s), 1.12 (3H, t, J=8.0 Hz).

Intermediate AI(2)

ethyl 4-(2-ethoxy-1-(4-fluorophenyl)-2-oxoethylamino)butanoate

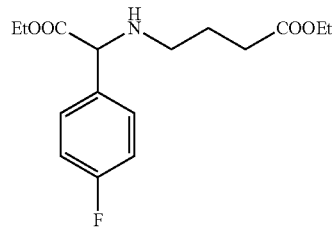 [SMILES: CCOC(=O)CCCNC(C(=O)OCC)c1ccc(F)cc1]

To a solution of Intermediate AI(1) (4.2 g, 21.3 mmol) in DMF was added cesium carbonate (8.3 g, 2.25 mmol) followed ethyl 4-bromobutyroate (4.98 g, 2.55 mmol) at room temperature. The reaction mixture was stirred at 70° C. for 18 h. The solvent was evaporated under reduced pressure and the crude compound was purified by column chromatography (Silica gel, 60-120 mesh) using 25% ethyl acetate in pet-ether as mobile phase to give ethyl 4-(2-ethoxy-1-(4-fluorophenyl)-2-oxoethylamino)butanoate (2.0 g, 30%) as yellowish oily liquid. LC-MS (M+H)$^+$=312.2. $^1$H NMR (400 MHz, CDCl$_3$): δ ppm 7.33 (2H, m), 7.06 (2H, m), 4.31 (1H, m), 4.18 (4H, m), 2.63 (1H, m), 2.49 (1H, m), 2.35 (2H, m), 1.81 (1H, m), 1.24 (6H, m).

Intermediate AI(3)

ethyl 4-((2-ethoxy-1-(4-fluorophenyl)-2-oxoethyl)(4-methoxybenzyl)amino)butanoate

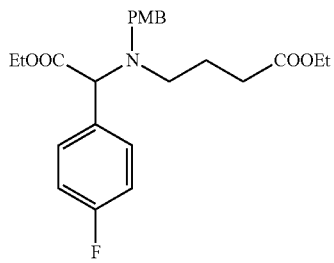

To a solution Intermediate AI(2) (15.0 g, 48.23 mmol) in acetone was added K$_2$CO$_3$ (7.9 g, 57.8 mmol) followed by 4-methoxybenzyl bromide (14.5 g, 72.3 mmol) at 0° C. The reaction mixture was heated at 70° C. for 18 h. The solvent was removed under reduced pressure and the residue was diluted with water. The aqueous layer was extracted with ethyl acetate (100×2). The combined organic layer was washed with brine solution (75 mL), dried over anhydrous Na$_2$SO$_4$ and evaporated under reduced pressure to get crude compound. The crude compound was purified by column chromatography (Silica gel, 60-120 mesh) using 30% ethyl acetate in pet-ether as mobile phase to give ethyl 4-((2-ethoxy-1-(4-fluorophenyl)-2-oxoethyl)(4-methoxybenzyl)amino)butanoate (12.0 g, 60%) as oily liquid. LC-MS (M+H)$^+$432.2. $^1$H NMR (400 MHz, CDCl$_3$): δ ppm 7.30 (2H, m), 7.22 (2H, m), 7.01 (2H, m), 6.99 (2H, m), 4.52 (1H, s), 4.22 (2H, m), 4.04 (2H, m), 3.79 (5H, m), 3.61 (1H, m), 2.71 (1H, m), 2.57 (1H, m), 2.20 (1H, m), 2.07 (1H, m), 1.70 (2H, m), 1.28 (3H, m, J=7.2 Hz), 1.20 (3H, m, J=7.2 Hz).

Intermediate AI(4)

ethyl 2-(4-fluorophenyl)-1-(4-methoxybenzyl)-3-oxopiperidine-4-carboxylate

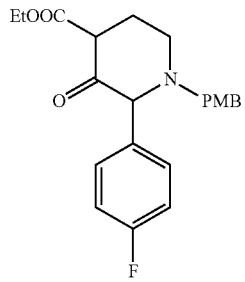

To a cooled solution of Intermediate AI(3) (12.0 g, 27.7 mmol) in THF was added t-BuOK (6.2 g, 55.5 mmol). The reaction mixture was stirred at room temperature for 3 h. The reaction mass was quenched with water then evaporated the solvent under reduced pressure. The residue was diluted with water and extracted with ethyl acetate (50 mL×4). The combined organic layer was washed with brine solution (50 mL), dried over anhydrous Na$_2$SO$_4$ and evaporated under reduced pressure to get crude compound. The crude compound was purified by column chromatography (Silica gel, 60-120 mesh) using 20% ethyl acetate in pet-ether as mobile phase to give ethyl 2-(4-fluorophenyl)-1-(4-methoxybenzyl)-3-oxopiperidine-4-carboxylate (7.0 g, 67%) as oily liquid. LC-MS (M+H)$^+$=386.2. $^1$H NMR (400 MHz, CDCl$_3$): δ ppm 12.02 (1H, s), 7.43 (2H, m), 7.15 (2H, m), 7.04 (2H, m), 6.84 (2H, m), 4.23 (2H, q, J=7.2 Hz), 4.05 (1H, s), 3.79 (3H, s), 3.65 (1H, d, J=13.6 Hz), 3.22 (1H, d, J=13.6 Hz), 2.92 (1H, m), 2.35 (3H, m), 1.32 (3H, t, J=7.2 Hz).

Intermediate AI(5)

8-(4-fluorophenyl)-7-(4-methoxybenzyl)-5,6,7,8-tetrahydropyrido[3,4-d]pyrimidine-2,4(1H,3H)-dione

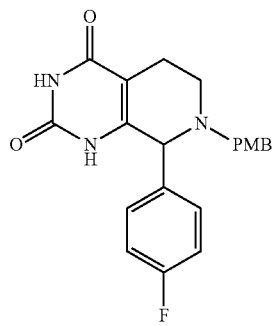

To a cooled solution of Intermediate AI(4) (7.0 g, 18.1 mmol) in ethanol was added t-BuOK (5.0 g 45.4 mmol) followed by urea (2.7 g, 45.4 mmol). The reaction mixture was heated at reflux for 18 h. The reaction mass was quenched with water and evaporated the solvent under reduced pressure. The residue was diluted with water and extracted with ethyl acetate (50 mL×3). The combined organic layer was washed with brine solution (75 mL), dried over Na$_2$SO$_4$ and evaporated under reduced pressure to get crude compound. The crude compound was purified by column chromatography (Silica gel, 60-120 mesh) using 50% pet-ether in ethyl acetate as mobile phase to give 8-(4-fluorophenyl)-7-(4-methoxybenzyl)-5,6,7,8-tetrahydropyrido[3,4-d]pyrimidine-2,4(1H,3H)-dione (3.0 g, 45%) as pale yellow solid. LC-MS (M+H)$^+$=382.0. $^1$H NMR (400 MHz, DMSO-d6): δ ppm 11.08 (1H, s), 10.44 (1H, s), 7.26-7.17 (6H, m), 6.92 (2H, m), 4.36 (1H, s), 3.75 (3H, s), 3.73 (1H, d, J=13.2 Hz) 3.58 (1H, d, J=13.2 Hz), 2.63 (2H, m), 2.51 (1H, m), 2.35 (1H, m).

Preparation AI 2,4-dichloro-8-(4-fluorophenyl)-7-(4-methoxybenzyl)-5,6,7,8-tetrahydropyrido[3,4-d]pyrimidine

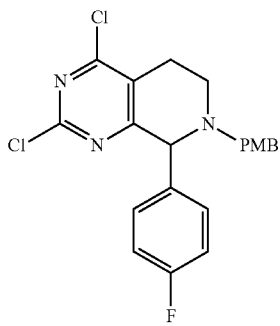

A solution of Intermediate AI(5) (2.0 g, 5.24 mmol) and catalytic amount of DMF in POCl$_3$ (30 vol.) was heated at 85° C. for 18 h. The excess of POCl$_3$ was evaporated under reduced pressure. The residue was poured in to crushed ice and stirred for 15 min. The aqueous solution was extracted with ethyl acetate (20 mL×3). The combined organic layer was washed with aqueous saturated NaHCO$_3$ (10 mL×4), brine solution (25 mL), dried over anhydrous Na$_2$SO$_4$ and evaporated under reduced pressure to give 2,4-dichloro-8-(4-fluorophenyl)-7-(4-methoxybenzyl)-5,6,7,8-tetrahydropyrido[3,4-d]pyrimidine (1.4 g, crude) as brown solid. LC-MS (M+H)$^+$=418.0.

Preparation AIa 2-chloro-N-ethyl-8-(4-fluorophenyl)-7-(4-methoxybenzyl)-5,6,7,8-tetrahydropyrido[3,4-d]pyrimidin-4-amine

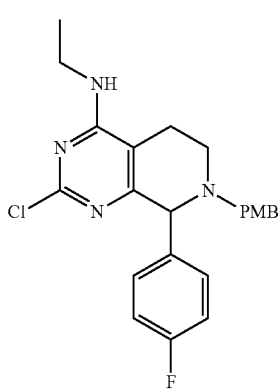

To a solution of Preparation AI (0.7 g, 1.67 mmol) in methanol was added diisopropylethylamine (0.43 g, 3.35 mmol) followed by ethylamine hydrochloride (0.27 g, 3.35 mmol) at room temperature. The reaction mixture was stirred at room temperature for 18 h. The solvent was removed under reduced pressure and the residue was purified by column chromatography (60-120 mesh) using 35% ethyl acetate in pet-ether as mobile phase to give chloro-N-ethyl-8-(4-fluorophenyl)-7-(4-methoxybenzyl)-5,6,7,8-tetrahydropyrido[3,4-d]pyrimidin-4-amine (0.36 g, 50%) as off-white solid. LC-MS (M+H)$^+$=427.2. $^1$H NMR: (400 MHz, DMSO-d6): δ ppm 7.38 (2H, m), 7.30 (2H, m), 7.20-7.13 (4H, m), 6.88 (2H, m), 4.45 (1H, s), 3.73 (3H, s), 3.45 (1H, m), 3.40-3.34 (3H, m), 2.88 (1H, m), 2.42 (2H, m), 1.16 (3H, t, J=7.2 Hz).

Preparation AIb 2-chloro-N-ethyl-8-(4-fluorophenyl)-7-(4-methoxybenzyl)-N-methyl-5,6,7,8-tetrahydropyrido[3,4-d]pyrimidin-4-amine

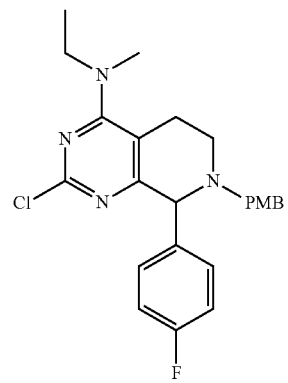

To a solution of Preparation AI (0.7 g, 1.67 mmol) in methanol was added diisopropylethylamine (0.43 g, 3.3 mmol) followed by ethylmethylamine HCl (0.19 g, 3.35 mmol) at room temperature. The reaction mixture was stirred at room temperature for 18 h. The solvent was removed under reduced pressure and the residue was purified by column chromatography (60-120 mesh) using 20% ethyl acetate in pet-ether as mobile phase to give 2-chloro-N-ethyl-8-(4-fluorophenyl)-7-(4-methoxybenzyl)-N-methyl-5,6,7,8-tetrahydropyrido[3,4-d]pyrimidin-4-amine (0.40 g, 54%) as off-white solid. LC-MS (M+H)$^+$=441.2. $^1$H NMR: (400 MHz, DMSO-d6) δ ppm 7.49 (2H, m), 7.19-7.14 (4H, m), 6.87 (2H, m), 4.42 (1H, s), 3.73 (3H, s), 3.55 (2H, m), 3.42 (1H, m), 3.21 (1H, m), 3.04 (3H, s), 2.95 (2H, m), 2.56 (1H, m), 2.25 (1H, m), 1.16 (3H, t, J=7.2 Hz).

Preparation AIc1 and AIc2

2-chloro-8-(4-fluorophenyl)-4-((R)-3-fluoropyrrolidin-1-yl)-7-(4-methoxybenzyl)-5,6,7,8-tetrahydropyrido[3,4-d]pyrimidine

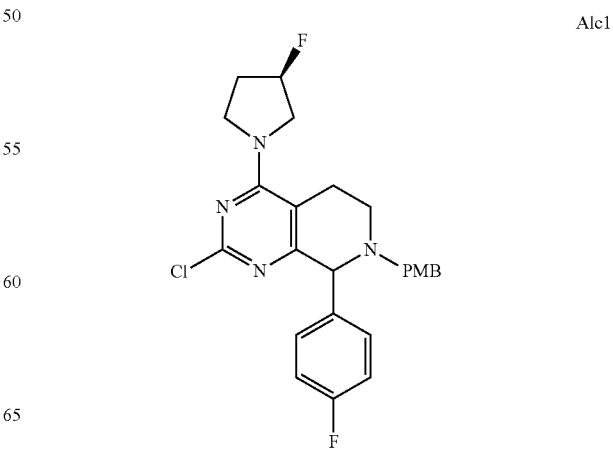

AIc1

-continued

Alc2

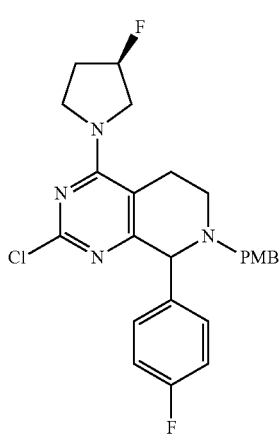

To a solution of Preparation AI (0.70 g, 1.6 mmol) in methanol was added diisopropylethylamine (0.40 g, 3.35 mmol) followed by (S)-3-fluoropyrrolidine (0.25 g, 2.14 mmol) at room temperature. The reaction mixture was stirred at room temperature for 18 h. The solvent was removed under reduced pressure and the residue was purified by pep-HPLC to give 2-chloro-8-(4-fluorophenyl)-4-((R)-3-fluoropyrrolidin-1-yl)-7-(4-methoxybenzyl)-5,6,7,8-tetrahydropyrido[3,4-d]pyrimidine (0.150 g, 37% & 190 mg, 43%).

AIc1: LC-MS (M+H)$^+$=471.1. $^1$H NMR (400 MHz, chlorofom-d): δ ppm 7.48 (2H, m), 7.15 (2H, m), 7.01 (2H, m), 6.83 (2H, m), 5.30 (1H, m), 4.43 (1H, s), 3.97-3.90 (4H, m), 3.88-3.72 (4H, m), 3.65 (1H, m), 3.17 (1H, m), 3.02 (2H, m), 2.33 (2H, m), 1.95 (1H, m).

AIc2: LC-MS (M+H)$^+$=471.1. $^1$H NMR (400 MHz, chlorofom-d): δ ppm 7.28 (2H, m), 7.18 (2H, m), 6.99 (2H, m), 6.84 (2H, m), 5.30 (1H, m), 4.58 (1H, s), 4.20-4.11 (2H, m), 3.97-3.80 (6H, m), 3.69 (1H, m), 3.35 (1H, m), 2.88 (2H, m), 2.35 (1H, m), 2.17 (1H, m), 2.05 (1H, m).

Preparation AId 2-chloro-8-(4-fluorophenyl)-4-((S)-3-fluoropyrrolidin-1-yl)-7-(4-methoxybenzyl)-5,6,7,8-tetrahydropyrido[3,4-d]pyrimidine

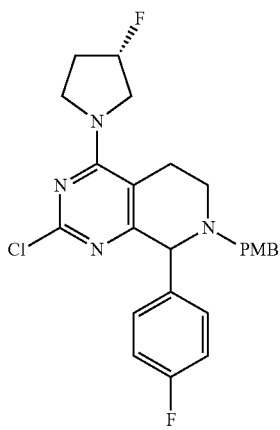

To a solution of Preparation AI (0.70 g, 1.6 mmol) in methanol was added diisopropylethylamine (0.43 g, 3.35 mmol) followed by (R)-3-fluoropyrrolidine (0.25 g, 2.2 mmol) at room temperature. The reaction mixture was stirred at room temperature for 18 h. The solvent was removed under reduced pressure and the residue was purified by pep-HPLC to give 2-chloro-8-(4-fluorophenyl)-4-((S)-3-fluoropyrrolidin-1-yl)-7-(4-methoxybenzyl)-5,6,7,8-tetrahydropyrido[3,4-d]pyrimidine (0.150 g, 37% & 190 mg, 43%). LC-MS (M+H)$^+$=471.2.

Preparation AJ 2-chloro-4-(methylamino)-8-phenyl-7,8-dihydroquinazolin-8-ol

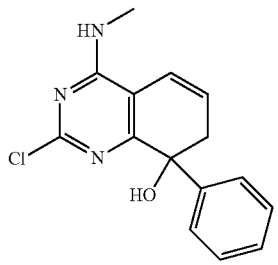 [SMILES: CNc1nc(Cl)nc2c1C=CCC2(O)c1ccccc1]

Intermediate AJ(1)

methyl 2-chloro-6-(methylamino)pyrimidine-4-carboxylate

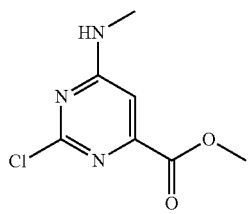

To a mixture of methyl 2,6-dichloropyrimidine-4-carboxylate (2 g), methylamine hydrochloride (0.72 g) in CH$_2$Cl$_2$ (48 mL) at 0° C. was added Hunig's base (3.7 mL) dropwise, and the reaction mixture was stirred at ice bath for 1 h and then rt for 1 h. The solvent was removed in vacuo, and the white residue was purified directly by Biotage eluting with 40-600% EtOAc/Hexanes (1000 mL) followed by 90% CH2Cl2/10% MeOH (4 L) to give the title compound as a white solid (1.8 g). These fractions were combined and evaporated in vacuo. During the solvent removal, some white solid was formed. Several filtrations gave the title compound as a white solid (1.8 g, very white solid).). LC-MS (M+H)$^+$= 202.00

Intermediate AJ(2)

2-chloro-N-methoxy-N-methyl-6-(methylamino)pyrimidine-4-carboxamide

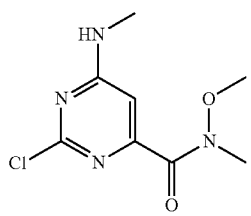

To a suspension of methyl 2-chloro-6-(methylamino)pyrimidine-4-carboxylate (1.95 g) and N,O-dimethylhydroxylamine hydrochloride (1.887 g, 19.34 mmol) in THF at −20° C. was added isopropylmagnesium chloride (23.60 mL, 47.2 mmol) dropwise through a dropping funnel over a period of 30 min, and the reaction mixture was stirred at −10° C. for 40 min. The reaction was worked up with sat. NH$_4$Cl and EtOAc, and the crude product was purified by Biotage eluting with 40-90% EtOAc/Hexanes to give the title compound as a colorless oil (786 mg). LC-MS (M+H)$^+$=231.01.

Intermediate AJ(3)

5-bromo-2-chloro-N-methoxy-N-methyl-6-(methylamino)pyrimidine-4-carboxamide

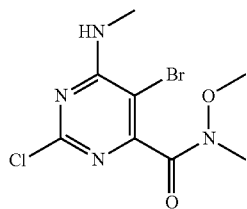 [SMILES: CNc1nc(Cl)nc(C(=O)N(C)OC)c1Br]

To a solution of 2-chloro-N-methoxy-N-methyl-6-(methylamino)pyrimidine-4-carboxamide (959 mg) in MeCN (21 mL) was added NBS (814 mg), and the reaction mixture was heated at 60° C. for 8 h. The solvent was removed, and the residue was purified by Biotage eluting with 50%-70 EtOAc/Hexanes (1.2 L) to give the title compound as a white solid (1.1 g). LC-MS (M+H)$^+$=310.95.

Intermediate AJ(4)

2-chloro-N-methoxy-N-methyl-6-(methylamino)-5-vinylpyrimidine-4-carboxamide

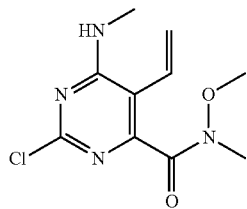 [SMILES: C=Cc1c(NC)nc(Cl)nc1C(=O)N(C)OC]

A solution of 5-bromo-2-chloro-N-methoxy-N-methyl-6-(methylamino)pyrimidine-4-carboxamide (100 mg), tributyl(vinyl)stannane (113 mg), tetrakis (23 mg) in toluene (1.6 mL) was heated at 95° C. for 12 h, and the solvent was removed. The residue was purified by preparative TLC eluting with 50% EtOAc/Hexanes to give the title compound as a colorless oil (23 mg). LC-MS (M+H)$^+$=257.06.

Intermediate AJ(5)

(2-chloro-6-(methylamino)-5-vinylpyrimidin-4-yl)(phenyl)methanone

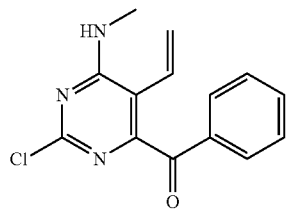 [SMILES: C=Cc1c(NC)nc(Cl)nc1C(=O)c1ccccc1]

To a solution of 2-chloro-N-methoxy-N-methyl-6-(methylamino)-5-vinylpyrimidine-4-carboxamide (136 mg) in THF (1.8 mL) at 0° C. was added phenylmagnesium bromide (1 M solution in THF, 1.3 mL)) dropwise, and the reaction mixture was stirred at 0° C. for 30 min. The reaction was worked up with EtOAc/sat. NH$_4$Cl, and the crude product was purified by preparative TLC eluting with 40% EtOAc/Hexanes to give the title compound as a colorless oil (87 mg). LC-MS (M+H)$^+$=274.03.

Intermediate AJ(6)

1-(2-chloro-6-(methylamino)-5-vinylpyrimidin-4-yl)-1-phenylbut-3-en-1-ol

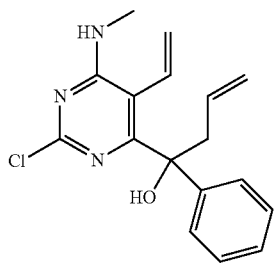 [SMILES: C=CCC(O)(c1ccccc1)c1nc(Cl)nc(NC)c1C=C]

To a solution of (2-chloro-6-(methylamino)-5-vinylpyrimidin-4-yl)(phenyl)methanone (142 mg) in THF (2.6 mL) at rt was added allylmagnesium bromide (1.0 M solution in THF, 1.1 mL) dropwise, and the reaction mixture was stirred at rt for 30 min. The reaction was worked up with EtOAc/sat. NH$_4$Cl, and the crude product was purified by prep. TLC eluting with 30% EtOAc/Hexanes to give the title compound as a colorless oil (133 mg). LC-MS (M−H$_2$O+H)$^+$=298.18.

Preparation AJ 2-chloro-4-(methylamino)-8-phenyl-7,8-dihydroquinazolin-8-ol

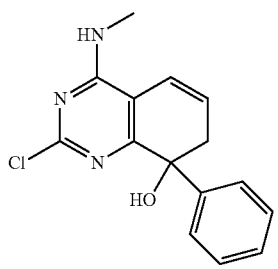 [SMILES: CNc1nc(Cl)nc2c1C=CCC2(O)c1ccccc1]

To a solution of 1-(2-chloro-6-(methylamino)-5-vinylpyrimidin-4-yl)-1-phenylbut-3-en-1-ol (60 mg) in benzene (5 mL) was added Grubbs I (16 mg), and the reaction mixture was heated at 85° C. for 1 h. The solvent was removed, and the residue was purified by preparative TLC eluting with 40% EtOAc/Hexanes to give the title compound as a colorless oil (50 mg). $^1$H NMR (500 MHz, CDCl$_3$) δ ppm 7.4 (5H, m), 6.25 (1H, m), 6.07 (1H, m), 5.14 (1H, br. S), 4.52 (1H, s), 3.10 (3H, d<J=5.0 Hz), 2.99 (2H, m). $^{13}$C NMR (125 MHz, CDCl$_3$) 164.32, 159.38, 158.85, 144.15, 128.24, 128.02, 127.83, 125.51, 117.54, 108.14, 60.51, 38.50, and 28.57. HRMS calcd. for $C_{15}H_{15}ClN_3O$ (M+H) 288.0904; found: 288.0899.

Preparation AK 2-chloro-4-(methylamino)-8-phenyl-5,6,7,8-tetrahydroquinazolin-8-ol

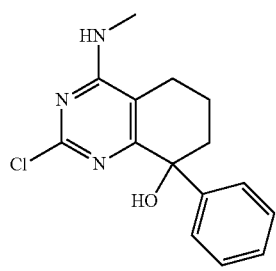 [SMILES: CNc1nc(Cl)nc2c1CCCC2(O)c1ccccc1]

To a solution of 2-chloro-4-(methylamino)-8-phenyl-7,8-dihydroquinazolin-8-ol (20 mg) in EtOAc (5 mL) was added 5% Pd/C (6 mg), and the resulting suspension was stirred under a hydrogen balloon for 1 h. The reaction mixture was filtered through a pad of Celite to give the title compound as a colorless oil (20 mg).

$^1$H NMR (500 MHz, CDCl$_3$) δ ppm 7.3 (5H, m), 4.9 (1H, br. S), 4.02 (1H, s), 3.14 (3H, br. S), 1.5-2.5 (6H, m) $^{13}$C NMR (125 MHz, CDCl$_3$) 164.82, 162.72, 158.56, 146.54, 128.02, 127.37, 126.72, 110.92, 74.81, 37.58, 28.61, 21.89, 17.47. HRMS calcd. for $C_{15}H_{17}ClN_3O$ (M+H) 290.1060; found: 290.1052.

Preparation AL 2-chloro-4-(dimethylamino)-7-phenyl-6,7-dihydro-5H-cyclopenta[d]pyrimidin-7-ol

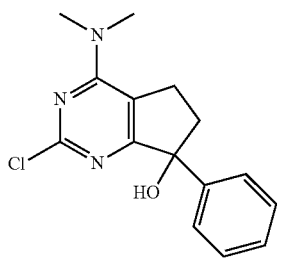 [SMILES: CN(C)c1nc(Cl)nc2c1CCC2(O)c1ccccc1]

2-chloro-4-(dimethylamino)-7-phenyl-7H-cyclopenta[d]pyrimidin-7-ol was prepared from methyl 2,6-dichloropyrimidine-4-carboxylate using the same transformations as shown in Preparation AJ/AK with the following differences:

Intermediate AL(1): dimethylamine was used instead of methylamine hydrochloride, and 1.1 equiv of Hünig's base was used; Intermediate AL(6): vinylmagnesium bromide was used instead of allylmagnesium bromide. $^1$H NMR (500 MHz, CDCl$_3$) δ ppm 7.3 (5H, m), 3.28 (6H, s), 1.5-3.4 (5H, m). $^{13}$C NMR (125 MHz, CDCl$_3$) 174.66, 161.76, 159.58, 144.61, 128.49, 127.58, 125.35, 113.92, 82.86, 41.07, 39.00, 28.59. HRMS calcd. for $C_{15}H_{17}ClN_3O$ (M+H) 290.1060; found: 290.1050.

Preparation AM (6S,7S)-2-chloro-4-(dimethylamino)-7-phenyl-6,7-dihydro-5H-cyclopenta[d]pyrimidin-6-ol

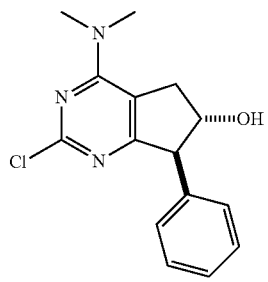 [SMILES: CN(C)c1nc(Cl)nc2c1C[C@H](O)[C@H]2c1ccccc1]

Intermediate AM(1)

2-chloro-N,N-dimethyl-7-phenyl-5H-cyclopenta[d]pyrimidin-4-amine

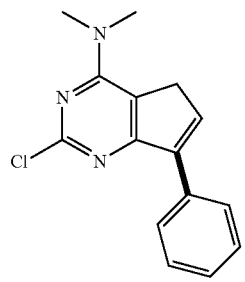

To a solution of 2-chloro-4-(dimethylamino)-7-phenyl-6,7-dihydro-5H-cyclopenta[d]pyrimidin-7-ol (85 mg) in i-PrOH (5 mL) was added HCl in ether (1M solution), and the reaction mixture was heated at 80° C. from 3 h. The solution was cloudy and turned to clear yellow solution by the end of the reaction. The solvents were removed, and the reaction mixture was worked up with EtOAc and saturated NaHCO$_3$ to give the title compound as a brownish solid (50 mg). LC-MS (M–H$_2$O+H)$^+$=272.07.

Preparation AM (6S,7S)-2-chloro-4-(dimethylamino)-7-phenyl-6,7-dihydro-5H-cyclopenta[d]pyrimidin-6-ol

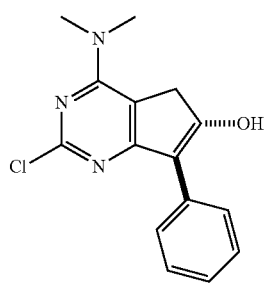

To a solution of 2-chloro-N,N-dimethyl-7-phenyl-5H-cyclopenta[d]pyrimidin-4-amine (113 mg) in THF (2 mL) at rt was added borane dimethyl sulfide complex in THF (2.0 M solution, 0.41 mL), and the reaction mixture was stirred at rt for 5 h. Water (0.50 mL) was added carefully, followed by 30% $H_2O_2$ (0.50 mL) and 1 N NaOH (1 mL). 5 mL EtOAc was added, and the reaction mixture was stirred at rt for 12 h. The crude product was purified by prep. TLC eluting with 50% EtOAc/Hexanes to give the title compound as a yellowish solid (44 mg). LC-MS $(M–H_2O+H)^+$=290.05.

Preparation AN 2-chloro-4-(methylamino)-7-phenyl-6,7-dihydro-5H-cyclopenta[d]pyrimidin-5-one

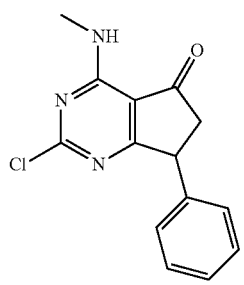 [SMILES: CNc1nc(Cl)nc2c1C(=O)CC2c1ccccc1]

Intermediate AN(1)

2,4-dichloro-6-(1-phenylvinyl)pyrimidin-5-yl)methanol

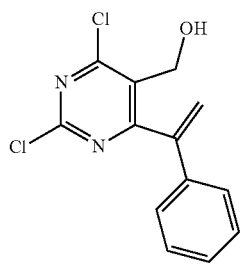 [SMILES: C=C(c1ccccc1)c1nc(Cl)nc(Cl)c1CO]

A mixture of 2,4,6-trichloropyrimidin-5-yl)methanol (1.1 g), 1-phenylvinylboronic acid (0.8 g), Tetrakis (0.3 g), sodium carbonate (1.64 g) in toluene (14 mL) and water (3 mL) was heated at 100° C. for 12 h. Water was added followed by ethyl acetate, the aqueous layer was extracted with ethyl acetate (×3), and the combined organic layers were dried over anhydrous sodium sulfate and then filtered. The filtrate was concentrated, and the residue was purified Biotage eluting with 10-40% EtOAc/Hexanes to give the title compound as a white solid (325 mg). LC-MS $(M+H)^+$=281.02. $^1$H NMR (500 MHz, chloroform-d) δ ppm 7.5 (5H, m), 6.01 (1H, s), 5.67 (1H, s), 4.62 (2H, s).

Intermediate AN(2)

2,4-dichloro-6-(1-phenylvinyl)pyrimidine-5-carbaldehyde

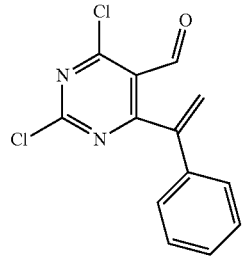 [SMILES: C=C(c1ccccc1)c1nc(Cl)nc(Cl)c1C=O]

To a solution of 2,4-dichloro-6-(1-phenylvinyl)pyrimidin-5-yl)methanol (327 mg) in $CH_2Cl_2$ was added PCC (600 mg) and 4A MS (600 mg), and the reaction mixture was stirred at rt for 30 min. The solution turned to dark brown from orange a few min after addition of PCC. The reaction mixture was filtered through a pad of silica gel eluting with $CH_2Cl_2$ to give the title compound as a s a brownish solid (209 mg) and used directly for the next step.

Intermediate AN(3)

1-(2,4-dichloro-6-(1-phenylvinyl)pyrimidin-5-yl)prop-2-en-1-ol

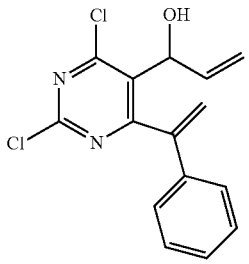 [SMILES: C=CC(O)c1c(Cl)nc(Cl)nc1C(=C)c1ccccc1]

To a solution of 2,4-dichloro-6-(1-phenylvinyl)pyrimidine-5-carbaldehyde (200 mg) in THF (3.6 mL) at −78 C was added vinylmagnesium bromide (0.79 mL, 1M solution in THF) dropwise, and the reaction mixture was stirred at −78° C. for 20 min. Saturated $NH_4Cl$ was added followed by ethyl acetate, the aqueous layer was extracted with ethyl acetate (×3), and the combined organic layers were dried over anhydrous sodium sulfate and then filtered. The filtrate was concentrated in vacuo to give the title compound (156 mg) as a colorless oil. The crude product was used directly for the next step.

Preparation AN 2-chloro-4-(methylamino)-7-phenyl-6,7-dihydro-5H-cyclopenta[d]pyrimidin-5-one

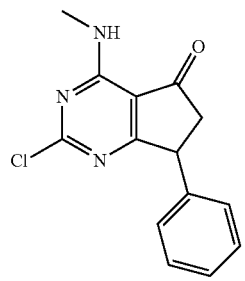 [SMILES: CNc1nc(Cl)nc2c1C(=O)CC2c1ccccc1]

To a solution of 1-(2,4-dichloro-6-(1-phenylvinyl)pyrimidin-5-yl)prop-2-en-1-ol (20 mg) in $CH_2Cl_2$ (6.5 mL) was added Grubbs II catalyst (6 mg), and the reaction mixture was heated under reflux for 30 min. The solvent was removed, and the residue was dissolved in EtOAc (4 mL), and 10% Pd/C (5 mg) was added. The reaction mixture was stirred under a hydrogen balloon for 35 min. Hydrogen balloon was removed, and then Hunig's base (23 mL) was added followed by methylamine (36 mL, 2 M solution in methanol). The reaction mixture was stirred at room temperature for 10 min, and the solvents were removed. The residue was purified by preparative TLC eluting with 35% EtOAc/Hexanes to give the title compound as a yellow solid (6.6 mg, 37% yield). $^1$H NMR (500 MHz, chloroform-d) δ ppm 7.1-7.4 (5H, m), 4.45 (1H, dd, J=3.0, 8.0 Hz), 3.24 (1H, dd, J=8.0, 19.5 Hz), 3.20 (3H, s), 3.19 (3H, s), 2.71 (1H, dd, J=3.0, 19.5 Hz). $^{13}$C NMR (125 MHz, chloroform-d) δ 203.12, 186.69, 166.52, 159.93, 139.88 129.16 (2C), 127.73 (2C), 127.59, 110.98, 46.50, 45.48, and 27.53. HRMS calcd. for $C_{14}H_{13}ClN_3O$ (M+H) 274.0742; found: 274.0741.

Preparation AO 3-methoxy-4-(1-methyl-1H-pyrazol-4-yl)aniline

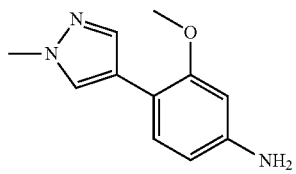

A DMF solution of diethyl 1-methyl-1H-pyrazol-4-ylboronate, 4-bromo-3-methoxy nitrobenzene together with Pd(dppf) and K2CO3 were heated at reflux overnight. The product obtained was reduced with Fe in MeOH/ammonium chloride to provide the title compound. LC-MS (M+H)$^+$= 204.2. $^1$H NMR (400 MHz, DMSO-d6): δ ppm 7.84 (1H, s), 7.66 (1H, s), 7.19 (1H, J=8.2 Hz, d), 6.29 (1H, s), 6.18 (1H, J=2.0, 8.2 Hz, dd), 5.31 (2H, br s), 3.80 (3H, s), 3.75 (3H, s).

Preparation AP 2,4-dichloro-7-(4-fluorophenyl)-7-methyl-6,7-dihydro-5H-cyclopenta[d]pyrimidine

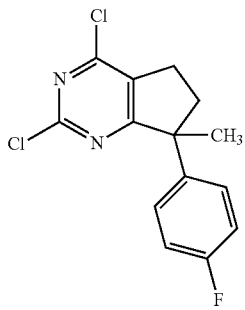 [SMILES: CC1(c2ccc(F)cc2)CCc2c(Cl)nc(Cl)nc21]

To a solution of Preparation H (300 mg, 1.060 mmol) in DME (Volume: 7064 μl) at −78° C. was added KHMDS (1281 μl, 1.166 mmol) (0.91 M in THF) dropwise. After 10 min, MeI (191 μl, 3.18 mmol) was added. The reaction was kept at −78° C. for 10 min, then allowed to come to rt. After 1 h at rt, the reaction was quenched with water and extracted three times with EtOAc. The combined organic extracts were dried over MgSO4, filtered, and the solvent removed in vacuo. $^1$H NMR (500 MHz, CDCl$_3$) δ ppm 7.21-7.27 (3 H, m), 6.95-7.03 (2 H, m), 2.87-3.01 (2 H, m), 2.62 (1 H, ddd, J=13.20, 7.86, 5.19 Hz), 2.26-2.34 (1 H, m).

Preparation APa 2-chloro-7-(4-fluorophenyl)-N,7-dimethyl-6,7-dihydro-5H-cyclopenta[d]pyrimidin-4-amine

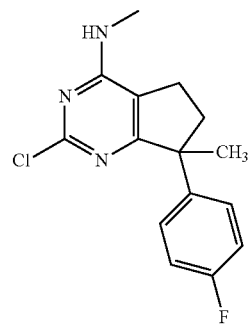 [SMILES: CNc1nc(Cl)nc2c1CCC2(C)c1ccc(F)cc1]

To a solution Preparation AP (123 mg, 0.414 mmol) in NMP (Volume: 4139 μl) was added 2 M Monomethylamine (414 μl, 0.828 mmol) in MeOH. After 2 h, LC/MS showed conversion to the desired product. Water was added, and the mixture was extracted three times into EtOAc. The combined organic extracts were dried over MgSO4, filtered, and concentrated in vacuo. The resulting material was used for further chemistry. LC-MS (M−H)$^−$=290.3.

Preparation AQ 2,4-dichloro-7-(2-methoxyphenyl)-6,7-dihydro-5H-cyclopenta[d]pyrimidine

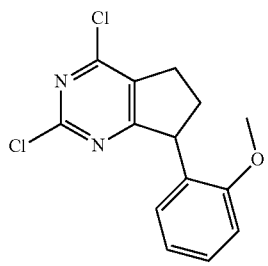 [SMILES: COc1ccccc1C1CCc2c(Cl)nc(Cl)nc21]

Intermediate AQ(1)

2-(2-methoxyphenyl)cyclopentanol

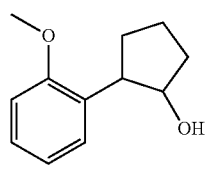

To a solution of (2-methoxyphenyl)magnesium bromide in THF (47.4 ml, 47.4 mmol) was added Copper(I) iodide (0.632 g, 3.32 mmol). The resulting solution was stirred at RT for 10 min. 6-oxabicyclo[3.1.0]hexane (4.11 ml, 47.4 mmol) was slowly added and the reaction mixture was stirred at RT overnight. Sat. NH4Cl was slowly added and the mixture was stirred at RT for 30 min. The product was extracted with CH$_2$Cl$_2$. The combined organic layers were washed with brine, dried over Na2SO4 and concentrated. The residue was purified by flash chromatography (SG, 0% to 60% EtOAc/Hex) to get 2-(2-methoxyphenyl)cyclopentanol (9.03 g, 47.0 mmol, 99% yield). LC-MS (M+Na)$^+$=215.1. $^1$H NMR (500 MHz, CDCl$_3$) δ 7.21 (t, J=5.8 Hz, 2H), 6.97 (t, J=7.3 Hz, 1H), 6.88 (d, J=8.2 Hz, 1H), 4.24 (q, J=5.9 Hz, 1H), 3.79 (s, 3H), 3.38-3.27 (m, 2H), 2.23-2.10 (m, 1H), 2.09-1.97 (m, 1H), 1.95-1.85 (m, 1H), 1.85-1.71 (m, 3H).

Intermediate AQ(2)

2-(2-methoxyphenyl)cyclopentanone

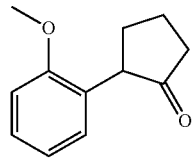

To a solution of 2-(2-methoxyphenyl)cyclopentanol (9.11 g, 47.4 mmol) in Acetone (Volume: 474 ml) was added Jones reagent (6.52 ml, 52.1 mmol) (8.0 M). After the addition was complete (the conversion of red reagent to green solid, and the supernatant solution took on the color of unreacted reagent), isopropanol was added to quench the excess reagent. The green solid was filtered off through ceilite and rinsed with acetone. The filtrate was concentrated and purified by flash chromatography to get 2-(2-methoxyphenyl)cyclopentanone (6.64 g, 34.9 mmol, 73.6% yield). LC-MS (M+H)$^+$=191.0. $^1$H NMR (500 MHz, CD$_3$OD) δ 7.24 (td, J=7.8, 1.8 Hz, 1H), 7.09 (dd, J=7.5, 1.7 Hz, 1H), 6.95 (d, J=8.2 Hz, 1H), 6.90 (td, J=7.4, 1.1 Hz, 1H), 3.77 (s, 3H), 3.43-3.37 (m, 1H), 2.48-2.30 (m, 3H), 2.23-2.11 (m, 2H), 2.00-1.88 (m, 1H).

Intermediate AQ (3)

methyl 3-(2-methoxyphenyl)-2-oxocyclopentanecarboxylate

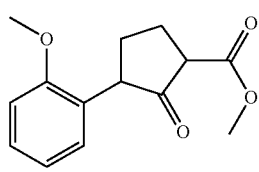 [SMILES: COC(=O)C1CCC(c2ccccc2OC)C1=O]

A mixture of 2-(2-methoxyphenyl)cyclopentanone (6.64 g, 34.9 mmol), dimethyl carbonate (58.8 ml, 698 mmol) and MeOH (4 drops) was stirred while sodium hydride (3.07 g, 60% wt, 77 mmol) was added slowly at 0° C. The mixture was warmed to RT and then heated to reflux for 2 hr and then stirred at RT overnight. The reaction was quenched with 1 N HCl (77 mL, 77 mmol) and extracted with ethyl acetate. The organic extracts were washed with water, dried with brine, and concentrated in vacuo. The crude product was purified by flash chromatography (SG, 0 to 75% EtOAc/Hexane) to get methyl 3-(2-methoxyphenyl)-2-oxocyclopentanecarboxylate (5.3 g, 21.35 mmol, 61.2% yield). LC-MS (M+Na)$^+$= 271.1. $^1$H NMR (500 MHz, CD$_3$OD) δ 7.26-7.16 (m, 1H), 7.08 (d, J=7.3 Hz, 1H), 6.92-6.84 (m, 2H), 3.73-3.69 (m, 3H), 3.68 (s, 3H), 3.60-3.49 (m, 1H), 3.49-3.40 (m, 1H), 2.40-2.31 (m, 1H), 2.31-2.17 (m, 2H), 2.16-2.01 (m, 1H).

Intermediate AQ(4)

7-(2-methoxyphenyl)-6,7-dihydro-5H-cyclopenta[d]pyrimidine-2,4-diol

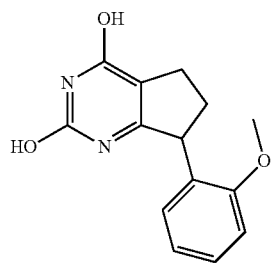 [SMILES: COc1ccccc1C1CCc2c(O)nc(O)nc21]

To a melt of urea (6.07 g, 101 mmol) (bath temp 150° C.) was added methyl 3-(2-methoxyphenyl)-2-oxocyclopentanecarboxylate (5.3 g, 20.21 mmol) dropwise. After stirring overnight, the reaction was cooled to rt. Added MeOH (30 ml), and broke up the solid mass with a spatula and stirred for 1 h. Added water (600 ml), and stirred for 3 hr. The mixture was added to a Buchner funnel, and washed with water. Dried overnight in the vacuum oven (45° C.) to obtain 7-(2-methoxyphenyl)-6,7-dihydro-5H-cyclopenta[d]pyrimidine-2,4-diol (4.03 g, 15.60 mmol, 77% yield) as a tan solid. LC-MS (M+H)$^+$=259.1.

Preparation AQ 2,4-dichloro-7-(2-methoxyphenyl)-6,7-dihydro-5H-cyclopenta[d]pyrimidine

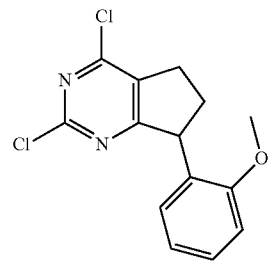 [SMILES: COc1ccccc1C1CCc2c(Cl)nc(Cl)nc21]

The mixture of Intermediate AQ(4) [7-(2-methoxyphenyl)-6,7-dihydro-5H-cyclopenta[d]pyrimidine-2,4-diol] (4.03 g, 15.60 mmol), phosphoryl trichloride (21.82 ml, 234 mmol) and N,N-diethylaniline (2.56 g, 17.16 mmol) was heated at 103° C. for 4 h. The reaction mixture was concentrated to remove POCl$_3$ and then poured into ice. The resulting aqueous mixture was extracted with diethyl ether. The combined ether extracts were concentrated. The crude product was purified by flash chromatography (SG, 5% to 45% EtOAc/Hexane) to get 2,4-dichloro-7-(2-methoxyphenyl)-6,7-dihydro-5H-cyclopenta[d]pyrimidine (1.82 g, 6.17 mmol, 39.5% yield). LC-MS (M+H)$^+$=295.1. $^1$H NMR (400 MHz, CD$_3$OD) δ 7.33-7.24 (m, 1H), 7.07 (dd, J=7.4, 1.6 Hz, 1H), 6.99 (d, J=8.3 Hz, 1H), 6.96-6.91 (m, 1H), 4.68 (t, J=8.9 Hz, 1H), 3.70 (s, 3H), 3.18-3.08 (m, 1H), 3.07-2.99 (m, 1H), 2.72-2.59 (m, 1H), 2.28-2.13 (m, 1H).

Preparation AQa 2-chloro-7-(2-methoxyphenyl)-N-methyl-6,7-dihydro-5H-cyclopenta[d]pyrimidin-4-amine

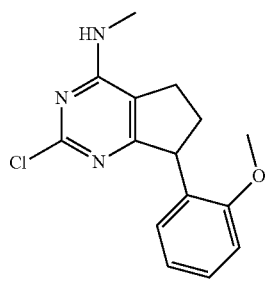 [SMILES: CNc1nc(Cl)nc2c1CCC2c1ccccc1OC]

A mixture of 2 M monomethylamine (1525 µl, 3.05 mmol) and Preparation AQ (450 mg, 1.525 mmol) in MeOH (Volume: 8565 µl) was stirred at RT overnight. The reaction was concentrated in vacuo and the residue was purified by flash chromatography (SG, 15% to 100% EtOAc/Hexane) to get 2-chloro-7-(2-methoxyphenyl)-N-methyl-6,7-dihydro-5H-cyclopenta[d]pyrimidin-4-amine (330 mg, 1.139 mmol, 74.7% yield).

LC-MS (M-H)$^-$=290.1.

Preparation AR 2,4-dichloro-7-(2-chlorophenyl)-6,7-dihydro-5H-cyclopenta[d]pyrimidine

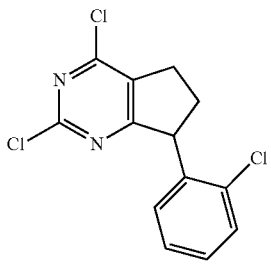 [SMILES: Clc1nc(Cl)c2c(n1)C(c1ccccc1Cl)CC2]

Intermediate AR(1)

ethyl 2-(2-chlorophenyl)acetate

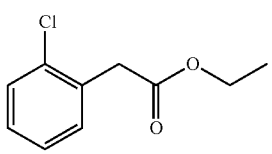

A mixture of 2-(2-chlorophenyl)acetic acid (10 g, 58.6 mmol) in EtOH (Volume: 152 ml) was treated with H2SO4 (1.719 ml, 32.2 mmol). The result mixture was refluxed overnight. The heat was removed, and the reaction mixture was concentrated. The resulting oil was dissolved in EtOAc and CAREFULLY treated with aqueous Na2CO3 (3.47 g, 32.8 mmol) (CAUTION: Gas evolution) until the solution remained basic and no further gas evolution was seen. The EtOAc layer was then removed and the aqueous layer was again extracted two times with EtOAc. The combined organic layers were then washed with brine, dried over Na2SO4 and concentrated in vacuo to obtain ethyl 2-(2-chlorophenyl)acetate (11.32 g, 57.0 mmol, 97% yield). LC-MS (M+H)$^+$= 199.1. $^1$H NMR (500 MHz, CD$_3$OD) δ 7.41 (ddd, J=16.8, 5.6, 3.5 Hz, 1H), 7.35 (dd, J=5.5, 3.7 Hz, 1H), 7.28 (dd, J=5.8, 3.7 Hz, 2H), 4.17 (q, J=7.0 Hz, 2H), 3.80 (s, 2H), 1.26 (t, J=7.2 Hz, 3H).

Intermediate AR(2)

diethyl 2-(2-chlorophenyl)hexanedioate

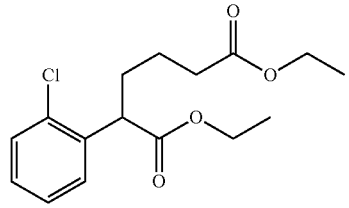 [SMILES: CCOC(=O)CCCC(C(=O)OCC)c1ccccc1Cl]

A mixture of ethyl 2-(2-chlorophenyl)acetate (11.32 g, 57.0 mmol), ethyl 4-bromobutanoate (33.3 g, 171 mmol) and Cs$_2$CO$_3$ (55.7 g, 171 mmol) in DMF (Volume: 57.0 ml) was heated at 60° C. overnight. The reaction was cooled to RT and diluted into a mixture of ethyl acetate and water. The organic layer was separated, and the aqueous layer was extracted three times with EtOAc. The combined organic layers were concentrated in vacuo. The residue was purified by flash chromatography (SG, 0 to 45% EtOAc/Hex) to get diethyl 2-(2-chlorophenyl)hexanedioate (17.82 g, 57.0 mmol, 100% yield). LC-MS (M+H)$^+$=313.2. $^1$H NMR (500 MHz, CD$_3$OD) δ 7.41 (ddd, J=17.0, 7.7, 1.5 Hz, 2H), 7.33-7.24 (m, 2H), 4.21-4.07 (m, 4H), 2.34 (td, J=7.3, 2.1 Hz, 2H), 2.16-2.05 (m, 1H), 1.82 (dddd, J=13.4, 10.3, 7.7, 5.5 Hz, 1H), 1.70-1.48 (m, 2H), 1.33-1.25 (m, 1H), 1.24 (t, J=7.2, 7.2 Hz, 3H), 1.21 (t, J=7.2 Hz, 3H).

Intermediate AR(3)

ethyl 3-(2-chlorophenyl)-2-oxocyclopentanecarboxylate

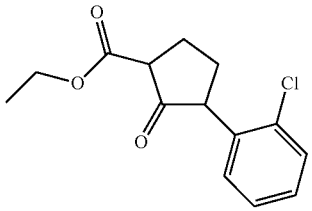

Intermediate AR(2) (17.82 g, 57.0 mmol) was dissolved in THF (Volume: 100 ml) and cooled to 5° C. To this solution was added 1 M Sodium bis(trimethylsilyl)amide in THF (68.4 ml, 68.4 mmol). The reaction mixture was stirred at 5° C. for 1 h and then 2 h at RT. The reaction was cooled to 0° C. and EtOAc (25 mL) was added. The pH was adjusted with 1.0 N HCl until neutral. The organic layer was isolated and the aqueous layer was extracted twice with EtOAc. The combined organic layers were dried over Na2SO4 and concentrated to get ethyl 3-(2-chlorophenyl)-2-oxocyclopentanecarboxylate (15.20 g, 57.0 mmol, 100% yield). LC-MS (M+H)$^+$=267.1. $^1$H NMR (500 MHz, CD$_3$OD) δ 7.43-7.38 (m, 1H), 7.31-7.22 (m, 3H), 4.22 (qd, J=7.1, 2.1 Hz, 2H), 3.58-3.51 (m, 1H), 2.53-2.42 (m, 2H), 2.40-2.25 (m, 2H), 2.21-2.11 (m, 1H), 1.30 (t, J=7.2 Hz, 3H).

Intermediate AR(4)

7-(2-chlorophenyl)-6,7-dihydro-5H-cyclopenta[d]pyrimidine-2,4-diol

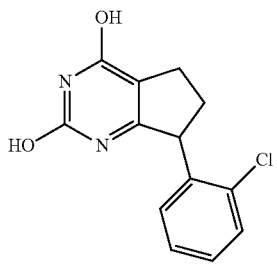 [SMILES: Oc1nc(O)c2c(n1)C(c1ccccc1Cl)CC2]

To a melt of urea (17.11 g, 285 mmol) (bath temp 150° C.) was added Intermediate AR(3) (15.20 g, 57.0 mmol) dropwise. After stirring overnight, the reaction was cooled to rt. Added MeOH (100 ml), and broke up the solid mass with a spatula and stirred for 1 h. Added water (1.8 L), and stirred for 3 hr. The mixture was added to a Buchner funnel, and washed with water. After drying overnight in vacuo, 7-(2-chlorophenyl)-6,7-dihydro-5H-cyclopenta[d]pyrimidine-2,4-diol (10.85 g, 41.3 mmol, 72.5% yield) was obtained as a tan solid. LC-MS (M+H)$^+$=263.1.

Preparation AR 2,4-dichloro-7-(2-chlorophenyl)-6,7-dihydro-5H-cyclopenta[d]pyrimidine

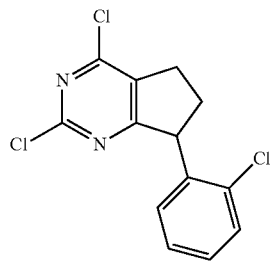 [SMILES: Clc1nc(Cl)c2c(n1)C(c1ccccc1Cl)CC2]

The mixture of Intermediate AR(4) [7-(2-chlorophenyl)-6,7-dihydro-5H-cyclopenta[d]pyrimidine-2,4-diol] (10.85 g, 41.3 mmol), phosphoryl trichloride (57.7 ml, 620 mmol) and N,N-diethylaniline (6.78 g, 45.4 mmol) was heated at 103° C. for 2 h. The reaction mixture was concentrated to remove POCl$_3$ and then poured into ice. The resulting aqueous mixture was extracted with diethyl ether. The combined ether extracts were concentrated. The crude product was purified by flash chromatography (SG, 0% to 40% EtOAc/Hexane) to get 2,4-dichloro-7-(2-chlorophenyl)-6,7-dihydro-5H-cyclopenta[d]pyrimidine (5.4 g, 18.03 mmol, 43.6% yield). LC-MS (M+H)$^+$=301.1.

Preparation ARa 2-chloro-7-(2-chlorophenyl)-N-methyl-6,7-dihydro-5H-cyclopenta[d]pyrimidin-4-amine

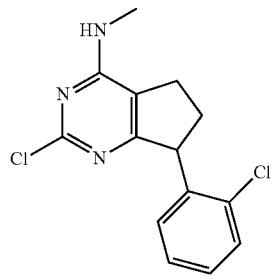 [SMILES: CNc1nc(Cl)nc2c1CCC2c1ccccc1Cl]

To a solution of Preparation AR [2,4-dichloro-7-(2-chlorophenyl)-6,7-dihydro-5H-cyclopenta[d]pyrimidine] (900 mg, 3.00 mmol) in NMP (Volume: 3.00E+04 μl) was added 2 M monomethanamine (7525 μl, 15.05 mmol). The resulting reaction mixture was stirred at RT for 1 h. Water was added (120 ml) to the mixture and stirred for 30 min. The mixture was filtered to get light green solid which was dried to get 2-chloro-7-(2-chlorophenyl)-N-methyl-6,7-dihydro-5H-cyclopenta[d]pyrimidin-4-amine (713 mg, 2.424 mmol, 81% yield). LC-MS (M+H)$^+$=295.9. $^1$H NMR (400 MHz, CD$_3$OD) δ 7.50-7.39 (m, 1H), 7.34-7.19 (m, 2H), 7.04-6.90 (m, 1H), 4.86-4.72 (m, 1H), 3.07 (s, 3H), 2.90-2.67 (m, 3H), 2.11-1.91 (m, 1H).

Preparation AS 2,4-dichloro-7-(2-fluorophenyl)-6,7-dihydro-5H-cyclopenta[d]pyrimidine

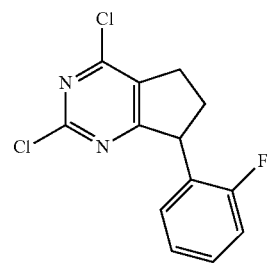 [SMILES: Fc1ccccc1C1CCc2c(Cl)nc(Cl)nc21]

Intermediate AS(1)

diethyl 2-(2-fluorophenyl)hexanedioate

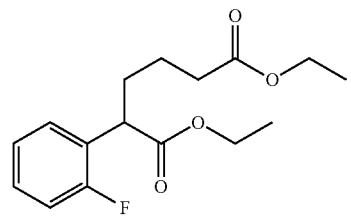 [SMILES: CCOC(=O)CCCC(C(=O)OCC)c1ccccc1F]

The procedure described for the preparation of Intermediate AR(2) was used with commercial ethyl 2-(2-fluorophenyl)acetate to obtain Intermediate AS(1). LC-MS (M+Na)$^+$= 319.1. $^1$H NMR (500 MHz, CD$_3$OD) δ 7.36 (td, J=7.6, 1.7 Hz, 1H), 7.33-7.26 (m, 1H), 7.17 (td, J=7.6, 1.2 Hz, 1H), 7.13-7.06 (m, 1H), 4.18-4.08 (m, 4H), 2.33 (td, J=7.3, 2.7 Hz, 1H), 2.18-2.05 (m, 2H), 1.81 (dddd, J=13.4, 10.3, 8.2, 5.6 Hz, 1H), 1.65-1.46 (m, 2H), 1.29-1.26 (m, 1H), 1.25-1.22 (m, 3H), 1.20 (t, J=7.0 Hz, 3H).

Intermediate AS(2)

ethyl 3-(2-fluorophenyl)-2-oxocyclopentanecarboxylate

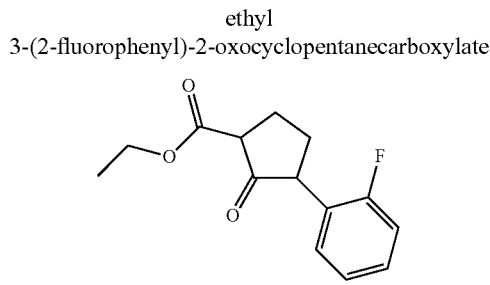

The procedure described for the preparation of Intermediate AR(3) was used with Intermediate AS(1) to obtain Intermediate AS(2). LC-MS (M+Na)$^+$=273.1. $^1$H NMR (500 MHz, CD$_3$OD) δ 7.34-7.20 (m, 2H), 7.19-7.02 (m, 3H), 4.26-4.17 (m, 2H), 2.54-2.41 (m, 2H), 2.37-2.22 (m, 1H), 2.11-1.98 (m, 1H), 1.30 (t, J=7.2 Hz, 3H), 1.26-1.17 (m, 1H).

Intermediate AS(3)

7-(2-fluorophenyl)-6,7-dihydro-5H-cyclopenta[d]pyrimidine-2,4-diol

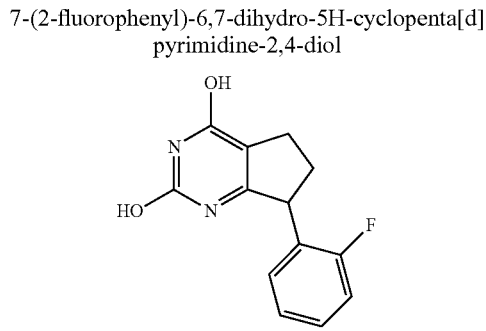

The procedure described for the preparation of Intermediate AR(4) was used with Intermediate AS(2) to obtain Intermediate AS(3). LC-MS (M+H)$^+$=247.1.

Preparation AS 2,4-dichloro-7-(2-fluorophenyl)-6,7-dihydro-5H-cyclopenta[d]pyrimidine

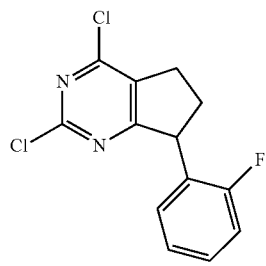 [SMILES: Fc1ccccc1C1CCc2c(Cl)nc(Cl)nc21]

The procedure described for the preparation of Preparation AR was used with Intermediate AS(3) to obtain Preparation AS. LC-MS (M+H)$^+$=283.0.

Preparation ASa 2-chloro-7-(2-fluorophenyl)-N-methyl-6,7-dihydro-5H-cyclopenta[d]pyrimidin-4-amine

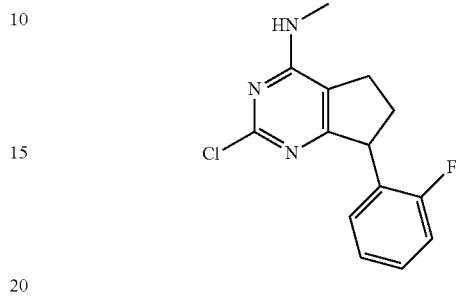

The procedure described for the preparation of Preparation ARa was used with Preparation AS to obtain Preparation ASa. LC-MS (M+H)$^+$=278.1. $^1$H NMR (400 MHz, CD$_3$OD) δ 7.34-7.25 (m, 1H), 7.17-7.12 (m, 1H), 7.12-7.08 (m, 1H), 7.07-7.03 (m, 1H), 4.61-4.52 (m, 1H), 3.05 (s, 3H), 2.89-2.67 (m, 3H), 2.12-2.00 (m, 1H).

Preparation AT 2,4-dichloro-7-(2,4,6-trifluorophenyl)-6,7-dihydro-5H-cyclopenta[d]pyrimidine

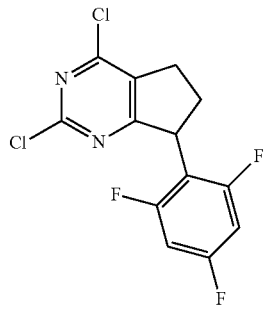 [SMILES: Fc1cc(F)c(C2CCc3c(Cl)nc(Cl)nc32)c(F)c1]

Intermediate AT(1)

ethyl 2-(2,4,6-trifluorophenyl)acetate

The procedure described for the preparation of Intermediate AR(1) was used to esterify 2,4,6-trifluorophenylacetic acid to obtain Intermediate AT(1). LC-MS (M+H)$^+$=247.1. $^1$H NMR (500 MHz, CD$_3$OD) δ 6.89 (dd, J=8.7, 8.1 Hz, 2H), 4.18 (q, J=7.1 Hz, 2H), 3.71 (s, 2H), 1.26 (t, J=7.2 Hz, 3H).

Intermediate AT(2)

diethyl 2-(2,4,6-trifluorophenyl)hexanedioate

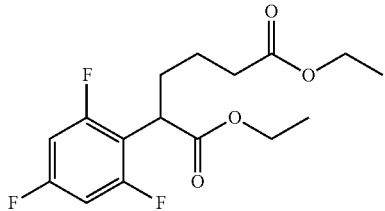 [SMILES: CCOC(=O)CCCC(C(=O)OCC)c1c(F)cc(F)cc1F]

The procedure described for the preparation of Intermediate AR(2) was used with Intermediate AT(1) to obtain Intermediate AT(2). LC-MS (M+Na)$^+$=355.2. $^1$H NMR (500 MHz, CD$_3$OD) δ 8.00 (s, 1H), 7.02-6.69 (m, 1H), 4.28-3.95 (m, 6H), 2.51-2.38 (m, 2H), 2.39-2.24 (m, 1H), 2.06-1.88 (m, 2H), 1.41-1.19 (m, 6H).

Intermediate AT(3)

ethyl 3-(2,4,6-trifluorophenyl)-2-oxocyclopentanecarboxylate

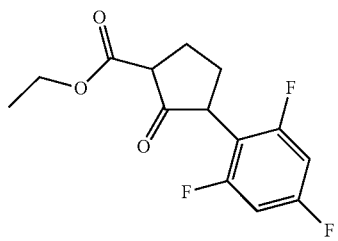 [SMILES: CCOC(=O)C1CCC(c2c(F)cc(F)cc2F)C1=O]

The procedure described for the preparation of Intermediate AR(3) was used with Intermediate AT(2) to obtain Intermediate AT(3). LC-MS (M+Na)$^+$=309.0.

Intermediate AT(4)

7-(2,4,6-trifluorophenyl)-6,7-dihydro-5H-cyclopenta[d]pyrimidine-2,4-diol

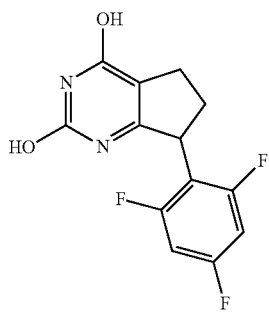 [SMILES: Oc1nc(O)c2c(n1)C(c1c(F)cc(F)cc1F)CC2]

The procedure described for the preparation of Intermediate AR(4) was used with Intermediate AT(3) to obtain Intermediate AT(4). LC-MS (M+H)$^+$=283.1.

Preparation AT 2,4-dichloro-7-(2,4,6-trifluorophenyl)-6,7-dihydro-5H-cyclopenta[d]pyrimidine

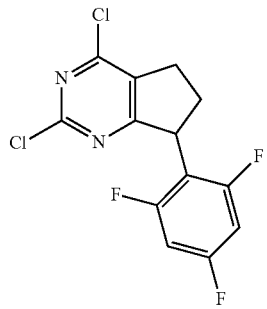 [SMILES: Fc1cc(F)c(C2CCc3c(Cl)nc(Cl)nc32)c(F)c1]

The procedure described for the preparation of Preparation AR was used with Intermediate AT(4) to obtain Preparation AT. LC-MS (M+H)$^+$=319.0.

Preparation ATa 2-chloro-7-(2,4,6-trifluorophenyl)-N-methyl-6,7-dihydro-5H-cyclopenta[d]pyrimidin-4-amine

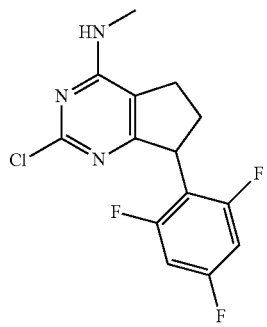 [SMILES: CNc1nc(Cl)nc2c1CCC2c1c(F)cc(F)cc1F]

The procedure described for the preparation of Preparation ARa was used with Preparation AT to obtain Preparation ATa. LC-MS (M+H)$^+$=314.1. $^1$H NMR (500 MHz, CD$_3$OD) δ 6.89-6.80 (m, 2H), 4.62 (t, J=9.0 Hz, 1H), 3.00 (s, 3H), 3.07-2.96 (m, 1H), 2.91-2.82 (m, 1H), 2.80-2.71 (m, 1H), 2.70-2.61 (m, 1H), 2.18-2.07 (m, 1H).

Preparation AU 2,4-dichloro-7-(4-chloro-2-fluorophenyl)-6,7-dihydro-5H-cyclopenta[d]pyrimidine

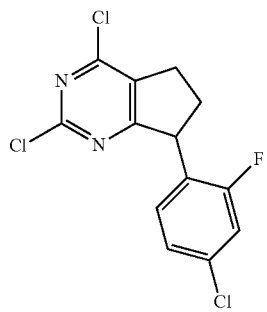 [SMILES: Fc1cc(Cl)ccc1C1CCc2c(Cl)nc(Cl)nc21]

Intermediate AU(1)

ethyl 2-(4-chloro-2-fluorophenyl)acetate

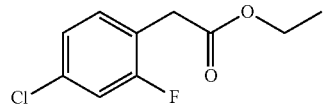

The procedure described for the preparation of Intermediate AR(1) was used to esterify 2-(4-chloro-2-fluorophenyl) acetic acid to obtain Intermediate AU(1). $^1$H NMR (500 MHz, CD$_3$OD) δ 7.32 (t, J=8.4 Hz, 1H), 7.25-7.13 (m, 2H), 4.17 (q, J=7.1 Hz, 2H), 3.70 (d, J=0.9 Hz, 2H), 1.26 (t, J=7.2 Hz, 3H).

Intermediate AU(2)

diethyl 2-(4-chloro-2-fluorophenyl)hexanedioate

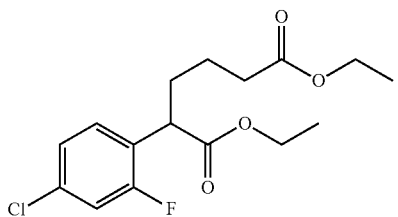 [SMILES: CCOC(=O)CCCC(C(=O)OCC)c1ccc(Cl)cc1F]

The procedure described for the preparation of Intermediate AR(2) was used with Intermediate AU(1) to obtain Intermediate AU(2). $^1$H NMR (500 MHz, CD$_3$OD) δ 7.41-7.32 (m, J=7.9 Hz, 1H), 7.25-7.17 (m, 2H), 4.20-4.07 (m, 4H), 3.51 (t, J=6.6 Hz, 1H), 2.34 (td, J=7.3, 2.1 Hz, 1H), 2.12-2.06 (m, 1H), 1.80 (dddd, J=13.5, 10.3, 8.2, 5.5 Hz, 1H), 1.67-1.48 (m, 2H), 1.30-1.18 (m, 7H).

Intermediate AU(3)

ethyl 3-(4-chloro-2-fluorophenyl)-2-oxocyclopentanecarboxylate

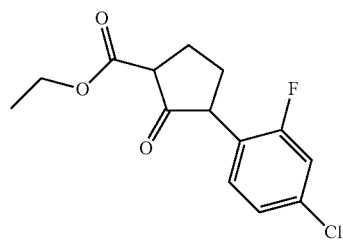 [SMILES: CCOC(=O)C1CCC(c2ccc(Cl)cc2F)C1=O]

The procedure described for the preparation of Intermediate AR(3) was used with Intermediate AU(2) to obtain Intermediate AU(3). LC-MS (M+Na)$^+$=307.0.

Intermediate AU(4)

7-(4-chloro-2-fluorophenyl)-6,7-dihydro-5H-cyclopenta[d]pyrimidine-2,4-diol

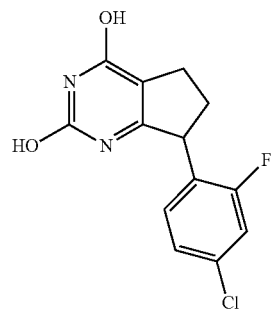 [SMILES: Oc1nc(O)c2c(n1)C(c1ccc(Cl)cc1F)CC2]

The procedure described for the preparation of Intermediate AR(4) was used with Intermediate AU(3) to obtain Intermediate AU(4). LC-MS (M+H)$^+$=281.0.

Preparation AU 2,4-dichloro-7-(4-chloro-2-fluorophenyl)-6,7-dihydro-5H-cyclopenta[d]pyrimidine

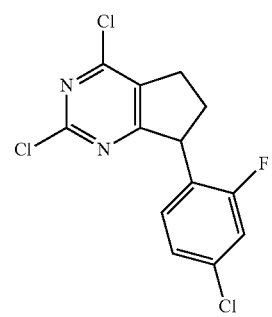 [SMILES: Fc1cc(Cl)ccc1C1CCc2c(Cl)nc(Cl)nc21]

The procedure described for the preparation of Preparation AR was used with Intermediate AU(4) to obtain Preparation AU. LC-MS (M+H)$^+$=317.0.

Preparation AUa 2-chloro-7-(4-chloro-2-fluorophenyl)-N-methyl-6,7-dihydro-5H-cyclopenta[d]pyrimidin-4-amine

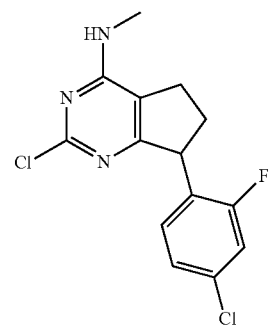 [SMILES: CNc1nc(Cl)nc2c1CCC2c1ccc(Cl)cc1F]

The procedure described for the preparation of Preparation ARa was used with Preparation AU to obtain Preparation AUa. LC-MS (M+H)⁺=313.9. ¹H NMR (500 MHz, CD₃OD) δ 7.19 (dd, J=10.2, 2.0 Hz, 1H), 7.16 (dd, J=8.2, 2.1 Hz, 1H), 7.07-7.01 (m, 1H), 4.51-4.44 (m, 1H), 3.01 (s, 3H), 2.87-2.61 (m, 3H), 2.11-1.98 (m, 1H).

Preparation AV 2,4-dichloro-7-(3-methoxyphenyl)-6,7-dihydro-5H-cyclopenta[d]pyrimidine

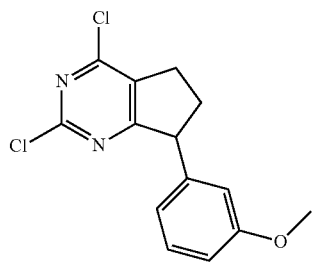 [SMILES: COc1cccc(C2CCc3c(Cl)nc(Cl)nc32)c1]

Intermediate AV(1)

diethyl 2-(3-methoxyphenyl)hexanedioate

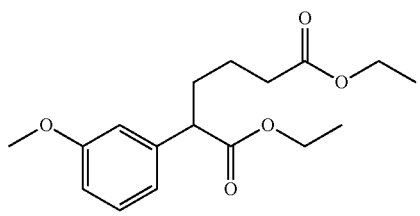 [SMILES: CCOC(=O)CCCC(C(=O)OCC)c1cccc(OC)c1]

The procedure described for the preparation of Intermediate AR(2) was used with commercial ethyl 2-(3-methoxyphenyl)acetate to obtain Intermediate AV(1). LC-MS (M+Na)⁺=331.1.

Intermediate AV(2)

ethyl 3-(3-methoxyphenyl)-2-oxocyclopentanecarboxylate

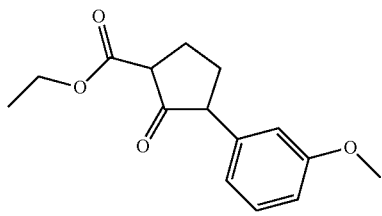 [SMILES: CCOC(=O)C1CCC(c2cccc(OC)c2)C1=O]

The procedure described for the preparation of Intermediate AR(3) was used with Intermediate AV(1) to obtain Intermediate AV(2). LC-MS (M+H)⁺=263.1.

Intermediate AV(3)

7-(3-methoxyphenyl)-6,7-dihydro-5H-cyclopenta[d]pyrimidine-2,4-diol

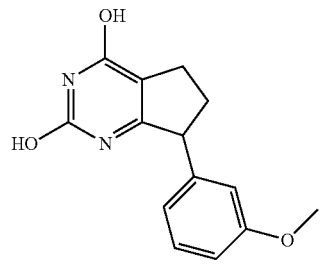 [SMILES: COc1cccc(C2CCc3c(O)nc(O)nc32)c1]

The procedure described for the preparation of Intermediate AR(4) was used with Intermediate AV(2) to obtain Intermediate AV(3). LC-MS (M+H)⁺=259.1.

Preparation AV 2,4-dichloro-7-(3-methoxyphenyl)-6,7-dihydro-5H-cyclopenta[d]pyrimidine

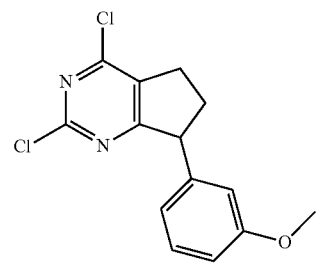 [SMILES: COc1cccc(C2CCc3c(Cl)nc(Cl)nc32)c1]

The procedure described for the preparation of Preparation AR was used with Intermediate AV(3) to obtain Preparation AV. LC-MS (M+H)⁺=295.0. ¹H NMR (400 MHz, CD₃OD) δ ppm 7.23-7.29 (1 H, m), 6.83-6.87 (1 H, m), 6.73-6.79 (2 H, m), 4.48 (1 H, t, J=8.53 Hz), 3.79 (3 H, s), 3.12-3.21 (1 H, m), 2.99-3.10 (1 H, m), 2.75 (1 H, dtd, J=13.21, 8.83, 8.83, 4.27 Hz), 2.19-2.36 (1 H, m).

Preparation AVa 2-chloro-7-(3-methoxyphenyl)-N-methyl-6,7-dihydro-5H-cyclopenta[d]pyrimidin-4-amine

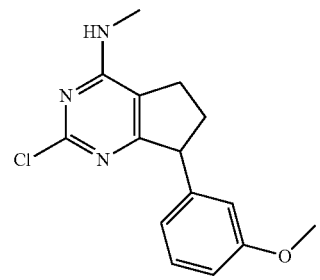 [SMILES: CNc1nc(Cl)nc2c1CCC2c1cccc(OC)c1]

The procedure described for the preparation of Preparation ARa was used with Preparation AV to obtain Preparation AVa. LC-MS (M+H)⁺=290.1.

Preparation AW 2,4-dichloro-7-(4-(dimethylamino)phenyl)-6,7-dihydro-5H-cyclopenta[d]pyrimidine

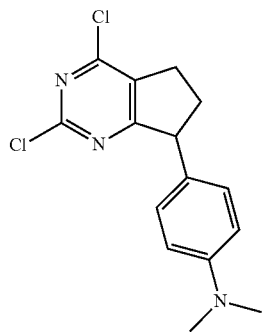 [SMILES: CN(C)c1ccc(C2CCc3c(Cl)nc(Cl)nc32)cc1]

Intermediate AW(1)

ethyl 2-(4-(dimethylamino)phenyl)acetate

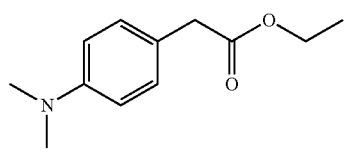

The procedure described for the preparation of Intermediate AR(1) was used to esterify 2-(4-(dimethylamino)phenyl) acetic acid to obtain Intermediate AW(1). LC-MS (M+H)$^+$=208.2.

Intermediate AW(2)

diethyl 2-(4-chloro-2-fluorophenyl)hexanedioate

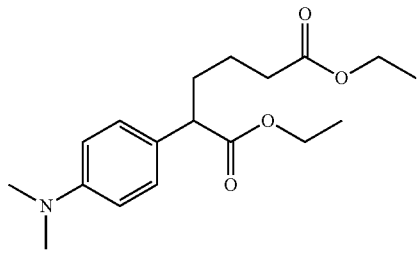 [SMILES: CCOC(=O)CCCC(C(=O)OCC)c1ccc(N(C)C)cc1]

The procedure described for the preparation of Intermediate AR(2) was used with Intermediate AW(1) to obtain Intermediate AW(2). LC-MS (M+H)$^+$=322.2.

Intermediate AW(3)

ethyl 3-(4-(dimethylamino)phenyl)-2-oxocyclopentanecarboxylate

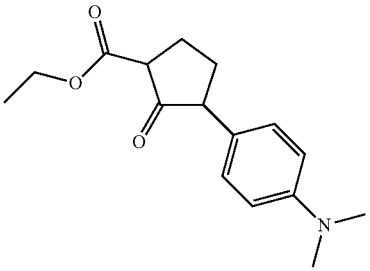 [SMILES: CCOC(=O)C1CCC(c2ccc(N(C)C)cc2)C1=O]

The procedure described for the preparation of Intermediate AR(3) was used with Intermediate AW(2) to obtain Intermediate AW(3). LC-MS (M+H)$^+$=276.1.

Intermediate AW(4)

7-(4-(dimethylamino)phenyl)-6,7-dihydro-5H-cyclopenta[d]pyrimidine-2,4-diol

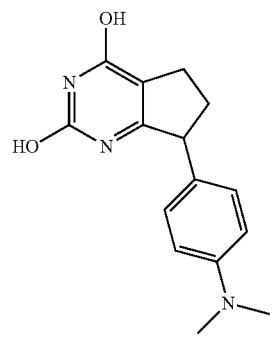 [SMILES: CN(C)c1ccc(C2CCc3c(O)nc(O)nc32)cc1]

The procedure described for the preparation of Intermediate AR(4) was used with Intermediate AW(3) to obtain Intermediate AW(4). LC-MS (M+H)$^+$=272.1.

Preparation AW 2,4-dichloro-7-(4-(dimethylamino)phenyl)-6,7-dihydro-5H-cyclopenta[d]pyrimidine

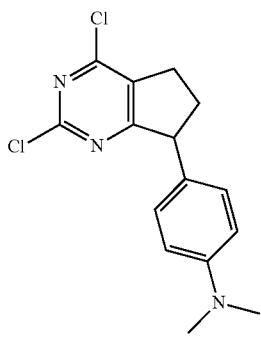 [SMILES: CN(C)c1ccc(C2CCc3c(Cl)nc(Cl)nc32)cc1]

The procedure described for the preparation of Preparation AR was used with Intermediate AW(4) to obtain Preparation AW. LC-MS (M+H)$^+$=308.0.

Preparation AWa 2-chloro-7-(4-(dimethylamino)phenyl)-N-methyl-6,7-dihydro-5H-cyclopenta[d]pyrimidin-4-amine

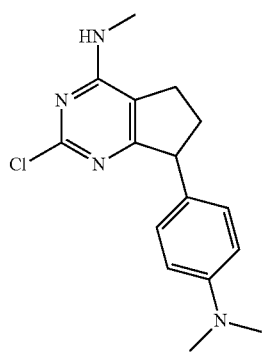 [SMILES: CNc1nc(Cl)nc2c1CCC2c1ccc(N(C)C)cc1]

The procedure described for the preparation of Preparation ARa was used with Preparation AW to obtain Preparation AWa. LC-MS (M+H)$^+$=303.1. $^1$H NMR (400 MHz, CD$_3$OD) δ 7.48 (d, J=8.8 Hz, 2H), 7.35 (d, J=8.5 Hz, 2H), 4.41-4.27 (m, J=8.5 Hz, 1H), 3.26 (s, 6H), 3.02 (s, 3H), 2.91-2.64 (m, 3H), 2.14-1.99 (m, 2H).

Preparation AX 2,4-dichloro-7-(2-fluoro-4-(trifluoromethyl)phenyl)-6,7-dihydro-5H-cyclopenta[d]pyrimidine

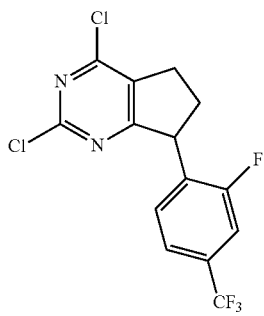 [SMILES: Fc1cc(C(F)(F)F)ccc1C1CCc2c(Cl)nc(Cl)nc21]

Intermediate AX(1)

ethyl 2-(2-fluoro-4-(trifluoromethyl)phenyl)acetate

The procedure described for the preparation of Intermediate AR(1) was used to esterify 2-(2-fluoro-4-(trifluoromethyl)phenyl)acetic acid to obtain Intermediate AX(1).

Intermediate AX(2)

diethyl 2-(2-fluoro-4-(trifluoromethyl)phenyl)hexanedioate

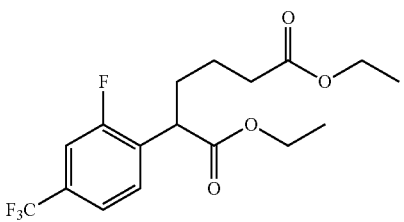 [SMILES: CCOC(=O)CCCC(C(=O)OCC)c1ccc(C(F)(F)F)cc1F]

The procedure described for the preparation of Intermediate AR(2) was used with Intermediate AX(1) to obtain Intermediate AX(2).

Intermediate AX(3)

ethyl 3-(2-fluoro-4-(trifluoromethyl)phenyl)-2-oxo-cyclopentanecarboxylate

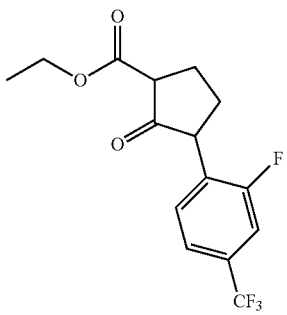 [SMILES: CCOC(=O)C1CCC(c2ccc(C(F)(F)F)cc2F)C1=O]

The procedure described for the preparation of Intermediate AR(3) was used with Intermediate AX(2) to obtain Intermediate AX(3).

Intermediate AX(4)

7-(2-fluoro-4-(trifluoromethyl)phenyl)-6,7-dihydro-5H-cyclopenta[d]pyrimidine-2,4-diol

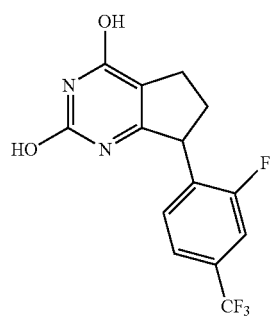 [SMILES: Oc1nc(O)c2c(n1)C(c1ccc(C(F)(F)F)cc1F)CC2]

The procedure described for the preparation of Intermediate AR(4) was used with Intermediate AX(3) to obtain Intermediate AX(4). LC-MS (M+H)$^+$=315.4.

Preparation AX 2,4-dichloro-7-(2-fluoro-4-(trifluoromethyl)phenyl)-6,7-dihydro-5H-cyclopenta[d]pyrimidine

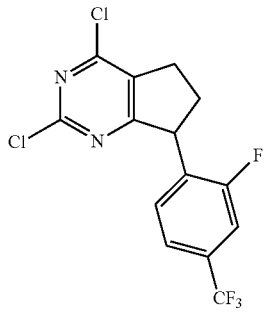 [SMILES: Fc1cc(C(F)(F)F)ccc1C1CCc2c(Cl)nc(Cl)nc21]

The procedure described for the preparation of Preparation AR was used with Intermediate AX(4) to obtain Preparation AX.

Preparation AXa 2-chloro-7-(2-fluoro-4-(trifluoromethyl)phenyl)-N-methyl-6,7-dihydro-5H-cyclopenta[d]pyrimidin-4-amine

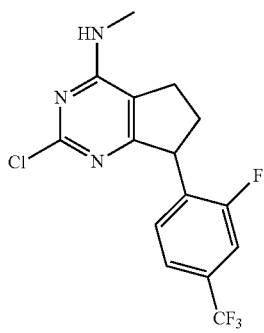 [SMILES: CNc1nc(Cl)nc2c1CCC2c1ccc(C(F)(F)F)cc1F]

The procedure described for the preparation of Preparation ARa was used with Preparation AX to obtain Preparation AXa. LC-MS (M+H)$^+$=346.4. $^1$H NMR (400 MHz, CD$_3$OD) δ ppm 7.46-7.52 (2 H, m), 7.32 (1 H, t, J=7.65 Hz), 4.64-4.70 (1 H, m), 3.07 (3 H, s), 2.73-2.93 (3 H, m), 2.05-2.17 (1 H, m).

Preparation AY 2,4-dichloro-7-(2-fluoro-4-(trifluoromethoxy)phenyl)-6,7-dihydro-5H-cyclopenta[d]pyrimidine

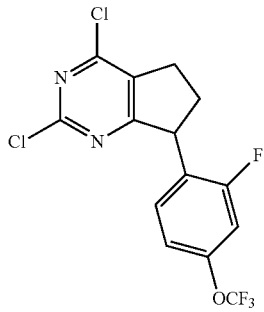 [SMILES: Fc1cc(OC(F)(F)F)ccc1C1CCc2c(Cl)nc(Cl)nc21]

Intermediate AY(1)

ethyl 2-(2-fluoro-4-(trifluoromethoxy)phenyl)acetate

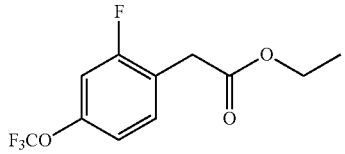 [SMILES: CCOC(=O)Cc1ccc(OC(F)(F)F)cc1F]

The procedure described for the preparation of Intermediate AR(1) was used to esterify 2-(2-fluoro-4-(trifluoromethoxy)phenyl)acetic acid to obtain Intermediate AY(1).

Intermediate AY(2) diethyl 2-(2-fluoro-4-(trifluoromethoxy)phenyl)hexanedioate

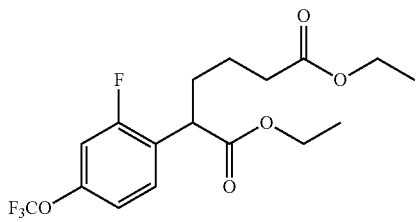 [SMILES: CCOC(=O)CCCC(C(=O)OCC)c1ccc(OC(F)(F)F)cc1F]

The procedure described for the preparation of Intermediate AR(2) was used with Intermediate AY(1) to obtain Intermediate AY(2).

Intermediate AY(3)

ethyl 3-(2-fluoro-4-(trifluoromethoxy)phenyl)-2-oxocyclopentanecarboxylate

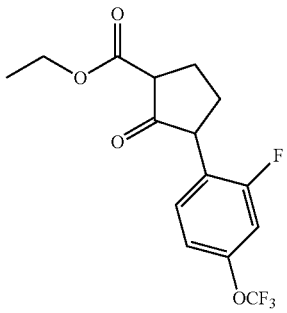 [SMILES: CCOC(=O)C1CCC(c2ccc(OC(F)(F)F)cc2F)C1=O]

The procedure described for the preparation of Intermediate AR(3) was used with Intermediate AY(2) to obtain Intermediate AY(3).

Intermediate AY(4)

7-(2-fluoro-4-(trifluoromethoxy)phenyl)-6,7-dihydro-5H-cyclopenta[d]pyrimidine-2,4-diol

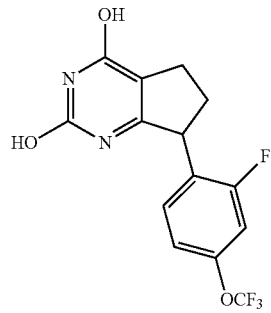 [SMILES: Oc1nc(O)c2c(n1)C(c1ccc(OC(F)(F)F)cc1F)CC2]

The procedure described for the preparation of Intermediate AR(4) was used with Intermediate AY(3) to obtain Intermediate AY(4). LC-MS (M+H)$^+$=331.4.

Preparation AY 2,4-dichloro-7-(2-fluoro-4-(trifluoromethoxy)phenyl)-6,7-dihydro-5H-cyclopenta[d]pyrimidine

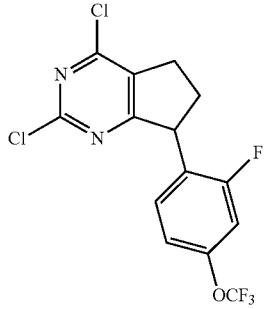 [SMILES: Fc1cc(OC(F)(F)F)ccc1C1CCc2c(Cl)nc(Cl)nc21]

The procedure described for the preparation of Preparation AR was used with Intermediate AY(4) to obtain Preparation AY. LC-MS (M+H)$^+$=367.3.

Preparation AYa 2-chloro-7-(2-fluoro-4-(trifluoromethoxy)phenyl)-N-methyl-6,7-dihydro-5H-cyclopenta[d]pyrimidin-4-amine

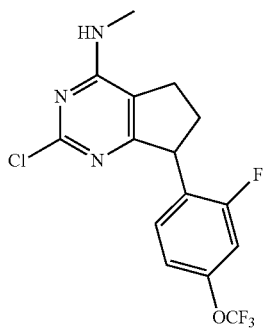 [SMILES: CNc1nc(Cl)nc2c1CCC2c1ccc(OC(F)(F)F)cc1F]

The procedure described for the preparation of Preparation ARa was used with Preparation AY to obtain Preparation AYa. LC-MS (M+H)$^+$=362.3/364.3. $^1$H NMR (400 MHz, CD$_3$OD) δ ppm 7.21 (1 H, t, J=8.28 Hz), 7.10-7.17 (2 H, m), 4.56-4.63 (1 H, m), 2.70-2.91 (3 H, m), 2.03-2.14 (1 H, m).

Preparation AZ 2,4-dichloro-7-(6-(trifluoromethyl)pyridin-3-yl)-6,7-dihydro-5H-cyclopenta[d]pyrimidine

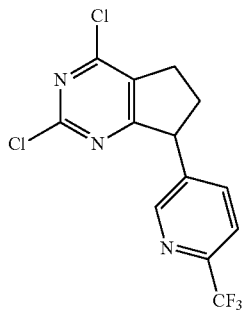 [SMILES: FC(F)(F)c1ccc(C2CCc3c(Cl)nc(Cl)nc32)cn1]

Intermediate AZ(1)

ethyl 2-oxo-3-(6-(trifluoromethyl)pyridin-3-yl)cyclopentanecarboxylate

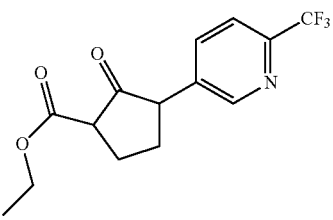 [SMILES: CCOC(=O)C1CCC(c2ccc(C(F)(F)F)nc2)C1=O]

2-(6-(trifluoromethyl)pyridin-3-yl)cyclopentanone (700 mg, 3.05 mmol) was added to a solution of LDA (2.291 mL, 4.58 mmol) at −78° C. After stirring for 30 min at −78° C., ethyl carbonocyanidate (0.329 mL, 3.36 mmol) was added to the reaction mixture. The resulting solution was warmed to room temperature with stirring over 3 h. The reaction mixture was quenched with 1 mL of water, washed with brine, dried over MgSO$_4$, and purified by Biotage (Hexanes/EtOAc 2:1) to afford ethyl 2-oxo-3-(6-(trifluoromethyl)pyridin-3-yl)cyclopentanecarboxylate (764 mg, 2.54 mmol, 83% yield). LC-MS (M+H)$^+$=302.2.

Intermediate AZ(2)

7-(6-(trifluoromethyl)pyridin-3-yl)-6,7-dihydro-5H-cyclopenta[d]pyrimidine-2,4-diol

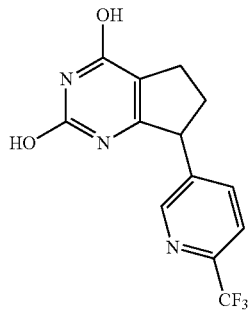 [SMILES: Oc1nc(O)c2c(n1)C(c1ccc(C(F)(F)F)nc1)CC2]

To a melt of urea (748 mg, 12.45 mmol) at 150° C. was added ethyl 2-oxo-3-(6-(trifluoromethyl)pyridin-3-yl)cyclopentanecarboxylate (750 mg, 2.49 mmol) dropwise. The reaction was stirred overnight. The reaction mixture was cooled and the resulting solid mass was broken up and suspended in MeOH. The mixture was diluted with a large excess of water and cooled in an ice bath. The suspension was filtered and the residue was washed with water and dried to afford the semi-pure product, 7-(6-(trifluoromethyl)pyridin-3-yl)-6,7-dihydro-5H-cyclopenta[d]pyrimidine-2,4-diol (334 mg, 1.124 mmol, 45.1% yield). LC-MS (M+H)$^+$=298.0.

Preparation AZ 2,4-dichloro-7-(6-(trifluoromethyl)pyridin-3-yl)-6,7-dihydro-5H-cyclopenta[d]pyrimidine

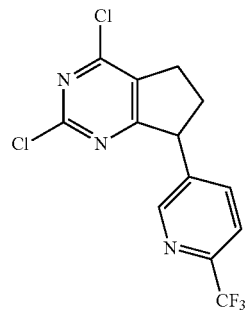 [SMILES: FC(F)(F)c1ccc(C2CCc3c(Cl)nc(Cl)nc32)cn1]

To a flask charged with 7-(6-(trifluoromethyl)pyridin-3-yl)-6,7-dihydro-5H-cyclopenta[d]pyrimidine-2,4-diol (334 mg, 1.124 mmol), phosphoryl trichloride (3142 μl, 33.7 mmol) and N,N-diethylaniline (198 μl, 1.236 mmol) were added. The reaction was heated at reflux (105° C.) for 4 h. The reaction mixture was concentrated to evaporate the excess POCl3 and was then poured into approx. 25 mL of ice. The mixture was extracted with diethyl ether (3×25 mL) and the combined extracts were dried & concentrated in vacuum. The crude product was purified by Biotage (Hexanes/EtOAc 4:1) to afford the purified product, 2,4-dichloro-7-(6-(trifluoromethyl)pyridin-3-yl)-6,7-dihydro-5H-cyclopenta[d]pyrimidine (33 mg, 0.099 mmol, 8.79% yield). LC-MS (M+H)$^+$=334.0.

Preparation AZa 2-chloro-N-methyl-7-(6-(trifluoromethyl)pyridin-3-yl)-6,7-dihydro-5H-cyclopenta[d]pyrimidin-4-amine

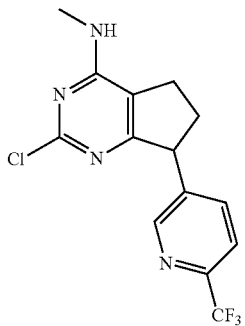 [SMILES: CNc1nc(Cl)nc2c1CCC2c1ccc(C(F)(F)F)nc1]

To a solution of 2,4-dichloro-7-(6-(trifluoromethyl)pyridin-3-yl)-6,7-dihydro-5H-cyclopenta[d]pyrimidine (33 mg, 0.099 mmol) in NMP (Volume: 5 mL) was added methanamine (0.247 mL, 0.494 mmol). The reaction mixture was stirred at room temperature for 2 h. The product was partitioned between ethyl acetate & water. The organic layers were combined and dried in vacuum to afford 2-chloro-N-methyl-7-(6-(trifluoromethyl)pyridin-3-yl)-6,7-dihydro-5H-cyclopenta[d]pyrimidin-4-amine (8 mg, 0.024 mmol, 24.64% yield). LC-MS (M+H)$^+$=329.0.

EXAMPLES

Examples 1A and 1B (S)-2-methoxy-4-(7-(2-methoxyphenyl)-4-(methylamino)-6,7-dihydro-5H-cyclopenta[d]pyrimidin-2-ylamino)benzonitrile and (R)-2-methoxy-4-(7-(2-methoxyphenyl)-4-(methylamino)-6,7-dihydro-5H-cyclopenta[d]pyrimidin-2-ylamino)benzonitrile

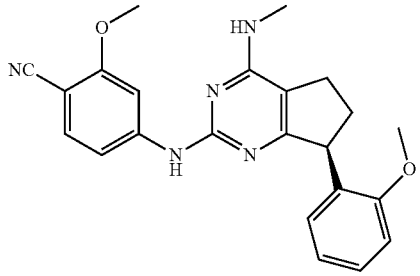

-continued

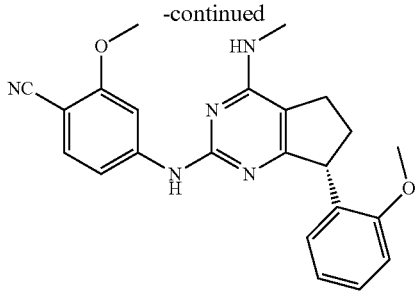

The mixture of 2-chloro-7-(2-methoxyphenyl)-N-methyl-6,7-dihydro-5H-cyclopenta[d]pyrimidin-4-amine (Preparation AQa) (165 mg, 0.569 mmol) and commercially available 4-amino-2-methoxybenzonitrile (84 mg, 0.569 mmol) was dissolved in NMP (Volume: 1134 μl) and was treated with sulfuric acid (39.5 μl, 0.740 mmol). The resulting mixture was heated at 90° C. for 24 h. After the heat was stopped, water (60 ml) was added dropwise. The crude product was purified by Prep-HPLC (Solvent A=10% MeOH-90% H2O-0.1% TFA, Solvent B=90% MeOH-10% H2O-0.1% TFA. Column. PHENOMENEX LUNA 30×100 mm, S10, Flow rate: 40 ml/min, 40-80% B, 35 min) to obtain 2-methoxy-4-(7-(2-methoxyphenyl)-4-(methylamino)-6,7-dihydro-5H-cyclopenta[d]pyrimidin-2-ylamino)benzonitrile, TFA (145 mg, 0.253 mmol, 44.5% yield). The racemate so obtained was separated into the enantiomers by chiral SFC purification (Chiralcel OJ-H 30×250 mm column, 30% MeOH (0.1% DEA) in CO$_2$ at 35° C. and 150 bar, 70 mL/min) Enantiomer A: LC-MS (M+H)$^+$=402.2. $^1$H NMR (400 MHz, CDCl$_3$) δ ppm 8.08 (d, J=1.8 Hz, 1H), 7.35 (d, J=8.5 Hz, 1H), 7.25-7.19 (m, 1H), 7.16 (s, 1H), 7.00 (dd, J=7.7, 1.6 Hz, 1H), 6.94-6.83 (m, 2H), 6.65 (dd, J=8.4, 1.9 Hz, 1H), 4.67-4.58 (m, 1H), 4.52 (d, J=5.0 Hz, 1H), 3.82 (s, 3H), 3.60 (s, 3H), 3.14 (d, J=4.8 Hz, 3H), 2.80-2.57 (m, 3H), 2.10-1.92 (m, 1H). The antipode had identical $^1$H NMR and LC/MS spectra.

Examples 2A and 2B (S)-4-(7-(4-fluorophenyl)-7-methyl-4-(methylamino)-6,7-dihydro-5H-cyclopenta[d]pyrimidin-2-ylamino)-2-methoxybenzonitrile and (R)-4-(7-(4-fluorophenyl)-7-methyl-4-(methylamino)-6,7-dihydro-5H-cyclopenta[d]pyrimidin-2-ylamino)-2-methoxybenzonitrile

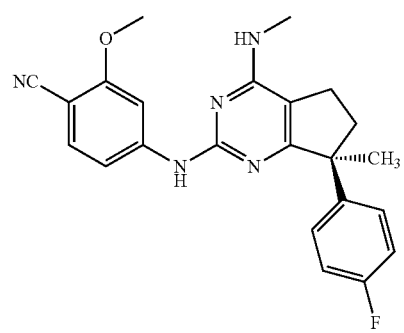

-continued

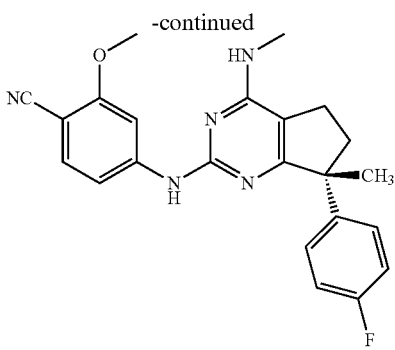

In a manner similar to that described in Example 1, commercially available 4-amino-2-methoxybenzonitrile and Preparation APa were reacted to give 4-(7-(4-fluorophenyl)-7-methyl-4-(methylamino)-6,7-dihydro-5H-cyclopenta[d]pyrimidin-2-ylamino)-2-methoxybenzonitrile. LC-MS (M+H)$^+$=404.2. $^1$H NMR (500 MHz, CDCl$_3$) δ ppm 12.3 (1H, br. s), 7.52 (1 H, s), 7.42-7.49 (2 H, m), 7.25-7.31 (2 H, m), 7.00 (2 H, t, J=8.6 Hz), 5.55 (1 H, d, J=4.3 Hz), 3.91 (3 H, s), 3.22 (3 H, d, J=4.9 Hz), 2.70-2.82 (2 H, m), 2.58 (1 H, ddd, J=13.4, 8.3, 4.6 Hz), 2.36 (1 H, ddd, J=13.6, 7.9, 7.8 Hz), 1.85 (3 H, s). The racemate so obtained was separated into the enantiomers by chiral SFC purification (Chiralcel OJ-H 30×250 mm column, 30% MeOH (0.1% DEA) in CO$_2$ at 35° C. and 150 bar, 70 mL/min)

Examples 3A and 3B (S)-2-methoxy-4-(7-(2-chlorophenyl)-4-(methylamino)-6,7-dihydro-5H-cyclopenta[d]pyrimidin-2-ylamino)benzonitrile and (R)-2-methoxy-4-(7-(2-chlorophenyl)-4-(methylamino)-6,7-dihydro-5H-cyclopenta[d]pyrimidin-2-ylamino)benzonitrile

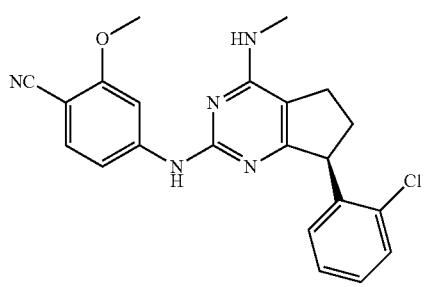

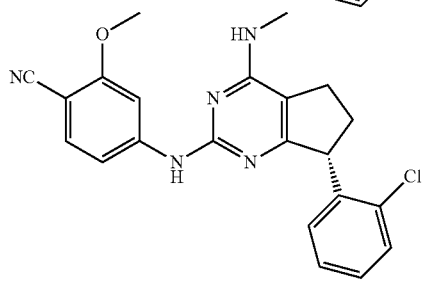

In a manner similar to that described in Example 1, commercially available 4-amino-2-methoxybenzonitrile and Preparation ARa were reacted to give (S)-2-methoxy-4-(7-(2-chlorophenyl)-4-(methylamino)-6,7-dihydro-5H-cyclopenta[d]pyrimidin-2-ylamino)benzonitrile. The racemate so obtained was separated into the enantiomers by chiral SFC purification (Chiralcel OJ-H 30×250 mm column, 35% MeOH (0.1% DEA) in CO$_2$ at 35° C. and 150 bar, 70 mL/min) Enantiomer A: LC-MS (M+H)$^+$=406.1. $^1$H NMR (500 MHz, CDCl$_3$) δ ppm 8.33 (br. s., 1H), 8.00 (d, J=1.8 Hz, 1H), 7.48-7.33 (m, 2H), 7.24-7.11 (m, 2H), 7.04-6.92 (m, 1H), 6.87 (dd, J=8.2, 1.8 Hz, 1H), 4.78-4.68 (m, 1H), 4.66 (d, J=4.6 Hz, 1H), 3.74 (s, 3H), 3.17 (d, J=4.9 Hz, 3H), 2.81-2.62 (m, 3H), 2.07-1.91 (m, 1H). The antipode had identical $^1$H NMR and LC/MS spectra.

Examples 4A and 4B (S)-2-methoxy-4-(7-(2-fluorophenyl)-4-(methylamino)-6,7-dihydro-5H-cyclopenta[d]pyrimidin-2-ylamino)benzonitrile and (R)-2-methoxy-4-(7-(2-fluorophenyl)-4-(methylamino)-6,7-dihydro-5H-cyclopenta[d]pyrimidin-2-ylamino)benzonitrile

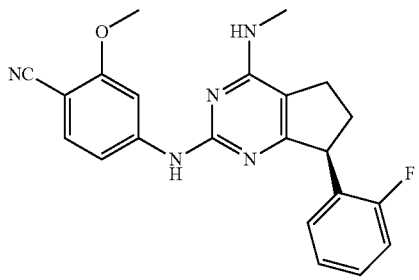

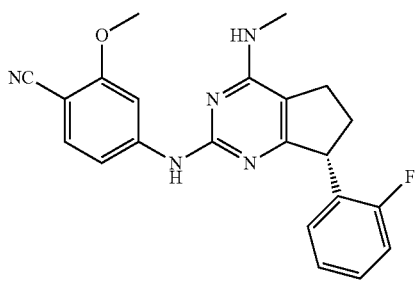

In a manner similar to that described in Example 1, commercially available 4-amino-2-methoxybenzonitrile and Preparation ASa were reacted to give (S)-2-methoxy-4-(7-(2-fluorophenyl)-4-(methylamino)-6,7-dihydro-5H-cyclopenta[d]pyrimidin-2-ylamino)benzonitrile. The racemate so obtained was separated into the enantiomers by chiral SFC purification (Chiralcel OJ-H 30×250 mm column, 25% MeOH (0.1% DEA) in CO$_2$ at 35° C. and 150 bar, 70 mL/min) Enantiomer A: LC-MS (M+H)$^+$=390.1. $^1$H NMR (500 MHz, CDCl$_3$) δ ppm 8.56 (br. s., 1H), 7.99 (d, J=1.8 Hz, 1H), 7.38 (d, J=8.5 Hz, 1H), 7.28-7.18 (m, 1H), 7.15-7.00 (m, 3H), 6.89 (dd, J=8.5, 1.8 Hz, 1H), 4.66 (d, J=4.6 Hz, 1H), 4.55-4.45 (m, 1H), 3.76 (s, 3H), 3.17 (d, J=4.9 Hz, 3H), 2.82-2.61 (m, 3H), 2.14-2.06 (m, 1H). The antipode had identical $^1$H NMR and LC/MS spectra.

Examples 5A and 5B (S)-2-methoxy-4-(4-(methylamino)-7-(2,4,6-trifluorophenyl)-6,7-dihydro-5H-cyclopenta[d]pyrimidin-2-ylamino)benzonitrile and (R)-2-methoxy-4-(4-(methylamino)-7-(2,4,6-trifluorophenyl)-6,7-dihydro-5H-cyclopenta[d]pyrimidin-2-ylamino)benzonitrile

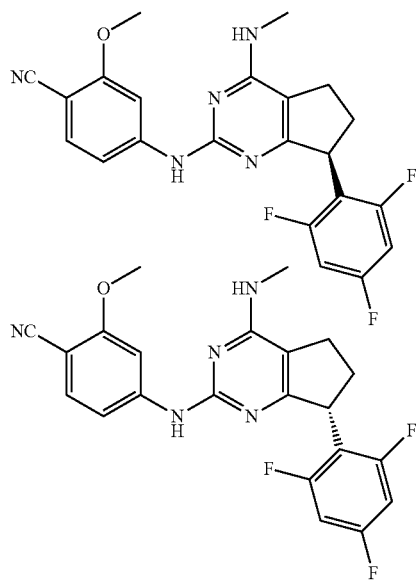

In a manner similar to that described in Example 1, commercially available 4-amino-2-methoxybenzonitrile and Preparation ATa were reacted to give 2-methoxy-4-(4-(methylamino)-7-(2,4,6-trifluorophenyl)-6,7-dihydro-5H-cyclopenta[d]pyrimidin-2-ylamino)benzonitrile. The racemate so obtained was separated into the enantiomers by chiral SFC purification (Chiralcel OJ-H 30×250 mm column, 15% MeOH (0.1% DEA) in $CO_2$ at 35° C. and 150 bar, 70 mL/min) Enantiomer A: LC-MS (M+H)$^+$=426.1. $^1$H NMR (500 MHz, CDCl$_3$) δ ppm 8.14 (br. s., 1H), 8.00 (d, J=1.8 Hz, 1H), 7.37 (d, J=8.5 Hz, 1H), 6.83 (dd, J=8.5, 1.8 Hz, 1H), 6.74-6.60 (m, 2H), 4.67-4.53 (m, 2H), 3.78 (s, 3H), 3.15 (d, J=4.9 Hz, 3H), 2.88-2.77 (m, 1H), 2.77-2.68 (m, 1H), 2.68-2.56 (m, 1H), 2.26-2.09 (m, 1H). The antipode had identical $^1$H NMR and LC/MS spectra.

Examples 6A and 6B (S)-4-(7-(4-chloro-2-fluorophenyl)-4-(methylamino)-6,7-dihydro-5H-cyclopenta[d]pyrimidin-2-ylamino)-2-methoxybenzonitrile and (R)-4-(7-(4-chloro-2-fluorophenyl)-4-(methylamino)-6,7-dihydro-5H-cyclopenta[d]pyrimidin-2-ylamino)-2-methoxybenzonitrile

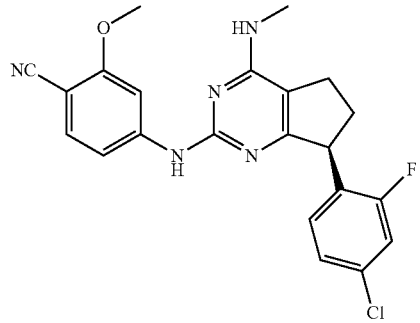

-continued

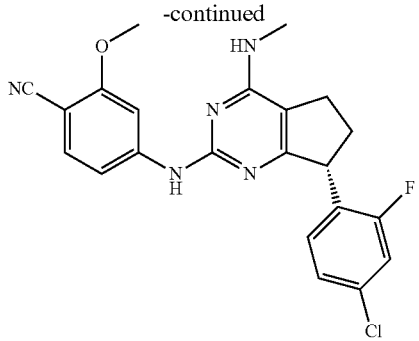

In a manner similar to that described in Example 1, commercially available 4-amino-2-methoxybenzonitrile and Preparation AUa were reacted to give 4-(7-(4-chloro-2-fluorophenyl)-4-(methylamino)-6,7-dihydro-5H-cyclopenta[d]pyrimidin-2-ylamino)-2-methoxybenzonitrile. The racemate so obtained was separated into the enantiomers by chiral SFC purification (Chiralcel OJ-H 30×250 mm column, 25% MeOH (0.1% DEA) in $CO_2$ at 35° C. and 150 bar, 70 mL/min) Enantiomer A: LC-MS (M+H)$^+$=424.1. $^1$H NMR (500 MHz, CDCl$_3$) δ ppm 7.99 (d, J=1.8 Hz, 1H), 7.67 (br. s., 1H), 7.37 (d, J=8.5 Hz, 1H), 7.16-6.99 (m, 3H), 6.76 (dd, J=8.5, 1.8 Hz, 1H), 4.61 (d, J=4.6 Hz, 1H), 4.52-4.41 (m, 1H), 3.72 (s, 3H), 3.14 (d, J=4.9 Hz, 3H), 2.82-2.61 (m, 3H), 2.15-1.98 (m, 1H). The antipode had identical $^1$H NMR and LC/MS spectra.

Examples 7A and 7B (S)-2-methoxy-4-(7-(3-methoxyphenyl)-4-(methylamino)-6,7-dihydro-5H-cyclopenta[d]pyrimidin-2-ylamino)benzonitrile and (R)-2-methoxy-4-(7-(3-methoxyphenyl)-4-(methylamino)-6,7-dihydro-5H-cyclopenta[d]pyrimidin-2-ylamino)benzonitrile

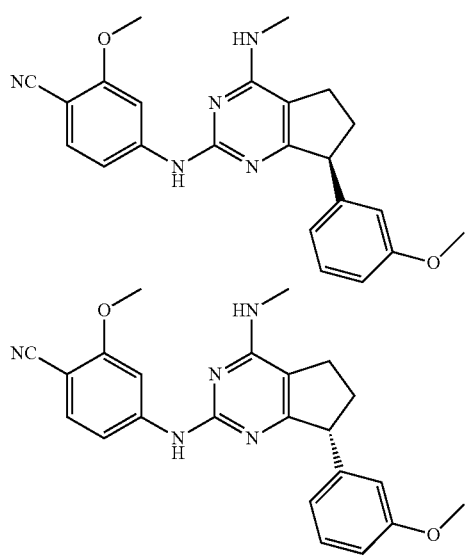

In a manner similar to that described in Example 1, commercially available 4-amino-2-methoxybenzonitrile and Preparation AVa were reacted to give 2-methoxy-4-(7-(3- methoxyphenyl)-4-(methylamino)-6,7-dihydro-5H-cyclopenta[d]pyrimidin-2-ylamino)benzonitrile. The racemate so obtained (Example 7) was separated into the enantiomers by chiral prep HPLC purification (Chiralpak AD 21×250 mm column, 35% EtOH:(0.1% DEA/Heptane), 15 mL/min) Enantiomer A: LC-MS (M+H)$^+$=402.6. $^1$H NMR (500 MHz, CDCl$_3$) δ ppm 8.04 (d, J=2.0 Hz, 1H), 7.35 (d, J=8.5 Hz, 1H), 7.24 (t, J=7.9 Hz, 2H), 6.84-6.70 (m, 3H), 6.66 (dd, J=8.5, 2.0 Hz, 1H), 4.60 (d, J=4.8 Hz, 1H), 4.25-4.10 (m, 1H), 3.79 (s, 3H), 3.63 (s, 3H), 3.13 (d, J=4.8 Hz, 3H), 2.84-2.65 (m, 3H), 2.17-2.00 (m, 1H). The antipode had identical $^1$H NMR and LC/MS spectra.

Example 8

4-(7-(2-fluoro-4-(trifluoromethyl)phenyl)-4-(methylamino)-6,7-dihydro-5H-cyclopenta[d]pyrimidin-2-ylamino)-2-methoxybenzonitrile

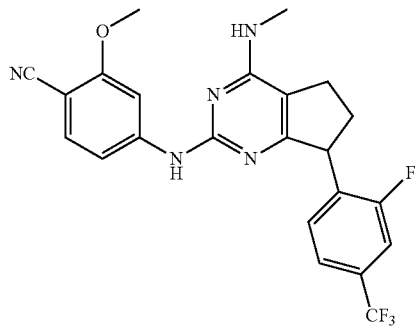 [SMILES: CNc1nc(Nc2ccc(C#N)c(OC)c2)nc2c1CCC2c1ccc(C(F)(F)F)cc1F]

In a manner similar to that described in Example 1, commercially available 4-amino-2-methoxybenzonitrile and Preparation AXa were reacted to give 4-(7-(2-fluoro-4-(trifluoromethyl)phenyl)-4-(methylamino)-6,7-dihydro-5H-cyclopenta[d]pyrimidin-2-ylamino)-2-methoxybenzonitrile. LC-MS (M+H)$^+$=458.6. $^1$H NMR (400 MHz, CD$_3$OD) δ ppm 7.70 (d, J=1.5 Hz, 1H), 7.66-7.54 (m, 3H), 7.51-7.44 (m, 1H), 7.22-7.11 (m, 1H), 4.89-4.77 (m, 1H), 3.94 (s, 3H), 3.20 (s, 3H), 3.01-2.75 (m, 3H), 2.18 (d, J=8.8 Hz, 1H).

Example 9

4-(7-(2-fluoro-4-(trifluoromethoxy)phenyl)-4-(methylamino)-6,7-dihydro-5H-cyclopenta[d]pyrimidin-2-ylamino)-2-methoxybenzonitrile

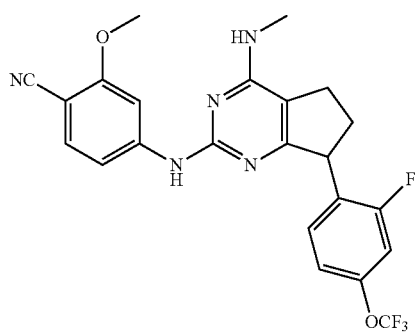 [SMILES: CNc1nc(Nc2ccc(C#N)c(OC)c2)nc2c1CCC2c1ccc(OC(F)(F)F)cc1F]

In a manner similar to that described in Example 1, commercially available 4-amino-2-methoxybenzonitrile and Preparation AYa were reacted to give 4-(7-(2-fluoro-4-(trifluoromethoxy)phenyl)-4-(methylamino)-6,7-dihydro-5H-cyclopenta[d]pyrimidin-2-ylamino)-2-methoxybenzonitrile. LC-MS (M+H)$^+$=474.6. $^1$H NMR (400 MHz, CDCl$_3$) δ ppm 12.07 (s, 1H), 7.58 (d, J=1.8 Hz, 1H), 7.53-7.34 (m, 2H), 7.34-7.16 (m, 1H), 7.11-6.89 (m, 2H), 5.62 (d, J=5.0 Hz, 1H), 4.64 (t, J=7.3 Hz, 1H), 3.94 (s, 3H), 3.27 (d, J=5.0 Hz, 3H), 2.99-2.87 (m, 1H), 2.87-2.74 (m, 2H), 2.40-2.14 (m, 1H).

Biological Methods

Cellular Assays for Inhibition of Aβ1-40 and Aβ1-42 Production

H4 cells stably transfected with APP751 containing the Swedish mutation (H4 APP751 SWE clone 8.20, developed at BMS) were maintained in log phase through twice weekly passage at a 1:20 split. For IC$_{50}$ determinations, 30 µl cells (1.5×10$^4$ cells/well) in DMEM media containing 0.0125% BSA (Sigma A8412) were plated directly into 384-well compound plates (Costar 3709) containing 0.1 µl serially diluted compound in DMSO. Following incubation for 19 h in 5% CO$_2$ at 37° C., plates were briefly centrifuged (1000 rpm, 5 min). A 10 µl aliquot from each well was transferred to a second assay plate (Costar 3709) for Aβ40 measurements. Antibody cocktails were freshly prepared by dilution into 40 mM Tris-HCl (pH 7.4) with 0.2% BSA and added to assay plates. For Aβ42 measurements, antibodies specific for the Aβ42 neoepitope (565, developed at BMS; conjugated to the Wallac reagent (Perkin Elmer)) and the N-terminal sequence of Aβ peptide (26D6, developed at SIBIA; conjugated to AβC (Perkin Elmer)) were mixed and 20 µl of the mixture was added to each well of the incubated cell plate yielding a final concentration of 0.8 ng/well 565 and 75 ng/well 26D6. For the Aβ40 measurements, antibodies specific for the Aβ40 neoepitope (TSD, developed at BMS; conjugated to the Wallac reagent (Perkin Elmer)) and 26D6 as described above were mixed and 20 µl of the mixture was added to the 10 µl aliquots which had been removed previously from the cell plate yielding a final concentration of 1.6 ng/well TSD and 17.5 ng/well 26D6. Assay plates containing antibodies were sealed with aluminum foil and incubated overnight at 4° C. Signal was determined using a Viewlux counter (Perkin Elmer) and IC$_{50}$ values determined using curve fitting in CurveMaster (Excel Fit based).

The activity of representative compounds of the present disclosure, based on Aβ42 cellular IC$_{50}$ values in H4 APP751 SWE clone 8.20, are illustrated in Table 1 (below).

TABLE 1

| Compound of Example | Activity Rating$^a$ | Compound of Example | Activity Rating$^a$ |
| --- | --- | --- | --- |
| 1A | 13 | 1B | ++ |
| 2A | 200 | 2B | + |
| 3A | +++ | 4A | ++ |
| 5A | 11 | 6A | ++ |
| 7 | ++ | 8 | ++ |
| 9 | 12 | | |

$^a$Activity based on Aβ42 cellular IC$_{50}$ values in H4 APP751 SWE clone 8.20.
+++ = 1.5 nM-0.0099M
++ = 0.010-0.100 µM
+ = 0.100-1.0 µM It will be evident to one skilled in the art that the present disclosure is not limited to the foregoing illustrative

What is claimed is:

1. A compound of formula (I)

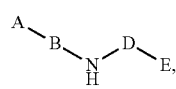
(I)

or a pharmaceutically acceptable salt thereof, wherein

A is a nitrile group;

B is selected from phenyl and pyridinyl, wherein the phenyl and pyridinyl are optionally substituted with one or two substituents independently selected from $C_{1-6}$alkoxy, $C_{1-6}$alkyl, $C_{1-3}$alkylamino-$C_{1-6}$alkoxy, cyano, $C_{1-3}$dialkylamino-$C_{1-6}$alkoxy, halo, halo$C_{1-6}$alkoxy, halo$C_{1-6}$alkyl, hydroxy, methylamino, and amino;

D is selected from the group of:

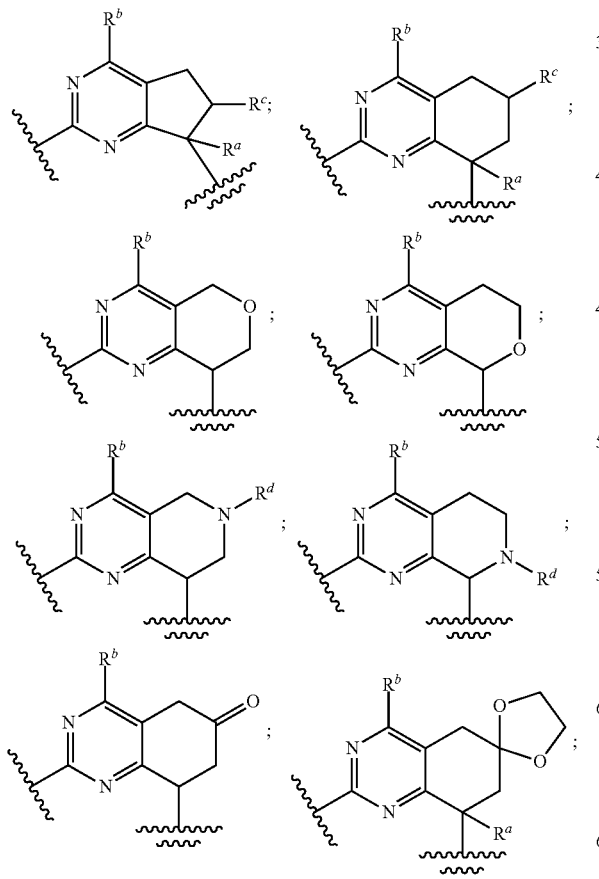

-continued

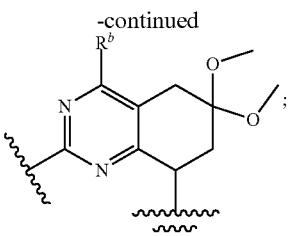

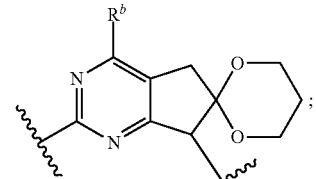

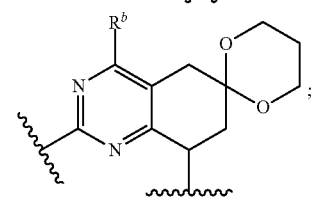

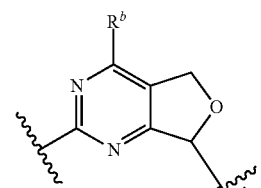

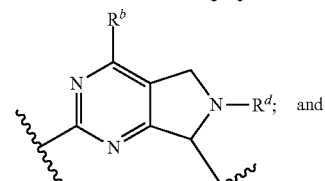

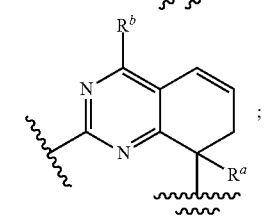

" $\xi$ " denotes the point of attachment to the nitrogen atom of the parent molecule;

" $\sim$ " denotes the point of attachment to the 'E' moiety;

$R^a$ is selected from hydrogen, $C_{1-6}$alkyl, $C_{2-6}$alkenyl, and hydroxy;

$R^b$ is —NR$^x$R$^y$, wherein R$^x$ and R$^y$ are independently selected from hydrogen, $C_{1-4}$alkoxy, $C_{1-4}$alkoxy$C_{1-4}$alkyl, $C_{1-4}$alkoxycarbonyl, $C_{1-6}$alkyl, $C_{3-7}$cycloalkyl, ($C_{3-7}$cycloalkyl)$C_{1-4}$alkyl, hydroxy$C_{1-4}$alkyl, and trideuteromethyl, wherein the alkyl part of the ($C_{3-7}$cycloalkyl)$C_{1-4}$alkyl can be optionally substituted with a $C_{1-4}$alkoxy group; or, R$^x$ and R$^y$, together with the nitrogen atom to which they are attached, form a four- to seven-membered monocyclic or bicyclic ring optionally containing one double bond and optionally containing one additional heteroatom selected from O, NR$^z$, and S; wherein R$^z$ is selected from hydrogen, $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —NR$^f$R$^g$, oxo, spirocyclic dioxolanyl; wherein R$^f$ and R$^g$ are independently selected from hydrogen, $C_{1-4}$alkoxycarbonyl, and $C_{1-6}$alkyl;

R$^c$ is selected from hydrogen, $C_{1-4}$alkylsulfonyl, $C_{1-4}$alkylsulfonylamido, amino, $C_{1-6}$alkylamino, $C_{1-6}$dialkylamino, $C_{3-7}$cycloalkylamino, hydroxy, and $C_{1-4}$alkoxy;

R$^d$ is selected from hydrogen, $C_{1-6}$alkyl, $C_{1-4}$alkoxy$C_{1-4}$alkylcarbonyl, $C_{1-6}$alkoxycarbonyl, $C_{1-6}$alkylcarbonyl, $C_{1-6}$alkylsulfonyl, $C_{3-7}$cycloalkylsulfonyl, $C_{3-7}$cycloalkylcarbonyl, $C_{1-6}$dialkylamino$C_{1-4}$alkylcarbonyl, and halo$C_{1-4}$alkyl, wherein the alkyl part of the alkoxycarbonyl, the alkylcarbonyl, and the alkylsulfonyl are optionally substituted with one substituent selected from $C_{1-4}$dialkylamino, and $C_{1-4}$alkoxy; and E is selected from $C_{1-6}$alkyl, $C_{4-6}$cycloalkyl, ($C_{4-7}$cycloalkyl)$C_{1-4}$alkyl, benzyl, phenyl, and a five- to six-membered heteroaromatic ring containing one or two nitrogen atoms, wherein the phenyl, the phenyl part of the benzyl, and the heteroaromatic ring are each optionally substituted with one, two, or three substituents independently selected from $C_{1-6}$alkyl, $C_{1-6}$alkoxy, cyano, halo, halo $C_{1-6}$alkoxy, and halo$C_{1-6}$alkyl.

2. A compound of claim 1, or a pharmaceutically acceptable salt thereof, wherein B is selected from phenyl and pyridinyl, wherein the phenyl and pyridinyl are optionally substituted with one or two substituents independently selected from $C_{1-6}$alkoxy and halo.

3. A compound of claim 2, or a pharmaceutically acceptable salt thereof, wherein E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl.

4. A compound of claim 3, or a pharmaceutically acceptable salt thereof, wherein D is selected from the group of:

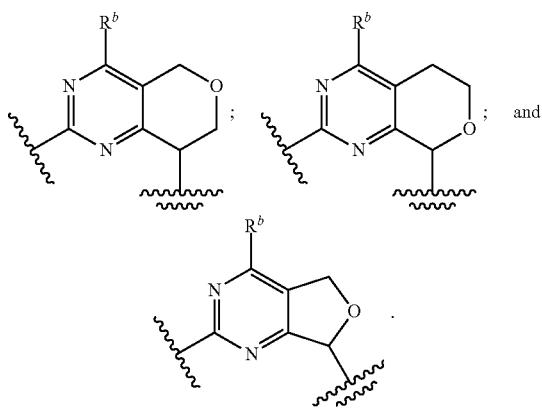

5. A compound of claim 4, or a pharmaceutically acceptable salt thereof, wherein R$^b$ is —NR$^x$R$^y$, wherein R$^x$ and R$^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the ($C_{3-7}$cycloalkyl)$C_{1-4}$alkyl can be optionally substituted with a $C_{1-4}$alkoxy group.

6. A compound of claim 4, or a pharmaceutically acceptable salt thereof, wherein R$^b$ is —NR$^x$R$^y$, wherein R$^x$ and R$^y$, together with the nitrogen atom to which they are attached, form a four- to seven-membered monocyclic or bicyclic ring optionally containing one additional heteroatom selected from O and NR$^z$; wherein R$^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —NR$^f$R$^g$, oxo, and spirocycle dioxolanyl; wherein R$^f$ and R$^g$ are independently selected from hydrogen, $C_{1-4}$alkoxycarbonyl, and $C_{1-6}$alkyl.

7. A compound of claim 3, or a pharmaceutically acceptable salt thereof, wherein D is selected from the group of:

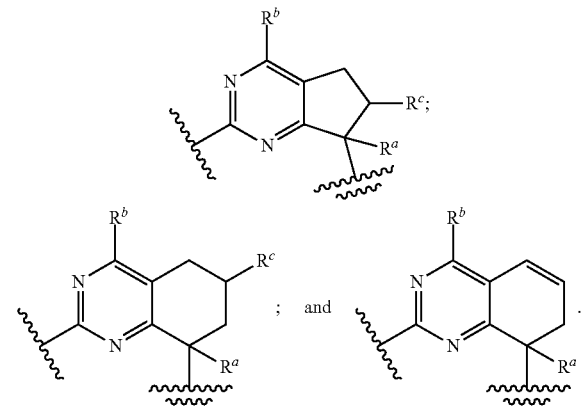

8. A compound of claim 7, or a pharmaceutically acceptable salt thereof, wherein R is —NR$^x$R$^y$, wherein R$^x$ and R$^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the ($C_{3-7}$cycloalkyl)$C_{1-4}$alkyl can be optionally substituted with a $C_{1-4}$alkoxy group.

9. A compound of claim 7, or a pharmaceutically acceptable salt thereof, wherein R$^b$ is —NR$^x$R$^y$, wherein R$^x$ and R$^y$, together with the nitrogen atom to which they are attached, form a four- to seven-membered monocyclic or bicyclic ring optionally containing one additional heteroatom selected from O and NR$^z$; wherein R$^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —NR$^f$R$^g$, oxo, and spirocycle dioxolanyl; wherein R$^f$ and R$^g$ are independently selected from hydrogen, $C_{1-4}$alkoxycarbonyl, and $C_{1-6}$alkyl.

10. A compound of claim 3, or a pharmaceutically acceptable salt thereof, wherein D is selected from

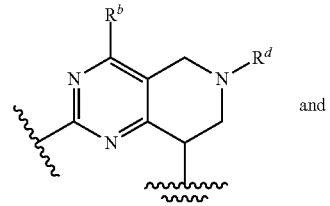

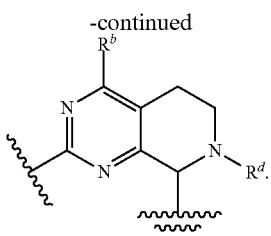

11. A compound of claim 10, or a pharmaceutically acceptable salt thereof, wherein $R^b$ is —$NR^xR^Y$, wherein $R^x$ and $R^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the $(C_{3-7}$cycloalkyl) $C_{1-4}$alkyl can be optionally substituted with a $C_{1-4}$alkoxy group.

12. A compound of claim 10, or a pharmaceutically acceptable salt thereof, wherein $R^b$ is —$NR^xR^y$, wherein $R^x$ and $R^Y$, together with the nitrogen atom to which they are attached, form a four- to seven-membered monocyclic or bicyclic ring optionally containing one additional heteroatom selected from O and $NR^z$; wherein $R^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —$NR^fR^g$, oxo, and spirocycle dioxolanyl; wherein $R^f$ and $R^g$ are independently selected from hydrogen, $C_{1-4}$alkoxycarbonyl, and $C_{1-6}$alkyl.

13. A compound selected from the group consisting of:
2-methoxy-4-(7-(2-methoxyphenyl)-4-(methylamino)-6,7-dihydro-5H-cyclopenta[d]pyrimidin-2-ylamino)benzonitrile
4-(7-(4-fluorophenyl)-7-methyl-4-(methylamino)-6,7-dihydro-5H-cyclopenta[d]pyrimid in-2-ylamino)-2-methoxybenzonitrile
2-methoxy-4-(7-(2-chlorophenyl)-4-(methylamino)-6,7-dihydro-5H-cyclopenta[d]pyrimidin-2-ylamino)benzonitrile
2-methoxy-4-(7-(2-fluorophenyl)-4-(methylamino)-6,7-dihydro-5H-cyclopenta[d]pyrimidin-2-ylamino)benzonitrile
2-methoxy-4-(4-(methylamino)-7-(2,4,6-trifluorophenyl)-6,7-dihydro-5H-cyclopenta[d]pyrimidin-2-ylamino)benzonitrile
4-(7-(4-chloro-2-fluorophenyl)-4-(methylamino)-6,7-dihydro-5H-cyclopenta[d]pyrimidin-2-ylamino)-2-methoxybenzonitrile
2-methoxy-4-(7-(3-methoxyphenyl)-4-(methylamino)-6,7-dihydro-5H-cyclopenta[d]pyrimidin-2-ylamino)benzonitrile
4-(7-(2-fluoro-4-(trifluoromethyl)phenyl)-4-(methylamino)-6,7-ihydro-5H-cyclopenta[d]pyrimidin-2-ylamino)-2-methoxybenzonitrile, and
4-(7-(2-fluoro-4-(trifluoromethoxy)phenyl)-4-(methylamino)-6,7-dihydro-5H-cyclopenta[d]pyrimidin-2-ylamino)-2-methoxybenzonitrile; or a pharmaceutically acceptable salt thereof.

14. A pharmaceutical composition for the treatment of disorders responsive to the reduction of β-amyloid peptide production comprising a therapeutically effective amount of a compound of claim 1, or a pharmaceutically acceptable salt thereof, in association with a pharmaceutically acceptable carrier or diluent.

15. A method for the treatment of disorders responsive to the reduction of β-amyloid peptide production in a mammal in need thereof, which comprises administering to said mammal a therapeutically effective amount of a compound of claim 1 or a pharmaceutically acceptable salt thereof.

16. A method of claim 15 wherein said disorder is selected from Alzheimer's Disease (AD), Down Syndrome, mild cognitive impairment (MCI), cerebral amyloid angiopathy (CAA), dementia with Lewy bodies (DLB), amyotrophic lateral sclerosis (ALS-D), inclusion body myositis (IBM), age-related macular degeneration, and cancer.

17. A method of claim 16 wherein said disorder is selected from Alzheimer's Disease and Down Syndrome.

18. A method of claim 17 wherein said disorder is Alzheimer's Disease.

* * * * *